United States Patent
Menear et al.

(10) Patent No.: US 8,129,380 B2
(45) Date of Patent: Mar. 6, 2012

(54) PHTHALAZINONE DERIVATIVES

(75) Inventors: Keith Allan Menear, Cambridge (GB); Muhammad Hashim Javaid, Cambridge (GB); Sylvie Gomez, Cambridge (GB); Marc Geoffrey Hummersone, Cambridge (GB); Carlos Fenandez Lence, Cambridge (GB); Niall Morrison Barr Martin, Cambridge (GB); David Alan Rudge, Alderley Park (GB); Craig Anthony Roberts, Alderley Park (GB); Kevin Blades, Alderley Park (GB)

(73) Assignee: AstraZeneca AB, Sodertalje (SE)

( * ) Notice: Subject to any disclaimer, the term of this patent is extended or adjusted under 35 U.S.C. 154(b) by 528 days.

(21) Appl. No.: 12/357,957

(22) Filed: Jan. 22, 2009

(65) Prior Publication Data
US 2009/0192156 A1    Jul. 30, 2009

Related U.S. Application Data

(60) Provisional application No. 61/022,900, filed on Jan. 23, 2008, provisional application No. 61/142,413, filed on Jan. 5, 2009.

(51) Int. Cl.
C07D 237/02 (2006.01)
A61K 31/502 (2006.01)
A61P 35/04 (2006.01)

(52) U.S. Cl. .................... 514/248; 544/237
(58) Field of Classification Search ........... 544/237; 514/248
See application file for complete search history.

(56) References Cited

U.S. PATENT DOCUMENTS

| | | | |
|---|---|---|---|
| 3,813,384 A | 5/1974 | Vogelsang et al. | |
| 4,665,181 A | 5/1987 | Thomas et al. | |
| 4,841,047 A | 6/1989 | Engel et al. | |
| 4,912,115 A | 3/1990 | Bomhard et al. | |
| 5,032,617 A | 7/1991 | Lee et al. | |
| 5,041,653 A | 8/1991 | Lee et al. | |
| 5,215,738 A | 6/1993 | Lee et al. | |
| 5,556,856 A | 9/1996 | Engel et al. | |
| 5,587,384 A | 12/1996 | Zhang et al. | |
| 5,648,355 A | 7/1997 | Theoharides | |
| 5,874,444 A | 2/1999 | West | |
| 5,886,178 A | 3/1999 | Allen et al. | |
| 6,197,785 B1 | 3/2001 | Jackson et al. | |
| 6,340,684 B1 | 1/2002 | Napoletano et al. | |
| 6,426,415 B1 | 7/2002 | Jackson et al. | |
| 6,476,048 B1 | 11/2002 | Szabo et al. | |
| 6,498,160 B2 | 12/2002 | Napoletano et al. | |
| 6,514,983 B1 | 2/2003 | Li | |
| 6,514,984 B1 | 2/2003 | Watanabe | |
| 6,635,642 B1 | 10/2003 | Jackson et al. | |
| 6,677,333 B1 | 1/2004 | Seko et al. | |
| 6,903,098 B1 | 6/2005 | Lubisch et al. | |
| 7,041,675 B2 | 5/2006 | Lubisch et al. | |
| 7,087,637 B2 | 8/2006 | Grandel et al. | |
| 7,151,102 B2 | 12/2006 | Martin et al. | |
| 7,196,085 B2 | 3/2007 | Martin et al. | |
| 7,402,580 B2 | 7/2008 | Seko et al. | |
| 7,981,890 B2 | 7/2011 | Javaid et al. | |
| 2004/0176361 A1 | 9/2004 | Fujio et al. | |
| 2005/0059663 A1 | 3/2005 | Martin et al. | |
| 2005/0080096 A1 | 4/2005 | Ishida et al. | |
| 2005/0227919 A1 | 10/2005 | Ashworth et al. | |
| 2006/0063767 A1 | 3/2006 | Javaid et al. | |
| 2006/0142293 A1 | 6/2006 | Martin et al. | |
| 2007/0093489 A1 | 4/2007 | Javaid et al. | |
| 2008/0161280 A1 | 7/2008 | Gandhi et al. | |
| 2008/0269234 A1 | 10/2008 | Gandhi et al. | |
| 2009/0023727 A1 | 1/2009 | Javaid et al. | |

FOREIGN PATENT DOCUMENTS

| | | |
|---|---|---|
| CA | 972755 | 8/1975 |
| CA | 2352194 | 4/2001 |
| DE | 2143745 | 3/1973 |
| DE | 3813531 | 4/1988 |
| DE | 287 032 | 2/1991 |

(Continued)

OTHER PUBLICATIONS

International Search Report, PCT/GB2009/000181, mailing date Jun. 5, 2009.*

(Continued)

*Primary Examiner* — Susanna Moore
(74) *Attorney, Agent, or Firm* — Morgan Lewis & Bockius LLP

(57) ABSTRACT

A compound of the formula (I):

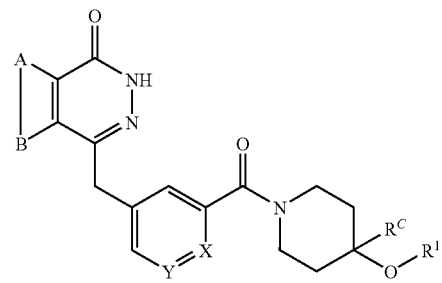

wherein:

A and B together represent an optionally substituted, fused aromatic ring; X and Y are selected from CH and CH, CF and CH, CH and CF and N and CH respectively; $R^C$ is selected from H, $C_{1-4}$ alkyl; and $R^1$ is selected from $C_{1-7}$ alkyl, $C_{3-20}$ heterocyclyl and $C_{5-20}$ aryl, which groups are optionally substituted; or $R^C$ and $R^1$ together with the carbon and oxygen atoms to which they are attached form a spiro-$C_{5-7}$ oxygen-containing heterocyclic group, which is optionally substituted or fused to a $C_{5-7}$ aromatic ring.

11 Claims, 3 Drawing Sheets

FOREIGN PATENT DOCUMENTS

| | | |
|---|---|---|
| EP | 0030861 | 6/1981 |
| EP | 0269968 | 6/1988 |
| EP | 0355750 | 2/1990 |
| EP | 0389995 | 10/1990 |
| EP | 0502575 | 9/1992 |
| EP | 0590551 | 4/1994 |
| EP | 0634404 | 1/1995 |
| EP | 0699754 | 3/1996 |
| EP | 0705903 | 4/1996 |
| EP | 0792643 | 9/1997 |
| EP | 1477175 | 11/2004 |
| EP | 1908481 | 4/2008 |
| FR | 2262513 | 9/1975 |
| GB | 721286 | 1/1955 |
| GB | 2384776 | 3/2004 |
| IT | MI98A001671 | 4/1999 |
| JP | 54156526 | 12/1979 |
| JP | 58164577 | 9/1983 |
| JP | 62-252774 | 11/1987 |
| WO | WO 91/18591 | 12/1991 |
| WO | WO 93/14086 | 7/1993 |
| WO | WO 94/10151 | 5/1994 |
| WO | WO 95/24379 | 9/1995 |
| WO | WO 96/19225 | 6/1996 |
| WO | WO 98/43477 | 10/1998 |
| WO | WO 98/51308 | 11/1998 |
| WO | WO 99/08680 | 2/1999 |
| WO | WO 99/11624 | 3/1999 |
| WO | WO 99/11645 | 3/1999 |
| WO | WO 99/11649 | 3/1999 |
| WO | WO 99/44612 | 9/1999 |
| WO | WO 99/47494 | 9/1999 |
| WO | WO 00/05219 | 2/2000 |
| WO | WO 00/42040 | 7/2000 |
| WO | WO 00/44726 | 8/2000 |
| WO | WO 00/67734 | 11/2000 |
| WO | WO 01/12199 | 2/2001 |
| WO | WO 01/16136 | 3/2001 |
| WO | WO 01/16137 | 3/2001 |
| WO | WO 01/21615 | 3/2001 |
| WO | WO 01/23390 | 4/2001 |
| WO | WO 01/57038 | 8/2001 |
| WO | WO 01/79184 | 10/2001 |
| WO | WO 01/85686 | 11/2001 |
| WO | WO 01/85687 | 11/2001 |
| WO | WO 01/87845 | 11/2001 |
| WO | WO 01/90077 | 11/2001 |
| WO | WO 02/36576 | 5/2002 |
| WO | WO 02/44157 | 6/2002 |
| WO | WO 02/068407 | 9/2002 |
| WO | WO 02/090334 | 11/2002 |
| WO | WO 02/094790 | 11/2002 |
| WO | WO 03/007959 | 1/2003 |
| WO | WO 03/051879 | 6/2003 |
| WO | WO 03/055865 | 7/2003 |
| WO | WO 03/057145 | 7/2003 |
| WO | WO 03/063874 | 8/2003 |
| WO | WO 03/070707 | 8/2003 |
| WO | WO 03/070726 | 8/2003 |
| WO | WO 03/080581 | 10/2003 |
| WO | WO 03/093261 | 11/2003 |
| WO | WO 2004/080976 | 9/2004 |
| WO | WO 2005/053662 | 6/2005 |
| WO | WO 2006021801 * | 3/2006 |
| WO | WO 2006/137510 | 12/2006 |
| WO | WO 2007/045877 | 4/2007 |
| WO | WO 2008/083027 | 7/2008 |

OTHER PUBLICATIONS

Affar, E. B. et al., "Immunodot blot method for the detection of poly(ADP-ribose) synthesized in vitro and in vivo," Anal. Biochem 259(2):280-283 (1998).

Al-Dabbagh and Smith, "Species differences in oxidative drug metabolism: some basic considerations." Archives of toxicology, Supplement. Archiv fur Toxikologie. Supplement, vol. 7, 219-231 (1984).

Ame, J-C. et al., "PARP-2, a novel mammalian DNA damage-dependent poly(ADP-ribose) polymerase," J. Biol. Chem. 274(25):17860-17868 (1999).

Ame, J-C. et al., "The PARP superfamily," BioEssays 26:882-893 (2004).

Angell, S.M. et al., "Consistent gene silencing in transgenic plants expressing a replicating potato virus X RNA," EMBO J. 16(12):3675-3684 (1997).

Arnaudeau, C. et al., "DNA double-strand breaks associated with replication forks are predominantly repaired by homologous recombination involving an exchange mechanism in mammalian cells," J. Mol. Biol 307:1235-1245 (2001).

Banasik, M. et al., "Inhibitors and activators of ADP-ribosylation reactions," Mol. Cell Biochem. 138:185-197 (1994).

Banasik, M. et al., "Specific Inhibitors of Poly (ADP-Ribose) Synthetase and Mono (ADP-Ribosyl) transferse", J. Biol. Chem., vol. 267, 1569-1575 (1992).

Ben-Hur, E. et al , "Inhibitors of poly (ADP-ribose) synthesis enhance radiation response by differentially affecting repair of potentially lethal versus sublethal damage," Br. J. Cancer 49(VI):39-42 (1984).

Berge et al., "Pharmaceutically Acceptable Salts," J. Pharm. Sci., vol. 66, 1-19. Protective Groups in Organic Synthesis (T. Green and P. Wuts, Wiley, 1991) (1977).

Berger, N. A. et al., "Poly (ADP-ribose) in cellular response to DNA damage", Radiation Research, 101:4-14 (1985).

Bhattacharyya, A. et al., "The breast cancer susceptibility gene BRCA1 is required for subnuclear assembly of Rad51 and survival following treatment with the DNA cross-linking agent cisplatin," J. Biol. Chem. 275(31): 23899-23903 (2000).

Bloch, W. et al., "Poly-adenosine diphosphate-ribose polymerase inhibition for myocardial protection: pathophysiologic and physiologic considerations," J. Thoracic Card. Surg. 128(2):323-324 (2004).

Bold, G. et al., "New anilinophthalazines as potent and orally well absorbed inhibitors of the VEGF receptor tyrosine kinases useful as antagonists of tumor-driven angiogenesis," J. Med. Chem. 43:3200 (Abstract) (2000).

Bold, G. et al., "New anilinophthalazines as potent and orally well absorbed inhibitors of the FEBF receptor tyrosine kinases useful as antagonists of tumour-driven angiogenesis", J. Med. Chem., 43(12):2310-2323 (2000).

Bowman et al., "Differential effects of the poly (ADP-ribose) polymerase (PARP) inhibitor NU 1025 on topoisomerase I and II inhibitor cytotoxicity in L1210 cells in vitro," British Journal of Cancer, 84(1):106-112 (2001).

Brummelkamp, T. R. et al., "A system for stable expression of short interfering RNAs in mammalian cells," Science 296:550-553 (2002).

Bundgaard, H., "Design of prodrugs: Bioreversible derivatives for various functional groups and chemical entities" Design of Prodrugs, Chapter 1 Elsevier Science Publishers (1985).

Burzio, L. et al., "Poly (adenosine diphosphoribose) synthase activity of isolated nuclei of normal and leukemic leukocytes (38930)", Proc. Soc. Exp. Bio. Med., 149:933-938 (1975).

Calabrese, C.R. et al., "Identification of potent nontoxic poly(ADP-ribose) polymerase-1 inhibitors: chemopotentiation and pharmacological studies," Clin. Can. Res. 9:2711-2718 (2003).

Caldecott, K.W., "DNA single-strand break repair and spinocerebellar ataxia," Cell 112:7-10 (2003).

Cantoni, O. et al., "Hydrogen peroxide insult in cultured mammalian cells: relationships between DNA single-strand breakage, poly (ADP-ribose) metabolism and cell killing", Biochim. Biophys. Acta, 1014:1-7 (1989).

Catteau, A. et al., "Methylation of the BRCA1 promoter region in sporadic breast and ovarian cancer: correlation with disease characteristics," Oncogene 18:1957-1965 (1999).

Chalmers, A.J. , "Poly(ADP-ribose) polymerase-1 and ionizing radiation: sensor, signaller and therapeutic target," Clin. Onc. 16:29-39 (2004).

Chappuis, P. O. et al., "Risk Assessment and Genetic Testing," Cancer Treat. Res., 107:29-59 (2002).

Chiarugi, A., "Poly(ADP-ribose) polymerase: killer or conspirator? The 'suicide hypothesis' revisted," Trends in Pharm. Sci. 23(3):122-129 (2002).

Cockcroft, X-L. et al., "Phthalazinones 2: optimisation and synthesis of novel potent inhibitors of poly(ADP-ribose)polymerase," Biorg. Med. Chem. Lett. 16:1040-1044 (2006).

Cosi, C. et al., "Poly (ADP-ribose) polymerase: early involvement in glutamate-induced neurotoxicity in cultured cerebellar granule cells", J.Neurosci. Res., 39:38-46 (1994).

Cosi, C., "New inhibitors of poly(ADP-ribose) polymerase and their potential therapeutic targets," Expert Opin. Ther. Patents 12(7): 1047-1071 (2002).

Couzin, J., "The twists and turns in BRCA's path," Science 302:591-592 (2003).

Crooke, S.T., "Therapeutic applications of oligonucleotides," Ann. Rev. Pharmacol. Toxicol. 32:329-376 (1992).

Cuzzocrea, S., "Shock, inflammation and PARP," Pharmacological Res. 52:72-82 (2005).

D'Adda Di Fagagna, F. et al., "Functions of poly(ADP-ribose) polymerase in controlling telomere length and chromosomal stability", Nature Gen., 23(1): 76-80 (1999).

D'Amours, D. et al., "Poly(ADP-ribosyl)ation reactions in the regulation of nuclear functions", Biochem. J., 342:249-268 (1999).

D'Amours, D. et al., "The MRE11 complex: at the crossroads of DNA repair and checkpoint signalling," Mol. Cell Biol. 3:317-327 (2002).

D'Andrea, A. D. et al., "The fanconi anaemia/BRCA pathway," Nat. Rev. Cancer 3:23-34 (2003).

Dantzer, F. et al., "Base excision repair is imparied in mammalian cells lacking poly(ADP-ribose) polymerase-1," Biochemistry 39:7559-7569 (2000).

Dantzer, F. et al., "Involvement of poly(ADP-ribose) polymerase in base excision repair," Biochimie 81:69-75 (1999).

Davies, A. A. et al., "Role of BRCA2 in control of the RAD51 recombination and DNA repair protein," Mol. Cell 7:273-282 (2001).

Dillon, K. J. et al., "A flashplate assay for the identification of PARP-1 inhibitors," J. Biomolecular Screening 8(3):347-352 (2003).

Durkacz, B. W. et al., "(ADP-ribose)n participates in DNA excision repair", Nature, 283(7):593-596 (1980).

Dusemund, "Isochino [3,2-a]phthalazin-5,8-dione", Arch. Pharm., (Weinhein) 925-930 (English Abstract) (1982).

Dusemund, J., "Einfache synthese von isochino[2,3-c][2,3]benzoxazepinon und-[2,3]benzodiazepinonen sowie ihrer vorstufen," Arch. Pharm. 321:41-44 (1988).

Egawa, C. et al., "Decreased expression of BRCA2 mRNA predicts favorable response to docetaxel in breast cancer," Int. J. Cancer 95:255-259 (2001).

Egawa, C. et al., "Quantitative analysis of estrogen receptor-? and-? messenger RNA expression in normal and malignant thyroid tissues by real-time polymerase chain reaction," Oncology 61:293-298 (2001).

Ehrlich, H.A. et al., "Recent advances in the polymerase chain reaction," Science 252:1643-1650 (1991).

Elbashir, S. M. et al., "Duplexes of 21-nucleotide RNAs mediate RNA interference in cultured mammalian cells," Nature 411:494-498 (2001).

El-Tamaty et al., Synthesis and biological activity of some 4-benzyl-1(2H)-phthalazinone derivatives, Indian J. Chemistry, v. 35B, 1067-1072 (1996).

El-Tamaty, E-S.H. et al., "Synthesis and biological activity of some 4-benzyl-1(2H)-phthalazinone derivatives," Chem. Abs. 125:23, 125:300924j (1996).

Esteller, M. et al., "Promoter hypermethylation and BRCA1 inactivation in sporadic breast and ovarian tumors," J. Natl. Cancer Inst. 92(7):564-569 (2000).

Ferraris, D. et al., "Design and synthesis of poly ADP-ribose polymerase-1 inhibitors. 2. Biological evaluation of Aza-5[H]-phenanthridin-6-ones as potent, aqueous-soluble compounds for the treatment of ischemic injuries," J. Med. Chem. 46:3138-3151 (2003).

Fire, A. et al., "Potent and specific genetic interference by double-stranded RNA in Caenorhabditis elegans," Nature 391:806-811 (1998).

Foray, N. et al., "A subset of ATM- and ATR-dependent phosphorylation events requires the BRCA1 protein," Embo J. 22(11):2860-2871 (2003).

Fujisawa Pharmaceutical Co., "Preaparation of 2-carboxyalkyl-4-aralkylphthalazine derivaties as aldose reductase inhibitors and a process for preparing them," Chemical Abstracts 109:6531 (1987).

Fuska, J. et al., "New Cytotoxic and antitumor agents," Chemical Abstracts, 104:102050 (1985).

Gaken, J. A. et al., "Efficient retroviral infection of mammalian cells is blocked by inhibition of poly(ADP-ribose) polymerase activity", J. Virology, 70(6): 3992-4000 (1996).

Greene, T.W. et al., Protective Groups in Organic Synthesis, Chapters 2 and 7, John Wiley & Sons Inc. 17-23 and 494-503 (1999).

Griffin et al., "The role of inhibitors of poly (ADP-ribose) polymerase as resistance-modifying agents in cancer therapy," Biochimie 77:408-422 (1995).

Griffin, C.S. et al., "Mammalian recombination-repair genes XRCC2 and XRCC3 promote correct chromosome segregation," Nature Cell Biol. 2:757-761 (2000).

Grube, K. et al., "Direct stimulation of poly(ADP ribose) polymerase in permeabilized cells by double-stranded DNA oligomers," Anal. Biochem. 193:236-239 (1991).

Haber, J. E., "DNA recombination: the replication connection," Trends Biochem. Sci. 24:271-275 (1999).

Hall, I.H. et al., "Cytotoxicity of imides-N-alkyl semicarbazones, thiosemicarbazones, acetylhydrazones and related derivatives," Anti-Cancer Drugs (and abstract 122:204573), V.6, 147-153 (1995).

Halldorsson, H. et al., "Poly(ADP-ribose) polymerase activity in nucleotide permeable cells," FEBS Lett. 85(2):349-352 (1978).

Hawley's Condensed Chemical Dictionary, 13th ed., Van Nostrand Reinhold eds. 716 and 825 (1997).

Herceg, Z. et al., "Functions of poly(ADP-ribose) polymerase (PARP) in DNA repair, genomic intergrity and cell death," Mut. Res. 477:97-110 (2001).

Hirai, K. et al., "Aberration of poly(adenosine diphosphate-ribose) metabolism in human colon adenomatous polyps and cancers", Cancer Res., 43:3441-3446 (1983).

Hiramoto, T. et al., "Mutations of a novel human RAD54 homologue, RAD54B, in primary cancer," Oncogene 18:3422-3426 (1999).

Hoeijmakers, J. H.J., "Genome maintenance mechanisms for preventing cancer," Nature 411:366-374 (2001).

Hughes-Davies, L. et al., "EMSY links the BRCA2 pathway to sporadic breast and ovarian cancer," Cell 115:523-535 (2003).

Islam, A.M. et al., "4, 5, 6, 7-Tetraiodo-3-benzalphthalides and related compounds," (1981) Chemical Abstracts 95:187182.

Islam, A.M. et al., "Action of phosphorus pentasulfide on the products of interaction of p-sulfamoylphenylacetic acids with phthalic anhydride," Chemical Abstracts 95:62106 (1981).

Islam, A.M. et al., "Thioarylidenephthalides and related compounds: Part II. Reactions with amino compounds," Chemical Abstracts 87:67943 (1977).

Jackson, S.P., "Sensing and repairing DNA double-strand breaks," Carcinogenesis 23(5):687-696 (2002).

Janatova, M. et al., "Detection of the most frequent mutations in BRCA1 gene on polyacrylamide gels containing spreadex polymer NAB," Neoplasma 50(4):246-250 (2003).

Jancarkova, N., "Detection and incidence of mutations of BRCA1 gene in patients with cancer of the breast and ovary," Ceska Gynekol. 68(1):11-16 (2003).

Jantzen et al., "B. Prodrugs" taken from Modern Pharmaceutics, Third Edition, Banker and Rhodes, editors p. 596 (1996).

Jasin, M., "Homologous repair of DNA damage and tumorigenesis: the BRCA connection," Oncogene 21(58):8981-8993 (2002).

Jijon, H.B. et al., "Inhibition of poly(ADP-ribose) polymerase attenuates inflammation in a model of chronic colitis," Am. J. Physiol. Gastrointest. Liver Physiol. 279:G641-G651 (2000).

Johnson, R.D. et al., "Mammalian XRCC2 promotes the repair of DNA double-strand breaks by homologous recombination," Nature 401:397-399 (1999).

Kanaar, R. et al., "Molecular mechanisms of DNA double-strand break repair," Trends Cell Biol. 8:483-489 (1998).

Kashani-Sabet, M. et al., "Application of ribozymes to cancer gene therapy," Cancer Gene Therapy 2(3):213-223 (1995).

Kawamura, I. et al., "Ponalrestat, an aldose reductase inhibitor," Chemical Abstract 132:273943 (1999).
Kerr, P. et al., "New complexities for BRCA1 and BRCA2," Curr. Biol. 11:R668-676 (2001).
Kerrigan, F. et al. "Imide-substituted 4-benzyl-2H-phthalazin-1-ones: potent inhibitors of poly(ADP-ribose) polymerase-1 (PARP-1)," Poster at 12th SCI-RSC Medicinal Chemistry Symposium, Cambridge, 7-10 (2003).
Khanna, K. K. et al., "DNA double-strand breaks: signaling, repair and the cancer connection," Nat. Genet. 27(3):247-254 (2001).
Kraakman-Van Der Zwet, M. et al., "Brca2 (XRCC11) deficiency results in radioresistant DNA synthesis and a higher frequency of spontaneous deletions," Mol. Cell Biol. 22(2):669-679 (2002).
Kuperstein, G. et al., "A rapid fluorescent multiplexed-PCR analysis (FMPA) for founder mutations in the BRCA1 and BRCA2 genes," Clin. Genet. 57:213-220 (2000).
Kupper, J-H. et al., "Trans-dominant inhibition of poly(ADP-ribosyl)ation potentiates carcinogen-induced gene amplification in SV40-transformed Chinese hamster cells," Cancer Res. 56:2715-2717 (1996).
Lakhani, S. R. et al., "The pathology of familial breast cancer: predictive value of immunohistochemical markers estrogen receptor, progesterone receptor, HER-2, and p53 in patients with mutations in BRCA1 and BRCA2," J. Clin. Oncol. 20(9):2310-2318 (2002).
Le Rhun, Y. et al., "Cellular responses to DNA damage in the absence of poly(ADP-ribose)polymerase", Biochem. Biophys. Res. Commun., 245:1-10 (1998).
LeMay, M. et al., "Detection of DNA damage and identification of UV-induced photoproducts using the cometassay kit," Biotechniques 27:846-851 (1999).
Liaudet, L. et al., "Protection against hemorrhagic shock in mice genetically deficient in poly(ADP-ribose)polymerase", Proc. Natl. Acad. Sci. U.S.A., 97(3):10203-10208 (2000).
Lindahl, T. et al, "Post-translational modification of poly(ADP-ribose) polymerase induced by DNA strand breaks," TIBS 20:405-411 (1995).
Lindahl, T. et al, "Quality control by DNA repair," Science 286:1897-1905 (1999).
Loh, V.M. et al., "Phthalazinones. Part 1: The design and synthesis of a novel series of potent inhibitors of poly(ADP-ribose)polymerase," Bioorg. Med. Chem. Lett. 15:2235-2238 (2005).
Lundin, C. et al., "Different roles for nonhomologous end joining and homologous recombination following replication arrest in mammalian cells," Mol. Cell. Biol. (2002) 22(16):5869-5878.
Lundin, C. et al., "RAD51 is involved in repair of damage associated with DNA replication in mammalian cells," J. Mol. Biol. 328:521-535 (2003).
Magnusson, J. et al , "Inhibitor of poly(ADP-ribose)transferase potentiates the recombinogenic but not the mutagenic action of alkylating agents in somatic cells in vivo in *Drosophila melanogaster*," Mutagenesis 5(5):511-514 (1990).
Martin, N. et al., "DNA repair inhibition and cancer therapy," J. Photochem. and PhotoBiol. B: Biology 63:162-170 (2001).
Martin, N. et al., "Phthalazinone derivatives as potent PARP-1 inhibitors", 13th Intl. Symposium on ADP-ribosylation, Abstract 107 (2001).
Matsuda, M. et al., "Mutations in the RAD54 recombination gene in primary cancers," Oncogene 18:3427-3430 (1999).
McNealy, T. et al., "Intrinsic presence of poly (ADP-ribose) is significantly increased in malignant prostate compared to benign prostate cell lines," Anticancer Res. 23:1473-1478 (2003).
Menear et al. "4-[3-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1" Journal of Medicinal Chemistry, Web Release Date: Sep. 19, 2008.
Menissier De Murcia, J. et al., "Functional interaction between PARP-1 and PARP-2 in chromosome stability and embryonic development in mouse," EMBO J. 22(9):2255-2263 (2003).
Menissier De Murcia, J. et al., "Requirement of poly(ADP-ribose)polymerase in recovery from DNA damage in mice and cells", Proc. Natl. Acad. Sci. U.S.A., 94:7303-7307 (1997).
Mercola, D. et al., "Antisense approaches to cancer gene therapy," Cancer Gene Therapy 2(1):47-59 (1995).
Miller, B.A., "Inhibition of TRPM2 function by PARP inhibitors protects cells from oxidative stress-induced death," Br. J. Pharmacology 143:515-516 (2004).
Miwa, M. et al., "Cell density-dependent increase in chromatin-associated ADP-ribosyltransferase activity in simian virus 40-transformed cells", Arch. Biochem. Biophys., 181:313-321 1977.
Morrison, C. et al., "Genetic interaction between PARP and DNA-PK in V(D)J recombination and tumorigenesis," Nature Genetics 17:479-482 (1997).
Moynahan, M. E. et al., "Brca1 controls homology-directed DNA repair," Mol. Cell 4:511-518 (1999).
Moynahan, M. E. et al., "BRCA2 is required for homology-directed repair or chromosomal breaks," Mol. Cell 7:263-272 (2001).
Mullis, K. et al., "Specific enzymatic amplification of DNA in vitro: the polymerase chain reaction," Cold Spring Harbor Symp. Quant. Biol. 51:263-273 (1987).
Nakamura, J. et al., "Quantitation of intracellular NAD(P)H can monitor an imbalance of DNA single strand break repair in base excision repair deficient cells in real time," Nuc. Acids Res. 31(17):e104 1-7 (2003).
Nathanson, K. L. et al., "Breast cancer genetics: what we know and what we need," Nat. Med. 7(5):552-556 (2001).
Neuhausen, S. L. et al., "Mutation testing of early-onset breast cancer genes BRCA1 and BRCA2," Genet. Test 1(2):75-83 (1997).
Noel, G. et al., "Poly(ADP-ribse) polymerase (PARP-1) is not involved in DNA double-strand break recovery," BMC Cell Biol. 4:7-17 (2003).
Pacher et al., "The Role of Poly(ADP-Ribose) Polymerase Activation in the Development of Myocardial and Endothelial Dysfunction in Diabetes," Diabetes, 51:514-521 (2002).
Perkins, E. et al., "Novel inhibitors of poly(ADP-ribose)polymerase/PARP1 and PARP2 identified using a cell-based screen in yeast", Cancer Res., vol. 61, 4175-4183 (2001).
Pierce, A.J. et al., "XRCC3 promotes homology-directed repair of DNA damage in mammalian cells," Genes & Dev. 13:2633-2638 (1999).
Radice, P. J., "Mutations of BRCA genes in hereditary breast and ovarian cancer," Exp. Clin. Cancer Res. 21(3 Suppl.):9-12 (2002).
Rattan, S. I. et al., "Kinetin delays the onset of ageing characteristics in human fibroblasts", Biochem. Biophys. Res. Commun., 201(2):665-672 (1994).
Said, S. I. et al., "Excitotoxicity in the lung: N-methy-D-aspartate-induced, nitric oxide-dependent, pulmonary edema is attenuated by vasoactive intestinal peptide and by inhibitors of poly(ADP-ribose)polymerase", Proc. Natl. Acad. Sci. U.S.A., 93:4688-4692 (1996).
Samper, E. et al., "Normal telomere length and chromosomal end capping in poly(ADP-ribose) polymerase-deficient mice and primary cells despite increased chromosomal instability," J. Cell Biol. 154(1):49-60 (2001).
Satoh, M.S. et al., "Role of poly(ADP-ribose) formation in DNA repair," Nature 356:356-358 (1992).
Schlicker, A. et al., "4-Amino-1,8-napthalimide: a novel inhibitor of poly(ADP-ribose)polymerase and radiation sensitizer", Int. J. Radiat. Bio., 75(1):91-100 (1999).
Schreiber, V. et al., "A dominant-negative mutant of human poly(ADP-ribose) polymerase affects cell recovery, apoptosis, and sister chromatid exchange following DNA damage," Proc. Natl. Acad. Sci. USA 92:4753-4757 (1995).
Schreiber, V. et al., "Poly(ADP-ribose) polymerase-2 (PARP-2) is required for efficient base excision DNA repair in association with PARP-1 and XRCC1," J. Biol. Chem. 277(25):23028-23036 (2002).
Schultz, N. et al., "Poly(ADP-ribose) polymerase (PARP-1) has a controlling role in homologous recombination," Nucleic Acids Res. 31:4959-4964 (2003).
Semionov, A. et al., "Inhibition of poly(ADP-ribose)polymerase stimulates extrachromosomal homologous recombination in mouse Ltk-fibroblasts," Nuc. Acids Res. 27(22):4526-4531 (1999).
Shah, G.M. et al., "Complete inhibition of poly(ADP-ribose) polymerase activity prevents the recovery of C3H10T1/2 cells from oxidative stress," Biochimica et Biophysica Acta 1312:1-7 (1996).

Shall, S. et al., "Poly(ADP-ribose) polymerase-1: what have we learned from the deficient mouse model?" Mutat. Res. 460:1-15 (2000).

Shimizu, T. et al., "Inhibitory effects of azelastine and tranilast on leukotriene B4 and leukotriene C4 generation by rat colonic mucosa", Prostaglandins Leukotrienes and Essential Fatty Acids, 53:355-358 (1995).

Silverman, R.B., "Chapter 8. Prodrugs and drug delivery system" The Organic Chemistry of Drug Design and Drug Action, 352-400 Academic Press, Inc. (1992).

Simbulan-Rosenthal, C.M. et al., "Chromosomal aberrations in PARP-/-mice: genome stabilization in immortalized cells by reintroduction of poly(ADP-ribose) polymerase cDNA," Proc. Natl. Acad. Sci. USA 96(23):13191-13196 (1999).

Skehan, P. et al., "New colorimetric cytotoxicity assay for anticancer-drug screening", J. Natl. Cancer Inst., 82(13):1107-1112 (1990).

Southan, G.J. and Szabo, C., "Poly (ADP-ribose) polymerase inhibitors," Current Medicinal Chemistry, 10(4):321-340 (2003).

Suto, M.J. et al., "Dihydroisoquinolinones: the design and synthesis of a new series of potent inhibitors of poly(ADP-ribose) polymerase," Anticancer Drug Des. 7:107-117 (1991).

Szabo, "9. Role of poly(ADP-ribose) polymerase activation in the pathogenesis of shock and inflammation" PARP as a Therapeutic Target, Zhang, Ed. CRC Press 169-204 (2002).

Szabo, C. et al., "Endothelial dysfunction in a rat model of endotoxic shock", J. Clin. Invest., 100, 723-25 (1997).

Szabo, G. et al., "Poly-ADP-ribose polymerase inhibition protects against myocardial and endothelial reperfusion injury after hypothermic cardiac arrest," J. Thoracic Cardiovas. Surg. 126(3):651-658 (2003).

Taniguchi, T. et al., "Disruption of the Fanconi anemia-BRCA pathway in cisplatin-sensitive ovarian tumors," Nat. Med. 9(5):568-574 (2003).

Tarsounas, M. et al., "BRCA2-dependent and independent formation of RAD51 nuclear foci," Oncogene 22:1115-1123 (2003).

Tasatargil, A. et al., "Poly(ADP-ribose) polymerase inhibition prevents homocysteine-induced endothelial dysfunction in the isolated rat aorta," Pharmacology 72:99-105 (2004).

Tebbs, R.S. et al., "Correction of chromosomal instability and sensitivity to diverse mutagens by a cloned cDNA of the XRCC3 DNA repair gene," Proc. Natl. Acad. Sci. USA 92:6354-6358 (1995).

Tentori, L. et al., "Potential clinical applications of poly(ADP-ribose) polymerase (PARP) inhibitors," Pharm. Res. 45(2):73-85 (2002).

Thompson, L. H. et al., "Recombinational DNA repair and human disease," Mutat. Res. 509:49-78 (2002).

Tracey, W. et al., "Aldose reductase inhibition alone or combined with an adenosine A3 agonist reduces ischemic myocardial injury," Chemical Abstract 134:65983 (2000).

Tutt, A N.J. et al., "Disruption of Brca2 increases the spontaneous mutation rate in vivo: synergism with ionizing radiation," Embo Reports 3(3):255-260 (2002).

Tutt, A. et al., "Mutation in Brca2 stimulates error-prone homology-directed repair of DNA double-strand breaks occurring between repeated sequences," EMBO J. 20(17):4704-4716 (2001).

Tutt, A. et al., "The relationship between the roles of BRCA genes in DNA repair and cancer predisposition," Trends Mol. Med. 8(12):571-576 (2002).

Uhlmann, E. et al., Antisense oligonucleotides: a new therapeutic principle, Chem. Rev. 90(4):543-584 (1990).

Van Gent, D.C. et al., "Chromosomal stability and the DNA double-stranded break connection," Nature Reviews 2:196-206 (2001).

Venkitaraman, A. R., "Cancer susceptibility and the functions of BRCA1 and BRCA2," Cell 108:171-182 (2002).

Vippagunta, S.R. et al., "Crystalline solids," Adv. Drug Delivery Reviews 48:3-26 (2001).

Virag and Szabo, "The Therapeutic Potential of Poly(ADP-Ribose) Polymerase Inhibitors," Pharmacological Reviews, 54(3):375-429 (2002).

Voinnet, O. et al. "Systemic signalling in gene silencing," Nature 389:553 (1997).

Waldman, A.S. et al., "Stimulation of intrachromosomal homologous recombination in mammalian cells by an inhibitor of poly(ADP-ribosylation)," Nuc. Acids Res. 19(21):5943-5947 (1991).

Wang, Z.-Q. et al., "Mice lacking ADPRT and poly(ADP-ribosyl)ation develop normally but are susceptible to skin disease", Genes Dev., 9:509-520 (1995).

Wang, Z.-Q. et al., "PARP is important for genomic stability but dispensable in apoptosis," Genes Dev. 11:2347-2358 (1997).

West, A.R. "Solid State Chemistry and its Applications" Wiley, New York, 358 and 365 (1988).

Wood, R.D. et al., "Human DNA repair genes," Science 291:1284-1289 (2001).

Yamaguchi, M. et al., "Novel antiasthmatic agents with dual activities of thromboxane A2 synthetase inhibition and bronchodilation. 1. 2-[2-(1-Imidazolyl)alkyl]-1(2H)-phthalazinones", J. Med. Chem., 36(25):4052-4060 (1993).

Yamaguchi, M. et al., "Novel antiasthmatic agents with dual activities of thromboxane A2 synthetase inhibition and bronchodilation. 2. 4-(3-Pyridyl)-1(2H)-phthalazinones", J. Med. Chem., , vol. 36, No. 25, 4061-4068 (1993).

Zamore, P. D., "RNA interference: listening to the sound of silence," Nature Structural Biology 8(9):746-750 (2001).

Zamore, P. D., "RNAi: double-stranded RNA directs the ATP-dependent cleavage of mRNA at 21 to 23 nucleotide intervals," Cell 101:25-33 (2000).

Zhang, J. et al., "Neuroprotective effects of poly(ADP-ribose) polymerase inhibition on focal cerebral ischemia," Portland Press Proc. 15:125 (1998).

Zhong, Q. et al., "Association of BRCA1 with the hRad50-hMre11-p95 complex and the DNA damage response," Science 285:747-750 (1999).

Zingarelli, B. et al., "Activator protein-1 signalling pathway and apoptosis are modulated by poly(ADP-ribose) polymerase-1 in experimental colitis," Immunology 113:509-517 (2004).

\* cited by examiner

PHTHALAZINONE DERIVATIVES

The present invention relates to phthalazinone derivatives and their use as pharmaceuticals. In particular, the present invention relates to the use of these compounds to inhibit the activity of the enzyme poly (ADP-ribose)polymerase-1, also known as poly(ADP-ribose)synthase and poly ADP-ribosyl-transferase, and commonly referred to as PARP-1.

The mammalian enzyme PARP-1 (a 113-kDa multidomain protein) has been implicated in the signalling of DNA damage through its ability to recognize and rapidly bind to DNA single or double strand breaks (D'Amours, et al., *Biochem. J.*, 342, 249-268 (1999)).

The family of Poly (ADP-ribose) polymerases now includes around 18 proteins, that all display a certain level of homology in their catalytic domain but differ in their cellular functions (Ame et al., *Bioessays.*, 26(8), 882-893 (2004)). Of this family PARP-1 (the founding member) and PARP-2 are so far the sole enzymes whose catalytic activity are stimulated by the occurrence of DNA strand breaks, making them unique in the family.

It is now known that PARP-1 participates in a variety of DNA-related functions including gene amplification, cell division, differentiation, apoptosis, DNA base excision repair as well as effects on telomere length and chromosome stability (d'Adda di Fagagna, et al., *Nature Gen.*, 23(1), 76-80 (1999)).

Studies on the mechanism by which PARP-1 modulates DNA repair and other processes has identified its importance in the formation of poly (ADP-ribose) chains within the cellular nucleus (Althaus, F. R. and Richter, C., ADP-Ribosylation of Proteins: Enzymology and Biological Significance, Springer-Verlag, Berlin (1987)). The DNA-bound, activated PARP-1 utilizes $NAD^+$ to synthesize poly (ADP-ribose) on a variety of nuclear target proteins, including topoisomerases, histones and PARP itself (Rhun, et al., *Biochem. Biophys. Res. Commun.*, 245, 1-10 (1998))

Poly (ADP-ribosyl)ation has also been associated with malignant transformation. For example, PARP-1 activity is higher in the isolated nuclei of SV40-transformed fibroblasts, while both leukaemic and colon cancer cells show higher enzyme activity than the equivalent normal leukocytes and colon mucosa (Miwa, et al., *Arch. Biochem. Biophys.*, 181, 313-321 (1977); Burzio, et al., *Proc. Soc. Exp. Biol. Med.*, 149, 933-938 (1975); and Hirai, et al., *Cancer Res.*, 43, 3441-3446 (1983)). More recently in malignant prostate tumours compared to benign prostate cells significantly increased levels of active PARP (predominantly PARP-1) have been identified associated with higher levels of genetic instability (Mc-Nealy, et al., *Anticancer Res.*, 23, 1473-1478 (2003)).

A number of low-molecular-weight inhibitors of PARP-1 have been used to elucidate the functional role of poly (ADP-ribosyl)ation in DNA repair. In cells treated with alkylating agents, the inhibition of PARP leads to a marked increase in DNA-strand breakage and cell killing (Durkacz, et al., *Nature*, 283, 593-596 (1980); Berger, N. A., *Radiation Research*, 101, 4-14 (1985)).

Subsequently, such inhibitors have been shown to enhance the effects of radiation response by suppressing the repair of potentially lethal damage (Ben-Hur, et al., *British Journal of Cancer*, 49 (Suppl. VI), 34-42 (1984); Schlicker, et al., *Int. J. Radiat. Biol.*, 75, 91-100 (1999)). PARP inhibitors have been reported to be effective in radio sensitising hypoxic tumour cells (U.S. Pat. No. 5,032,617; U.S. Pat. No. 5,215,738 and U.S. Pat. No. 5,041,653). In certain tumour cell lines, chemical inhibition of PARP-1 (and PARP-2) activity is also associated with marked sensitisation to very low doses of radiation (Chalmers, *Clin. Oncol.*, 16(1), 29-39 (2004))

Furthermore, PARP-1 knockout (PARP –/–) animals exhibit genomic instability in response to alkylating agents and γ-irradiation (Wang, et al., *Genes Dev.*, 9, 509-520 (1995); Menissier de Murcia, et al., *Proc. Natl. Acad. Sci. USA*, 94, 7303-7307 (1997)). More recent data indicates that PARP-1 and PARP-2 possess both overlapping and non-redundant functions in the maintenance of genomic stability, making them both interesting targets (Menissier de Murcia, et al., *EMBO. J.*, 22(9), 2255-2263 (2003)).

PARP inhibition has also recently been reported to have antiangiogenic effects. Where dose dependent reductions of VEGF and basic-fibroblast growth factor (bFGF)-induced proliferation, migration and tube formation in HUVECS has been reported (Rajesh, et al., *Biochem. Biophys. Res. Comm.*, 350, 1056-1062 (2006)).

A role for PARP-1 has also been demonstrated in certain vascular diseases, septic shock, ischaemic injury and neurotoxicity (Cantoni, et al., *Biochim. Biophys. Acta*, 1014, 1-7 (1989); Szabo, et al., *J. Clin. Invest.*, 100, 723-735 (1997)). Oxygen radical DNA damage that leads to strand breaks in DNA, which are subsequently recognised by PARP-1, is a major contributing factor to such disease states as shown by PARP-1 inhibitor studies (Cosi, et al., *J. Neurosci. Res.*, 39, 38-46 (1994); Said, et al., *Proc. Natl. Acad. Sci. U.S.A.*, 93, 4688-4692 (1996)). More recently, PARP has been demonstrated to play a role in the pathogenesis of haemorrhagic shock (Liaudet, et al., *Proc. Natl. Acad. Sci. U.S.A.*, 97(3), 10203-10208 (2000)).

It has also been demonstrated that efficient retroviral infection of mammalian cells is blocked by the inhibition of PARP-1 activity. Such inhibition of recombinant retroviral vector infections was shown to occur in various different cell types (Gaken, et al., *J. Virology*, 70(6), 3992-4000 (1996)). Inhibitors of PARP-1 have thus been developed for the use in anti-viral therapies and in cancer treatment (WO 91/18591).

Moreover, PARP-1 inhibition has been speculated to delay the onset of aging characteristics in human fibroblasts (Rattan and Clark, *Biochem. Biophys. Res. Comm.*, 201(2), 665-672 (1994)). This may be related to the role that PARP plays in controlling telomere function (d'Adda di Fagagna, et al., *Nature Gen.*, 23(1), 76-80 (1999)).

PARP inhibitors are also thought to be relevant to the treatment of inflammatory bowel disease (Szabo C., Role of Poly(ADP-Ribose) Polymerase Activation in the Pathogenesis of Shock and Inflammation, In PARP as a Therapeutic Target; Ed J. Zhang, 2002 by CRC Press; 169-204), ulcerative colitis (Zingarelli, B, et al., *Immunology*, 113(4), 509-517 (2004)) and Crohn's disease (Jijon, H. B., et al., *Am. J. Physiol. Gastrointest. Liver Physiol.*, 279, G641-G651 (2000).

Some of the present inventors have previously described (WO 2004/080976) a class of 1(2H)-phthalazinone compounds which act as PARP inhibitors. The compounds have the general formula:

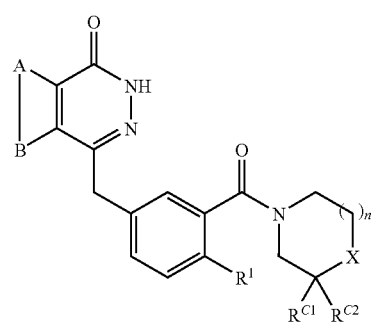

wherein:
A and B together represent an optionally substituted, fused aromatic ring;
X can be $NR^X$ or $CR^X R^Y$;
if $X=NR^X$ then n is 1 or 2 and if $X=CR^X R^Y$ then n is 1;
$R^X$ is selected from the group consisting of H, optionally substituted $C_{1-20}$ alkyl, $C_{5-20}$ aryl, $C_{3-20}$ heterocyclyl, amido, thioamido, sulfonamino, ester, acyl, and sulfonyl groups;
$R^Y$ is selected from H, hydroxy, amino;
or $R^X$ and $R^Y$ may together form a spiro-$C_{3-7}$ cycloalkyl or heterocyclyl group;
$R^{C1}$ and $R^{C2}$ are both hydrogen, or when X is $CR^X R^Y$, $R^{C1}$, $R^{C2}$, $R^X$ and $R^Y$, together with the carbon atoms to which they are attached, may form an optionally substituted fused aromatic ring; and
$R^1$ is selected from H and halo.

The present inventors have now discovered that compounds where X is $CHR^X$, and $R^X$ is an ether group exhibit a surprising increase in the level of inhibition of the activity of PARP, and/or of potentiation of tumour cells to radiotherapy and various chemotherapies. These compounds may also exhibit improved solubility and may be less amenable to efflux from cells, thus increasing bioavailability.

Accordingly, the first aspect of the present invention provides a compound of the formula (I):

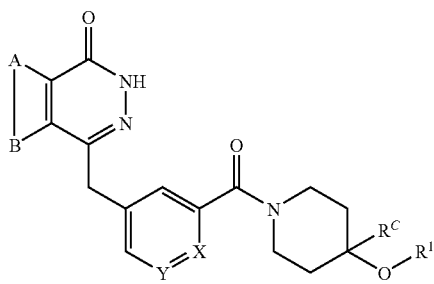

wherein:
A and B together represent an optionally substituted, fused aromatic ring;
X and Y are selected from CH and CH, CF and CH, CH and CF and N and CH respectively;
$R^C$ is selected from H, $C_{1-4}$ alkyl; and
$R^1$ is selected from $C_{1-7}$ alkyl, $C_{3-20}$ heterocyclyl and $C_{5-20}$ aryl, which groups are optionally substituted; or
$R^C$ and $R^1$ together with the carbon and oxygen atoms to which they are attached form a spiro-$C_{5-7}$ oxygen-containing heterocyclic group, which is optionally substituted or fused to a $C_{5-7}$ aromatic ring.

Thus, when $R^C$ is H and Y is CH, the compound is of formula (Ia):

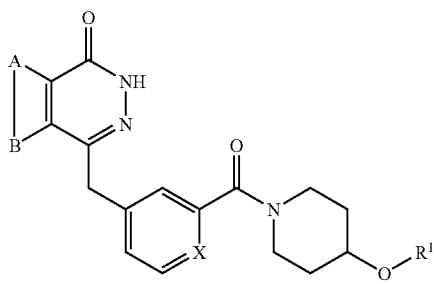

A second aspect of the present invention provides a pharmaceutical composition comprising a compound of the first aspect and a pharmaceutically acceptable carrier or diluent.

A third aspect of the present invention provides the use of a compound of the first aspect in a method of treatment of the human or animal body.

A fourth aspect of the present invention provides the use of a compound as defined in the first aspect of the invention in the preparation of a medicament for:
(a) preventing poly(ADP-ribose) chain formation by inhibiting the activity of cellular PARP (PARP-1 and/or PARP-2);
(b) the treatment of: vascular disease; septic shock; ischaemic injury, both cerebral and cardiovascular; reperfusion injury, both cerebral and cardiovascular; neurotoxicity, including acute and chronic treatments for stroke and Parkinson's disease; haemorraghic shock; inflammatory diseases, such as arthritis, inflammatory bowel disease, ulcerative colitis and Crohn's disease; multiple sclerosis; secondary effects of diabetes; as well as the acute treatment of cytoxicity following cardiovascular surgery or diseases ameliorated by the inhibition of the activity of PARP;
(c) use as an adjunct in cancer therapy or for potentiating tumour cells for treatment with ionizing radiation or chemotherapeutic agents.

In particular, compounds as defined in the first aspect of the invention can be used in anti-cancer combination therapies (or as adjuncts) along with alkylating agents, such as methyl methanesulfonate (MMS), temozolomide and dacarbazine (DTIC), also with topoisomerase-1 inhibitors like Topotecan, Irinotecan, Rubitecan, Exatecan, Lurtotecan, Gimetecan, Diflomotecan (homocamptothecins); as well as 7-substituted non-silatecans; the 7-silyl camptothecins, BNP 1350; and non-camptothecin topoisomerase-1 inhibitors such as indolocarbazoles also dual topoisomerase-1 and 11 inhibitors like the benzophenazines, XR 11576/MLN 576 and benzopyridoindoles. Such combinations could be given, for example, as intravenous preparations or by oral administration as dependent on the preferred method of administration for the particular agent.

Other further aspects of the invention provide for the treatment of disease ameliorated by the inhibition of PARP, comprising administering to a subject in need of treatment a therapeutically-effective amount of a compound as defined in the first aspect, preferably in the form of a pharmaceutical composition and the treatment of cancer, comprising administering to a subject in need of treatment a therapeutically-effective amount of a compound as defined in the first aspect in combination, preferably in the form of a pharmaceutical composition, simultaneously or sequentially with radiotherapy (ionizing radiation) or chemotherapeutic agents.

In further aspects of the present invention, the compounds may be used in the preparation of a medicament for the treatment of cancer which is deficient in Homologous Recombination (HR) dependent DNA double strand break (DSB) repair activity, or in the treatment of a patient with a cancer which is deficient in HR dependent DNA DSB repair activity, comprising administering to said patient a therapeutically-effective amount of the compound.

The HR dependent DNA DSB repair pathway repairs double-strand breaks (DSBs) in DNA via homologous mechanisms to reform a continuous DNA helix (K. K. Khanna and S. P. Jackson, Nat. Genet. 27(3): 247-254 (2001)). The components of the HR dependent DNA DSB repair pathway include, but are not limited to, ATM (NM_000051), RAD51 (NM_002875), RAD51 L1 (NM_002877), RAD51C (NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY (Hughes-Davies, et al., *Cell*, 115, pp 523-535). HR components are also described in Wood, et al., *Science*, 291, 1284-1289 (2001).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterised in the art (see for example, Wood, et al., *Science*, 291, 1284-1289 (2001)) and include the components listed above.

In some preferred embodiments, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (Hughes-Davies, et al., *Cell*, 115, 523-535) or by an epigenetic mechanism such as gene promoter methylation.

BRCA1 and BRCA2 are known tumour suppressors whose wild-type alleles are frequently lost in tumours of heterozygous carriers (Jasin M., *Oncogene*, 21(58), 8981-93 (2002); Tutt, et al., *Trends Mol. Med.*, 8(12), 571-6, (2002)). The association of BRCA1 and/or BRCA2 mutations with breast cancer is well-characterised in the art (Radice, P. J., *Exp. Clin. Cancer Res.*, 21(3 Suppl), 9-12 (2002)). Amplification of the EMSY gene, which encodes a BRCA2 binding factor, is also known to be associated with breast and ovarian cancer.

Carriers of mutations in BRCA1 and/or BRCA2 are also at elevated risk of cancer of the ovary, prostate and pancreas.

In some preferred embodiments, the individual is heterozygous for one or more variations, such as mutations and polymorphisms, in BRCA1 and/or BRCA2 or a regulator thereof. The detection of variation in BRCA1 and BRCA2 is well-known in the art and is described, for example in EP 699 754, EP 705 903, Neuhausen, S. L. and Ostrander, E. A., *Genet. Test*, 1, 75-83 (1992); Janatova M., et al., *Neoplasma*, 50(4), 246-50 (2003). Determination of amplification of the BRCA2 binding factor EMSY is described in Hughes-Davies, et al., *Cell*, 115, 523-535).

Mutations and polymorphisms associated with cancer may be detected at the nucleic acid level by detecting the presence of a variant nucleic acid sequence or at the protein level by detecting the presence of a variant (i.e. a mutant or allelic variant) polypeptide.

FIGURES

DEFINITIONS

Figure 1:
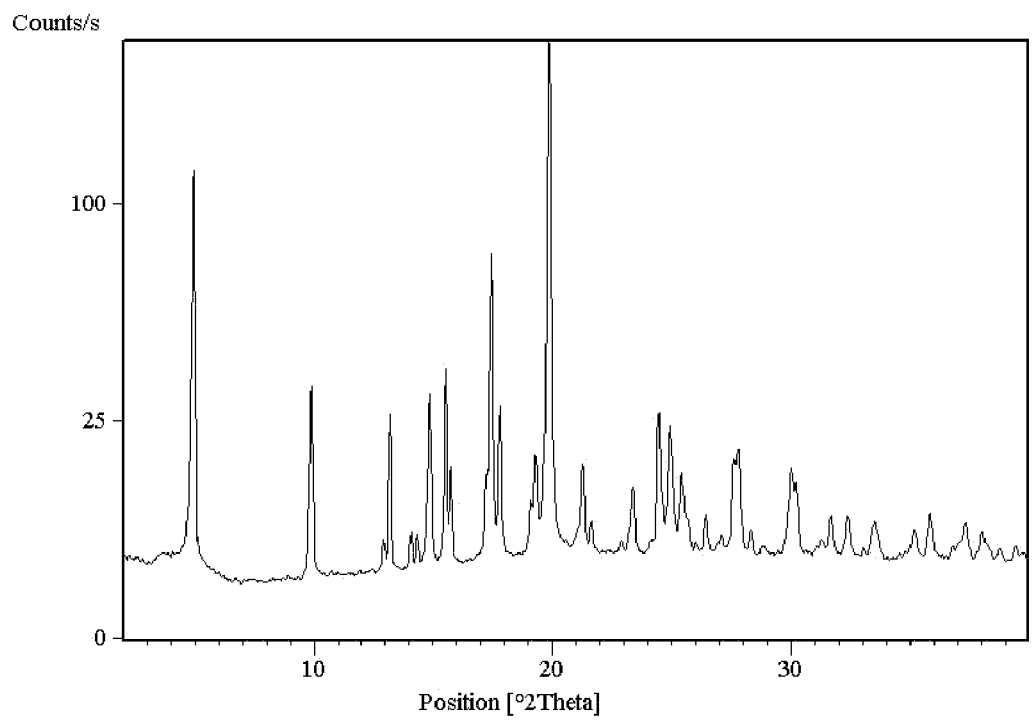
FIG. 1 is a powder XRD pattern of a crystalline form of a compound of the present invention.

The term "aromatic ring" is used herein in the conventional sense to refer to a cyclic aromatic structure, that is, a cyclic structure having delocalised π-electron orbitals.

The aromatic ring fused to the main core, i.e. that formed by -A-B—, may bear further fused aromatic rings (resulting in, e.g. naphthyl or anthracenyl groups). The aromatic ring(s) may comprise solely carbon atoms, or may comprise carbon atoms and one or more heteroatoms, including but not limited to, nitrogen, oxygen, and sulfur atoms. The aromatic ring(s) preferably have five or six ring atoms.

The aromatic ring(s) may optionally be substituted. If a substituent itself comprises an aryl group, this aryl group is not considered to be a part of the aryl group to which it is attached. For example, the group biphenyl is considered herein to be a phenyl group (an aryl group comprising a single aromatic ring) substituted with a phenyl group. Similarly, the group benzylphenyl is considered to be a phenyl group (an aryl group comprising a single aromatic ring) substituted with a benzyl group.

In one group of preferred embodiments, the aromatic group comprises a single aromatic ring, which has five or six ring atoms, which ring atoms are selected from carbon, nitrogen, oxygen, and sulfur, and which ring is optionally substituted. Examples of these groups include, but are not limited to, benzene, pyrazine, pyrrole, thiazole, isoxazole, and oxazole. 2-Pyrone can also be considered to be an aromatic ring, but is less preferred.

If the aromatic ring has six atoms, then preferably at least four, or even five or all, of the ring atoms are carbon. The other ring atoms are selected from nitrogen, oxygen and sulphur, with nitrogen and oxygen being preferred. Suitable groups include a ring with: no hetero atoms (benzene); one nitrogen ring atom (pyridine); two nitrogen ring atoms (pyrazine, pyrimidine and pyridazine); one oxygen ring atom (pyrone); and one oxygen and one nitrogen ring atom (oxazine).

If the aromatic ring has five ring atoms, then preferably at least three of the ring atoms are carbon. The remaining ring atoms are selected from nitrogen, oxygen and sulphur. Suitable rings include a ring with: one nitrogen ring atom (pyrrole); two nitrogen ring atoms (imidazole, pyrazole); one oxygen ring atom (furan); one sulphur ring atom (thiophene); one nitrogen and one sulphur ring atom (isothiazole, thiazole); and one nitrogen and one oxygen ring atom (isoxazole or oxazole).

The aromatic ring may bear one or more substituent groups at any available ring position. These substituents are selected from halo, nitro, hydroxy, ether, thiol, thioether, amino, $C_{1-7}$ alkyl, $C_{3-20}$ heterocyclyl and $C_{5-20}$ aryl. The aromatic ring may also bear one or more substituent groups which together form a ring. In particular these may be of formula —$(CH_2)_m$— or —O—$(CH_2)_p$—O—, where m is 2, 3, 4 or 5 and p is 1, 2 or 3.

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g. partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g. $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkyl", as used herein, pertains to an alkyl group having from 1 to 4 carbon atoms. Examples of groups of alkyl groups include $C_{1-4}$ alkyl ("lower alkyl"), $C_{1-7}$ alkyl, and $C_{1-20}$ alkyl. Note that the first prefix may vary according to other limitations; for example, for unsaturated alkyl groups, the first prefix must be at least 2; for cyclic alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl", as used herein, pertains to an alkyl group having one or more carbon-carbon double bonds. Examples of groups of alkenyl groups include $C_{2-4}$ alkenyl, $C_{2-7}$ alkenyl, $C_{2-20}$ alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

Alkynyl: The term "alkynyl", as used herein, pertains to an alkyl group having one or more carbon-carbon triple bonds. Examples of groups of alkynyl groups include $C_{2-4}$ alkynyl, $C_{2-7}$ alkynyl, $C_{2-20}$ alkynyl.

Examples of (unsubstituted) unsaturated alkynyl groups include, but are not limited to, ethynyl (ethinyl, —C≡CH) and 2-propynyl (propargyl, —CH$_2$—C≡CH).

Cycloalkyl: The term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3 to 20 carbon atoms (unless otherwise specified), including from 3 to 20 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_{3-20}$ cycloalkyl, $C_{3-15}$ cycloalkyl, $C_{3-10}$ cycloalkyl, $C_{3-7}$ cycloalkyl.

Examples of cycloalkyl groups include, but are not limited to, those derived from:
saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds:
camphene ($C_{10}$), limonene ($C_{10}$), pinene ($C_{10}$);

polycyclic hydrocarbon compounds having an aromatic ring:
indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);
$S_1$: thiirane ($C_3$), thietane ($C_4$), thiolane (tetrahydrothiophene) ($C_5$), thiane (tetrahydrothiopyran) ($C_6$), thiepane ($C_7$);
$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
$N_1S_1$: thiazoline ($C_5$), thiazolidine ($C_5$), thiomorpholine ($C_6$);
$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Spiro-$C_{3-7}$ cycloalkyl or heterocyclyl: The term "spiro $C_{3-7}$ cycloalkyl or heterocyclyl" as used herein, refers to a $C_{3-7}$ cycloalkyl or $C_{3-7}$ heterocyclyl ring joined to another ring by a single atom common to both rings.

Spiro-oxygen containing $C_{5-7}$ heterocyclyl: The term "spiro-oxygen containing $C_{5-7}$ heterocyclyl" as used herein, refers to a spiro-$C_{5-7}$ heterocyclyl where one of the ring atoms is oxygen.

$C_{5-20}$ aryl: The term "$C_{5-20}$ aryl" as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups" in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

The heteroaryl group may be bonded via a carbon or hetero ring atom.

Examples of $C_{5-20}$ heteroaryl groups which comprise fused rings, include, but are not limited to, $C_9$ heteroaryl groups derived from benzofuran, isobenzofuran, benzothiophene, indole, isoindole; $C_{10}$ heteroaryl groups derived from quinoline, isoquinoline, benzodiazine, pyridopyridine; $C_{1-4}$ heteroaryl groups derived from acridine and xanthene.

The above alkyl, heterocyclyl, and aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —$NO_2$.

Cyano (nitrile, carbonitrile): —CN.

Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)O$CH_3$, —C(=O)O$CH_2CH_3$, —C(=O)OC($CH_3$)$_3$, and —C(=O)OPh.

Amido (carbamoyl, carbamyl, aminocarbonyl, carboxamide): —C(=O)N$R^1R^2$, wherein $R^1$ and $R^2$ are independently amino substituents, as defined for amino groups. Examples of amido groups include, but are not limited to, —C(=O)$NH_2$, —C(=O)NH$CH_3$, —C(=O)N($CH_3$)$_2$, —C(=O)NH$CH_2CH_3$, and —C(=O)N($CH_2CH_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —N$R^1R^2$, wherein $R^1$ and $R^2$ are independently amino substituents, for example, hydrogen, a $C_{1-7}$ alkyl group (also referred to as a $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —NH$CH_3$, —NHCH($CH_3$)$_2$, —N($CH_3$)$_2$, —N($CH_2CH_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. The cyclic amino groups may be substituted on their ring by any of the substituents defined here, for example carboxy, carboxylate and amido.

Acylamido (acylamino): —N$R^1$C(=O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and $R^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl:

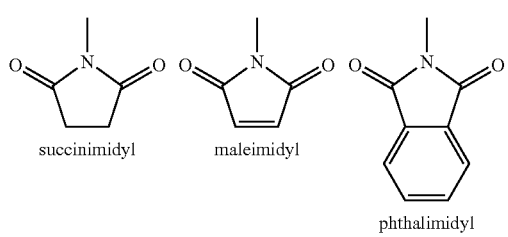

succinimidyl    maleimidyl    phthalimidyl

Ureido: —N($R^1$)CON$R^2R^3$ wherein $R^2$ and $R^3$ are independently amino substituents, as defined for amino groups, and $R^1$ is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCON$H_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, —NMeCONEt$_2$ and —NHC(=O)NHPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Thiol: —SH.

Thioether (sulfide): —SR, wherein R is a thioether substituent, for example, a C$_{1-7}$ alkyl group (also referred to as a C$_{1-7}$ alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a C$_{1-7}$ alkyl group, a C$_{3-20}$ heterocyclyl group, or a C$_{5-20}$ aryl group, preferably a C$_{1-7}$ alkyl group. Examples of sulfoxide groups include, but are not limited to, —S(=O)CH$_3$ and —S(=O)CH$_2$CH$_3$.

Sulfonyl (sulfone): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

As mentioned above, the groups that form the above listed substituent groups, e.g. C$_{1-7}$ alkyl, C$_{3-20}$ heterocyclyl and C$_{5-20}$ aryl, may themselves be substituted. Thus, the above definitions cover substituent groups which are substituted.

FURTHER EMBODIMENTS

The following embodiments can apply to each aspect of the present invention, where applicable.

In some embodiments, R$^C$ is H and Y is CH; in these embodiments, the compounds are of formula (Ia).

In embodiments where R$^C$ is C$_{1-4}$ alkyl, it may be methyl.

If R$^C$ and R$^1$ together with the carbon and oxygen atoms to which they are attached form a spiro-C$_{5-7}$ oxygen-containing heterocyclic group, these may be tetrahydrofuran (which may be fused to a benzene ring to form 1,3-dihydro-isobenzofuran).

In some embodiments, Y is CH and therefore X may be selected from CH, CF and N.

In other embodiments, Y is CF and therefore X is CH.

In the present invention, the fused aromatic ring(s) represented by -A-B— may consist of solely carbon ring atoms, and thus may be benzene, naphthalene, and in particular may be benzene. As described above, these rings may be substituted, but in some embodiments are unsubstituted.

In alternate embodiments, the fused aromatic ring represented by -A-B— may comprise a nitrogen ring atom, and thus may be, for example, pyrrole. The compound of the present invention may therefore be of the formula:

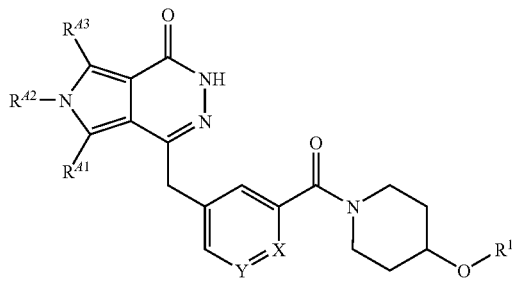

where R$^{A1}$, R$^{A2}$ and R$^{A3}$ may be independently selected from H and C$_{1-4}$ alkyl (e.g. methyl). In some embodiments, at least one of R$^{A1}$ and R$^{A3}$ is C$_{1-4}$ alkyl (e.g. methyl). In further embodiments:

(a) R$^{A1}$ and R$^{A3}$ are methyl and R$^{A2}$ is hydrogen;

(b) R$^{A1}$, R$^{A2}$ and R$^{A3}$ are methyl;

(c) R$^{A1}$ is methyl and R$^{A2}$ and R$^{A3}$ are hydrogen.

If the fused aromatic ring represented by -A-B— bears one or more substituent groups, it may bear two substituent groups or a divalent substituent group. The group or groups may be attached to the atoms which themselves are attached to the central ring α- to the carbon atom in the central ring. Thus, if the fused aromatic ring is a benzene ring, places of substitution in some embodiments are shown in the formula below by *:

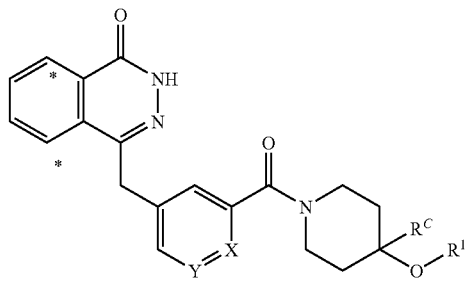

These substituents may be halo groups, and in particular F. In these embodiments, X may be CH. The halo group may also by chloro.

In further embodiments the benzene ring may be substituted by one or more, e.g. two, NH$_2$ groups. These may be in the positions indicated in the formula above, and one or two substitutent groups may be present. In some embodiments, the NH$_2$ is in the position closest the benzyl group.

In further embodiments the benzene ring may be substituted by one or more, e.g. two, C$_{1-4}$ alkoxy (e.g. methoxy) groups. These may be in the positions indicated in the formula above, and one or two substitutent groups may be present. In some embodiments, the alkoxy group is in the position closest the benzyl group.

In further embodiments, the benzene ring may be substituted in one or two of the positions shown in the in the formula below by $^+$:

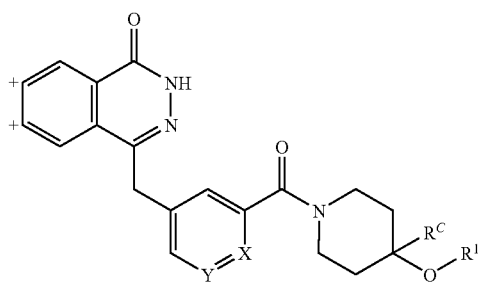

These substituents may be halo groups, and in particular chloro or bromo, or $NH_2$. In some of these embodiments, there is one substituent. In others of these embodiments, there are two of these substituents.

In some embodiments X may be CH or CF. In particular X may be CF.

In other embodiments X may be N.

When $R^1$ is $C_{1-7}$ alkyl, it may be a saturated $C_{1-7}$ alkyl group, e.g. methyl, ethyl, iso-propyl, cyclopropylmethyl. Further examples include propyl, butyl, cyclobutyl and cyclopentyl. It may also be unsaturated, e.g. propenyl. If the $C_{1-7}$ alkyl group is substituted the substituents may be selected from those listed above, or may more particularly be: $C_{5-7}$ aryl (e.g. furanyl, benzyl, pyridyl), $C_{3-7}$ heterocyclyl (e.g. tetrahydrofuranyl, pyrrolyl, morpholino, thiomorpholino), halo, hydroxy, $C_{1-7}$ alkyloxy and $NH_2$. Further substituents include $C_{1-4}$ alkoxy (e.g. methoxy), carboxy and amido (wherein the amino substituents may be methyl, or where the amino substituents together with the nitrogen atom to which they are attached form a heterocyclic group, for example, morpholino, 3,3-difluoro-azetidinyl, pyrrolidinyl, or piperidinyl. In some embodiments, the substituted $C_{1-7}$ alkyl group is methyl or ethyl.

When $R^1$ is $C_{5-20}$ aryl, it may be $C_{5-7}$ aryl. The aryl group may be a $C_6$ aryl group, such as phenyl or pyridyl. Further possible $C_6$ aryl groups include pyridazinyl, pyrimidinyl and pyrazinyl. The aryl group may be unsubstituted or substituted. If the aryl group is substituted, the substituent may be selected from those listed above, or may more particularly be: $C_{1-4}$ alkyl (e.g. methyl), $C_{5-7}$ aryl (e.g. furanyl, benzyl, pyridyl), $C_{3-7}$ heterocyclyl (e.g. tetrahydrofuranyl, pyrrolyl, morpholino, thiomorpholino), halo, hydroxy, $C_{1-7}$ alkyloxy and $NH_2$. Further possible substituents include cyano. The substituents may be selected from halo (e.g. F, Cl), hydroxy and $NH_2$, and in particular halo (e.g. F, Cl). In other embodiments, the substituents may be selected from halo, $C_{1-4}$ alkoxy (e.g. methoxy), cyano and $C_{1-4}$ alkyl (e.g. methyl).

When $R^1$ is $C_{3-20}$ heterocyclyl, it may be $C_{5-7}$ heterocyclyl. The heterocyclyl group may be, for example, pyrrolyl, piperidyl, oxazolyl, isoxazolyl, piperazinyl, morpholinyl and thiomorpholinyl. The heterocyclyl group may be unsubstituted or substituted. If the heterocyclyl group is substituted, the substituent may be selected from those listed above, or may more particularly be: $C_{5-7}$ aryl (e.g. furanyl, benzyl, pyridyl), $C_{3-7}$ heterocyclyl (e.g. tetrahydrofuranyl, pyrrolyl, morpholino, thiomorpholino), halo, hydroxy, $C_{1-7}$ alkyloxy and $NH_2$.

In certain embodiments of the present invention, $R^1$ may be methyl or ethyl.

In certain embodiments of the present invention, $R^1$ may be methyl or ethyl, and $R^C$ is H.

In certain embodiments of the present invention, $R^1$ may be methyl or ethyl, Y is CH and $R^C$ is H.

Further aspects of the present invention are the compounds of the examples below. Where appropriate, the above preferences may be taken in combination with each other.

Includes Other Forms

Included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

If the compound is in crystalline form, it may exist in a number of different polymorphic forms.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Particularly relevant to the present invention is the tautomeric pair illustrated below:

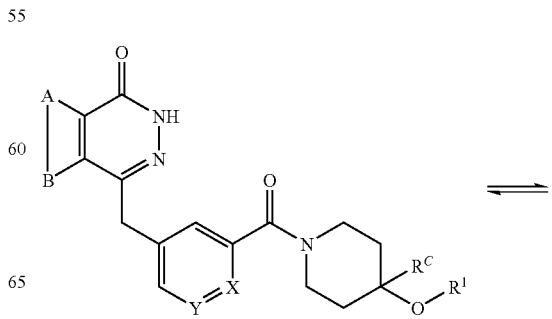

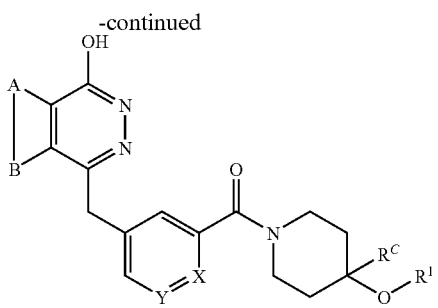

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic and salt forms thereof, for example as discussed below.

Unless otherwise specified, a reference to a particular compound also includes solvates thereof, for example as discussed below.

Unless otherwise specified, a reference to a particular compound also includes prodrugs thereof, for example as discussed below.

Unless otherwise specified, a reference to a particular compound also includes protected forms thereof, for example as discussed below.

Unless otherwise specified, a reference to a particular compound also includes different polymorphic forms thereof, for example as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., "Pharmaceutically Acceptable Salts", *J. Pharm. Sci.*, 66, 1-19 (1977).

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (T. Green and P. Wuts; 3rd Edition; John Wiley and Sons, 1999).

For example, a hydroxy group may be protected as an ether (—OR) or an ester (—OC(═O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(═O)CH$_3$, —OAc).

For example, an aldehyde or ketone group may be protected as an acetal or ketal, respectively, in which the carbonyl group (>C═O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an C$_{1-7}$ alkyl ester (e.g. a methyl ester; a t-butyl ester); a C$_{1-7}$ haloalkyl ester (e.g. a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-20}$ alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxycarbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(=O)(OH)$_2$. Such a group can be cleared by phosphotase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis

Compounds of the present invention may be synthesised by reaction of a compound of Formula 1:

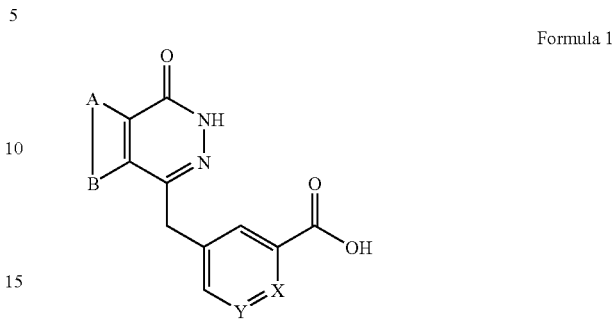

Formula 1 in which A, B and X are as previously defined, with a compound of Formula 2:

Formula 2 in which $R^1$ is as previously defined, in the presence of a coupling reagent system, for example 2-(1H-benzotriazol-1-yl)-1,1,3,3-tetramethyluronium tetrafluoroborate, 2-(1H-benzotriazol-1-yl)-1,1,3,3-tetramethyluronium hexafluorophosphate or (dimethylaminopropyl)ethylcarbodiimide hydrochloride/hydroxybenzotriazole, in the presence of a base, for example diisopropylethylamine, in a solvent, for example dimethylacetamide or dichloromethane, at a temperature in the range of 0° C. to the boiling point of the solvent used.

Alternatively, compounds of the present invention may be synthesised by conversion of a compound of Formula 1 into an activated species, for example an acid chloride or an activated ester such as an N-hydroxysuccinimide ester, using well-known methodologies, and reaction of the activated species with a compound of Formula 2.

The synthesis of compounds of Formula 1 in which Y is CH and X is CH or CF are described in WO 2004/080976, which description is incorporated herein by reference. The synthesis of compounds of Formula 1 in which Y is CH and X is N are described in WO 2006/021801, which description is incorporated herein by reference.

Compounds of Formula 2 are commercially available or may be synthesised by methods reported in the chemical literature.

Compounds of Formula 2 where $R^C$ is H may also be synthesised from compounds of Formula 3:

Formula 3

In which R¹ is as previously defined, by hydrogenation in the presence of a suitable catalyst, for example, 5% rhodium on alumina, in a suitable solvent, for example, ethanol.

Compounds of Formula 3 are commercially available or may be synthesised by methods reported in the chemical literature.

Compounds of Formula 1 may also be synthesised by reaction of a compound of formula 4:

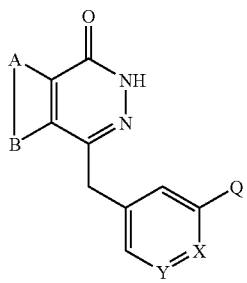

Formula 4 in which A, B and X are as previously defined, and Q is a suitable leaving group, for example bromide, in the presence of carbon monoxide and a suitable catalyst, such as, for example, trans-di-mu-acetatobis[2-(di-o-tolylphosphino)benzyl]dipalladium(II).

Compounds of formula 4 may be synthesised by the methods previously referenced in WO 2004/080976 & WO 2006/021801, or by the reaction of a compound of Formula 5:

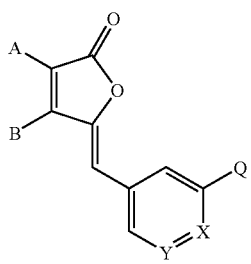

Formula 5 in which A, B, X Y and Q are as previously defined, or a compound of formula 6 (and/or its related ring-open form Formula 7):

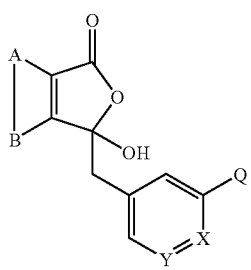

Formula 6

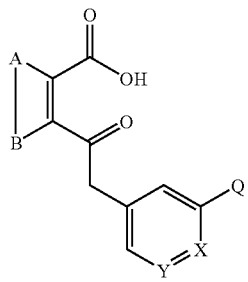

Formula 7 in which A, B, X Y and Q are as previously defined, or a mixture of compounds of formula 5, 6 and 7, with a source of hydrazine, for example hydrazine hydrate or hydrazine monohydrate, optionally in the presence of a base for example triethylamine, or an acid, for example acetic acid, optionally in the presence of solvent such as, for example water, DMF or THF.

Compounds of Formula 5 may be synthesised by methods analogous to those described in WO 2004/080976 & WO 2006/021801, or by reaction of a compound of Formula 8:

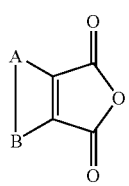

Formula 8 in which A and B are as previously defined, with a compound of Formula 9:

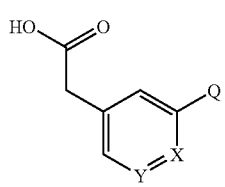

Formula 9 in which X, Y and Q are as previously defined, in the presence of a base, for example sodium acetate, at a temperature above the melting points of the compounds used.

Compounds of Formula 8 and compounds of Formula 9 are commercially available or may be synthesised by methods reported in the chemical literature.

In another embodiment, compounds of the present invention may be synthesised by reaction of a compound of Formula 10, which is itself a compound of the present invention:

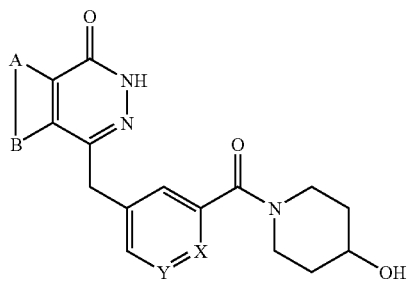

Formula 10 in which A, B, X and Y are as previously defined, with a compound of formula 11:

T-R¹          Formula 11 in which R¹ is as previously defined, typically optionally substituted $C_6$-heteroaryl, T is a leaving group, for example fluoride or chloride, in the presence of a suitable base, for example sodium hydride or sodium tert-butoxide.

Furthermore compounds of the present invention may be synthesised by reaction of a compound of Formula 10, in which A, B, X and Y are as previously defined, with a compound of Formula 11, in which R¹ is as previously defined, typically optionally substituted $C_6$-aryl and Y is a hydroxyl, by an arylation reaction involving the use of, for example, triphenylphosphine and diethylazodicarboxylate.

In a further embodiment, compounds of the present invention may be synthesised by reaction of a compound of Formula 12 or a compound of Formula 13:

Formula 12

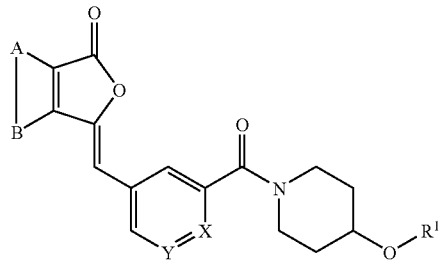

Formula 13

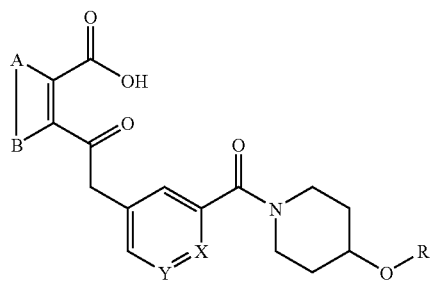

in which A, B, X and Y are as previously defined, and which are compounds of the present invention, and the carboxylic acid functionality may optionally be esterified, for example as a methyl ester, with a source of hydrazine, for example hydrazine hydrate or hydrazine monohydrate, optionally in the presence of a base for example triethylamine, or an acid, for example acetic acid, optionally in the presence of solvent such as, for example water, DMF or THF.

Compounds of Formula 12 may be synthesised by reaction of a compound of formula 8:

Formula 8

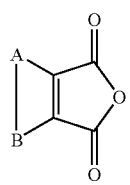

in which A & B are as previously defined, with a compound of Formula 14

Formula 14

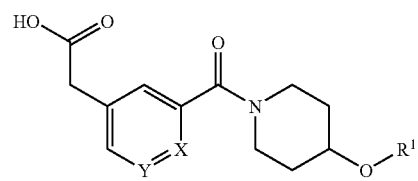

in which X, Y and R¹ are as previously defined, in the presence of a base, for example sodium acetate, at a temperature above the melting points of the compounds used.

Compounds of Formula 14 may be synthesised from compounds of Formula 15:

Formula 15

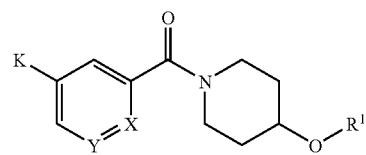

in which X, Y and R¹ are as previously defined and K is a leaving group, typically iodide, by reaction with diethyl malonate, in the presence of a suitable catalyst, for example copper (I) iodide and a suitable base, for example caesium carbonate, followed by subsequent decarboxylation and ester hydrolysis, for example, using a base such as Lithium hydroxide in a suitable solvent mixture, such as THF/Water.

Compounds of Formula 15 may be synthesised by reaction of a compound of Formula 16:

Formula 16

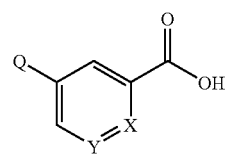

in which X, Y and Q are as previously defined, with a compound of Formula 2:

Formula 2

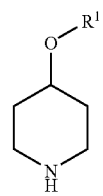

in which R¹ is as previously defined, in the presence of a coupling reagent system, for example 2-(1H-benzotriazol-1-yl)-1,1,3,3-tetramethyluronium tetrafluoroborate, 2-(1H-benzotriazol-1-yl)-1,1,3,3-tetramethyluronium hexafluorophosphate or (dimethylaminopropyl)ethylcarbodiimide hydrochloride/hydroxybenzotriazole, in the presence of a base, for example diisopropylethylamine, in a solvent, for example dimethylacetamide or dichloromethane, at a temperature in the range of 0° C. to the boiling point of the solvent used.

Alternatively, compounds of the present invention may be synthesised by conversion of a compound of Formula 1 into an activated species, for example an acid chloride or an activated ester such as an N-hydroxysuccinimide ester, using well-known methodologies, and reaction of the activated species with a compound of Formula 2.

Compounds of Formula 8 and compounds of Formula 16 are commercially available or may be synthesised by methods reported in the chemical literature.

Compounds of Formula 13, especially where A and B form:

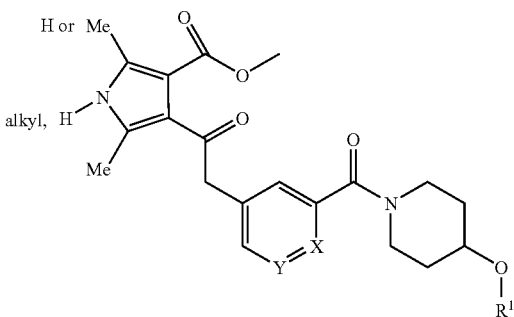

and X, Y and $R^1$ are as previously defined, may be synthesised from a compound of Formula 17:

Formula 17

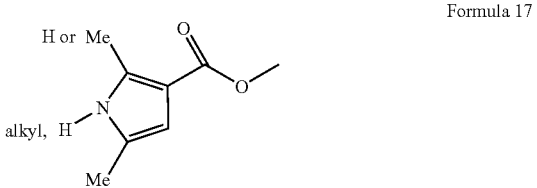

by acylation with a compound of Formula 14

Formula 14

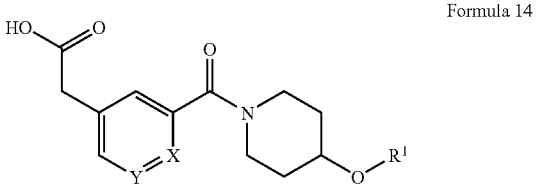

in which X, Y and $R^1$ are as previously defined, following conversion of a compound of Formula 14 into an activated species, for example an acid chloride, and subsequent reaction in the presence of a Lewis acid, for example aluminium trichloride.

Compounds of Formula 17 are commercially available or may be synthesised by methods reported in the chemical literature.

Use

The present invention provides active compounds, specifically, active in inhibiting the activity of PARP.

The term "active" as used herein, pertains to compounds which are capable of inhibiting PARP activity, and specifically includes both compounds with intrinsic activity (drugs) as well as prodrugs of such compounds, which prodrugs may themselves exhibit little or no intrinsic activity.

One assay which may conveniently be used in order to assess the PARP inhibition offered by a particular compound is described in the examples below.

The present invention further provides a method of inhibiting the activity of PARP in a cell, comprising contacting said cell with an effective amount of an active compound, preferably in the form of a pharmaceutically acceptable composition. Such a method may be practiced in vitro or in vivo.

For example, a sample of cells may be grown in vitro and an active compound brought into contact with said cells, and the effect of the compound on those cells observed. As examples of "effect", the amount of DNA repair effected in a certain time may be determined. Where the active compound is found to exert an influence on the cells, this may be used as a prognostic or diagnostic marker of the efficacy of the compound in methods of treating a patient carrying cells of the same cellular type.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "adjunct" as used herein relates to the use of active compounds in conjunction with known therapeutic means. Such means include cytotoxic regimes of drugs and/or ionising radiation as used in the treatment of different cancer types. In particular, the active compounds are known to potentiate the actions of a number of cancer chemotherapy treatments, which include the topoisomerase class of poisons (e.g. topotecan, irinotecan, rubitecan), most of the known alkylating agents (e.g. DTIC, temozolamide) and platinum based drugs (e.g. carboplatin, cisplatin) used in treating cancer.

Active compounds may also be used as cell culture additives to inhibit PARP, for example, in order to sensitize cells to known chemotherapeutic agents or ionising radiation treatments in vitro.

Active compounds may also be used as part of an in vitro assay, for example, in order to determine whether a candidate host is likely to benefit from treatment with the compound in question.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

Formulations

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, N.Y., USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g. compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

Polymorphic Forms

The following forms are as prepared in Example 47 below.

Compound 2b Form A (Anhydrous)

Compound 2b (Form A anhydrous) is characterised in providing at least one of the following 2θ values measured using CuKα radiation: 19.9° and 4.9°. Compound 2b (Form A anhydrous) is characterised in providing an X-ray powder diffraction pattern, substantially as shown in FIG. 1. The ten most prominent peaks are shown in Table 1:

TABLE 1

Ten most Prominent X-Ray Powder Diffraction peaks for Compound 2b Form A anhydrous

| Angle 2-Theta (2θ) | Intensity % | Relative Intensity |
|---|---|---|
| 4.9 | 60 | vs |
| 9.9 | 17 | s |
| 13.2 | 13 | s |
| 14.9 | 15 | s |
| 15.5 | 19 | s |
| 17.4 | 40 | vs |
| 17.8 | 13 | s |
| 19.9 | 100 | vs |
| 24.4 | 12 | s |
| 24.9 | 10 | s | vs = very strong
s = strong

Therefore according to a further aspect of the present invention there is provided a crystalline form of Compound 2b, Form A anhydrous, which has an X-ray powder diffraction pattern with at least one specific peak at about 2-theta=19.9°.

According to a further aspect of the present invention there is provided a crystalline form of Compound 2b, Form A anhydrous, which has an X-ray powder diffraction pattern with at least one specific peak at about 2-theta=4.9°.

According to a further aspect of the present invention there is provided a crystalline form of Compound 2b, Form A anhydrous, which has an X-ray powder diffraction pattern with at least two specific peaks at about 2-theta=19.9° and 4.9°.

According to a further aspect of the present invention there is provided a crystalline form of Compound 2b, Form A anhydrous, which has an X-ray powder diffraction pattern with specific peaks at about 2-theta=4.9°, 9.9°, 13.2°, 14.9°, 15.5°, 17.4°, 17.8°, 19.9°, 24.4° and 24.9°.

According to a further aspect of the present invention there is provided crystalline form, Compound 2b Form A anhydrous, which has an X-ray powder diffraction pattern substantially the same as the X-ray powder diffraction pattern shown in FIG. 1.

Figure 2:
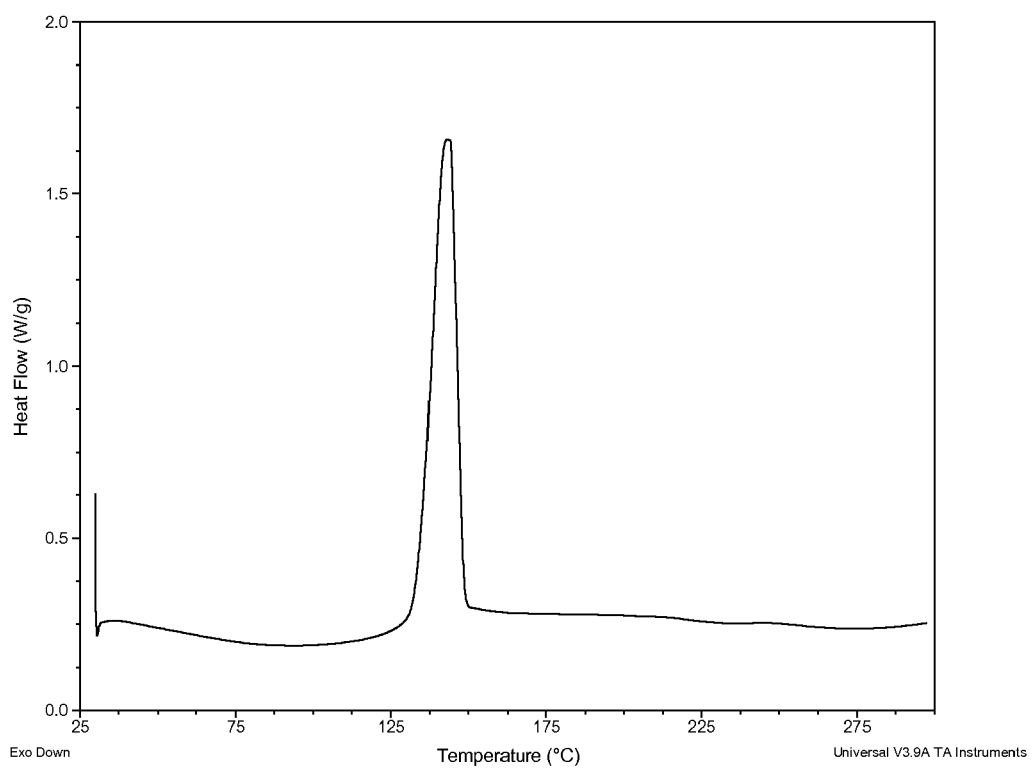
FIG. 2 is a DSC trace of a the form of the compound shown in FIG. 1.

DSC analysis shows Compound 2b, Form A anhydrous, is a high melting solid with an onset of melting at 134° C. and a peak at 143° C. (FIG. 2) when heated at a rate of 10° C. per minute.

When it is stated that aspects of the present invention relates to a crystalline form of Compound 2b, the degree of crystallinity is conveniently greater than about 60%, more conveniently greater than about 80%, preferably greater than about 90% and more preferably greater than about 95%. Most preferably the degree of crystallinity is greater than about 98%.

Compound 2b Form A anhydrous provides X-ray powder diffraction patterns substantially the same as the X-ray powder diffraction patterns shown in FIG. 1 and has substantially the ten most prominent peaks (angle 2-theta values) shown in Table 1. It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that 2b Form A of the present invention is not limited to the crystals that provide X-ray powder diffraction patterns identical to the X-ray powder diffraction pattern shown in FIG. 1, and any crystals providing X-ray powder diffraction patterns substantially the same as those shown in FIG. 1 fall within the scope of the present invention. A person skilled in the art of X-ray powder diffraction is able to judge the substantial identity of X-ray powder diffraction patterns.

Compound 2b Form B (Hydrate)

Figure 3:
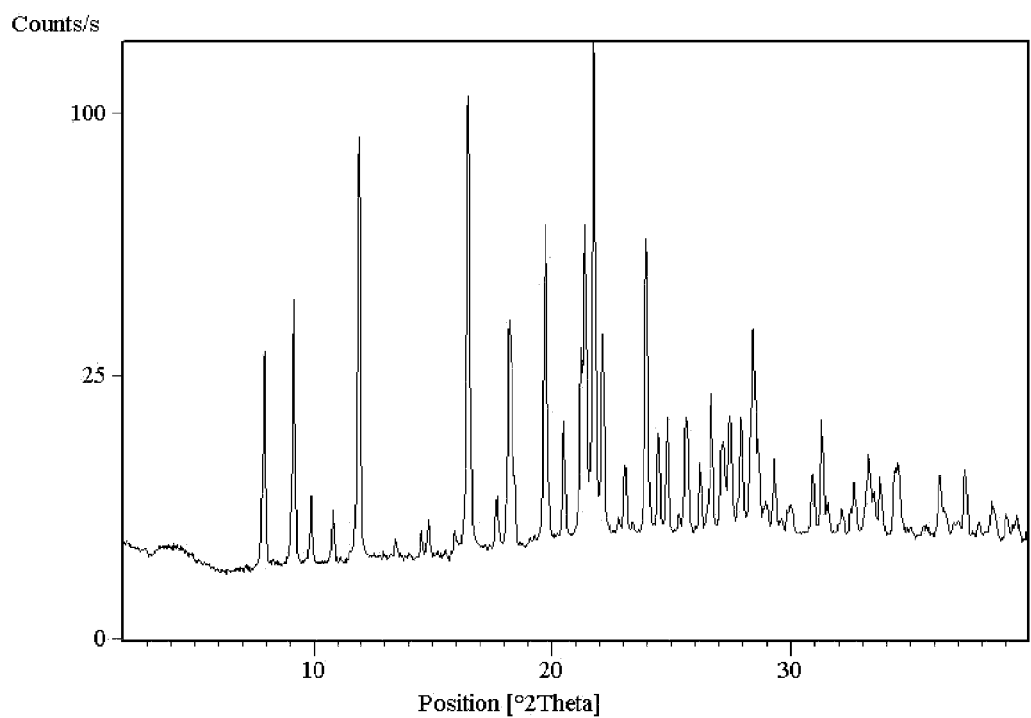
FIG. 3 is a powder XRD pattern of a further crystalline form of the compound shown in FIG. 1.

Compound 2b (Form B hydrate) is characterised in providing at least one of the following 2θ values measured using CuKα radiation: 21.7° and 16.5°. 2b (Form B hydrate) is characterised in providing an X-ray powder diffraction pattern, substantially as shown in FIG. 3. The ten most prominent peaks are shown in Table 2:

TABLE 2

Ten most Prominent X-Ray Powder Diffraction peaks for Compound 2b Form B hydrate

| Angle 2-Theta (2θ) | Intensity % | Relative Intensity |
|---|---|---|
| 9.2 | 27 | vs |
| 11.9 | 68 | vs |
| 16.5 | 82 | vs |
| 18.2 | 29 | vs |
| 19.7 | 47 | vs |
| 21.4 | 46 | vs |
| 21.7 | 100 | vs |

TABLE 2-continued

Ten most Prominent X-Ray Powder Diffraction peaks for Compound 2b Form B hydrate

| Angle 2-Theta (2θ) | Intensity % | Relative Intensity |
|---|---|---|
| 22.1 | 23 | s |
| 23.9 | 42 | vs |
| 28.4 | 25 | vs | vs = very strong
s = strong

Therefore according to a further aspect of the present invention there is provided a crystalline form of Compound 2b, Form B hydrate, which has an X-ray powder diffraction pattern with at least one specific peak at about 2-theta=21.7°.

According to a further aspect of the present invention there is provided a crystalline form of Compound 2b, Form B hydrate, which has an X-ray powder diffraction pattern with at least one specific peak at about 2-theta=16.5°.

According to a further aspect of the present invention there is provided a crystalline form of Compound 2b, Form B hydrate, which has an X-ray powder diffraction pattern with at least two specific peaks at about 2-theta=21.7° and 16.5°.

According to a further aspect of the present invention there is provided a crystalline form of Compound 2b, Form B hydrate, which has an X-ray powder diffraction pattern with specific peaks at about 2-theta=9.2°, 11.9°, 16.5°, 18.2°, 19.7°, 21.4°, 21.7°, 22.1°, 23.9° and 28.4°.

According to a further aspect of the present invention there is provided a crystalline form of Compound 2b, Form B hydrate, which has an X-ray powder diffraction pattern substantially the same as the X-ray powder diffraction pattern shown in FIG. 3.

Figure 4:
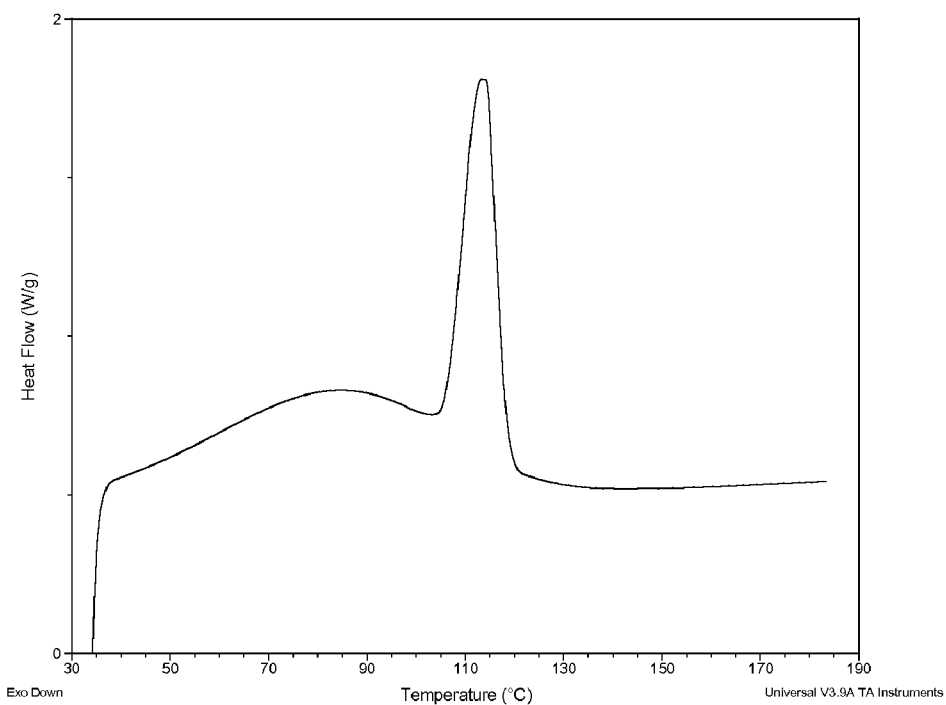
FIG. 4 is a DSC trace of a the form of the compound shown in FIG. 3.

DSC analysis shows Compound 2b, Form B hydrate, is a solid with an endothermic dehydration onsetting at 31° C. and a second endothermic transition at an onset of 105° C. (FIG. 4) when heated at a rate of 10° C. per minute.

When it is stated that the present invention relates to a crystalline form of Compound 2b, Form B hydrate, the degree of crystallinity is conveniently greater than about 60%, more conveniently greater than about 80%, preferably greater than about 90% and more preferably greater than about 95%. Most preferably the degree of crystallinity is greater than about 98%.

Compound 2b, Form B hydrate, provides X-ray powder diffraction patterns substantially the same as the X-ray powder diffraction patterns shown in FIG. 3 and has substantially the ten most prominent peaks (angle 2-theta values) shown in Table 2. It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that Compound 2b, Form B hydrate, of the present invention is not limited to the crystals that provide X-ray powder diffraction patterns identical to the X-ray powder diffraction pattern shown in FIG. 3, and any crystals providing X-ray powder diffraction patterns substantially the same as those shown in FIG. 3 fall within the scope of the present invention. A person skilled in the art of X-ray powder diffraction is able to judge the substantial identity of X-ray powder diffraction patterns.

Compound 2f Form A (Anhydrous)

Figure 5:
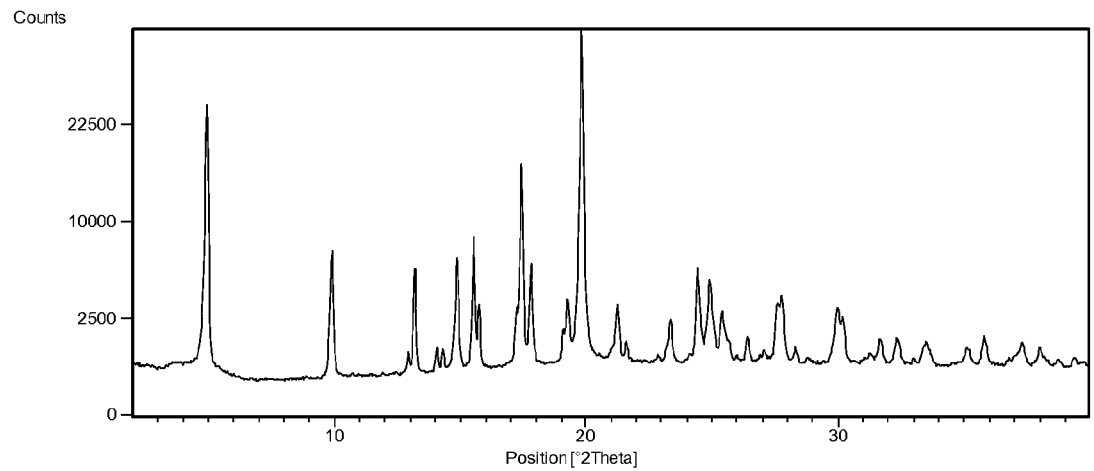
FIG. 5 is a powder XRD pattern of a crystalline form of a further compound of the present invention.

Compound 2f (Form A) is characterised in providing at least one of the following 2θ values measured using CuKα radiation: 19.9° and 4.9°. Compound 2f (Form A) is characterised in providing an X-ray powder diffraction pattern, substantially as shown in FIG. 5. The ten most prominent peaks are shown in Table 3:

TABLE 3

Ten most Prominent X-Ray Powder Diffraction peaks for Compound 2f Form A

| Angle 2-Theta (2θ) | Intensity % | Relative Intensity |
|---|---|---|
| 19.9 | 100.0 | vs |
| 4.9 | 64.5 | vs |
| 17.4 | 41.8 | vs |
| 15.5 | 20.4 | s |
| 9.9 | 17.5 | s |
| 14.9 | 15.3 | s |
| 13.2 | 14.2 | s |
| 17.8 | 13.8 | s |
| 24.4 | 12.7 | s |
| 24.9 | 10.5 | s | vs = very strong
s = strong
m = medium
w = weak

Therefore according to a further aspect of the present invention there is provided a crystalline form of Compound 2f, Form A, which has an X-ray powder diffraction pattern with at least one specific peak at about 2-theta=19.9°.

According to a further aspect of the present invention there is provided a crystalline form Compound 2f, Form A, which has an X-ray powder diffraction pattern with at least one specific peak at about 2-theta=4.9°.

According to a further aspect of the present invention there is provided a crystalline form Compound 2f, Form A, which has an X-ray powder diffraction pattern with at least two specific peaks at about 2-theta=19.9° and 4.9°.

According to a further aspect of the present invention there is provided a crystalline form Compound 2f, Form A, which has an X-ray powder diffraction pattern with specific peaks at about 2-theta=4.9°, 9.9°, 13.2°, 14.9°, 15.5°, 17.4°, 17.8°, 19.9°, 24.4° and 24.9°.

According to a further aspect of the present invention there is provided a crystalline form Compound 2f, Form A, which has an X-ray powder diffraction pattern substantially the same as the X-ray powder diffraction pattern shown in FIG. 5.

Figure 6:
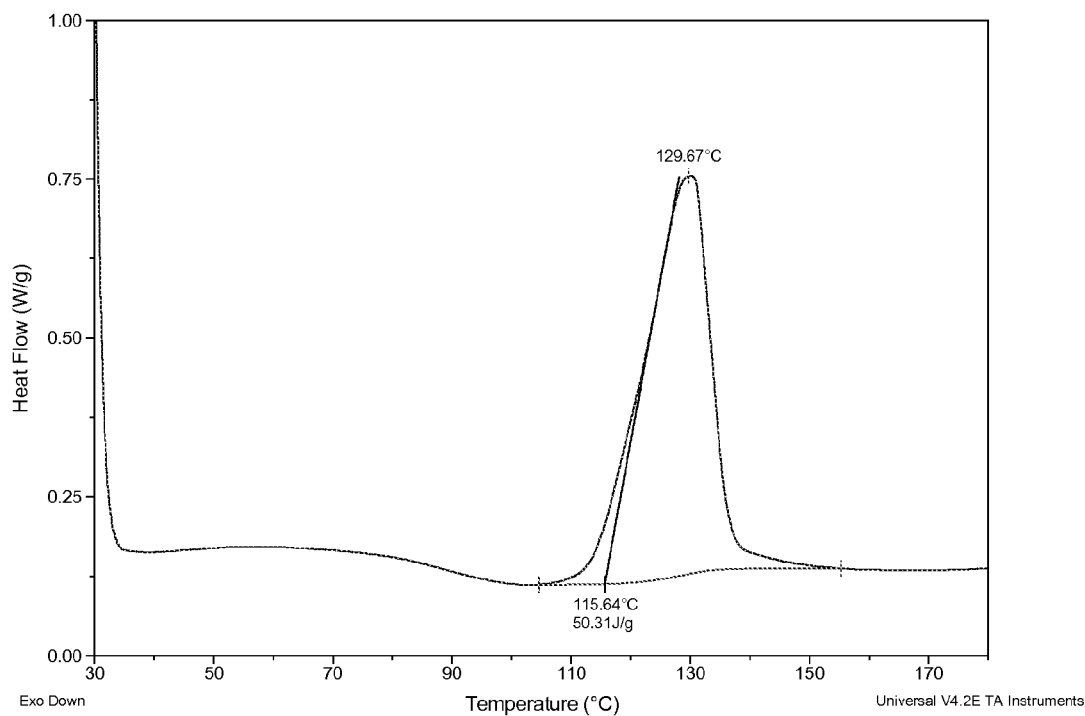
FIG. 6 is a DSC trace of a the form of the compound shown in FIG. 5.

DSC analysis shows Compound 2f, Form A, is a high melting solid with an onset of melting at 116° C. (FIG. 6) when heated at a rate of 10° C. per minute.

When it is stated that the present invention relates to a crystalline form of Compound 2f, the degree of crystallinity is conveniently greater than about 60%, more conveniently greater than about 80%, preferably greater than about 90% and more preferably greater than about 95%. Most preferably the degree of crystallinity is greater than about 98%.

Compound 2f Form A provides X-ray powder diffraction patterns substantially the same as the X-ray powder diffraction patterns shown in FIG. 5 and has substantially the ten most prominent peaks (angle 2-theta values) shown in Table 3. It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that Compound 2f Form A of the present invention is not limited to the crystals that provide X-ray powder diffraction patterns identical to the X-ray powder diffraction pattern shown in FIG. 5, and any crystals providing X-ray powder diffraction patterns substantially the same as those shown in FIG. 5 fall within the scope of the present invention. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is plus or minus 0.1° 2-theta, and such degree of a measurement error should be taken into account when considering the X-ray powder diffraction patterns in FIGS. 1, 3 and 5 and when reading Tables 1, 2 and 3. Furthermore, it should be understood that intensities may fluctuate depending on experimental conditions and sample preparation (preferred orientation).

Details of Techniques Used
X-Ray Powder Diffraction

TABLE 4

| % Relative Intensity* | Definition |
|---|---|
| 25-100 | vs (very strong) |
| 10-25 | s (strong) |
| 3-10 | m (medium) |
| 1-3 | w (weak) |

*The relative intensities are derived from diffractograms measured with fixed slits Analytical Instrument: PANalytical Cubix PRO The X-ray powder diffraction spectra were determined by mounting a sample of the crystalline salt on single silicon crystal wafer mounts (zero background holder) and spreading out the sample into a thin layer. The sample was spun to improve counting statistics and irradiated with X-rays generated by a copper long-fine focus tube operated at 45 kV and 40 mA with a wavelength of 1.5418 angstroms. The collimated X-ray source was passed through an automatic variable divergence slit set at V20 and the reflected radiation directed through a 2 mm anti-scatter slit and a 0.2 mm detector slit. The sample was exposed for 100 second per 0.02 degree 2-theta increment (continuous scan mode) over the range 2 degrees to 40 degrees 2-theta in theta-theta mode. Persons skilled in the art of X-ray powder diffraction will realise that the relative intensity of peaks can be affected by, for example, grains above 30 microns in size and non-unitary aspect ratios which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Differential Scanning Calorimetry

Analytical Instrument: TA Instruments Q1000.

Typically less than 5 mg of material contained in a 40 μl aluminium pan fitted with a pierced lid was heated over the temperature range 25° C. to 300° C./25° C. to 180° C. at a constant heating rate of 10° C. per minute. Nitrogen was used as purge gas-flow rate 50 ml per minute.

EXAMPLES

General Experimental Methods for Examples 1-3

Preparative HPLC

Instrument: Waters ZMD LC-MS system No. LD352 operating in Electrospray ionisation mode.

Mobile Phase A: 0.1% Formic acid in water

Mobile Phase B: 0.1% Formic acid in acetonitrile

Column: Genesis C18 4 μm 50×4.6 mm

Gradient:

| Time (mins.) | % B |
| --- | --- |
| 0 | 5 |
| 7 | 95 |
| 9 | 95 |
| 9.5 | 5 |
| 13 | 5 |

Flow rate: 1.0 ml/min.

PDA Scan range: 210-400 nm.

Long Method

Instrument: Waters ZQ LC-MS system No. LAA 254 operating in Electrospray ionisation mode.

Mobile Phase A: 0.1% Formic acid in water

Mobile Phase B: 0.1% Formic acid in acetonitrile

Column: Genesis C18 4 μm 50×4.6 mm

Gradient:

| Time (mins.) | % B |
| --- | --- |
| 0 | 5 |
| 20 | 95 |
| 23 | 95 |
| 24 | 5 |
| 25 | 5 |

Flow rate: 2.0 ml/min.

PDA Scan range: 210-400 nm.

Example 1

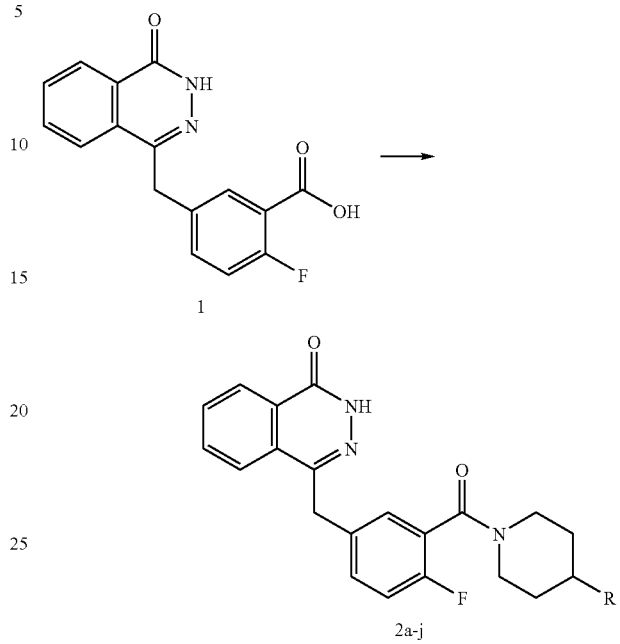

(a) Library Synthesis (2a-j)

To a solution of 2-fluoro-5-(4-oxo-3,4-dihydro-phthalazin-1-ylmethyl)-benzoic acid (1) (29 mg, 0.1 mmol) in DMA (0.5 ml) was added DIPEA (0.02 μL, 0.11 mmol), HBTU (42 mg, 0.10 mmol) followed by the appropriate piperidine derivative (0.10 mmol). The reaction was stirred at ambient temperature for 16 hours. The crude sample were then submitted for preparative HPLC purification.

| | R | Purity | RT (min) | M + H |
| --- | --- | --- | --- | --- |
| 2a | *⟋OH | 89% | 6.79* | 382.3 |
| 2b | *⟋O⟍ | 96% | 8.21* | 396.3 |
| 2c | *⟋O-(4-F-C6H4) | 97% | 5.34 | 476.3 |

-continued

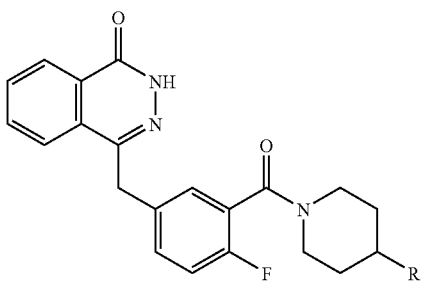

| | R | Purity | RT (min) | M + H |
|---|---|---|---|---|
| 2d | *—O—C₆H₄—Cl (4-Cl-phenoxy) | 97% | 5.34 | 476.3 |
| 2e | *—O—phenyl | 99% | 5.64 | 492.3 |
| 2f | *—O—ethyl | 90% | 4.53 | 410.2 |
| 2g | *—O—CH₂—cyclopropyl | 99% | 10.21* | 436.2 |
| 2h | *—O—isobutyl | 98% | 5.37 | 438.3 |
| 2i | *—O—2-pyridyl | 100 | 9.92 | 459.2 |
| 2j | *—O—4-pyridyl | 99% | 3.58 | 459.1 |

*= long method

Example 2

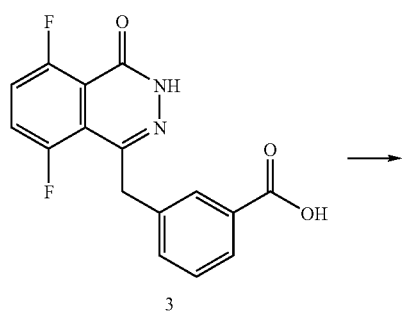

3

-continued

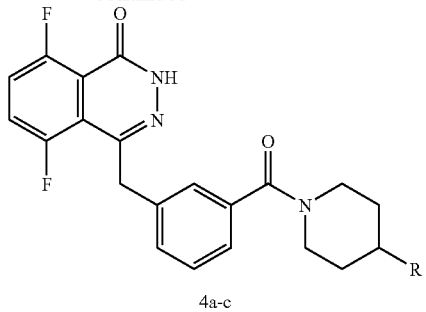
4a-c (a) Library Synthesis (4a-c)

To a solution of 3-(5,8-difluoro-4-oxo-3,4-dihydro-phthalazin-1-ylmethyl)-benzoic acid (3) (32 mg, 0.1 mmol) in DMA (0.5 ml) was added DIPEA (0.02 μL, 0.11 mmol), HBTU (42 mg, 0.10 mmol) followed by the appropriate piperidine derivative (0.10 mmol). The reaction was stirred at ambient temperature for 16 hours. The crude sample were then submitted for preparative HPLC purification.

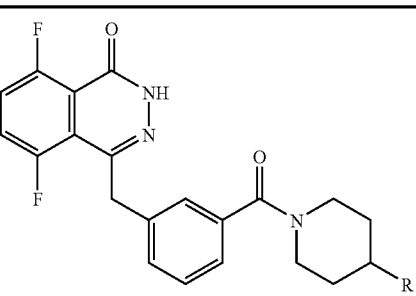

| | R | Purity | RT (min) | M + H |
|---|---|---|---|---|
| 4a | *—O—CH₂—cyclopropyl | 99% | 4.88 | 454.3 |
| 4b | *—O—2-pyridyl | 100% | 4.84 | 477.2 |
| 4c | *—O—isobutyl | 98% | 5.43 | 456.3 |

Example 3

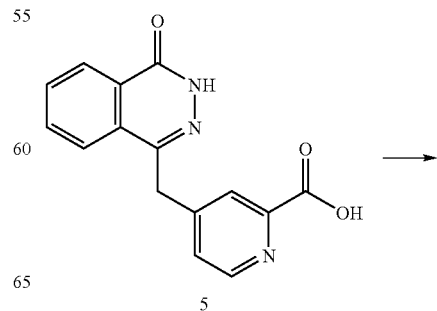

5

-continued

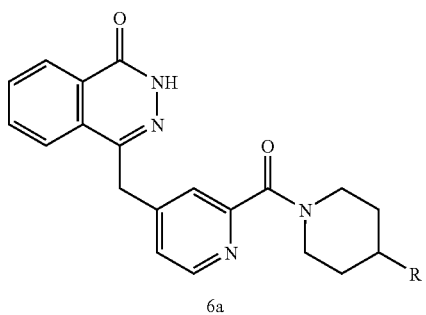

6a (a) Library Synthesis (6a-c)

To a solution of 4-(4-oxo-3,4-dihydro-phthalazin-1-ylmethyl)-pyridine-2-carboxylic acid (5) (28 mg, 0.1 mmol) in DMA (0.5 ml) was added DIPEA (0.02 μL, 0.11 mmol), HBTU (42 mg, 0.10 mmol) followed by the appropriate piperidine derivative (0.10 mmol). The reaction was stirred at ambient temperature for 16 hours. The crude sample were then submitted for preparative HPLC purification.

| R | | Purity | RT (min) | M + H |
|---|---|---|---|---|
| 6a | 4-chlorophenoxy | 99% | 10.81* | 475.2 |
| 6b | 4-fluorophenoxy | 100% | 2.71+ | 459.1 |
| 6c | methoxy | 100% | 1.87+ | 379.1 |
| 6d | phenoxy | 100% | 2.67+ | 441.1 |

-continued

| R | | Purity | RT (min) | M + H |
|---|---|---|---|---|
| 6e | 4-pyridyloxy | 97% | 3.34 | 442.1 |
| 6f | 2-pyridyloxy | 100% | 2.42+ | 442.1 |

*long method
+analytical LC-MS method below

General Experimental Methods for Examples 4-45

Analytical LC-MS

LC-MS data was generated on a system where the HPLC component comprised generally either an Agilent 1100, Waters Alliance HT (2790 & 2795) equipment or an HP1100 pump and Diode Array with CTC autosampler and was run on a Phenomenex Gemini C18 5 mm, 50×2 mm column (or similar) eluting with either acidic eluent (for example, using a gradient, over 4 minutes, between 0-95% water/acetonitrile with 5% of a 1% formic acid in 50:50 water:acetonitrile (v/v) mixture; or using an equivalent solvent system with methanol instead of acetonitrile), or basic eluent (for example, using a gradient, over 4 minutes, between 0-95% water/acetonitrile with 5% of a 0.1% 880 Ammonia in acetonitrile mixture); and the MS component comprised generally a Waters ZQ mass spectrometer scanning over an appropriate mass range. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is the $(M+H)^+$ for positive ion mode and $(M-H)-$ for negative ion mode NMR Spectra Where given NMR data was determined at 400 MHz using, for example, a Bruker DPX-400 spectrometer and is in the form of delta values, for major diagnostic protons, given in parts per million (ppm). Solvents used were $CDCl_3$ (with tetramethylsilane (TMS) as an internal standard) or DMSO-$d_6$ unless otherwise indicated; the following abbreviations have been used: s, singlet; d, doublet; t, triplet; q, quartet; m, multiplet; br, broad.

Example 4

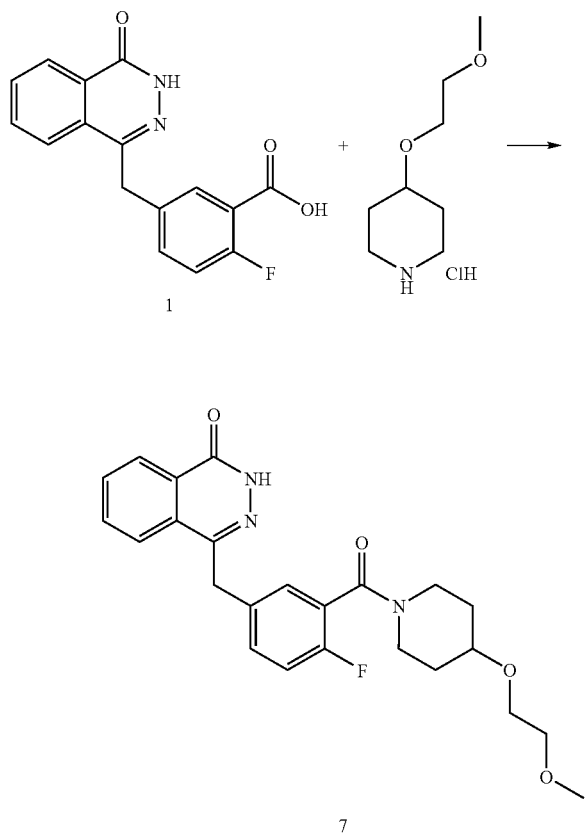

4-(4-fluoro-3-(4-(2-methoxyethoxy)piperidine-1-carbonyl)benzyl)phthalazin-1(2H)-one (7)

A solution of 2-fluoro-5-((4-oxo-3,4-dihydrophthalazin-1-yl)methyl)benzoic acid (1) (150 mg, 0.50 mmol) in N,N-dimethylacetamide (4 mL) was treated with 4-(2-methoxyethoxy)piperidine hydrochloride (103 mg, 0.53 mmol) and triethylamine (0.210 mL, 1.51 mmol). O-Benzotriazol-1-yl-N,N,N',N'-tetra-methyluronium hexafluorophosphate (253 mg, 0.67 mmol) was added and the resulting solution was stirred at ambient temperature for 4.5 hours. The crude reaction mixture was filtered before being purified by preparative HPLC (Waters XBridge Prep C18 OBD column, 5μ silica, 19 mm diameter, 100 mm length), using decreasingly polar mixtures of water (containing 1% NH3) and MeCN as eluents. Fractions containing the desired compound were evaporated to dryness and lyophilised to afford a gum, which was taken up in a small amount of diethyl ether and dichloromethane and allowed to evaporate before drying under vacuum, at 55° C., for 2 hours to afford the desired compound as a white solid (151 mg, 68.3% yield); $^1$H NMR (400.132 MHz, DMSO) δ 1.28-1.36 (1H, m), 1.40-1.49 (1H, m), 1.68-1.75 (1H, m), 1.82-1.90 (1H, m), 2.99-3.06 (1H, m), 3.25 (3H, s), 3.26-3.32 (2H, m), 3.44 (2H, t), 3.53-3.58 (3H, m), 3.90-3.98 (1H, m), 4.33 (2H, s), 7.21 (1H, t), 7.33-7.35 (1H, m), 7.39-7.43 (1H, m), 7.81-7.91 (2H, m), 7.97 (1H, d), 8.27 (1H, dd), 12.56 (1H, s); m/z (LC-MS, ESI+), RT=1.65 (M+H 440.6).

Example 5

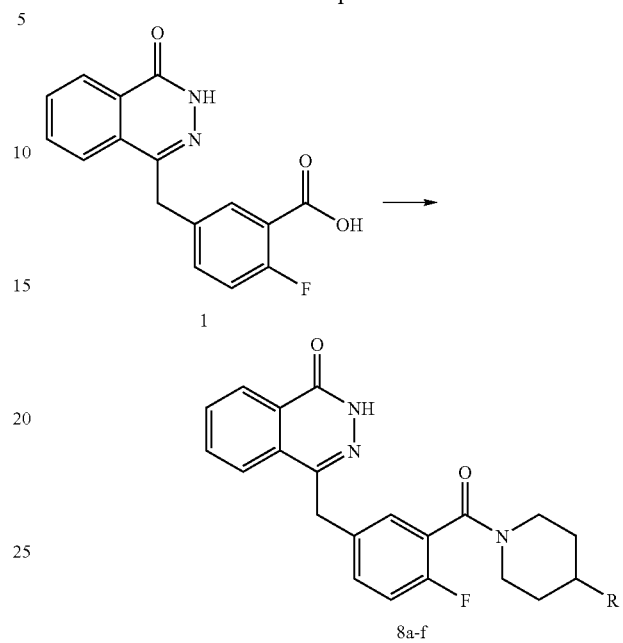

Multiple Parallel Synthesis (8a-f)

A solution of 2-fluoro-5-((4-oxo-3,4-dihydrophthalazin-1-yl)methyl)benzoic acid (1) (120 mg, 0.40 mmol), triethylamine (144 uL, 1.03 mmol) and O-Benzotriazol-1-yl-N,N,N',N'-tetra-methyluronium hexafluorophosphate (200 mg, 0.53 mmol) in N,N-dimethylacetamide (3 mL) was added to the appropriate piperidine (0.50 mmol) and the mixture was allowed to stir at ambient temperature overnight. The reaction mixture was then filtered through a 0.45 μm syringe filter and filtrate purified directly by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired product were combined, evaporated to dryness and lyophilised to afford the final products, which were dissolved in a few drops of dichloromethane and diethyl ether (1-2 mL). The solvents were allowed to evaporate before drying residue, under vacuum, at 60° C., for 3 hours to afford the desired compounds.

| R | | Purity | RT (min) | M + H |
|---|---|---|---|---|
| 8a | *-O-[3-methoxyphenyl]-O- | 99% | 2.28 | 488.6 |

-continued

| R | Purity | RT (min) | M + H |
|---|---|---|---|
| 8b  *\O\<phenyl>\OMe (4-methoxyphenoxy) | 99% | 2.27 | 488.6 |
| 8c  *\O\propyl | 100% | 2.09 | 424.6 |
| 8d  *\O\<phenyl>\OMe (2-methoxyphenoxy) | 100% | 2.23 | 488.6 |
| 8e  *\O\CH2\phenyl | 100% | 2.32 | 472.6 |
| 8f  *\O\<phenyl>\CH2CN | 100% | 2.17 | 497.6 |

8a:—4-[[4-fluoro-3-[4-(3-methoxyphenoxy)piperidine-1-carbonyl]phenyl]methyl]-2H-phthalazin-1-one; ¹H NMR (400.132 MHz, DMSO) δ 1.46-1.67 (2H, m), 1.80-1.87 (1H, m), 1.95-2.03 (1H, m), 3.13-3.20 (1H, m), 3.33-3.50 (2H, m), 3.73 (3H, s), 3.92-4.01 (1H, m), 4.33 (2H, s), 4.60-4.66 (1H, m), 6.51-6.58 (3H, m), 7.16-7.25 (2H, m), 7.36-7.44 (2H, m), 7.80-7.90 (2H, m), 7.98 (1H, d), 8.26 (1H, dd), 12.57 (1H, s).

8b:—4-[[4-fluoro-3-[4-(4-methoxyphenoxy)piperidine-1-carbonyl]phenyl]methyl]-2H-phthalazin-1-one; ¹H NMR (400.132 MHz, DMSO) δ 1.44-1.65 (2H, m), 1.76-1.84 (1H, m), 1.91-1.99 (1H, m), 3.10-3.17 (1H, m), 3.32-3.49 (2H, m), 3.70 (3H, s), 3.92-3.99 (1H, m), 4.33 (2H, s), 4.45-4.51 (1H, m), 6.83-6.94 (4H, m), 7.22 (1H, t), 7.35-7.44 (2H, m), 7.80-7.90 (2H, m), 7.97 (1H, d), 8.26 (1H, dd), 12.57 (1H, s).

8c:—4-[[4-fluoro-3-(4-propoxypiperidine-1-carbonyl)phenyl]methyl]-2H-phthalazin-1-one; ¹H NMR (400.132 MHz, DMSO) δ 0.87 (3H, t), 1.27-1.36 (1H, m), 1.39-1.55 (3H, m), 1.66-1.74 (1H, m), 1.82-1.89 (1H, m), 2.99-3.07 (1H, m), 3.24-3.29 (2H, m), 3.36 (2H, td), 3.48-3.54 (1H, m), 3.89-3.98 (1H, m), 4.33 (2H, s), 7.21 (1H, t), 7.33-7.35 (1H, m), 7.39-7.43 (1H, m), 7.81-7.91 (2H, m), 7.97 (1H, d), 8.27 (1H, dd), 12.56 (1H, s).

8d:—4-[[4-fluoro-3-[4-(2-methoxyphenoxy)piperidine-1-carbonyl]phenyl]methyl]-2H-phthalazin-1-one; ¹H NMR (400.132 MHz, DMSO) δ 1.49-1.68 (2H, m), 1.76-1.84 (1H, m), 1.91-1.99 (1H, m), 3.10-3.17 (1H, m), 3.35-3.50 (2H, m), 3.76 (3H, s), 3.93-4.00 (1H, m), 4.34 (2H, s), 4.47-4.53 (1H, m), 6.85-7.05 (4H, m), 7.22 (1H, t), 7.36-7.43 (2H, m), 7.80-7.90 (2H, m), 7.98 (1H, d), 8.26 (1H, dd), 12.57 (1H, s).

8e:—4-[[4-fluoro-3-(4-phenylmethoxypiperidine-1-carbonyl)phenyl]methyl]-2H-phthalazin-1-one; ¹H NMR (400.132 MHz, DMSO) δ 1.37-1.59 (2H, m), 1.72-1.79 (1H, m), 1.88-1.94 (1H, m), 3.01-3.08 (1H, m), 3.27-3.38 (2H, m), 3.63-3.68 (1H, m), 3.90-3.98 (1H, m), 4.33 (2H, s), 4.52 (2H, s), 7.21 (1H, t), 7.26-7.31 (1H, m), 7.33-7.38 (5H, m), 7.39-7.43 (1H, m), 7.81-7.91 (2H, m), 7.97 (1H, d), 8.27 (1H, dd), 12.56 (1H, s).

8f:—2-[4-[1-[2-fluoro-5-[(4-oxo-3H-phthalazin-1-yl)methyl]benzoyl]piperidin-4-yl]oxyphenyl]acetonitrile; ¹H NMR (399.902 MHz, DMSO) δ 1.47-1.68 (2H, m), 1.81-1.88 (1H, m), 1.96-2.04 (1H, m), 3.13-3.21 (1H, m), 3.32-3.40 (1H, m), 3.43-3.51 (1H, m), 3.92-4.03 (3H, m), 4.34 (2H, s), 4.62-4.68 (1H, m), 7.00-7.03 (2H, m), 7.21-7.28 (3H, m), 7.37-7.44 (2H, m), 7.80-7.90 (2H, m), 7.98 (1H, d), 8.27 (1H, dd), 12.58 (1H, s).
[Starting piperidine:—CAS 1000516-48-2]

Example 6

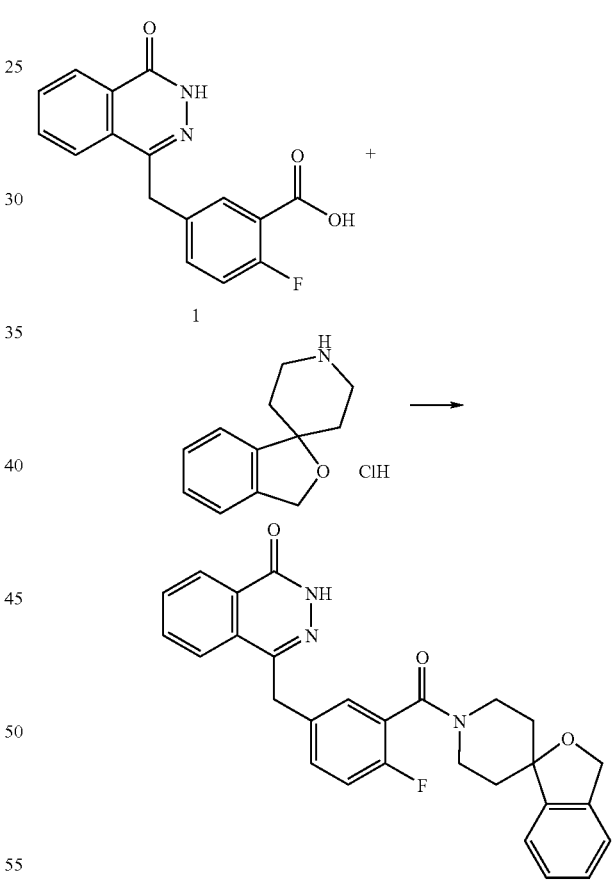

4-(4-fluoro-3-(3H-spiro[isobenzofuran-1,4'-piperidine]-1'-ylcarbonyl)benzyl)phthalazin-1(2H)-one (9)

A solution of 2-fluoro-5-((4-oxo-3,4-dihydrophthalazin-1-yl)methyl)benzoic acid (1) (144 mg, 0.48 mmol) and 3H-spiro[isobenzofuran-1,4'-piperidine]hydrochloride (109 mg, 0.48 mmol) in N,N-dimethylacetamide (2 mL) was treated with triethylamine (0.168 mL, 1.21 mmol) and O-Benzotriazol-1-yl-N,N,N',N'-tetra-methyluronium hexafluorophosphate (256 mg, 0.68 mmol). The resulting mixture was stirred at ambient temperature for 5 hours, before being filtered and purified by preparative HPLC (Waters XBridge Prep C18 OBD column, 5μ silica, 19 mm diameter, 100 mm length), using decreasingly polar mixtures of water (containing 0.1% NH$_3$) and MeCN as eluents. Fractions containing the desired compound were evaporated to dryness and lyophilised to afford the desired compound as a white solid (118 mg, 52.1% yield); $^1$H NMR (400.132 MHz, DMSO) δ 1.53-1.62 (2H, m), 1.73-1.83 (3H, m), 1.91-1.99 (1H, m), 3.10-3.18 (1H, m), 4.40 (2H, s), 4.54-4.60 (1H, m), 5.03-5.11 (2H, m), 7.26-7.37 (5H, m), 7.45-7.50 (2H, m), 7.83-7.93 (2H, m), 8.02 (1H, d), 8.30 (1H, d), 12.13-12.59 (1H, br s); m/z (LC-MS, ESI+), RT=2.14 (M+H 470.9).

Example 7

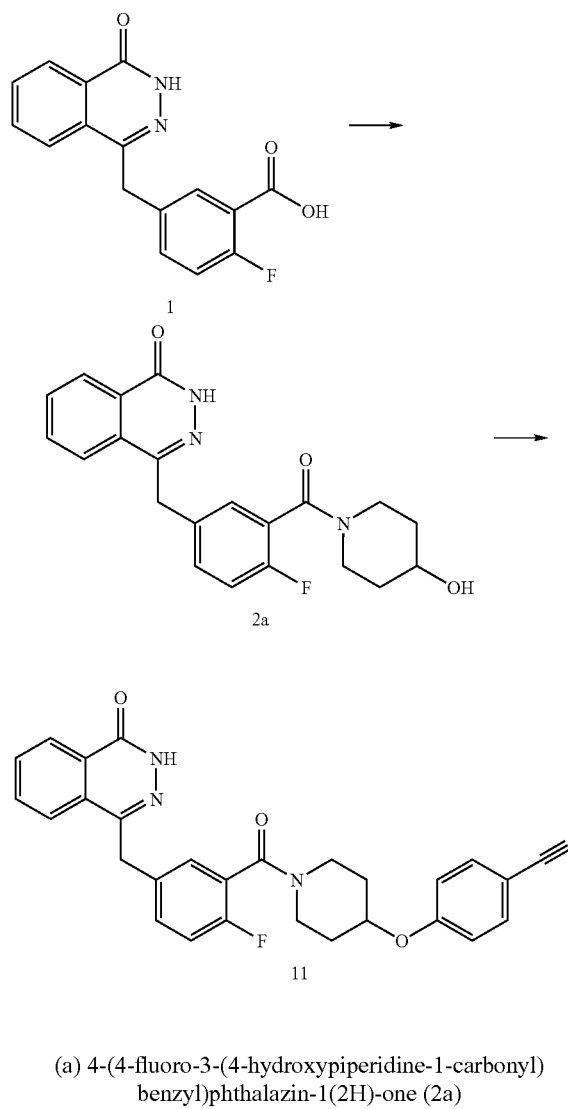

(a) 4-(4-fluoro-3-(4-hydroxypiperidine-1-carbonyl) benzyl)phthalazin-1(2H)-one (2a)

A solution of 2-fluoro-5-((4-oxo-3,4-dihydrophthalazin-1-yl)methyl)benzoic acid (1) (1 g, 3.35 mmol) in N,N-dimethylacetamide (30 mL) was treated with 4-hydroxypiperidine (396 mg, 3.92 mmol) and triethylamine (1 mL, 7.17 mmol). O-Benzotriazol-1-yl-N,N,N',N'-tetra-methyluronium hexafluorophosphate (1.77 g, 4.67 mmol) was added and the resulting solution was stirred at ambient temperature for 17 hours. The reaction mixture was then poured into water (300 mL) and extracted with dichloromethane (2×200 mL). Combined organic extracts were washed with brine, dried over magnesium sulfate, filtered and evaporated to afford the crude product, which was purified by flash silica chromatography, elution gradient 0 to 20% MeOH in dichloromethane. Pure fractions were evaporated to dryness to afford the desired compound as a pale yellow gum (1.24 g, 97% yield); $^1$H NMR (400.132 MHz, CDCl$_3$) δ 1.42-1.54 (1H, m), 1.55-1.67 (2H, m), 1.76-1.84 (1H, m), 1.92-2.01 (1H, m), 3.05-3.15 (1H, m), 3.38-3.55 (2H, m), 3.94-3.99 (1H, m), 4.14-4.22 (1H, m), 4.27 (2H, s), 7.02 (1H, t), 7.26-7.32 (2H, m), 7.70-7.79 (3H, m), 8.44-8.48 (1H, m), 10.07 (1H, s); m/z (LC-MS, ESI+), RT=1.44 (M+H 382.1).

(b) 4-[1-[2-fluoro-5-[(4-oxo-3H-phthalazin-1-yl) methyl]benzoyl]piperidin-4-yl]oxybenzonitrile (10)

A solution of 4-hydroxybenzonitrile (48 mg, 0.40 mmol) and 4-(4-fluoro-3-(4-hydroxypiperidine-1-carbonyl)benzyl) phthalazin-1(2H)-one (2a) (150 mg, 0.39 mmol) in dichloromethane (5 mL) was treated with polymer supported triphenylphosphine (ex-Biotage, 742 mg, 1.37 mmol) and di-tert-butyl azodicarboxylate (300 mg, 1.30 mmol). The reaction mixture was agitated at ambient temperature for 4-5 hours. Mixture was then filtered to remove resin, and filter cake washed through with methanol. Filtrate was evaporated to afford a waxy yellow solid, which was purified by repeated preparative HPLC (Waters XBridge Prep C18 OBD column, 5μ silica, 19 mm diameter, 100 mm length), firstly using decreasingly polar mixtures of water (containing 0.1% TFA) and MeCN as eluents, then using decreasingly polar mixtures of water (containing 1% ammonia) and MeCN as eluents (Waters Sunfire Prep C18 OBD column, 5μ silica, 19 mm diameter, 100 mm length). Fractions containing the desired compound were evaporated to dryness and lyophilised to afford the desired product (17 mg, 8% yield); $^1$H NMR (400.132 MHz, DMSO) δ 1.49-1.69 (2H, m), 1.83-1.91 (1H, m), 1.99-2.06 (1H, m), 3.14-3.22 (1H, m), 3.32-3.51 (2H, m), 3.94-4.04 (1H, m), 4.33 (2H, s), 4.78-4.84 (1H, m), 7.15-7.18 (2H, m), 7.23 (1H, t), 7.36-7.44 (2H, m), 7.75-7.78 (2H, m), 7.80-7.90 (2H, m), 7.97 (1H, d), 8.26 (1H, d), 12.56 (1H, s); m/z (LC-MS, ESI+), RT=2.20 (M+H 483.6).

Example 8

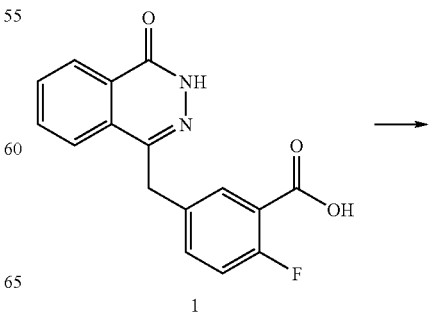

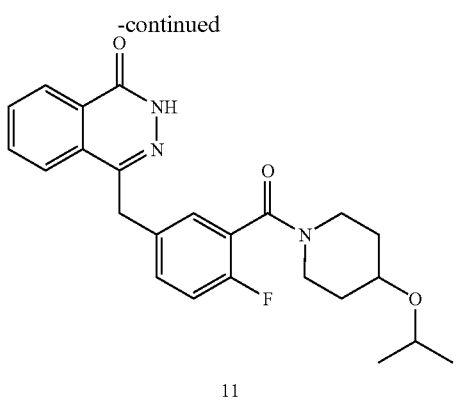

11

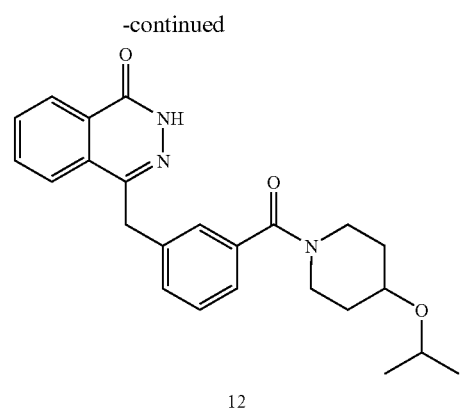

12

4-(4-fluoro-3-(4-isopropoxypiperidine-1-carbonyl)benzyl)phthalazin-1(2H)-one (11)

A solution of 4-isopropoxypiperidine hydrochloride (120 mg, 0.67 mmol) and triethylamine (0.206 mL, 1.48 mmol), in N,N dimethylformamide (2 mL) was added in one portion to a stirred solution of 2-fluoro-5-((4-oxo-3,4-dihydrophthalazin-1-yl)methyl)benzoic acid (1) (200 mg, 0.67 mmol), triethylamine (0.206 mL, 1.48 mmol) and O-Benzotriazol-1-yl-N,N,N',N'-tetra-methyluronium hexafluorophosphate (381 mg, 1.01 mmol) in N,N dimethylformamide (2 mL) at 25° C. The resulting solution was stirred at 25° C. for 4 hours. The crude product was purified by preparative HPLC (Waters XBridge Prep C18 OBD column, 5µ silica, 30 mm diameter, 100 mm length), using decreasingly polar mixtures of water (containing 1% NH3) and MeCN as eluents. Fractions containing the desired compound were evaporated to dryness to afford the desired compound (172 mg, 60.6% yield); $^1$H NMR (399.902 MHz, DMSO) δ 1.06-1.11 (6H, m), 1.21-1.46 (2H, m), 1.61-1.87 (2H, m), 3.04 (1H, t), 3.62 (2H, td), 3.70 (1H, quintet), 3.92-4.01 (1H, m), 4.07 (1H, q), 4.33 (2H, s), 7.19-7.25 (1H, m), 7.32-7.37 (1H, m), 7.38-7.44 (1H, m), 7.81-7.92 (2H, m), 7.96-8.00 (1H, m), 8.26-8.29 (1H, m), 12.58 (1H, s); m/z (LC-MS, ESI+), RT=1.98 (M+H 424.6).

Example 9

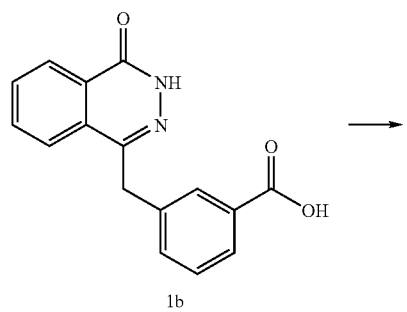

1b

A solution of 4-isopropoxypiperidine hydrochloride (128 mg, 0.71 mmol) and triethylamine (0.219 mL, 1.57 mmol) in N,N dimethylformamide (2 mL) was added in one portion to a stirred solution of 3-((4-oxo-3,4-dihydrophthalazin-1-yl)methyl)benzoic acid (1b) (200 mg, 0.71 mmol), triethylamine (0.219 mL, 1.57 mmol) and O-Benzotriazol-1-yl-N,N,N',N'-tetra-methyluronium hexafluorophosphate (406 mg, 1.07 mmol) in DMF (2 mL) at 25° C. The resulting solution was stirred at 25° C. for 4 hours. The crude product was purified by preparative HPLC (Waters XBridge Prep C18 OBD column, 5µ silica, 30 mm diameter, 100 mm length), using decreasingly polar mixtures of water (containing 1% NH3) and MeCN as eluents. Fractions containing the desired compound were evaporated to dryness to afford the desired compound (172 mg, 59.4% yield); $^1$H NMR (399.902 MHz, DMSO) δ 1.06-1.10 (6H, m), 1.21-1.46 (2H, m), 1.57-1.90 (2H, m), 3.00-3.13 (2H, m), 3.55-3.64 (2H, m), 3.64-3.75 (1H, m), 3.88-4.02 (1H, m), 4.33-4.38 (2H, m), 7.21 (1H, dt), 7.31-7.42 (3H, m), 7.85 (2H, m), 7.96 (1H, m), 8.27 (1H, m), 12.59 (1H, s); m/z (LC-MS, ESI+), RT=1.89 (M+H 406.6).

Example 10

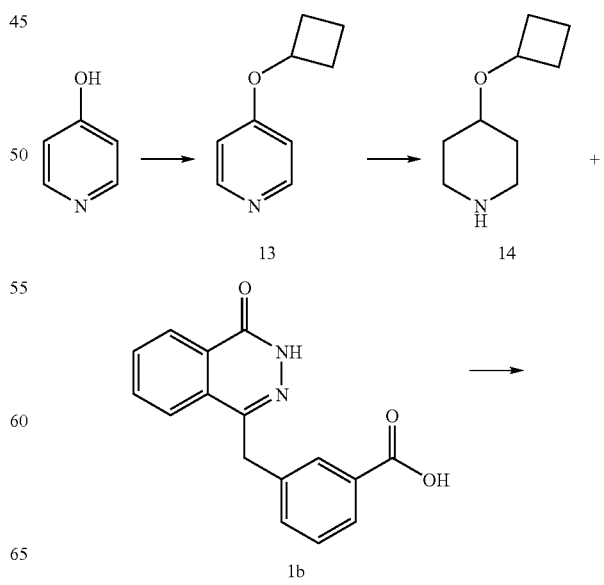

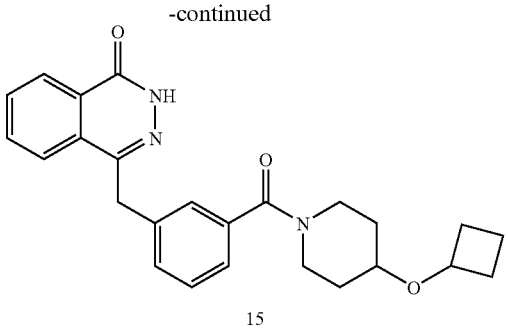

15

(a) 4-cyclobutoxypyridine (13)

Pyridin-4-ol (6.0 g, 63.09 mmol), cyclobutanol (5.00 g, 69.40 mmol) and triphenylphosphine (18.20 g, 69.40 mmol) were added to THF (250 mL) and stirred for 10 minutes. To this was slowly added diisopropylazodicarboxylate (13.49 mL, 69.40 mmol). Once the addition was complete the reaction was stirred at 50° C. for 1 hour. The solvent was evaporated and the crude residue was dissolved in diethyl ether. To this was added a small amount of triphenylphoshine oxide and the reaction was stirred for 30 minutes to afford a solid, this was filtered and discarded. The solvent was evaporated and the pale yellow gum was acidified with 2.0M HCl, extracted with diethyl ether (1×75 mL) and the aqueous was then basified with solid potassium hydroxide. This was then extracted with diethyl ether (3×75 mL), the organic layer was dried over MgSO$_4$, filtered and evaporated to afford yellow gum. This was purified by distillation at 0.60 mBar, collecting fractions that distilled at 80° C. to afford the desired compound as a colourless oil (4.70 g, 49.9%); $^1$H NMR (400.132 MHz, CDCl$_3$) δ 1.78-1.66 (1H, m), 1.95-1.86 (1H, m), 2.24-2.14 (2H, m), 2.51-2.43 (2H, m), 4.69 (1H, quintet), 6.70 (2H, d), 8.40 (2H, d); m/z (LC-MS, ESI+), RT=1.76 (M+H 150).

(b) 4-cyclobutoxypiperidine (14)

4-cyclobutoxypyridine (13) (3.8 g, 25.47 mmol) and rhodium 5% on alumina (0.38 g, 0.05 mmol) in EtOH (50 mL) were stirred under an atmosphere of hydrogen at 5 bar and 25° C. for 16 hours. GCMS analysis indicated no reaction so the mixture was heated to 60° C. for 5 hours but analysis still only indicated trace product formation. Platinum Oxide (0.2 g) catalyst was added and stirred overnight at 60° C., 5 bar, but still no more product formation. The reaction mixture was transferred to a high pressure autoclave and heated overnight at 80° C. and 50 bar no more product formation was observed, thus temperature increased to 100° C. and pressure to 80 bar and left overnight bar but analysis, once more, indicated no more product formation. Thus added 5% ruthenium on Carbon (0.2 g) and heated overnight at 120° C. and 100 bar. Analysis showed no remaining starting material. The reaction was cooled and filtered and solvent evaporated to afford a yellow oil. The crude product was purified by distillation at 0.55 mBar, collecting fractions that distilled at 55° C. to afford the product as a colourless oil, which was used in next step without any further purification.

(c) 4-(3-(4-cyclobutoxypiperidine-1-carbonyl)-4-fluorobenzyl)phthalazin-1(2H)-one (15)

2-fluoro-5-((4-oxo-3,4-dihydrophthalazin-1-yl)methyl) benzoic acid (1b) (0.20 g, 0.67 mmol) and O-benzotriazol-1-yl-N,N,N',N'-tetra-methyluronium hexafluorophosphate (0.381 g, 1.01 mmol) were added to N,N-dimethylformamide (30 mL), and to this was added N-ethyl-N-isopropylpropan-2-amine (0.179 mL, 1.01 mmol) and then 4-cyclobutoxypiperidine (14) (0.104 g, 0.67 mmol). The reaction was stirred for 2 hours before being purified by preparative HPLC (Waters XBridge Prep C18 OBD column, 5µ silica, 21 mm diameter, 100 mm length), using decreasingly polar mixtures of water (containing 1% NH3) and MeCN as eluents. Fractions containing the desired compound were evaporated to dryness to afford the desired compound as a white solid (0.017 g, 5.82%); $^1$H NMR (400.132 MHz, CDCl$_3$) δ 1.56-1.44 (2H, m), 1.72-1.64 (2H, m), 2.00-1.84 (4H, m), 2.23-2.14 (2H, m), 3.14-3.04 (1H, m), 3.48-3.41 (2H, m), 3.58-3.52 (1H, m), 4.00 (1H, quintet), 4.10-4.03 (1H, m), 4.26 (2H, s), 7.01 (1H, t), 7.31-7.24 (2H, m), 7.77-7.70 (3H, m), 8.47-8.44 (1H, m), 9.90 (1H, s); m/z (LC-MS, ESI+), RT=2.15 (M+H 436).

Example 11

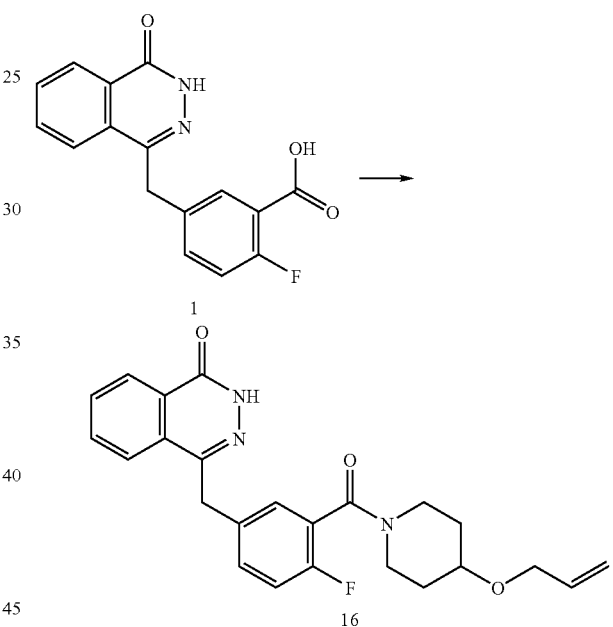

2-fluoro-5-((4-oxo-3,4-dihydrophthalazin-1-yl)methyl) benzoic acid (1) (0.2 g, 0.67 mmol), 4-(allyloxy)piperidine (0.095 g, 0.67 mmol) and O-benzotriazol-1-yl-N,N,N',N'-tetra-methyluronium hexafluorophosphate (0.381 g, 1.01 mmol) were added to N,N-diemthylformamide (30 mL). To this was added N-ethyl-N-isopropylpropan-2-amine (0.179 mL, 1.01 mmol) and the reaction was stirred for 2 hours before being purified by preparative HPLC (Waters XBridge Prep C18 OBD column, 5µ silica, 21 mm diameter, 100 mm length), using decreasingly polar mixtures of water (containing 1% NH3) and MeCN as eluents. Fractions containing the desired compound were evaporated to dryness to afford the desired material as a white solid (0.225 g, 80%); $^1$H NMR (400.132 MHz, DMSO) δ 1.37-1.31 (1H, m), 1.51-1.42 (1H, m), 1.74-1.70 (1H, m), 1.90-1.86 (1H, m), 3.07-3.00 (1H, m), 3.35-3.26 (2H, m), 3.60-3.54 (1H, m), 3.94-3.90 (1H, m), 3.98 (2H, d), 4.33 (2H, s), 5.13 (1H, dq), 5.26 (1H, dq), 5.94-5.85 (1H, m), 7.21 (1H, t), 7.35-7.33 (1H, m), 7.43-7.39 (1H, m), 7.83 (1H, t), 7.89 (1H, t), 7.97 (1H, d), 8.27 (1H, d), 12.58 (1H, s); m/z (LC-MS, ESI+), RT=1.93 (M+H 422).

Example 12

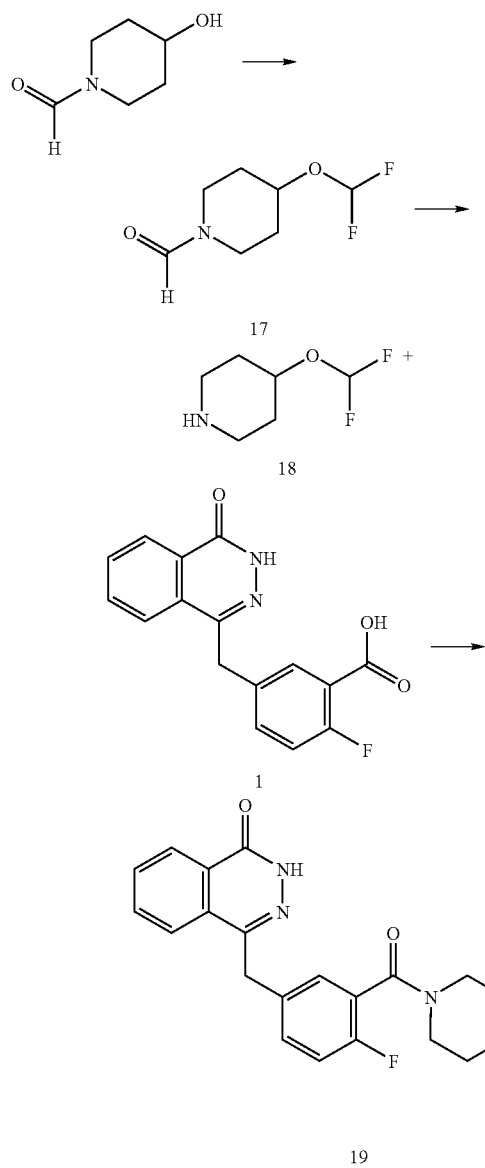

(a) 4-(difluoromethoxy)piperidine-1-carbaldehyde (17)

4-hydroxypiperidine-1-carbaldehyde (10.8 g, 83.62 mmol) was dissolved in tetrahydrofuran (150 mL). To this was added sodium hydride (5.22 g, 108.70 mmol) and the reaction was stirred for 30 minutes. 15-crown-5 (9.21 g, 41.81 mmol) was added and the reaction was stirred for a further 30 minutes before the slow addition of chlorodifluoromethane (8.68 g, 100.34 mmol), after the addition the reaction was stirred for 30 minutes. The reaction mixture was quenched with saturated brine (75 mL), extracted with diethyl ether (3×100 mL), the organic layer was dried over MgSO4, filtered and evaporated to afford a yellow liquid. The crude product was purified by distillation at 0.8 mBar, collecting fractions that distilled at 80° C. to afford the desired material as a colourless liquid (2.70 g, 18.02%); $^1$H NMR (400.132 MHz, CDCl$_3$) δ 1.93-1.70 (4H, m), 3.32-3.26 (1H, m), 3.60-3.47 (2H, m), 3.74-3.67 (1H, m), 4.50 (1H, septet), 6.28 (1H, t), 8.03 (1H, s).

(b) 4-(difluoromethoxy)piperidine (18)

4-(difluoromethoxy)piperidine-1-carbaldehyde (17) (2.7 g, 15.07 mmol) and potassium hydroxide (2.96 g, 52.74 mmol) were dissolved in water (40 mL) and stirred vigorously for 3 hours. The reaction was extracted with diethyl ether (3×75 mL), the organic layer was dried over MgSO4, filtered and evaporated to afford an orange liquid. The crude product was purified by distillation at 0.70 mBar, collecting fractions that distilled at 25° C. to afford the desired material as a colourless oil (1.100 g, 48.3%); $^1$H NMR (400.132 MHz, CDCl$_3$) δ 1.50 (1H, s), 1.66-1.57 (2H, m), 1.95-1.89 (2H, m), 2.70-2.64 (2H, m), 3.09 (2H, dt), 4.25-4.19 (1H, m), 6.24 (1H, t).

(c) 4-(3-(4-(difluoromethoxy)piperidine-1-carbonyl)-4-fluorobenzyl)phthalazin-1(2H)-one (19)

2-fluoro-5-((4-oxo-3,4-dihydrophthalazin-1-yl)methyl) benzoic acid (1) (0.2 g, 0.67 mmol), 4-(difluoromethoxy) piperidine (18) (0.101 g, 0.67 mmol) and O-benzotriazol-1-yl-N,N,N',N'-tetra-methyluronium hexafluorophosphate (0.381 g, 1.01 mmol) were added to N,N-dimethylformamide (30 mL). To this was added N-ethyl-N-isopropylpropan-2-amine (0.179 mL, 1.01 mmol) and the reaction was stirred for 2 hours before being purified by preparative HPLC (Waters XBridge Prep C18 OBD column, 5µ silica, 21 mm diameter, 100 mm length), using decreasingly polar mixtures of water (containing 1% NH3) and MeCN as eluents. Fractions containing the desired compound were evaporated to dryness to the desired compound as a white solid (0.266 g, 92%); $^1$H NMR (400.132 MHz, DMSO) δ 1.53-1.45 (1H, m), 1.65-1.56 (1H, m), 1.83-1.74 (1H, m), 1.98-1.92 (1H, m), 3.15-3.09 (1H, m), 3.40-3.26 (2H, m), 4.01-3.91 (1H, m), 4.33 (2H, s), 4.41-4.35 (1H, m), 6.75 (1H, t), 7.22 (1H, t), 7.38-7.36 (1H, m), 7.44-7.40 (1H, m), 7.83 (1H, t), 7.88 (1H, t), 7.97 (1H, d), 8.27 (1H, d), 12.58 (1H, s); m/z (LC-MS, ESI+), RT=1.98 (M+H 432).

Example 13

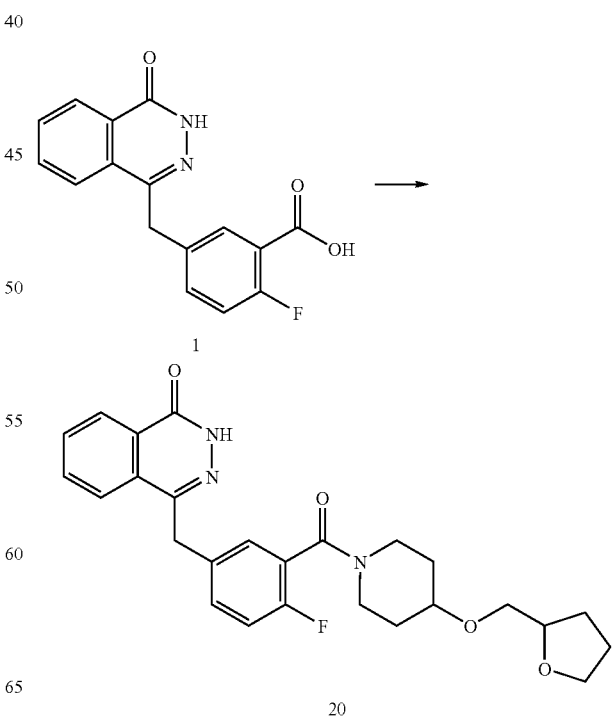

4-[[4-fluoro-3-[4-(oxolan-2-ylmethoxy)piperidine-1-carbonyl]phenyl]methyl]-2H-phthalazin-1-one (20)

O-Benzotriazol-1-yl-N,N,N',N'-tetra-methyluronium hexafluorophosphate (509 mg, 1.34 mmol) was added, in one portion, to 2-fluoro-5-((4-oxo-3,4-dihydrophthalazin-1-yl)methyl)benzoic acid (200 mg, 0.67 mmol) and triethylamine (0.206 mL, 1.48 mmol) in N,N-dimethylformamide (2.5 mL), at 25° C. under an air atmosphere. The resulting solution was stirred at 25° C. for 10 minutes. A solution of 4-((tetrahydrofuran-2-yl)methoxy)piperidine hydrochloride (164 mg, 0.74 mmol) and triethylamine (0.206 mL, 1.48 mmol) in N,N-dimethylformamide (1 mL) was then added dropwise and the resulting solution stirred at 25° C. for 10 hours. The crude mixture was purified by preparative HPLC (Waters XBridge Prep C18 OBD column, 5μ silica, 30 mm diameter, 100 mm length), using decreasingly polar mixtures of water (containing 1% NH3) and MeCN as eluents. Fractions containing the desired compound were evaporated to dryness to afford the desired compound as a solid (238 mg, 76%); $^1$H NMR (400.132 MHz, DMSO) δ 1.01 (2H, dt), 1.31-1.37 (1H, m), 1.43-1.50 (1H, m), 1.51-1.58 (1H, m), 1.68-1.73 (1H, m), 1.74-1.93 (4H, m), 3.00-3.07 (1H, m), 3.17-3.18 (1H, m), 3.39 (2H, d), 3.53-3.59 (1H, m), 3.70-3.75 (1H, m), 3.90 (2H, ddd), 4.33 (2H, s), 7.21 (1H, t), 7.33-7.35 (1H, m), 7.39-7.43 (1H, m), 7.83 (1H, td), 7.89 (1H, td), 7.97 (1H, d), 8.27 (1H, dd), 12.56 (1H, s) m/z (LC-MS, ESI+), RT=1.71 (M+H 466.5).

Example 14

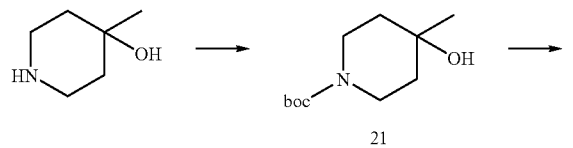

21

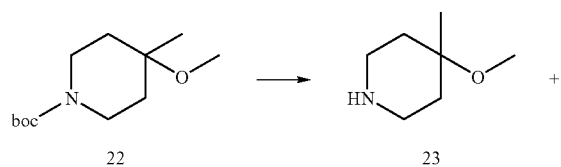

22    23

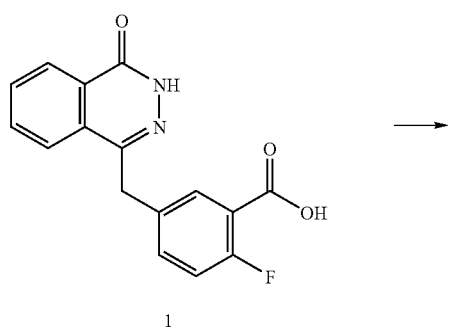

1

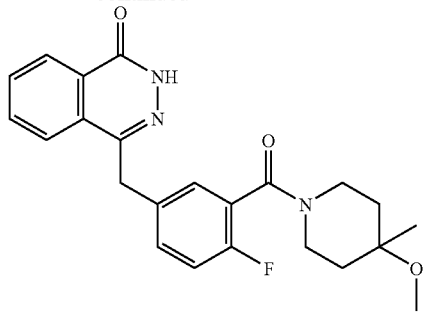

24

(a) tert-butyl 4-hydroxy-4-methylpiperidine-1-carboxylate (21)

Sodium hydride (60% dispersion on mineral oil) (158 mg, 3.96 mmol) was added portionwise to 4-methylpiperidin-4-ol hydrochloride (500 mg, 3.30 mmol) and triethylamine (0.506 mL, 3.63 mmol) in N,N-dimethylformamide (8 mL) at 25° C. over a period of 1 minute under an air atmosphere. The resulting suspension was stirred at 25° C. for 20 minutes. A solution of Di-tert-butyl dicarbonate (1.668 mL, 7.25 mmol) in DMF (2 mL) was then added in one portion and the resulting suspension was stirred at 25° C. for 18 hours. The reaction mixture was diluted with water (125 mL) and saturated brine (25 mL), then washed sequentially with dichloromethane (3×50 mL). The organic layer was dried over MgSO$_4$, filtered and evaporated to afford crude desired product, which was used without further purification; $^1$H NMR (400.132 MHz, CDCl3) δ 1.46 (9H, s), 1.51-1.56 (7H, m), 3.21-3.28 (2H, m), 3.65-3.73 (2H, m)

(b) tert-butyl 4-methoxy-4-methylpiperidine-1-carboxylate (22)

Sodium hydride (60% dispersion on mineral oil) (198 mg, 4.95 mmol) was added portionwise to tert-butyl 4-hydroxy-4-methylpiperidine-1-carboxylate (21) (710 mg, 3.30 mmol) in N,N-dimethylformamide (12 mL) at ambient temperature over a period of 30 seconds under an air atmosphere. The resulting suspension was stirred at 25° C. for 20 minutes. Methyl iodide (0.411 mL, 6.60 mmol) was then and the resulting suspension was stirred at 25° C. for 18 hours. The reaction mixture was diluted with water (150 mL) and saturated brine (25 mL), then washed sequentially with dichloromethane (3×100 mL). The organic layer was dried over MgSO$_4$, filtered and evaporated to afford crude product, which was used directly in the next stage.

(c) 4-methoxy-4-methylpiperidine (23)

Trifluoroacetic acid (2.54 mL, 32.97 mmol) was added dropwise to tert-butyl 4-methoxy-4-methylpiperidine-1-carboxylate (22) (756 mg, 3.30 mmol) in dichloromethane (10 mL) at 25° C. under an air atmosphere. The resulting solution was stirred at 25° C. for 15 hours. The crude product was purified by ion exchange chromatography, using an SCX column. The desired product was eluted from the column using 7M NH$_3$/MeOH and pure fractions were evaporated to dryness to afford the desired compound as an oil (235 mg, 55.2%); $^1$H NMR (400.132 MHz, CDCl3) δ 1.15 (3H, s), 1.41-1.49 (2H, m), 1.68-1.74 (2H, m), 2.76 (2H, dt), 2.93 (2H, dt), 3.19 (3H, s), 3.49 (1H, s).

(d) 4-[[4-fluoro-3-(4-methoxy-4-methylpiperidine-1-carbonyl)phenyl]methyl]-2H-phthalazin-1-one (24)

O-(1H-Benzotriazol-1-yl)-N,N,N',N'-tetramethyluronium hexafluorophosphate (0.597 g, 1.57 mmol) was added in one portion to 2-fluoro-5-((4-oxo-3,4-dihydrophthalazin-1-yl)methyl)benzoic acid (1) (0.188 g, 0.63 mmol) and triethylamine (0.193 mL, 1.39 mmol) in N,N-dimethylformamide (2 mL) at ambient temperature under an air atmosphere. The resulting solution was stirred at 25° C. for 15 minutes. A solution of 4-methoxy-4-methylpiperidine (23) (89.5 mg, 0.69 mmol) in N,N-dimethylformamide (1 mL) was added dropwise and the resulting solution was stirred at 25° C. for 4 hours. The crude mixture was purified by preparative HPLC (Waters XBridge Prep C18 OBD column, 5μ silica, 21 mm diameter, 100 mm length), using decreasingly polar mixtures of water (containing 1% $NH_3$) and MeCN as eluents. Fractions containing the desired compound were evaporated to dryness to the desired compound as a solid (0.110 g, 42.7%); $^1$H NMR (400.132 MHz, DMSO) δ 1.11 (3H, s), 1.25-1.34 (1H, m), 1.42 (1H, td), 1.56 (1H, d), 1.75 (1H, dd), 3.10-3.18 (4H, m), 4.09 (3H, q), 4.32 (2H, s), 7.21 (1H, t), 7.31 (1H, dd), 7.39-7.43 (1H, m), 7.83 (1H, td), 7.88 (1H, td), 7.96 (1H, dd), 8.27 (1H, dd), 12.57 (1H, s); m/z (LC-MS, ESI+), RT=1.79 (M+H 409).

Example 15

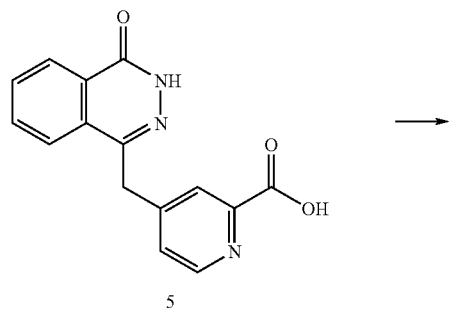

5

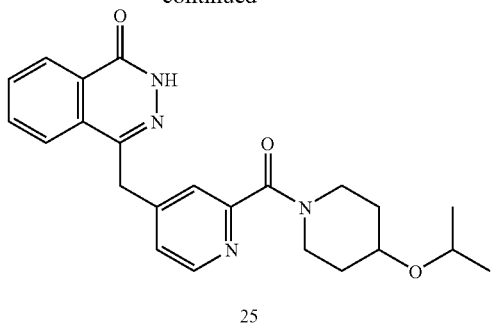

25

4-[[2-(4-propan-2-yloxypiperidine-1-carbonyl)pyridin-4-yl]methyl]-2H-phthalazin-1-one (25)

A solution of 4-isopropoxypiperidine hydrochloride (192 mg, 1.07 mmol) and triethylamine (0.327 mL, 2.35 mmol) in N,N-dimethylformamide (3 mL) was added in one portion to a stirred solution of 4-((4-oxo-3,4-dihydrophthalazin-1-yl)methyl)picolinic acid (5)(300 mg, 1.07 mmol), triethylamine (0.327 mL, 2.35 mmol) and O-benzotriazol-1-yl-N,N,N',N'-tetra-methyluronium hexafluorophosphate (607 mg, 1.60 mmol) in DMF (3 mL) at 25° C. The resulting solution was stirred at 25° C. for 4 hours. The crude mixture was purified by preparative HPLC (Waters XBridge Prep C18 OBD column, 5μ silica, 30 mm diameter, 100 mm length), using decreasingly polar mixtures of water (containing 1% $NH_3$) and MeCN as eluents. Fractions containing the desired compound were evaporated to dryness and lyophilised to afford the desired compound as a solid (257 mg, 59.3%); $^1$H NMR (400.132 MHz, DMSO) δ 1.08 (6H, dd), 1.28-1.46 (2H, m), 1.65-1.74 (1H, m), 1.78-1.87 (1H, m), 3.12 (1H, ddd), 3.23-3.31 (1H, m), 3.42-3.51 (1H, m), 3.62 (1H, m), 3.69 (1H, quintet), 3.91-4.00 (1H, m), 4.40 (2H, s), 7.39 (1H, dd), 7.49 (1H, d), 7.83-7.97 (3H, m), 8.28 (1H, dd), 8.46-8.49 (1H, m), 12.60 (1H, s); m/z (LC-MS, ESI+), RT=1.54 (M+H 407).

Example 16

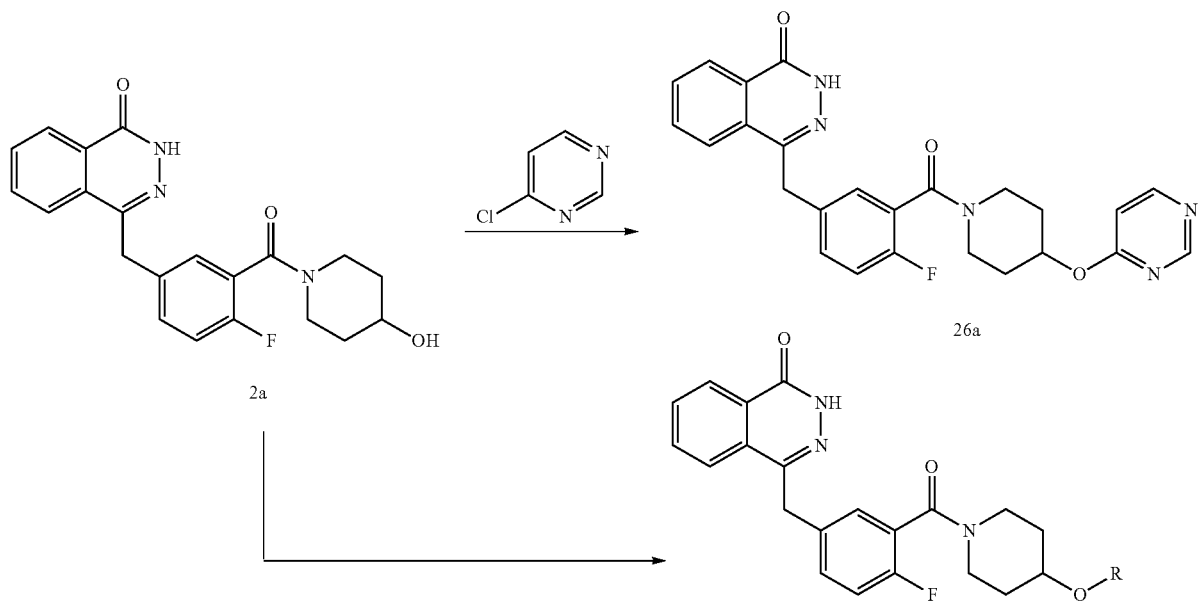

(a) 4-(4-fluoro-3-(4-(pyrimidin-4-yloxy)piperidine-1-carbonyl)benzyl)phthalazin-1(2H)-one (26a)

Sodium tert-butoxide (125 mg, 1.30 mmol) was added in one portion to 4-(4-fluoro-3-(4-hydroxypiperidine-1-carbonyl)benzyl)phthalazin-1(2H)-one (2a) (150 mg, 0.39 mmol) in tetrahydrofuran (2 ml) at 20° C. The resulting suspension was stirred at 20° C. for 10 minutes. 4-chloropyrimidine hydrochloride (49.5 mg, 0.43 mmol) was added in one portion and the resulting mixture was stirred at 50° C. for 2 hours. Sodium tert-butoxide (41 mg, 0.43 mmol) was added in one portion followed by 4-chloropyrimidine hydrochloride (65 mg, 0.43 mmol) and the mixture heated at 50° C. for 2 hours and then stirred at ambient temperature overnight. The crude product was purified by ion exchange chromatography using an SCX column. The desired product was eluted from the column using 2M $NH_3$/MeOH and pure fractions were evaporated to dryness to afford crude product. This was purified by preparative HPLC (Sunfire column, 5μ silica, 19 mm diameter, 100 mm length), using decreasingly polar mixtures of water (containing 0.1% TFA) and MeCN as eluents. Fractions containing the desired compound were evaporated to dryness to afford the desired compound as a solid (91 mg, 50.4%); $^1$H NMR (400.132 MHz, DMSO) δ 1.53-1.61 (1H, m), 1.66-1.73 (1H, m), 1.88-1.94 (1H, m), 2.02-2.09 (1H, m), 3.14-3.25 (1H, m), 3.32-3.48 (2H, m), 3.98-4.07 (1H, m), 4.34 (2H, s), 5.33-5.39 (1H, m), 6.95 (1H, d), 7.21-7.25 (1H, m), 7.37-7.44 (2H, m), 7.80-7.84 (1H, m), 7.87-7.90 (1H, m), 7.97 (1H, d), 8.26 (1H, d), 8.54 (1H, d), 8.79 (1H, s), 12.56 (1H, s); m/z (LC-MS, ESI+), RT=1.69 (M+H 460.6).

(b) Multiple Parallel Synthesis (26b-m)

4-(4-fluoro-3-(4-hydroxypiperidine-1-carbonyl)benzyl)phthalazin-1(2H)-one (2a) (150 mg, 0.39 mmol) was reacted with the appropriate chloroheterocycle according to the procedure described above to afford the desired compounds

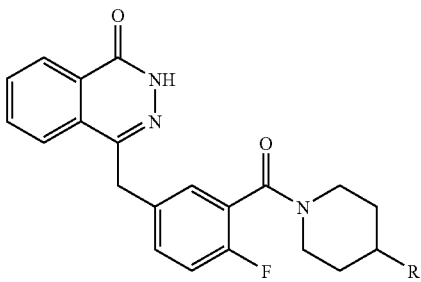

| R | | Purity | RT (min) | M + H |
|---|---|---|---|---|
| 26b | *O-pyridazine-methyl | 96.9% | 1.76 | 474.5 |
| 26c | *O-pyridine-CN | 97.5% | 2.10 | 484.5 |
| 26d | *O-pyrazine | 90.8% | 1.82 | 460.6 |
| 26e | *O-pyrimidine | 97.3% | 1.71 | 460.6 |
| 26f | *O-pyridine-CN | 100% | 2.16 | 484.0 |
| 26g | *O-pyridine-C(O)NH₂ | 97.2% | 1.65 | 501.9 |
| 26h | *O-methylpyrazine | 100% | 1.92 | 474.0 |
| 26i | *O-dimethylpyrazine | 100% | 2.02 | 488.0 |
| 26j | *O-dimethylpyrazine | 100% | 2.10 | 488.0 |
| 26k | *O-methoxypyridine | 100% | 2.11 | 489.0 |
| 26l | *O-cyanopyrazine | 100% | 2.01 | 485.6 |

-continued

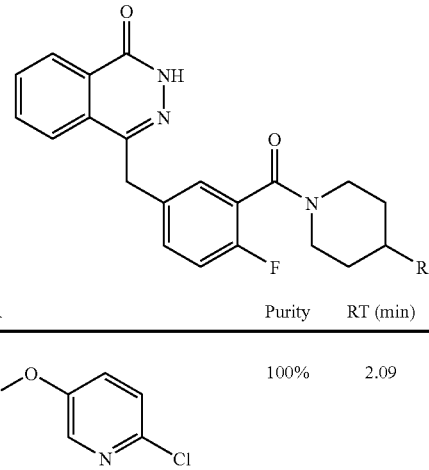

| R | | Purity | RT (min) | M + H |
|---|---|---|---|---|
| 26m | *—O—(5-pyridyl-2-Cl) | 100% | 2.09 | 493.2 |

26b:—¹H NMR (400.132 MHz, DMSO) δ 1.55-1.64 (1H, m), 1.68-1.78 (1H, m), 1.91-1.99 (1H, m), 2.07-2.13 (1H, m), 2.55 (3H, s), 3.18-3.26 (1H, m), 3.34-3.42 (1H, m), 3.45-3.53 (1H, m), 3.97-4.06 (1H, m), 4.34 (2H, s), 5.36-5.42 (1H, m), 7.21-7.28 (2H, m), 7.36-7.39 (1H, m), 7.40-7.44 (1H, m), 7.65 (1H, d), 7.80-7.83 (1H, m), 7.86-7.90 (1H, m), 7.98 (1H, d), 8.26 (1H, d), 12.56 (1H, s)

26c:—¹H NMR (400.132 MHz, DMSO) δ 1.51-1.62 (1H, m), 1.64-1.73 (1H, m), 1.87-1.93 (1H, m), 2.02-2.09 (1H, m), 3.17-3.24 (1H, m), 3.32-3.49 (2H, m), 3.99-4.06 (1H, m), 4.34 (2H, s), 5.31-5.37 (1H, m), 7.00 (1H, d), 7.20-7.25 (1H, m), 7.36-7.38 (1H, m), 7.40-7.44 (1H, m), 7.80-7.84 (1H, m), 7.86-7.90 (1H, m), 7.97 (1H, d), 8.16 (1H, d), 8.26 (1H, d), 8.69 (1H, s), 12.56 (1H, s)

26d:—¹H NMR (400.132 MHz, CDCl3) δ 1.79-2.16 (4H, m), 3.29-3.37 (1H, m), 3.52-3.63 (1H, m), 3.74-3.87 (1H, m), 3.97-4.07 (1H, m), 4.33 (2H, s), 5.32-5.39 (1H, m), 7.04-7.08 (1H, m), 7.29-7.33 (1H, m), 7.35-7.37 (1H, m), 7.79-7.87 (3H, m), 8.14 (1H, d), 8.18 (1H, s), 8.24 (1H, s), 8.48 (1H, d), 11.30 (1H, s)

26e:—¹H NMR (400.132 MHz, DMSO) δ 1.55-1.74 (2H, m), 1.89-1.94 (1H, m), 2.04-2.10 (1H, m), 3.18-3.24 (1H, m), 3.34-3.48 (2H, m), 3.99-4.06 (1H, m), 4.34 (2H, s), 5.19-5.25 (1H, m), 7.12-7.15 (1H, m), 7.21-7.25 (1H, m), 7.39-7.43 (2H, m), 7.80-7.83 (1H, m), 7.86-7.90 (1H, m), 7.98 (1H, d), 8.26 (1H, d), 8.61 (2H, d), 12.57 (1H, s)

26f:—¹H NMR (400.132 MHz, DMSO) δ 1.51-1.59 (1H, m), 1.64-1.73 (1H, m), 1.86-1.93 (1H, m), 2.02-2.08 (1H, m), 3.17-3.22 (1H, m), 3.34-3.47 (2H, m), 3.98-4.07 (1H, m), 4.34 (2H, s), 5.26-5.32 (1H, m), 7.21-7.25 (1H, m), 7.36-7.44 (4H, m), 7.80-7.84 (1H, m), 7.86-7.90 (1H, m), 7.97 (1H, d), 8.25 (1H, d), 8.40 (1H, d), 12.57 (1H, s)

26g:—¹H NMR (400.132 MHz, DMSO) δ 1.51-1.60 (1H, m), 1.64-1.72 (1H, m), 1.87-1.93 (1H, m), 2.02-2.09 (1H, m), 3.19-3.24 (1H, m), 3.34-3.49 (2H, m), 3.99-4.07 (1H, m), 4.34 (2H, s), 5.26-5.31 (1H, m), 7.19 (1H, s), 7.21-7.25 (1H, m), 7.34-7.44 (3H, m), 7.64 (1H, s), 7.80-7.83 (1H, m), 7.87-7.90 (1H, m), 7.98 (1H, d), 8.13 (1H, s), 8.25-8.27 (2H, m), 12.56 (1H, s)

26h:—¹H NMR (400.132 MHz, DMSO) δ 1.57-1.63 (1H, m), 1.71-1.77 (1H, m), 1.83-1.90 (1H, m), 2.00-2.06 (1H, m), 2.40 (3H, s), 3.23-3.28 (1H, m), 3.34-3.41 (1H, m), 3.59-3.64 (1H, m), 3.85-3.91 (1H, m), 4.34 (2H, s), 5.27-5.31 (1H, m), 7.21-7.25 (1H, m), 7.36-7.38 (1H, m), 7.41-7.44 (1H, m), 7.79-7.83 (1H, m), 7.86-7.90 (1H, m), 7.96-8.01 (2H, m), 8.05 (1H, d), 8.25 (1H, d), 12.56 (1H, s)

26i:—¹H NMR (400.132 MHz, CDCl3) δ 1.61-1.67 (1H, m), 1.72-1.80 (1H, m), 1.88-1.95 (1H, m), 2.03-2.10 (1H, m), 2.42 (3H, s), 2.44 (3H, s), 3.25-3.32 (1H, m), 3.47-3.55 (1H, m), 3.76-3.99 (2H, m), 4.29 (2H, s), 5.26-5.31 (1H, m), 7.01-7.05 (1H, m), 7.27-7.31 (1H, m), 7.33-7.35 (1H, m), 7.71-7.79 (4H, m), 8.46 (1H, d), 10.45 (1H, s)

26j:—¹H NMR (400.132 MHz, DMSO) δ 1.55-1.63 (1H, m), 1.69-1.77 (1H, m), 1.81-1.89 (1H, m), 1.97-2.05 (1H, m), 2.35 (6H, s), 3.20-3.25 (1H, m), 3.34-3.39 (1H, m), 3.60-3.69 (1H, m), 3.80-3.88 (1H, m), 4.34 (2H, s), 5.27-5.32 (1H, m), 7.21-7.25 (1H, m), 7.37 (1H, d), 7.41-7.45 (1H, m), 7.79-7.83 (1H, m), 7.87-7.90 (1H, m), 7.92 (1H, s), 7.97 (1H, d), 8.25 (1H, d), 12.56 (1H, s)

26k:—¹H NMR (400.132 MHz, DMSO) δ 1.46-1.56 (1H, m), 1.60-1.68 (1H, m), 1.82-1.91 (1H, m), 1.98-2.06 (1H, m), 3.13-3.22 (1H, m), 3.32-3.45 (2H, m), 3.80 (3H, s), 3.99-4.07 (1H, m), 4.34 (2H, s), 5.22-5.26 (1H, m), 6.33 (1H, s), 6.57-6.59 (1H, m), 7.20-7.24 (1H, m), 7.36-7.44 (2H, m), 7.80-7.84 (1H, m), 7.86-7.91 (1H, m), 7.94-7.99 (2H, m), 8.26 (1H, d), 12.56 (1H, s)

26l:—¹H NMR (400.132 MHz, DMSO) δ 1.66-1.72 (1H, m), 1.77-1.83 (1H, m), 1.89-1.96 (1H, m), 2.05-2.12 (1H, m), 3.21-3.42 (2H, m), 3.55-3.65 (1H, m), 3.88-3.97 (1H, m), 4.34 (2H, s), 5.40-5.44 (1H, m), 7.21-7.25 (1H, m), 7.40-7.43 (2H, m), 7.80-7.84 (1H, m), 7.87-7.91 (1H, m), 7.99 (1H, d), 8.26 (1H, d), 8.44 (1H, d), 8.58 (1H, d), 12.56 (1H, s)

26m:—¹H NMR (400.132 MHz, DMSO) δ 1.48-1.55 (1H, m), 1.60-1.66 (1H, m), 1.81-1.88 (1H, m), 1.98-2.03 (1H, m), 3.11-3.20 (1H, m), 3.33-3.48 (2H, m), 3.93-4.02 (1H, m), 4.33 (2H, s), 4.70-4.76 (1H, m), 7.20-7.25 (1H, m), 7.36-7.45 (3H, m), 7.54-7.57 (1H, m), 7.80-7.84 (1H, m), 7.87-7.90 (1H, m), 7.97 (1H, d), 8.16 (1H, s), 8.26 (1H, d), 12.57 (1H, s)

Example 17

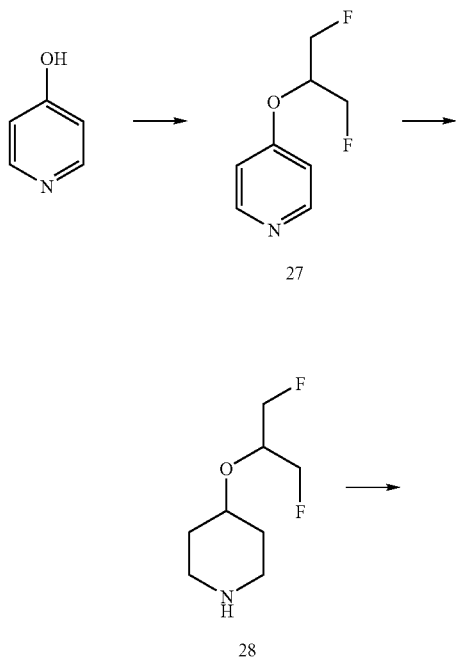

-continued

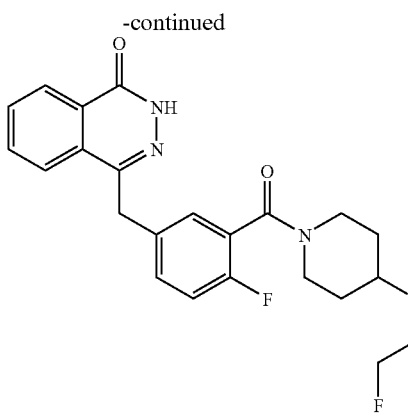

29

(a) 4-(1,3-difluoropropan-2-yloxy)pyridine (27)

Di-tert-butyl azodicarboxylate (719 mg, 3.12 mmol) was added in one portion to pyridin-4-ol (YY) (297 mg, 3.12 mmol), 1,3-difluoropropan-2-ol (100 mg, 1.04 mmol) and Polymer supported triphenylphosphine (1.89 mmol/g; 1016 mg, 3.12 mmol) in dichloromethane (10 mL) at 20° C. under air. The resulting suspension was stirred at 20° C. for 4 hours. The mixture was filtered and the solvent evaporated to a yellow oil. The reaction mixture was diluted with dichloromethane (25 mL), and washed sequentially with 2M NaOH (2×10 mL) and saturated brine (10 mL). The organic layer was dried over MgSO4, filtered and evaporated to afford crude product. This was re-dissolved in dichloromethane (25 mL), and washed with 2M HCl (10 mL). The aqueous layer was basified with 2M NaOH and extracted with dichloromethane (×3). The combined organic layers were dried over $MgSO_4$, filtered and evaporated to afford the desired compound as a viscous oil (90 mg, 50%); $^1$H NMR (400.132 MHz, $CDCl_3$) δ 4.60-4.67 (2H, m), 4.71-4.76 (2H, m), 4.78-4.90 (1H, m), 6.92 (2H, d), 8.48 (2H, d); m/z (LC-MS, ESI+), RT=1.53 (M+H 174).

(b) 4-(1,3-difluoropropan-2-yloxy)piperidine (28)

4-(1,3-difluoropropan-2-yloxy)pyridine (27) (0.098 mg, 0.57 μmol) and 5% rhodium on alumina (0.02 g, 2.56 μmol) in MeOH (50 mL) were stirred under an atmosphere of hydrogen at 5 bar and 25° C. for 16 hours. The catalyst was filtered and washed with MeOH and the solvent evaporated to afford the desired compound as a gum (0.082 g, 81%); $^1$H NMR (400.132 MHz, $CDCl_3$) δ 1.43-1.48 (1H, m), 1.60-1.71 (1H, m), 1.82-2.15 (3H, m), 2.42 (1H, s), 2.84-2.92 (1H, m), 3.09-3.14 (1H, m), 3.25-3.30 (1H, m), 3.82-3.95 (1H, m), 4.35-4.44 (2H, m), 4.47-4.56 (2H, m).

(c) 4-(3-(4-(1,3-difluoropropan-2-yloxy)piperidine-1-carbonyl)-4-fluorobenzyl)phthalazin-1(2H)-one (29)

O-Benzotriazol-1-yl-N,N,N',N'-tetra-methyluronium hexafluorophosphate (0.227 g, 0.60 mmol) was added in one portion to 2-fluoro-5-((4-oxo-3,4-dihydrophthalazin-1-yl)methyl)benzoic acid (1) (0.137 g, 0.46 mmol), 4-(1,3-difluoropropan-2-yloxy)piperidine (28) (0.082 g, 0.46 mmol) and triethylamine (0.194 mL, 1.38 mmol) in N,N-dimethylformamide (3 mL) at 20° C. under air. The resulting solution was stirred at 20° C. for 24 hours. The crude mixture was purified by preparative HPLC (Waters XBridge Prep C18 OBD column, 5μ silica, 19 mm diameter, 100 mm length), using decreasingly polar mixtures of water (containing 0.1% NH3) and MeCN as eluents. Fractions containing the desired compound were evaporated to dryness to afford the desired compound as a colourless gum (34 mg, 15.90%); $^1$H NMR (400.132 MHz, DMSO) δ 1.10-1.19 (1H, m), 1.21-1.30 (1H, m), 1.46-1.55 (2H, m), 1.62-1.70 (2H, m), 2.78-2.86 (1H, m), 3.54-3.60 (1H, m), 3.69-3.79 (2H, m), 4.11 (2H, s), 4.15-4.20 (1H, m), 4.22-4.32 (2H, m), 4.34-4.39 (1H, m), 6.97-7.02 (1H, m), 7.13-7.20 (2H, m), 7.59-7.69 (2H, m), 7.76 (1H, d), 8.05 (1H, d), 12.34 (1H, s); m/z (LC-MS, ESI+), RT=1.99 (M+H 460).

Example 18

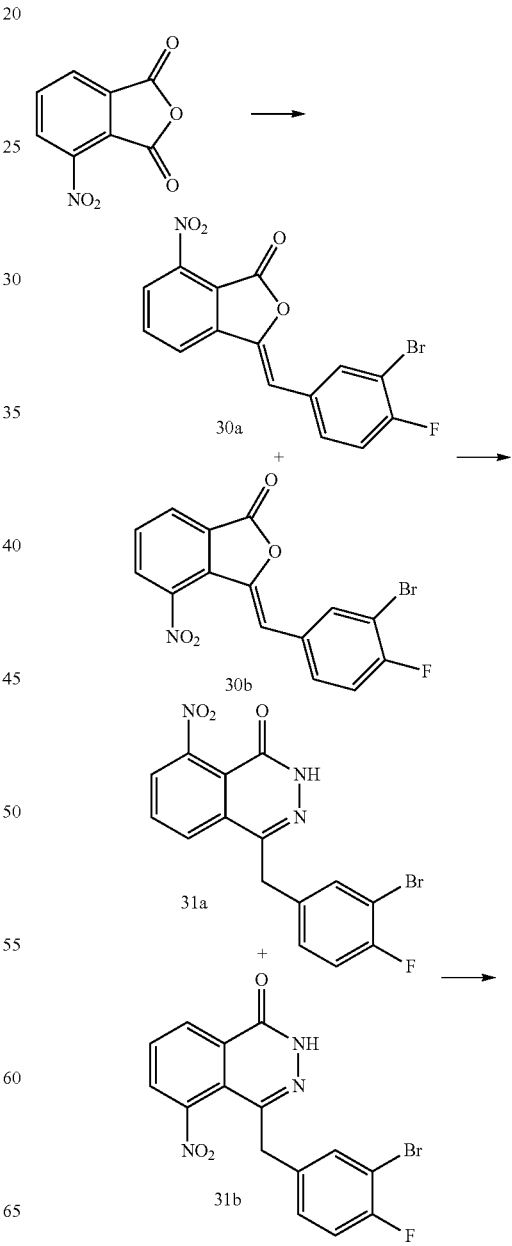

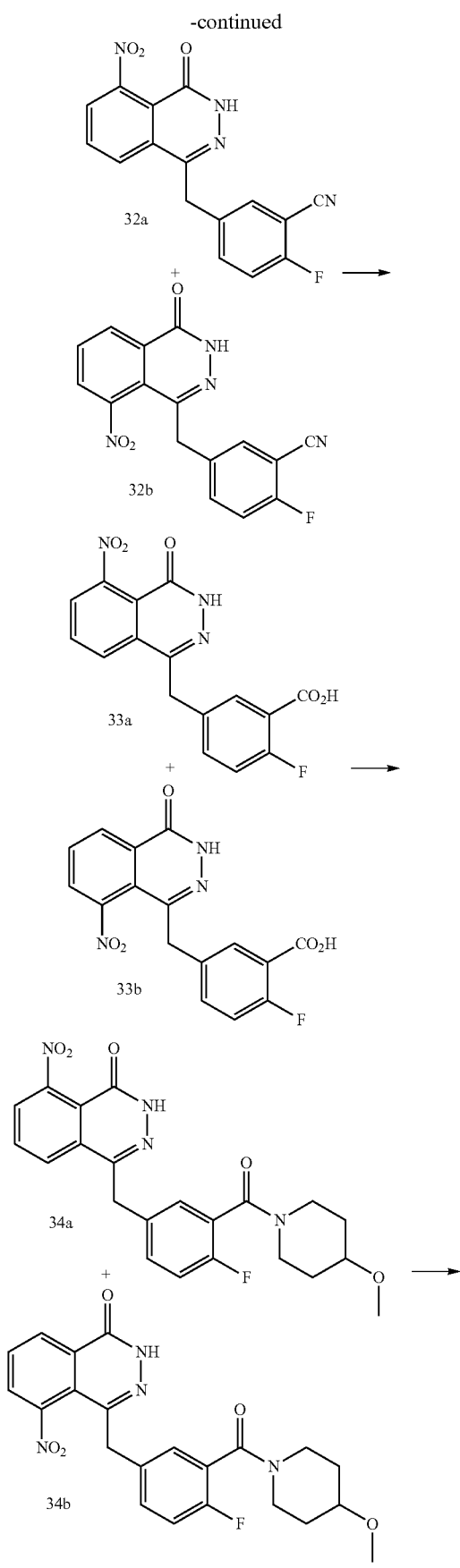

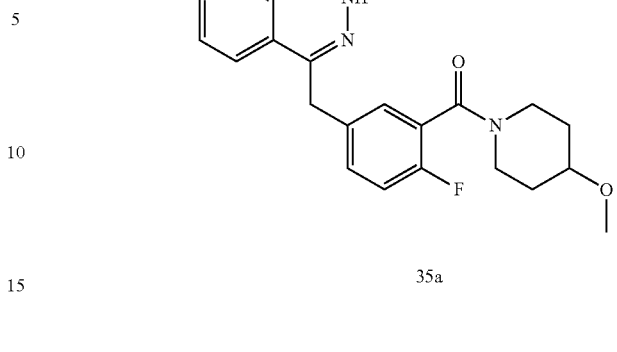

(a) (Z)-3-(3-bromo-4-fluorobenzylidene)-7-nitroisobenzofuran-1(3H)-one (30a) & (Z)-3-(3-bromo-4-fluorobenzylidene)-4-nitroisobenzofuran-1(3H)-one (30b)

Sodium acetate (0.018 g, 0.21 mmol) was added to 4-nitroisobenzofuran-1,3-dione (1.409 g, 7.30 mmol) and 2-(3-bromo-4-fluorophenyl)acetic acid (1 g, 4.29 mmol) under air. The resulting mixture was stirred at 240° C. for 30 minutes. The cooled mixture was triturated with ethanol, filtered and dried to afford a mixture of the desired compounds as a yellow solid (0.111 g, 3.55%); m/z (LC-MS, ESI+), RT=2.92 (78.7%) & 3.02 (21.3%). This was taken onto the next stage without further purification.

The ethanol liquors from the filtration were evaporated to a dark brown residual gum, which was purified by chromatography on silica eluting with 0-100% EtOAc/isohexane to afford (Z)-3-(3-bromo-4-fluorobenzylidene)-4-nitroisobenzofuran-1(3H)-one (JME3a') (45 mg, 2.9%); $^1$H NMR (400.132 MHz, DMSO) δ 7.16 (1H, s), 7.51-7.56 (1H, m), 7.84-7.89 (1H, m), 8.10-8.14 (2H, m), 8.21 (1H, d), 8.40 (1H, d); m/z (LC-MS, ESI+), RT=2.97 (M+H not found); and (Z)-3-(3-bromo-4-fluorobenzylidene)-7-nitroisobenzofuran-1(3H)-one (JME3a) (4 mg, 0.3%); $^1$H NMR (400.132 MHz, DMSO) δ 7.12 (1H, s), 7.50-7.54 (1H, m), 7.90-7.95 (2H, m), 8.21-8.23 (1H, m), 8.37 (1H, d), 8.53 (1H, d); m/z (LC-MS, ESI+), RT=3.07 (M+H not found).

(b) 4-(3-bromo-4-fluorobenzyl)-5-nitrophthalazin-1(2H)-one compound (31b) and 4-(3-bromo-4-fluorobenzyl)-8-nitrophthalazin-1(2H)-one (31a)

Hydrazine hydrate (0.215 mL, 4.43 mmol) was added to a mixture of (Z)-3-(3-bromo-4-fluorobenzylidene)-4-nitroisobenzofuran-1(3H)-one (30b) with (Z)-3-(3-bromo-4-fluorobenzylidene)-7-nitroisobenzofuran-1(3H)-one (30a) (4:1) (403 mg, 0.55 mmol) and N,N-dimethylformamide (0.214 mL, 2.77 mmol) in water (10 mL) at 20° C. under air. The resulting mixture was stirred at 100° C. for 18 hours. The solvent was evaporated and the residue dissolved in dichloromethane/MeOH. The solvent volume was reduced to afford a mixture of 4-(3-bromo-4-fluorobenzyl)-5-nitrophthalazin-1(2H)-one with 4-(3-bromo-4-fluorobenzyl)-8-nitrophthalazin-1(2H)-one as a dark brown solid (429 mg, 103%), which was taken on without further purification; $^1$H NMR (400.132 MHz, DMSO) δ 4.37 & 4.05 (2H, 2xs), 7.20-7.39 (2H, m), 7.53-7.72 (1H, m), 7.92-8.40 (3H, m), 9.04 (1H, s); m/z (LC-MS, ESI+), RT=2.38 (M+H 380).

(c) 2-fluoro-5-((5-nitro-4-oxo-3,4-dihydro-phthalazin-1-yl)methyl)benzonitrile (32b) and 2-fluoro-5-((8-nitro-4-oxo-3,4-dihydrophthalazin-1-yl)methyl)benzonitrile (32a)

Copper(I) cyanide (71.7 mg, 0.80 mmol) was added to a mixture of 4-(3-bromo-4-fluorobenzyl)-5-nitrophthalazin-1 (2H)-one (31b) with 4-(3-bromo-4-fluorobenzyl)-8-nitrophthalazin-1(2H)-one (31a) (429 mg, 0.57 mmol) in N,N-dimethylformamide (4 mL) at 20° C. under air. The resulting brown solution was stirred at 160° C. for 17 hours. Copper (I) cyanide (11 mg, 0.12 mmol) was added and reaction continued for a further 5 hours. The cooled mixture was diluted with ethyl acetate (50 ml) and washed with saturated brine (2×25 ml). The organic solution was dried over $MgSO_4$, filtered and evaporated to afford a brown gum (150 mg, 40.8% yield), which was used without further purification; m/z (LC-MS, ESI+), RT=2.05 (M–H 323).

(d) 2-fluoro-5-((5-nitro-4-oxo-3,4-dihydro-phthalazin-1-yl)methyl)benzoic acid (33b) and 2-fluoro-5-((8-nitro-4-oxo-3,4-dihydrophthalazin-1-yl)methyl)benzoic acid (33a)

Potassium hydroxide (14 mg, 0.25 mmol) in water (1 ml) was added to a mixture of 2-fluoro-5-((5-nitro-4-oxo-3,4-dihydrophthalazin-1-yl)methyl)benzonitrile (32a) with 2-fluoro-5-((8-nitro-4-oxo-3,4-dihydrophthalazin-1-yl)methyl)benzonitrile (32b) (162 mg, 0.25 mmol) in ethanol (4 mL) at 20° C. under air. The resulting solution was stirred at ambient temperature for 2 hours and then at 50° C. for 2 hours. Further potassium hydroxide (93 mg, 1.66 mmol, 7 eq) was then added and the solution heated at 90° C. for 16 hours. The reaction mixture was cooled and diluted with water (10 mL) and extracted with diethyl ether (2×10 ml). The aqueous solution was acidified with 1M citric acid and the solid product filtered and dried, under vacuum at 60° C., to afford the desired mixture (26 mg, 15% yield). The remaining aqueous solution was extracted with EtOAc and combined extracts dried over magnesium sulfate, filtered and evaporated to afford more of the desired mixture as a gum (27 mg, 15% yield); m/z (LC-MS, ESI+), RT=0.84 (M+H 344). The two batches were combined and used without further purification.

(e) 4-(4-fluoro-3-(4-methoxypiperidine-1-carbonyl)benzyl)-5-nitrophthalazin-1(2H)-one (34b) with 4-(4-fluoro-3-(4-methoxypiperidine-1-carbonyl)benzyl)-8-nitrophthalazin-1(2H)-one (34a)

O-Benzotriazol-1-yl-N,N,N',N'-tetra-methyluronium hexafluorophosphate (38.1 mg, 0.10 mmol) was added in one portion to a mixture of 2-fluoro-5-((5-nitro-4-oxo-3,4-dihydrophthalazin-1-yl)methyl)benzoic acid (33b) with 2-fluoro-5-((8-nitro-4-oxo-3,4-dihydrophthalazin-1-yl)methyl)benzoic acid (33a) (53 mg, 0.08 mmol), 4-methoxypiperidine (17.8 mg, 0.15 mmol) and Triethylamine (0.033 mL, 0.24 mmol) in DMF (2 mL) at 20° C. under air. The resulting solution was stirred at 20° C. for 24 hours. The reaction mixture was diluted with ethyl acetate and washed with water (×2). The organic layer was dried over MgSO4, filtered and evaporated to afford the desired mixture as a gum (8.50 mg, 12.50% yield), which was used without further purification; m/z (LC-MS, ESI+), RT=1.76 (M+H 441.3).

(f) 8-amino-4-(4-fluoro-3-(4-methoxypiperidine-1-carbonyl)benzyl)phthalazin-1(2H)-one (35a)

A mixture of 4-(4-fluoro-3-(4-methoxypiperidine-1-carbonyl)benzyl)-5-nitrophthalazin-1 (2H)-one (34b) with 4-(4- fluoro-3-(4-methoxypiperidine-1-carbonyl)benzyl)-8-nitrophthalazin-1 (2H)-one (34a) (6 mg, 6.81 µmol) in ethanol (2 ml) was added to 5% palladium on carbon (2 mg, 0.94 µmol) in ethanol (5 mL) at 20° C. and the resulting mixture stirred at 20° C. for 5 hours, under an atmosphere of hydrogen. The catalyst was filtered and washed with ethanol and the solvent evaporated to a foam. Further ethanol and 5% palladium on charcoal (10 mg) were added and mixture stirred for a further 5 hours, under an atmosphere of hydrogen. The catalyst was filtered and washed with ethanol. Evaporation gave a gum, which was purified by preparative HPLC (Waters XBridge Prep C18 OBD column, 5µ silica, 19 mm diameter, 100 mm length), using decreasingly polar mixtures of water (containing 1% NH3) and MeCN as eluents. Fractions containing the desired compound were evaporated to dryness to afford the desired compound as a colourless gum (1.700 mg, 60.8%); $^1$H NMR (400.132 MHz, CDCl3) δ 1.25-1.31 (1H, m), 1.51-1.82 (2H, m), 1.89-1.98 (1H, m), 3.09-3.17 (1H, m), 3.38 (3H, s), 3.46-3.51 (2H, m), 3.55-3.63 (1H, m), 3.98-4.05 (1H, m), 4.16 (2H, s), 6.43 (2H, s), 6.79 (1H, d), 6.85 (1H, d), 7.00-7.04 (1H, m), 7.25-7.31 (2H, m), 7.41-7.45 (1H, m), 9.56 (1H, s); m/z (LC-MS, ESI+), RT=1.71 (M+H 411.5).

Example 19

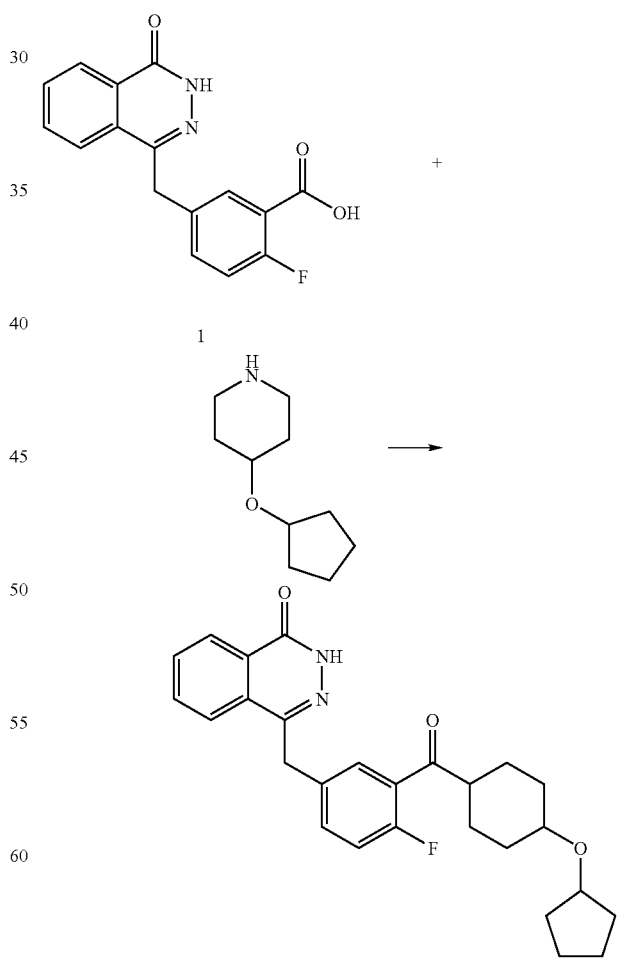

4-(3-(4-(cyclopentyloxy)piperidine-1-carbonyl)-4-fluorobenzyl)phthalazin-1(2H)-one (36)

Triethylamine (0.280 ml, 2.01 mmol) was added in one portion to 2-fluoro-5-((4-oxo-3,4-dihydrophthalazin-1-yl)methyl)benzoic acid (1) (200 mg, 0.67 mmol), 4-(cyclopentyloxy)piperidine hydrochloride (113 mg, 0.67 mmol) and O-benzotriazol-1-yl-N,N,N',N'-tetra-methyluronium hexafluorophosphate (331 mg, 0.87 mmol) in DMA (2 ml) at 20° C. under air. The resulting mixture was stirred at 20° C. for 3 days. The crude product was purified by preparative HPLC (Waters XBridge Prep C18 OBD column, 5µ silica, 19 mm diameter, 100 mm length), using decreasingly polar mixtures of water (containing 1% NH$_3$) and MeCN as eluents. Fractions containing the desired compound were evaporated to dryness to afford the desired material as a white solid (112 mg, 37.2% yield); $^1$H NMR (400.132 MHz, DMSO) δ 1.23-1.72 (11H, m), 1.81-1.87 (1H, m), 3.00-3.06 (1H, m), 3.22-3.27 (2H, m), 3.52-3.59 (1H, m), 3.96-4.04 (2H, m), 4.33 (2H, s), 7.18-7.23 (1H, m), 7.34 (1H, d), 7.38-7.42 (1H, m), 7.81-7.91 (2H, m), 7.97 (1H, d), 8.26 (1H, d), 12.56 (1H, s); m/z (LC-MS, ESI+), RT=2.30 (M+H 450.1).

Example 20

4-(3-(4-(cyclopentyloxy)piperidine-1-carbonyl)benzyl)phthalazin-1(2H)-one (37)

Triethylamine (0.298 ml, 2.14 mmol) was added in one portion to 3-((4-oxo-3,4-dihydrophthalazin-1-yl)methyl)benzoic acid (1b) (200 mg, 0.71 mmol), 4-(cyclopentyloxy)piperidine hydrochloride (121 mg, 0.71 mmol) and O-benzotriazol-1-yl-N,N,N',N'-tetra-methyluronium hexafluorophosphate (352 mg, 0.93 mmol) in DMA (2 ml) at 20° C. under air. The resulting mixture was stirred at 20° C. for 3 days. The crude product was purified by preparative HPLC (Waters XBridge Prep C18 OBD column, 5µ silica, 19 mm diameter, 100 mm length), using decreasingly polar mixtures of water (containing 1% NH3) and MeCN as eluents. Fractions containing the desired compound were evaporated to dryness to afford the desired material as a white solid (120 mg, 39% yield); $^1$H NMR (400.132 MHz, DMSO) δ 1.22-1.86 (11H, m), 3.00-3.20 (2H, m), 3.25-3.43 (2H, m), 3.52-3.56 (1H, m), 3.91-4.05 (2H, m), 4.35 (2H, s), 7.20 (1H, d), 7.31 (1H, s), 7.34-7.40 (2H, m), 7.80-7.89 (2H, m), 7.96 (1H, d), 8.26 (1H, d), 12.57 (1H, s); m/z (LC-MS, ESI+), RT=2.18 (M+H 432.1)

Example 21

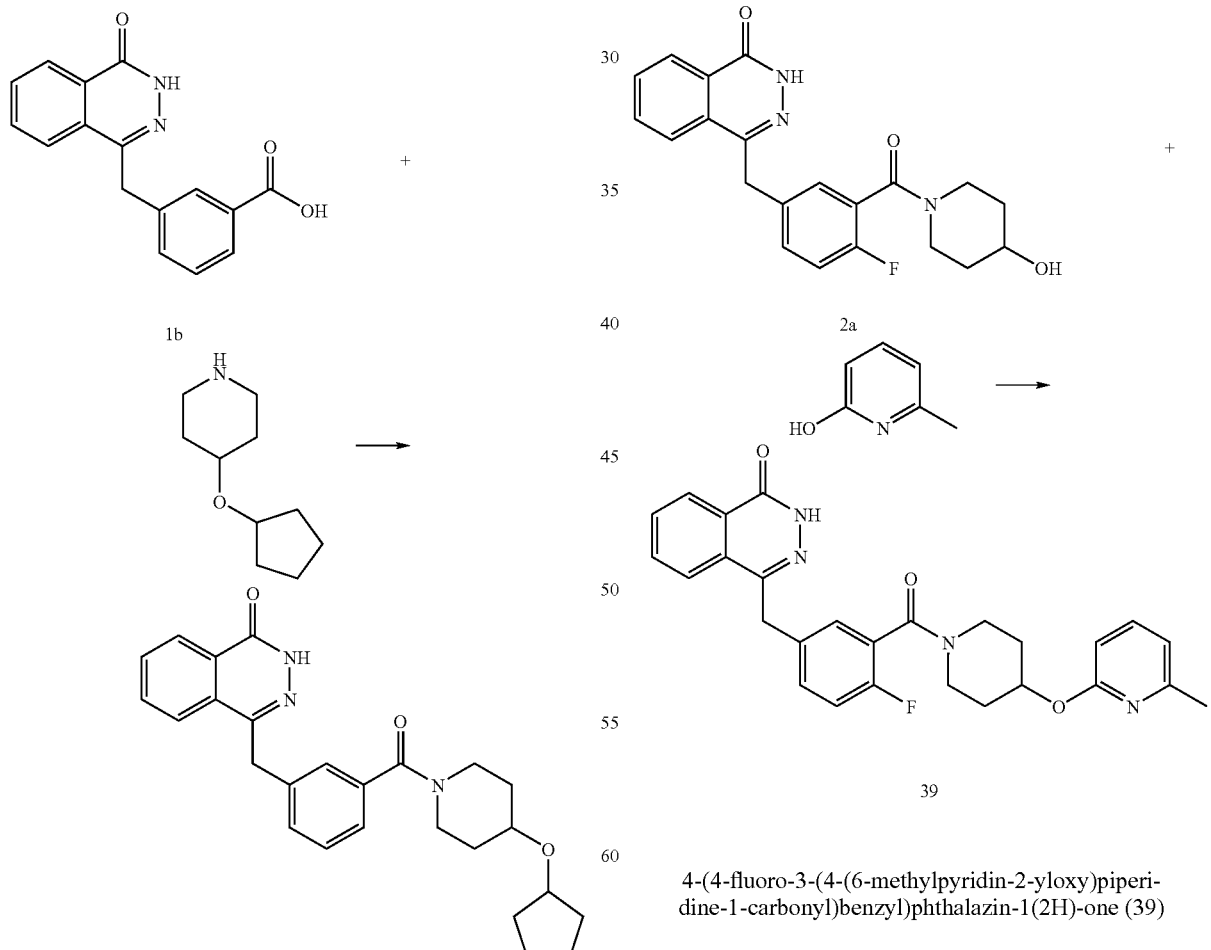

4-(4-fluoro-3-(4-(6-methylpyridin-2-yloxy)piperidine-1-carbonyl)benzyl)phthalazin-1(2H)-one (39)

6-methylpyridin-2-ol (95 mg, 0.87 mmol) was added in one portion to polymer supported triphenylphosphine (1.89 mmol/g; 460 mg, 0.87 mmol) in DCM (5 ml). Di-tert-butyl azodicarboxylate (201 mg, 0.87 mmol) and 4-(4-fluoro-3-(4- hydroxypiperidine-1-carbonyl)benzyl)phthalazin-1(2H)-one (2a) (111 mg, 0.29 mmol) in DCM (1 ml) was added and the resulting mixture was stirred at 20° C. for 4 hours. The reaction mixture was diluted with DCM and washed with water (×2). The organic layer was dried over MgSO$_4$, filtered and evaporated to afford crude product. The crude product was purified by preparative HPLC (Waters XTerra C18 column, 5μ silica, 19 mm diameter, 100 mm length), using decreasingly polar mixtures of water (containing 1% formic acid) and MeCN as eluents. Fractions containing the desired compound were evaporated to dryness to afford the desired material as a white solid (10 mg, 7.3% yield); $^1$H NMR (400.132 MHz, CDCl$_3$) δ 1.70-1.80 (1H, m), 1.85-1.95 (2H, m), 2.02-2.08 (1H, m), 2.41 (3H, s), 3.22-3.28 (1H, m), 3.51-3.57 (1H, m), 3.74-3.83 (1H, m), 3.95-4.03 (1H, m), 4.28 (2H, s), 5.32-5.35 (1H, m), 6.50 (1H, d), 6.69 (1H, d), 7.02 (1H, t), 7.26-7.29 (1H, m), 7.33-7.35 (1H, m), 7.44 (1H, t), 7.71-7.79 (3H, m), 8.45-8.48 (1H, m), 10.33 (1H, s); m/z (LC-MS, ESI+), RT=2.26 (M+H 473.6).

Example 22

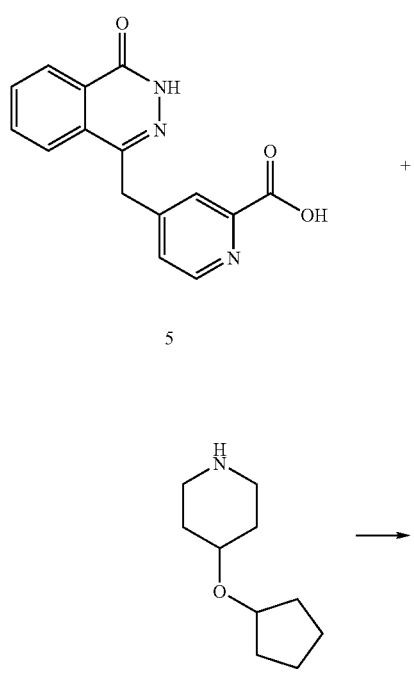

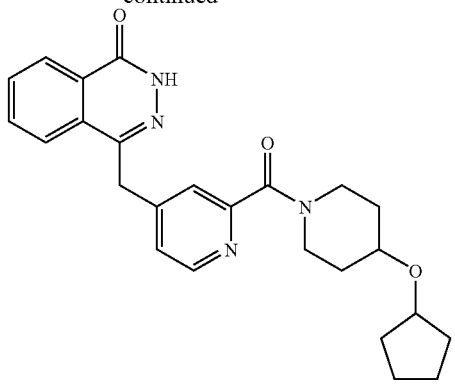

4-((2-(4-(cyclopentyloxy)piperidine-1-carbonyl)pyridin-4-yl)methyl)phthalazin-1(2H)-one (40)

Triethylamine (0.452 ml, 3.24 mmol) was added in one portion to 4-((4-oxo-3,4-dihydrophthalazin-1-yl)methyl)picolinic acid (5) (304 mg, 1.08 mmol), 4-(cyclopentyloxy)piperidine hydrochloride (183 mg, 1.08 mmol) and O-benzotriazol-1-yl-N,N,N',N'-tetra-methyluronium hexafluorophosphate (533 mg, 1.41 mmol) in DMA (3 ml) at 20° C. under air. The resulting mixture was stirred at 20° C. for 3 days. The crude product was purified by preparative HPLC (Waters XBridge Prep C18 OBD column, 5μ silica, 19 mm diameter, 100 mm length), using decreasingly polar mixtures of water (containing 1% NH3) and MeCN as eluents. Fractions containing the desired compound were evaporated to dryness to afford the desired material as a white solid (39 mg, 8.3% yield); $^1$H NMR (400.132 MHz, DMSO) δ 1.28-1.74 (11H, m), 1.82-1.88 (1H, m), 3.08-3.14 (1H, m), 3.20-3.27 (1H, m), 3.44-3.49 (1H, m), 3.53-3.59 (1H, m), 3.96-4.05 (2H, m), 4.40 (2H, s), 7.39 (1H, d), 7.49 (1H, s), 7.83-7.96 (3H, m), 8.28 (1H, d), 8.47 (1H, d), 12.60 (1H, s); m/z (LC-MS, ESI+), RT=1.88 (M+H 433.1).

Example 23

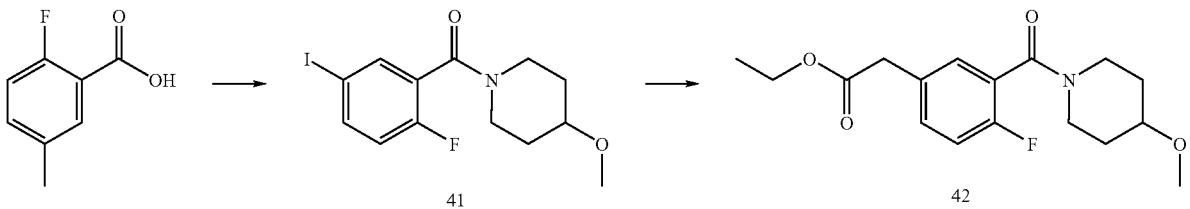

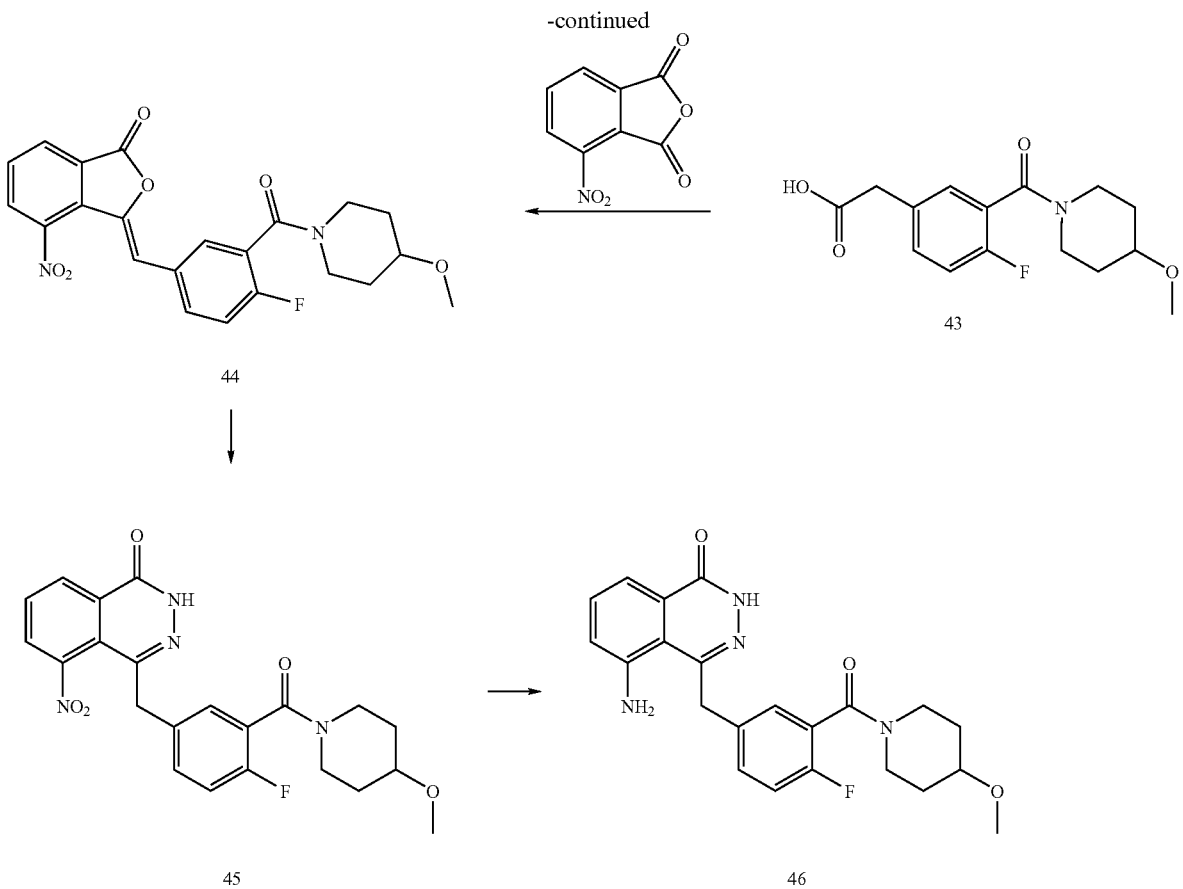

(a) (2-fluoro-5-iodophenyl)(4-methoxypiperidin-1-yl)methanone (41)

2-(1H-benzo[d][1,2,3]triazol-1-yl)-1,1,3,3-tetramethylisouronium hexafluorophosphate(V) (5.99 g, 15.79 mmol) was added portionwise to 2-fluoro-5-iodobenzoic acid (3.000 g, 11.28 mmol), 4-methoxypiperidine (1.364 g, 11.84 mmol) and triethylamine (3.93 mL, 28.19 mmol) in DMF (40 mL). The resulting solution was stirred at room temperature for 7 hours. The reaction mixture was poured into water (350 mL), extracted with Et2O (2×200 mL), the combined organic layers were washed with saturated brine (100 mL), dried over Na2SO4, filtered and evaporated to afford a dark orange gum. The crude product was purified by flash silica chromatography, elution gradient 0 to 50% EtOAc in isohexane. Pure fractions were evaporated to dryness to afford the desired material as a colourless gum (0.348 g, 67% yield); $^1$H NMR (400.132 MHz, CDCl$_3$) δ1.57-1.99 (4H, m), 3.18 (1H, m), 3.39 (3H, s), 3.50 (2H, m), 3.63 (1H, m), 3.98 (1H, m), 6.89 (1H, t), 7.69 (2H, m); m/z (LC-MS, ESI+), RT=2.05 (M+H 364.0).

(b) Ethyl 2-(4-fluoro-3-(4-methoxypiperidine-1-carbonyl)phenyl)acetate (42)

Cesium carbonate (2.308 g, 7.08 mmol) was added in one portion to (2-fluoro-5-iodophenyl)(4-methoxypiperidin-1-yl)methanone (41) (1.06 g, 2.92 mmol), diethyl malonate (1.329 mL, 8.76 mmol), 2-phenylphenol (0.099 g, 0.58 mmol) and copper(I) iodide (0.056 g, 0.29 mmol) in THF (10 mL) at 25° C. under nitrogen. The resulting mixture was stirred at 160° C. in the microwave reactor for 90 minutes. The reaction mixture was evaporated to dryness and redissolved in Et$_2$O (200 mL), and washed sequentially with water (100 mL) and saturated brine (50 mL). The organic layer was dried over MgSO$_4$, filtered and evaporated to afford crude product. The crude product was purified by flash silica chromatography, elution gradient 0 to 50% ethyl acetate in isohexane. Pure fractions were evaporated to dryness to afford the desired material as a colourless gum (2.03 g, 72% yield); $^1$H NMR (400.132 MHz, CDCl$_3$) δ 1.25 (3H, t), 1.53-1.61 (1H, m), 1.67-1.74 (1H, m), 1.77-1.84 (1H, m), 1.89-1.97 (1H, m), 3.12-3.20 (1H, m), 3.36 (3H, s), 3.44-3.62 (3H, m), 3.59 (2H, s), 3.96-4.05 (1H, m), 4.15 (2H, q), 7.02-7.06 (1H, m), 7.26-7.33 (2H, m); m/z (LC-MS, ESI+), RT=1.08 (M+H 324.3).

(c) 2-(4-fluoro-3-(4-methoxypiperidine-1-carbonyl)phenyl)acetic Acid (43)

Lithium hydroxide (0.752 g, 31.39 mmol) was added in one portion to ethyl 2-(4-fluoro-3-(4-methoxypiperidine-1-carbonyl)phenyl)acetate (42) (2.03 g, 6.28 mmol) in THF (20 mL) and water (20 ml) at 25° C. under air. The resulting mixture was stirred at room temperature for 2 hours. The THF was evaporated and the mixture diluted with water (30 mL). The aqueous solution was acidified with 2N HCl and the product extracted into EtOAc (3×30 ml). The combined extracts were dried (MgSO₄), filtered and evaporated to a give the desired material as a white solid (1.580 g, 85% yield); ¹H NMR (400.132 MHz, CDCl₃) δ 1.54-1.84 (3H, m), 1.89-1.96 (1H, m), 3.12-3.20 (1H, m), 3.36 (3H, s), 3.45-3.53 (2H, m), 3.58 (2H, s), 3.60-3.66 (1H, m), 3.93-4.02 (1H, m), 7.01-7.06 (1H, m), 7.28-7.32 (2H, m); m/z (LC-MS, ESI+), RT=0.78 (M+H 296.3).

(d) (Z)-3-(4-fluoro-3-(4-methoxypiperidine-1-carbonyl)benzylidene)-4-nitroisobenzofuran-1(3H)-one (44)

Sodium acetate (6.97 mg, 0.08 mmol) was added to 4-nitroisobenzofuran-1,3-dione (558 mg, 2.89 mmol) and 2-(4-fluoro-3-(4-methoxypiperidine-1-carbonyl)phenyl)acetic acid (43) (502 mg, 1.70 mmol) under air. The resulting mixture was stirred at 240° C. for 30 minutes. The cooled mixture was purified by flash silica chromatography, elution gradient 0 to 100% ethyl acetate in isohexane. Pure fractions were evaporated to dryness to afford the desired material as a yellow gum (50 mg, 6.90% yield); ¹H NMR (400.132 MHz, CDCl₃) δ 1.59-2.00 (4H, m), 3.10-3.26 (1H, m), 3.37 (3H, s), 3.43-3.57 (2H, m), 3.61-3.71 (1H, m), 3.88-4.05 (1H, m), 7.16-7.20 (1H, m), 7.30 (1H, s), 7.70-7.76 (1H, m), 7.86-7.88 (1H, m), 7.97-8.01 (1H, m), 8.27 (1H, d), 8.39 (1H, d); m/z (LC-MS, ESI+), RT=2.29 (M+H 427.3).

(e) 4-(4-fluoro-3-(4-methoxypiperidine-1-carbonyl)benzyl)-5-nitrophthalazin-1(2H)-one (45)

Hydrazine hydrate (0.046 mL, 0.94 mmol) was added in one portion to (Z)-3-(4-fluoro-3-(4-methoxypiperidine-1-carbonyl)benzylidene)-4-nitroisobenzofuran-1(3H)-one (44) (50 mg, 0.12 mmol) and N,N-Dimethylformamide (0.045 mL, 0.59 mmol) in water (2 mL) at 25° C. under air. The resulting mixture was stirred at 100° C. for 18 hours. The mixture was cooled to ambient temperature and the solvent evaporated to give crude desired product as a pale brown solid (40.0 mg, 77% yield); ¹H NMR: (400.132 MHz, DMSO) δ 1.23-1.33 (1H, m), 1.36-1.50 (1H, m), 1.65-1.72 (1H, m), 1.79-1.92 (1H, m), 3.25-3.27 (4H, m), 3.33 (3H, s), 3.82-3.97 (1H, m), 4.10 (2H, s), 7.10-7.21 (3H, m), 7.99-8.03 (1H, m), 8.27 (1H, d), 8.59 (1H, d); m/z (LC-MS, ESI+), RT=1.85 (M+H 441.3).

(f) 5-amino-4-(4-fluoro-3-(4-methoxypiperidine-1-carbonyl)benzyl)phthalazin-1(2H)-one (46)

4-(4-fluoro-3-(4-methoxypiperidine-1-carbonyl)benzyl)-5-nitrophthalazin-1 (2H)-one (45) (40 mg, 0.09 mmol) was added to 5% palladium on carbon (4 mg, 0.04 mmol) in ethanol (7 ml) at 25° C. under air. The resulting mixture was hydrogenated at 25° C. for 22 hours. The catalyst was filtered and washed with ethanol and the solvent evaporated to a pale brown gum. The crude product was purified by preparative HPLC (Waters XBridge Prep C18 OBD column, 5µ silica, 19 mm diameter, 100 mm length), using decreasingly polar mixtures of water (containing 1% NH3) and MeCN as eluents. Fractions containing the desired compound were evaporated to dryness to afford the desired material as a beige solid (11 mg, 29.5% yield); ¹H NMR (400.132 MHz, DMSO) δ 1.66-1.81 (2H, m), 1.86-1.96 (2H, m), 3.10-3.19 (1H, m), 3.36 (3H, s), 3.44-3.50 (2H, m), 3.55-3.64 (1H, m), 3.91-3.99 (1H, m), 4.08 (2H, s), 4.44 (2H, s), 6.99 (1H, d), 7.05-7.10 (1H, m), 7.23-7.28 (2H, m), 7.50-7.54 (1H, m), 7.94 (1H, d), 9.95 (1H, s); m/z (LC-MS, ESI+), RT=1.50 (M+H 411.3).

Example 24

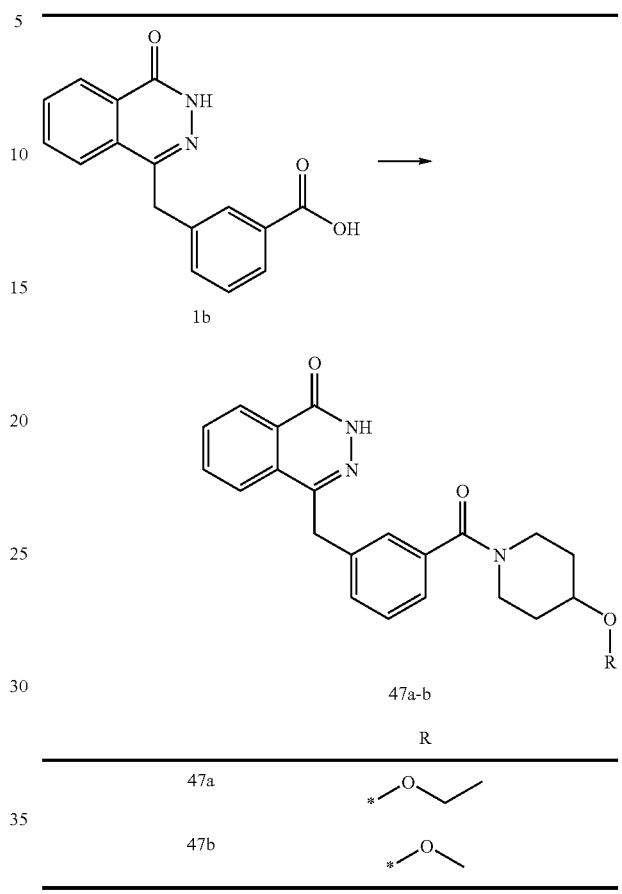

(a) 4-(3-(4-ethoxypiperidine-1-carbonyl)benzyl)phthalazin-1(2H)-one (47a)

2-(1H-Benzo[d][1,2,3]triazol-1-yl)-1,1,3,3-tetramethylisouronium hexafluorophosphate(V) (0.379 g, 1.00 mmol) was added to 3-((4-oxo-3,4-dihydrophthalazin-1-yl)methyl)benzoic acid (1b) (0.200 g, 0.71 mmol), 4-ethoxypiperidine (0.101 g, 0.78 mmol) and triethylamine (0.249 mL, 1.78 mmol) in DMF (3 mL). The resulting solution was stirred at room temperature for 3 days. The crude product was purified by preparative HPLC (Waters XBridge Prep C18 OBD column, 5µ silica, 19 mm diameter, 100 mm length), using decreasingly polar mixtures of water (containing 1% NH₃) and MeCN as eluents. Fractions containing the desired compound were evaporated to dryness to afford the desired compound (0.175 g, 62.6% yield); ¹H NMR (400.132 MHz, DMSO) δ 1.11 (3H, t), 1.20-1.93 (4H, m), 2.98-3.27 (2H, m), 3.33-3.41 (1H, m), 3.42-3.54 (3H, m), 3.93 (1H, s), 4.35 (2H, s), 7.21 (1H, m), 7.31 (1H, s), 7.33-7.42 (2H, m), 7.79-7.90 (2H, m), 7.95 (1H, m), 8.26 (1H, m), 12.58 (1H, s); m/z (LC-MS, ESI+), RT=1.81 min (M+H=392.13).

(b) 4-(3-(4-methoxypiperidine-1-carbonyl)benzyl)phthalazin-1(2H)-one (47b)

2-(1H-Benzo[d][1,2,3]triazol-1-yl)-1,1,3,3-tetramethylisouronium hexafluorophosphate(V) (0.379 g, 1.00 mmol) was added to 3-((4-oxo-3,4-dihydrophthalazin-1-yl)methyl)benzoic acid (1b) (0.200 g, 0.71 mmol), 4-methoxypiperidine (0.090 g, 0.78 mmol) and triethylamine (0.249 mL, 1.78 mmol) in DMF (3 mL). The resulting solution was stirred at room temperature for 16 hours. The crude product was purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired compound (0.211 g, 78% yield); $^1$H NMR (400.132 MHz, DMSO) δ 1.24-1.49 (2H, m), 1.63-1.93 (2H, m), 2.94-3.14 (2H, m), 3.30 (3H, s), 3.34-3.44 (2H, m), 3.88 (1H, s), 4.35 (2H, s), 7.21 (1H, m), 7.30-7.43 (3H, m), 7.80-7.90 (2H, m), 7.96 (1H, d), 8.27 (1H, m), 12.58 (1H, s); m/z (LC-MS, ESI+), RT=1.57 min (M+H=378.20).

C., under nitrogen. The resulting suspension was stirred at 0° C. for 10 minutes. A solution of 2-(3-bromophenyl)acetyl chloride (48) (0.500 g, 2.14 mmol) in anhydrous DCM (5 mL) was added dropwise to the stirred suspension at 0° C. The resulting suspension was allowed to warm to room temperature and then stirred at room temperature for a further 18 hours. The reaction mixture was poured onto ice (50 mL) and conc HCl (2 mL). The layers were separated and the aqueous layer extracted with DCM (2×50 mL). The combined organics were washed sequentially with 2M HCl (2×75 mL), water (50 mL), and saturated NaHCO$_3$ (50 mL). The organic layer was dried over Na$_2$SO$_4$, filtered and evaporated to afford crude product, which was used directly in the next stage; m/z (LC-MS, ESI−), RT=2.46 min (M−H=350.00).

Example 25

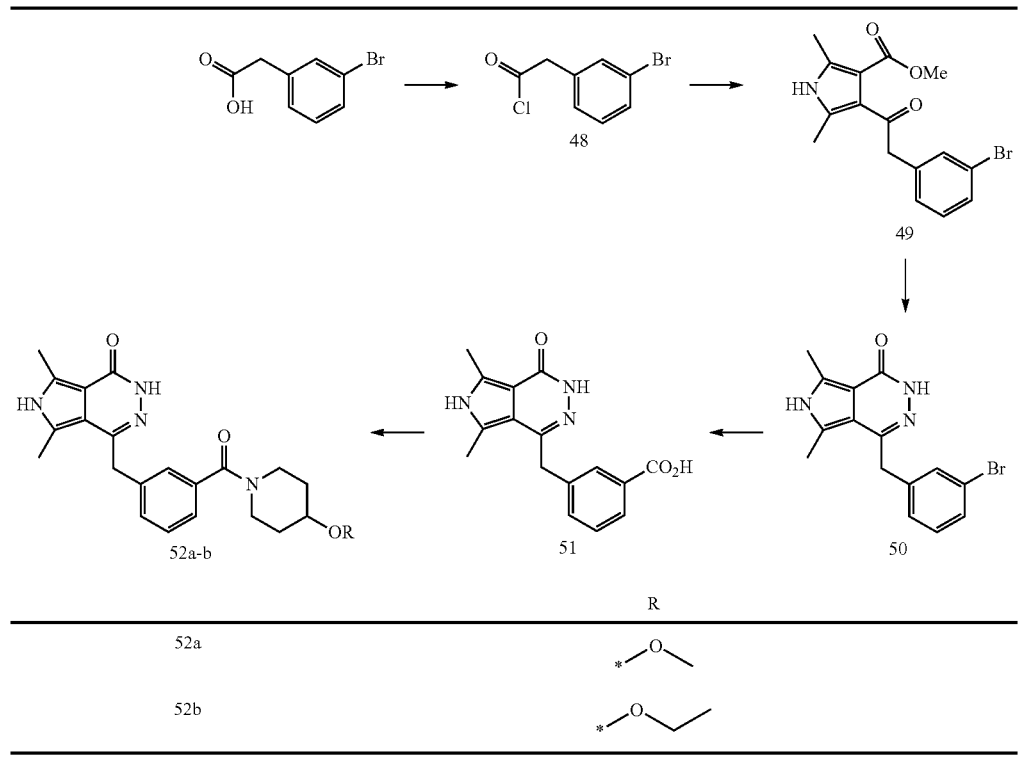

(a) 2-(3-bromophenyl)acetyl Chloride (48)

Thionyl chloride (2.035 mL, 27.90 mmol) was added to 2-(3-bromophenyl)acetic acid (1.500 g, 6.98 mmol) in DCM (30 mL). The resulting solution was stirred at room temperature for 18 hours. The resulting mixture was evaporated to dryness and the residue was azeotroped with toluene to afford crude product (1.570 g, 96% yield), which was used without further purification.

(b) Methyl 4-(2-(3-bromophenyl)acetyl)-2,5-dimethyl-1H-pyrrole-3-carboxylate (49)

A solution of methyl 2,5-dimethyl-1H-pyrrole-3-carboxylate (0.295 g, 1.93 mmol) in anhydrous DCM (5 mL) was added dropwise to a stirred suspension of aluminum trichloride (0.714 g, 5.35 mmol) in anhydrous DCM (10 mL) at 0°

(c) 4-(3-bromobenzyl)-5,7-dimethyl-2,6-dihydro-1H-pyrrolo[3,4-d]pyridazin-1-one (50)

Hydrazine hydrate (0.110 mL, 1.48 mmol) was added to methyl 4-(2-(3-bromophenyl)acetyl)-2,5-dimethyl-1H-pyrrole-3-carboxylate (49) (0.470 g, 1.34 mmol) in acetic acid (20 mL). The resulting solution was stirred at room temperature for 2 days. The reaction mixture was evaporated to dryness and redissolved in EtOAc (200 mL), and washed sequentially with 2M NaOH (100 mL) and saturated brine (50 mL). The organic layer was dried over Na$_2$SO$_4$, filtered and evaporated to afford crude product. The crude product was purified by flash silica chromatography, elution gradient 0 to 100% ethyl acetate in isohexane. Pure fractions were evaporated to dryness to afford the desired material as a beige solid (0.253 g, 56.7% yield); $^1$H NMR (400.132 MHz, MeOD) δ 2.18 (3H, s), 2.50 (3H, s), 4.03 (2H, s), 7.04-7.11 (2H, m), 7.25 (2H, m); m/z (LC-MS, ESI+), RT=1.84 min (M+H=333.97).

(d) 3-((5,7-dimethyl-1-oxo-2,6-dihydro-1H-pyrrolo [3,4-d]pyridazin-4-yl)methyl)benzoic acid (51)

4-(3-Bromobenzyl)-5,7-dimethyl-2,6-dihydro-1H-pyrrolo[3,4-d]pyridazin-1-one (50) (0.188 g, 0.57 mmol), molybdenum hexacarbonyl (0.224 g, 0.85 mmol), N,N-dimethylpyridin-4-amine (0.138 g, 1.13 mmol), N-ethyl-N-isopropylpropan-2-amine (0.197 mL, 1.13 mmol) and acetoxy (2-(dio-tolylphosphino)benzyl)palladium (0.027 g, 0.03 mmol) were suspended in a mixture of dioxane (2.0 mL) and water (2.0 mL) and sealed into a microwave tube. The reaction was heated to 150° C. for 30 minutes in the microwave reactor and cooled to room temperature. The reaction mixture was diluted with water (50 mL) and EtOAc (50 mL). The mixture was filtered through celite. The layers were separated and the aqueous was adjusted to pH2 with 2M HCl. The resulting precipitate was collected by filtration, washed with water (50 mL), Et$_2$O (50 mL) and dried under vacuum to afford the desired material as a brown solid (0.200 g, >100% yield), which was used without further purification. $^1$H NMR (400.132 MHz, DMSO) δ 2.26 (3H, s), 2.51 (3H, s), 4.13 (2H, s), 7.39-7.48 (2H, m), 7.78 (2H, m), 11.08 (1H, s), 11.93 (1H, s), 12.86 (1H, s); m/z (LC-MS, ESI+), RT=1.41 min (M+H=298.08).

(e) 4-(3-(4-methoxypiperidine-1-carbonyl)benzyl)-5, 7-dimethyl-2,6-dihydro-1H-pyrrolo[3,4-d]pyridazin-1-one (52a)

2-(1H-Benzo[d][1,2,3]triazol-1-yl)-1,1,3,3-tetramethylisouronium hexafluorophosphate(V) (0.179 g, 0.47 mmol) was added to 3-((5,7-dimethyl-1-oxo-2,6-dihydro-1H-pyrrolo[3,4-d]pyridazin-4-yl)methyl)benzoic acid (51) (0.100 g, 0.34 mmol), 4-methoxypiperidine (0.043 g, 0.37 mmol) and triethylamine (0.117 mL, 0.84 mmol) in DMF (2 mL). The resulting solution was stirred at room temperature for 5 hours. The crude product was purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired compound (0.054 g, 40.9% yield). $^1$H NMR (400.132 MHz, DMSO) δ 1.18-1.93 (4H, m), 2.24 (3H, s), 2.51 (3H, s), 3.02-3.19 (2H, m), 3.25 (3H, s), 3.40 (2H, m), 3.76-3.97 (1H, m), 4.09 (2H, s), 7.14 (1H, s), 7.20 (1H, d), 7.27 (1H, d), 7.36 (1H, t), 11.08 (1H, s), 11.92 (1H, s); m/z (LC-MS, ESI+), RT=1.38 min (M+H=395.09).

(f) 4-(3-(4-ethoxypiperidine-1-carbonyl)benzyl)-5,7-dimethyl-2,6-dihydro-1H-pyrrolo[3,4-d]pyridazin-1-one (52b)

2-(1H-Benzo[d][1,2,3]triazol-1-yl)-1,1,3,3-tetramethylisouronium hexafluorophosphate(V) (0.163 g, 0.43 mmol) was added to 3-((5,7-dimethyl-1-oxo-2,6-dihydro-1H-pyrrolo[3,4-d]pyridazin-4-yl)methyl)benzoic acid (51) (0.091 g, 0.31 mmol), 4-ethoxypiperidine (0.044 g, 0.34 mmol) and triethylamine (0.107 mL, 0.77 mmol) in DMF (2 mL). The resulting solution was stirred at room temperature for 16 hours. The crude product was purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired material (0.028 g, 22.5% yield). $^1$H NMR (400.132 MHz, DMSO) δ 1.11 (3H, t), 1.16-1.95 (4H, m), 2.24 (3H, s), 2.51 (3H, s), 2.99-3.26 (2H, m), 3.33-3.54 (4H, m), 3.85-4.01 (1H, m), 4.09 (2H, s), 7.14 (1H, s), 7.20 (1H, d), 7.27 (1H, d), 7.35 (1H, t), 11.08 (1H, s), 11.92 (1H, s); m/z (LC-MS, ESI+), RT=1.53 min (M+H=409.13).

Example 26

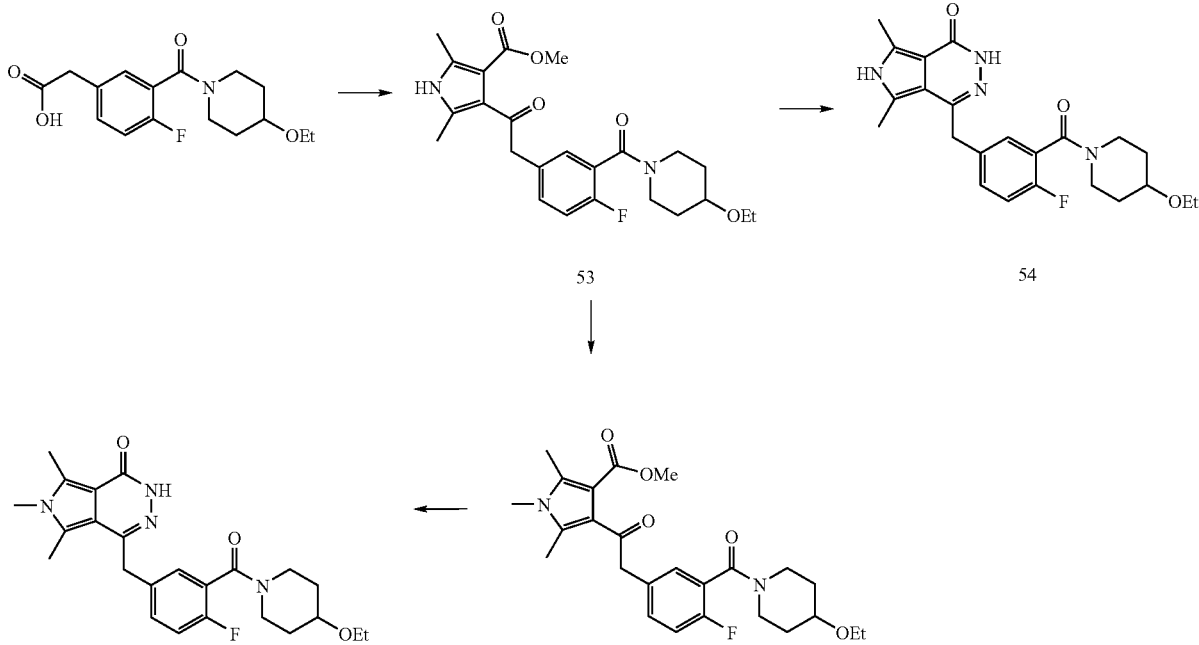

(a) methyl 4-(2-(3-(4-ethoxypiperidine-1-carbonyl)-4-fluorophenyl)acetyl)-2,5-dimethyl-1H-pyrrole-3-carboxylate (53)

A solution of methyl 2,5-dimethyl-1H-pyrrole-3-carboxylate (0.545 g, 3.56 mmol) in anhydrous DCM (10 mL) was added dropwise to a stirred suspension of aluminum trichloride (1.078 g, 8.08 mmol) in anhydrous DCM (20 mL) at 0° C., under nitrogen. The resulting suspension was stirred at 0° C. for 10 minutes. A solution of the requisite acid chloride [prepared earlier; by stirring 1-chloro-N,N,2-trimethylprop-1-en-1-amine (0.428 mL, 3.23 mmol) was added to a solution of 2-(3-(4-ethoxypiperidine-1-carbonyl)-4-fluorophenyl)acetic acid (1.000 g, 3.23 mmol) in anhydrous DCM (10 mL) at 0° C. and stirred for 2 hours] was added dropwise to the stirred suspension at 0° C. The resulting suspension was allowed to warm to room temperature and then stirred at room temperature for a further 18 hours. The reaction was incomplete and further aluminum trichloride (1.078 g, 8.08 mmol) was added and the solution was stirred at room temperature for a further 1 hour. The reaction mixture was poured onto ice (100 mL) and concentrated HCl (5 mL). The layers were separated and the aqueous layer extracted with DCM (2×100 mL). The combined organics were washed sequentially with 2M HCl (2×150 mL), water (100 mL), and saturated NaHCO$_3$ (100 mL). The organic layer was dried over Na$_2$SO$_4$, filtered and evaporated to afford crude product. The crude product was purified by flash silica chromatography, elution gradient 0 to 100% ethyl acetate in isohexane. Pure fractions were evaporated to dryness to afford the desired material as a beige solid (1.241 g, 86% yield); $^1$H NMR (400.132 MHz, CDCl$_3$) δ 1.14 (3H, t), 1.42-1.66 (2H, m), 1.71 (1H, m), 1.85 (1H, m), 2.00 (3H, s), 2.32 (3H, s), 3.06 (1H, m), 3.39-3.52 (5H, m), 3.75 (3H, s), 3.93-4.02 (3H, m), 6.92 (1H, t), 7.07 (1H, m), 7.17 (1H, m), 8.43 (1H, s); m/z (LC-MS, ESI+), RT=2.02 min (M+H=445.24).

(b) 4-(3-(4-ethoxypiperidine-1-carbonyl)-4-fluorobenzyl)-5,7-dimethyl-2,6-dihydro-1H-pyrrolo[3,4-d]pyridazin-1-one (54)

Hydrazine hydrate (0.037 mL, 0.49 mmol) was added to methyl 4-(2-(3-(4-ethoxypiperidine-1-carbonyl)-4-fluorophenyl)acetyl)-2,5-dimethyl-1H-pyrrole-3-carboxylate (53) (0.200 g, 0.45 mmol) in acetic acid (8 mL). The resulting solution was stirred at room temperature for 2 days. The resulting mixture was evaporated to dryness and the residue was azeotroped with toluene to afford a crude gum, which was triturated with a mixture of NMP, DMSO and water to give a solid which was collected by filtration, washed with ether and dried under vacuum to give the desired compound as a white solid (0.112 g, 58.4% yield); $^1$H NMR (400.132 MHz, DMSO) δ 1.11 (3H, t), 1.29 (1H, m), 1.42 (1H, m), 1.71 (1H, m), 1.86 (1H, m), 2.27 (3H, s), 2.51 (3H, s), 3.04 (1H, m), 3.24-3.39 (2H, m), 3.46 (2H, m), 3.52 (1H, m), 3.97 (1H, s), 4.07 (2H, s), 7.13-7.30 (3H, m), 11.07 (1H, s), 11.94 (1H, s); m/z (LC-MS, ESI+), RT=1.62 min (M+H=427.12).

(c) Methyl 4-(2-(3-(4-ethoxypiperidine-1-carbonyl)-4-fluorophenyl)acetyl)-1,2,5-trimethyl-1H-pyrrole-3-carboxylate (55)

Iodomethane (0.056 mL, 0.90 mmol) was added to methyl 4-(2-(3-(4-ethoxypiperidine-1-carbonyl)-4-fluorophenyl)acetyl)-2,5-dimethyl-1H-pyrrole-3-carboxylate (53) (0.200 g, 0.45 mmol) and potassium carbonate (0.249 g, 1.80 mmol) in DMF (10 mL). The resulting suspension was stirred at room temperature for 2 hours. The reaction mixture was poured into water (75 mL) and extracted with EtOAc (3×50 mL). The combined organic layers were washed with water (50 mL) and saturated brine (50 mL). The organic layer was dried over Na$_2$SO$_4$, filtered and evaporated to afford crude product. The crude product was purified by flash silica chromatography, elution gradient 0 to 100% ethyl acetate in isohexane. Pure fractions were evaporated to dryness to afford the desired material as a yellow gum (0.158 g, 77% yield); $^1$H NMR (400.132 MHz, CDCl$_3$) δ 1.14 (3H, t), 1.43-1.65 (2H, m), 1.72 (1H, m), 1.85 (1H, m), 2.05 (3H, s), 2.38 (3H, s), 3.06 (1H, m), 3.32 (3H, s), 3.45 (5H, m), 3.74 (3H, s), 3.91 (2H, s), 3.99 (1H, m), 6.93 (1H, t), 7.08 (1H, m), 7.17 (1H, m); m/z (LC-MS, ESI+), RT=2.15 min (M+H=459.36).

(d) 4-(3-(4-ethoxypiperidine-1-carbonyl)-4-fluorobenzyl)-5,6,7-trimethyl-2,6-dihydro-1H-pyrrolo[3,4-d]pyridazin-1-one (56)

Hydrazine hydrate (0.028 mL, 0.38 mmol) was added to methyl 4-(2-(3-(4-ethoxypiperidine-1-carbonyl)-4-fluorophenyl)acetyl)-1,2,5-trimethyl-1H-pyrrole-3-carboxylate (55) (0.158 g, 0.34 mmol) in acetic acid (4 mL). The resulting solution was stirred at room temperature for 2 days. The resulting mixture was evaporated to dryness and the residue was azeotroped with toluene to afford the crude product, which was purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired compound (0.049 g, 32.3% yield); $^1$H NMR (400.132 MHz, DMSO) δ 1.11 (3H, t), 1.29 (1H, m), 1.41 (1H, m), 1.72 (1H, m), 1.86 (1H, m), 2.29 (3H, s), 2.60 (3H, s), 3.05 (1H, m), 3.28 (3H, s), 3.46 (2H, m), 3.53 (3H, s), 3.96 (1H, m), 4.12 (2H, s), 7.16-7.28 (3H, m), 11.17 (1H, s); m/z (LC-MS, ESI+), RT=1.78 min (M+H=441.11).

Example 27

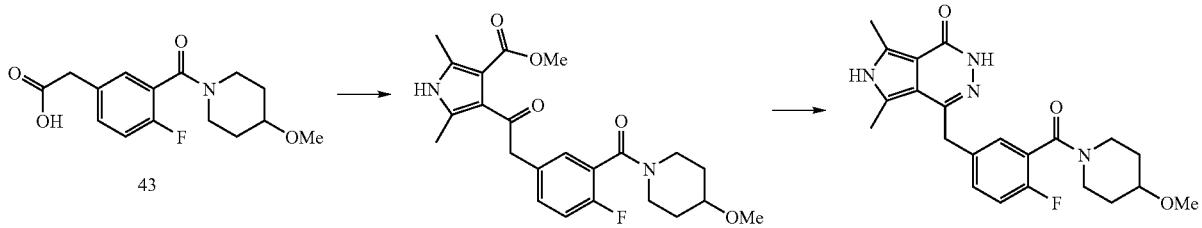

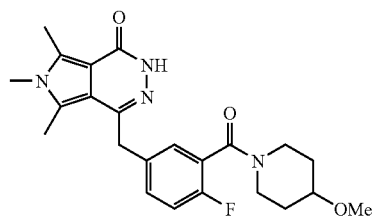

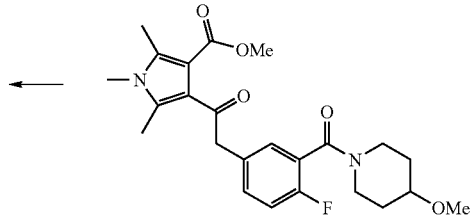

(a) Methyl 4-(2-(4-fluoro-3-(4-methoxypiperidine-1-carbonyl)phenyl)acetyl)-2,5-dimethyl-1H-pyrrole-3-carboxylate (57)

A solution of methyl 2,5-dimethyl-1H-pyrrole-3-carboxylate (0.114 g, 0.74 mmol) in anhydrous DCM (5 mL) was added dropwise to a stirred suspension of aluminum trichloride (0.226 g, 1.69 mmol) in anhydrous DCM (10 mL) at 0° C., under nitrogen. The resulting suspension was stirred at 0° C. for 10 minutes. A solution of the requisite acid chloride [prepared earlier; 1-chloro-N,N,2-trimethylprop-1-en-1-amine (0.090 mL, 0.68 mmol) was added to a solution of 2-(4-fluoro-3-(4-methoxypiperidine-1-carbonyl)phenyl)acetic acid (43) (0.200 g, 0.68 mmol) in anhydrous DCM (5 mL) at 0° C. and stirred for 2 hours] was added dropwise to the stirred suspension at 0° C. The resulting suspension was allowed to warm to room temperature and then stirred at room temperature for a further 18 hours. The reaction was incomplete and further aluminum trichloride (0.226 g, 1.69 mmol) was added and the solution was stirred at room temperature for a further 1 hour. The reaction mixture was poured onto ice (50 mL) and conc HCl (2 mL). The layers were separated and the aqueous layer extracted with DCM (2×50 mL). The combined organics were washed sequentially with 2M HCl (2×75 mL), water (50 mL), and saturated NaHCO$_3$ (50 mL). The organic layer was dried over Na$_2$SO$_4$, filtered and evaporated to afford crude product. The crude product was purified by flash silica chromatography, elution gradient 0 to 100% EtOAc in isohexane. Pure fractions were evaporated to dryness to afford methyl 4-(2-(4-fluoro-3-(4-methoxypiperidine-1-carbonyl)phenyl)acetyl)-2,5-dimethyl-1H-pyrrole-3-carboxylate (0.223 g, 76% yield) as a cream solid. $^1$H NMR (400.132 MHz, CDCl$_3$) δ 1.57-1.90 (4H, m), 1.98 (3H, s), 2.31 (3H, s), 3.07 (1H, m), 3.29 (3H, s), 3.36-3.55 (3H, m), 3.75 (3H, s), 3.92 (1H, m), 3.97 (2H, s), 6.93 (1H, t), 7.07 (1H, m), 7.17 (1H, m), 8.50 (1H, s); m/z (LC-MS, ESI+), RT=1.89 min (M+H=431.19).

(b) 4-(4-fluoro-3-(4-methoxypiperidine-1-carbonyl)benzyl)-5,7-dimethyl-2,6-dihydro-1H-pyrrolo[3,4-d]pyridazin-1-one (58)

Hydrazine hydrate (0.021 mL, 0.28 mmol) was added to methyl 4-(2-(4-fluoro-3-(4-methoxypiperidine-1-carbonyl)phenyl)acetyl)-2,5-dimethyl-1H-pyrrole-3-carboxylate (57) (0.108 g, 0.25 mmol) in acetic acid (4 mL). The resulting solution was stirred at room temperature for 2 days. The resulting mixture was evaporated to dryness and the residue was azeotroped with toluene to afford crude product, which was purified by preparative HPLC (Waters XBridge Prep C18 OBD column, 5µ silica, 19 mm diameter, 100 mm length), using decreasingly polar mixtures of water (containing 1% NH$_3$) and MeCN as eluents. Fractions containing the desired compound were evaporated to dryness to afford the desired material (0.033 g, 31.9% yield). $^1$H NMR (399.902 MHz, DMSO) δ 1.30 (1H, m), 1.44 (1H, m), 1.72 (1H, m), 1.87 (1H, m), 2.27 (3H, s), 2.51 (3H, s), 3.05 (1H, m), 3.26 (3H, s), 3.32 (2H, m), 3.42 (1H, m), 3.92 (1H, m), 4.08 (2H, s), 7.14-7.30 (3H, m), 11.08 (1H, s), 11.94 (1H, s); m/z (LC-MS, ESI+), RT=1.44 min (M+H=413.36).

(c) Methyl 4-(2-(4-fluoro-3-(4-methoxypiperidine-1-carbonyl)phenyl)acetyl)-1,2,5-trimethyl-1H-pyrrole-3-carboxylate (59)

Iodomethane (0.029 mL, 0.46 mmol) was added to methyl 4-(2-(4-fluoro-3-(4-methoxypiperidine-1-carbonyl)phenyl)acetyl)-2,5-dimethyl-1H-pyrrole-3-carboxylate (57) (0.100 g, 0.23 mmol) and potassium carbonate (0.048 g, 0.35 mmol) in DMF (5 mL). The resulting suspension was stirred at room temperature for 16 hours. The reaction was incomplete and further iodomethane (0.029 mL, 0.46 mmol) was added and the suspension was stirred at room temperature for a further 4 hours. The reaction was incomplete so the temperature was increased to 50° C. and the reaction mixture was stirred for a further 3 hours. The reaction mixture was poured into water (75 mL), extracted with EtOAc (3×50 mL), the combined organic layers were washed with water (50 mL) and saturated brine (50 mL). The organic layer was dried over Na$_2$SO$_4$, filtered and evaporated to afford crude product. The crude product was purified by flash silica chromatography, elution gradient 0 to 100% ethyl acetate in isohexane. Pure fractions were evaporated to dryness to afford the desired material as a colourless gum (0.082 g, 79% yield); m/z (LC-MS, ESI+), RT=2.06 min (M+H=445.30).

(d) 4-(4-fluoro-3-(4-methoxypiperidine-1-carbonyl)benzyl)-5,6,7-trimethyl-2,6-dihydro-1H-pyrrolo[3,4-d]pyridazin-1-one (60)

Hydrazine hydrate (0.014 mL, 0.19 mmol) was added to methyl 4-(2-(4-fluoro-3-(4-methoxypiperidine-1-carbonyl)phenyl)acetyl)-1,2,5-trimethyl-1H-pyrrole-3-carboxylate (59) (0.076 g, 0.17 mmol) in acetic acid (4 mL). The resulting solution was stirred at room temperature for 2 days. The resulting mixture was evaporated to dryness and the residue was azeotroped with toluene to afford crude product, which was purified by preparative HPLC (Waters XBridge Prep C18 OBD column, 5µ silica, 19 mm diameter, 100 mm length), using decreasingly polar mixtures of water (containing 1% NH$_3$) and MeCN as eluents. Fractions containing the desired compound were evaporated to dryness to afford the desired compound (4.00 mg, 5.49% yield); m/z (LC-MS, ESI+), RT=1.60 min (M+H=427.11).

Example 28

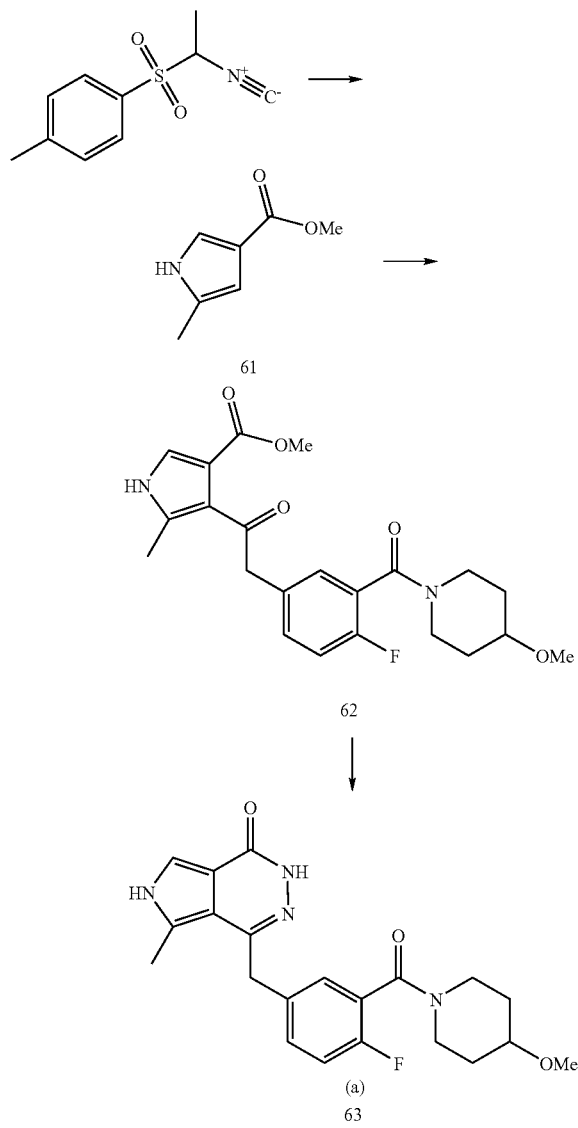

(a) Methyl 5-methyl-1H-pyrrole-3-carboxylate (61)

A solution of methyl acrylate (0.523 mL, 5.81 mmol) and 1-(1-isocyanoethylsulfonyl)-4-methylbenzene (1.215 g, 5.81 mmol) in diethyl ether (16.5 mL) and DMSO (8.5 mL) were added dropwise to a stirred suspension of sodium hydride (60% dispersion) (0.372 g, 9.29 mmol) in diethyl ether (25 mL) under nitrogen. The resulting suspension was stirred at room temperature for 2 hours. The reaction mixture was poured into 2% sodium chloride solution (200 mL), layers separated and the aqueous extracted with Et$_2$O (4×50 mL), the organic layers were combined washed with water (50 mL), dried over Na$_2$SO$_4$, filtered and evaporated to afford beige solid. The crude product was purified by flash silica chromatography, elution gradient 0 to 40% ethyl acetate in isohexane. Pure fractions were evaporated to dryness to afford the desired compound as a white solid (0.527 g, 65.2% yield); $^1$H NMR (400.132 MHz, CDCl$_3$) δ 2.19 (3H, s), 3.72 (3H, s), 6.23 (1H, m), 7.21 (1H, m), 8.09 (1H, s); m/z (LC-MS, ESI+), RT=1.30 min (no mass ion detected).

(b) Methyl 4-(2-(4-fluoro-3-(4-methoxypiperidine-1-carbonyl)phenyl)acetyl)-5-methyl-1H-pyrrole-3-carboxylate (62)

A solution of methyl 5-methyl-1H-pyrrole-3-carboxylate (61) (0.104 g, 0.74 mmol) in anhydrous DCM (5 mL) was added dropwise to a stirred suspension of aluminum trichloride (0.226 g, 1.69 mmol) in anhydrous DCM (10 mL) at 0° C., under nitrogen. The resulting suspension was stirred at 0° C. for 10 minutes. A solution of the requisite acid chloride [prepared earlier; 1-chloro-N,N,2-trimethylprop-1-en-1-amine (0.090 mL, 0.68 mmol) was added to a solution of 2-(4-fluoro-3-(4-methoxypiperidine-1-carbonyl)phenyl)acetic acid (0.200 g, 0.68 mmol) in anhydrous DCM (5 mL) at 0° C. and stirred for 2 hours] was added dropwise to the stirred suspension at 0° C. The resulting suspension was allowed to warm to room temperature and then stirred at room temperature for a further 18 hours. The reaction was incomplete and further aluminum trichloride (0.226 g, 1.69 mmol) was added and the solution was stirred at room temperature for a further 1 hour. The reaction mixture was poured onto ice (50 mL) and conc HCl (2 mL). The layers were separated and the aqueous layer extracted with DCM (2×50 mL). The combined organics were washed sequentially with 2M HCl (2×75 mL), water (50 mL), and saturated NaHCO$_3$ (50 mL). The organic layer was dried over Na$_2$SO$_4$, filtered and evaporated to afford crude product. The crude product was purified by flash silica chromatography, elution gradient 0 to 100% ethyl acetate in isohexane. Pure fractions were evaporated to dryness to afford the desired material as a colourless gum (0.117 g, 41.5% yield); $^1$H NMR (400.132 MHz, CDCl$_3$) δ 1.44-1.77 (3H, m), 1.85 (1H, m), 2.10 (3H, s), 3.08 (1H, m), 3.29 (3H, s), 3.36-3.55 (3H, m), 3.75 (3H, s), 3.92 (1H, m), 4.16 (2H, m), 6.93 (1H, t), 7.07-7.12 (2H, m), 7.21 (1H, m), 8.82 (1H, s); m/z (LC-MS, ESI+), RT=1.72 min (M+H=417.20).

(c) 4-(4-fluoro-3-(4-methoxypiperidine-1-carbonyl)benzyl)-5-methyl-2,6-dihydro-1H-pyrrolo[3,4-d]pyridazin-1-one (63)

Hydrazine hydrate (0.023 mL, 0.31 mmol) was added to methyl 4-(2-(4-fluoro-3-(4-methoxypiperidine-1-carbonyl)phenyl)acetyl)-5-methyl-1H-pyrrole-3-carboxylate (62) (0.117 g, 0.28 mmol) in acetic acid (4 mL). The resulting solution was stirred at room temperature for 2 days. The resulting mixture was evaporated to dryness and the residue was azeotroped with toluene to afford crude product, which was purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired compound (0.022 g, 19.65% yield); $^1$H NMR (400.132 MHz, DMSO) δ 1.21 (1H, m), 1.34 (1H, m), 1.62 (1H, m), 1.77 (1H, m), 2.25 (3H, s), 2.96 (1H, m), 3.15-3.36 (6H, m), 3.82 (1H, s), 4.05 (2H, s), 7.07-7.15 (2H, m), 7.19 (1H, m), 7.33 (1H, s), 11.22 (1H, s), 12.15 (1H, s); m/z (LC-MS, ESI+), RT=1.39 min (M+H=399.15).

Example 29

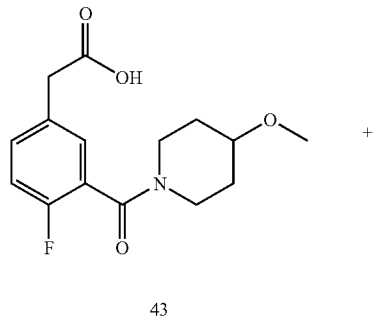

43

+

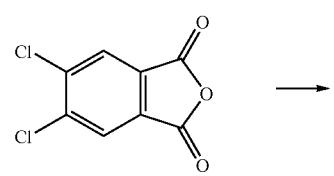

→

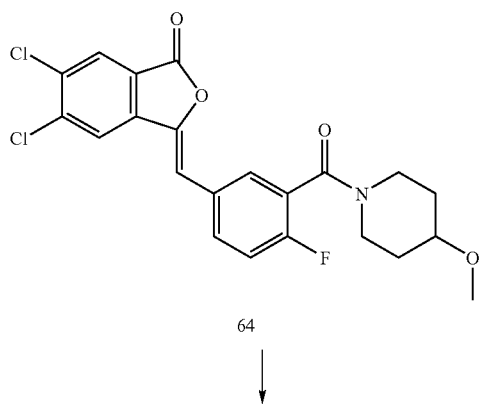

64

↓

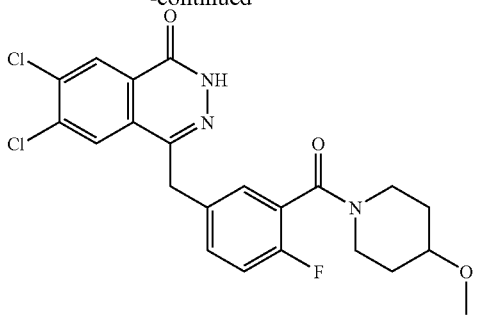

65

(a) (Z)-5,6-dichloro-3-(4-fluoro-3-(4-methoxypiperidine-1-carbonyl)benzylidene)isobenzofuran-1(3H)-one (64)

A flask charged with 5,6-dichloroisobenzofuran-1,3-dione (370 mg, 1.71 mmol), 2-(4-fluoro-3-(4-methoxypiperidine-1-carbonyl)phenyl)acetic acid (43) (496 mg, 1.68 mmol) and Sodium acetate (34 mg, 0.41 mmol) was lowered into a preheated aluminium block at 210° C. The resulting mixture was heated further and stirred at 240° C. for 1 hour then cooled. The residue was triturated, with sonication, under ethanol (~25 mL) and solid collected by suction filtration to afford crude product (128 mg, 16.92%), which was used directly without further purification; m/z (LC-MS, ESI+), RT=2.79 (M+H 450.1 & 452.0).

(b) 6,7-dichloro-4-(4-fluoro-3-(4-methoxypiperidine-1-carbonyl)benzyl)phthalazin-1(2H)-one (65)

(Z)-5,6-dichloro-3-(4-fluoro-3-(4-methoxypiperidine-1-carbonyl)benzylidene)isobenzofuran-1(3H)-one (64) (127 mg, 0.28 mmol) was taken up in water (2 mL) and N,N-dimethylformamide (0.500 mL). The resulting mixture was treated with hydrazine hydrate (0.080 mL, 1.65 mmol) and the reaction was heated to 105° C. with stirring for 90 minutes. The reaction mixture was cooled, diluted with water (~10 mL) and solid collected by suction filtration to afford the crude product, which was purified by flash silica chromatography, eluting with neat ethyl acetate. Pure fractions were evaporated to dryness and the residue triturated under diethyl ether and dried under vacuum to afford the desired material as a white solid (46.0 mg, 35% yield); $^1$H NMR (400.132 MHz, DMSO) δ 1.30-1.40 (1H, m), 1.44-1.53 (1H, m), 1.72-1.79 (1H, m), 1.87-1.94 (1H, m), 3.04-3.11 (1H, m), 3.29 (3H, s), 3.30-3.40 (2H, m), 3.44-3.49 (1H, m), 3.92-4.00 (1H, m), 4.37 (2H, s), 7.26 (1H, t), 7.38-7.45 (2H, m), 8.29 (1H, s), 8.40 (1H, s), 12.83 (1H, s); m/z (LC-MS, ESI+), RT=2.13 (M+H 464 & 465.9).

Example 30

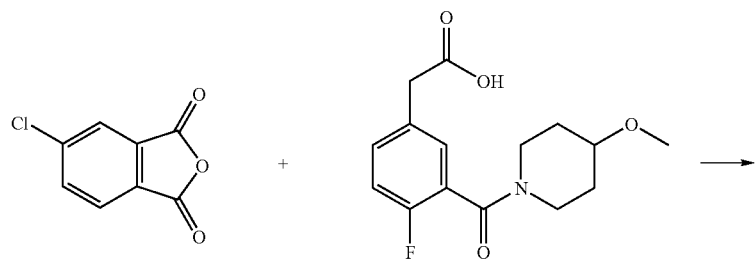

43

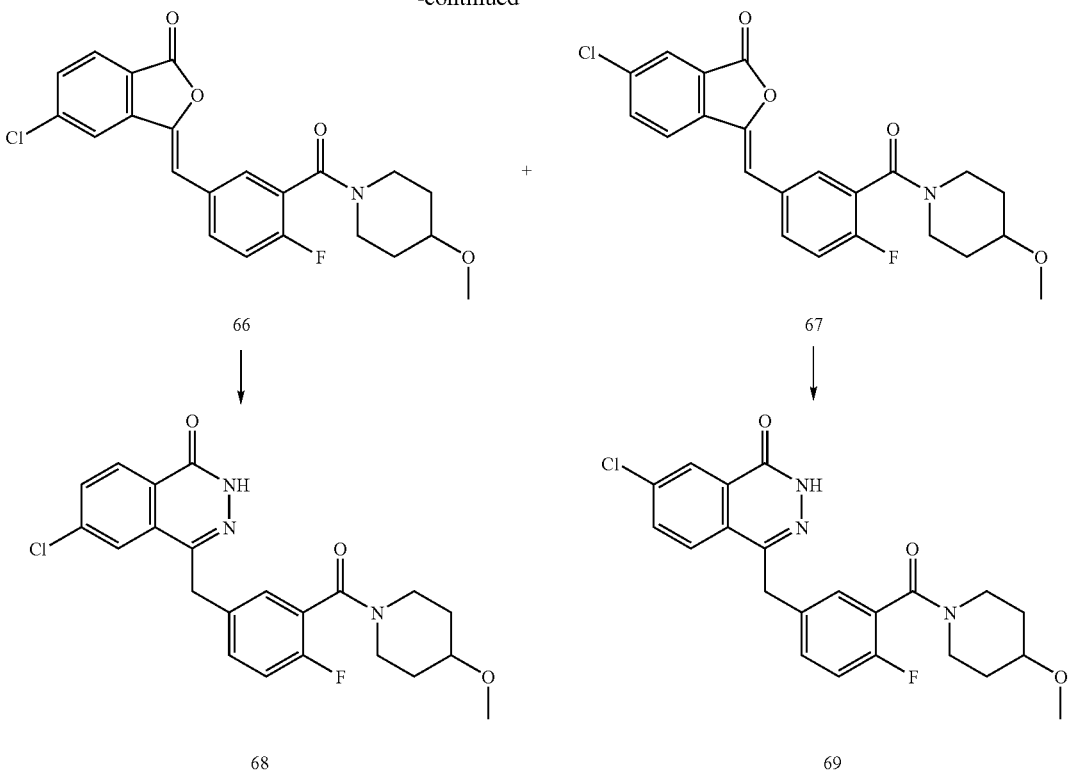

(a) (Z)-6-chloro-3-(4-fluoro-3-(4-methoxypiperidine-1-carbonyl)benzylidene)isobenzofuran-1(3H)-one (67) & (Z)-5-chloro-3-(4-fluoro-3-(4-methoxypiperidine-1-carbonyl)benzylidene)isobenzofuran-1(3H)-one (66)

A flask charged with 5-chloroisobenzofuran-1,3-dione (313 mg, 1.71 mmol), 2-(4-fluoro-3-(4-methoxypiperidine-1-carbonyl)phenyl)acetic acid (43) (496 mg, 1.68 mmol) and sodium acetate (37 mg, 0.45 mmol) was lowered into a pre-heated aluminium block at 210° C. The resulting mixture was heated further and stirred at 240° C. for 45 minutes then cooled. The residue was taken up in ethanol (~10 mL) and diethyl ether added (~40 mL). The resultant solid was collected by suction filtration. The filtrate was evaporated and the residue purified by flash silica chromatography, elution gradient 50 to 100% EtOAc in isohexane. Fractions of the required compounds were evaporated to dryness to afford the two regioisomers 67 as a beige solid (27.0 mg, 3.87%); $^1$H NMR (400.132 MHz, DMSO) δ 1.38-1.55 (2H, m), 1.79-1.86 (1H, m), 1.89-1.96 (1H, m), 3.12-3.19 (1H, m), 3.28 (3H, s), 3.36-3.43 (2H, m), 3.45-3.51 (1H, m), 3.96-4.03 (1H, m), 7.05 (1H, s), 7.45 (1H, t), 7.80 (1H, dd), 7.88-7.92 (1H, m), 7.98 (1H, dd), 8.07 (1H, d), 8.12 (1H, d); m/z (LC-MS, ESI+), RT=2.65 (M+H 416.1 & 417.9); and 66 as a beige solid (55.0 mg, 7.87%); $^1$H NMR (400.132 MHz, DMSO) δ 1.38-1.54 (2H, m), 1.79-1.85 (1H, m), 1.89-1.96 (1H, m), 3.11-3.19 (1H, m), 3.28 (3H, s), 3.35-3.43 (2H, m), 3.44-3.50 (1H, m), 3.95-4.02 (1H, m), 7.09 (1H, s), 7.44 (1H, t), 7.73 (1H, dd), 7.77 (1H, dd), 7.85-7.89 (1H, m), 7.99 (1H, d), 8.28 (1H, d); m/z (LC-MS, ESI+), RT=2.63 (M+H 416.1 &417.9) which were taken on directly to the next stage.

(b) 6-chloro-4-(4-fluoro-3-(4-methoxypiperidine-1-carbonyl)benzyl)phthalazin-1(2H)-one (68)

(Z)-5-chloro-3-(4-fluoro-3-(4-methoxypiperidine-1-carbonyl)benzylidene)isobenzofuran-1 (3H)-one (66) (53 mg, 0.13 mmol) was suspended in water (1.5 mL) and N,N-dimethylformamide (0.5 mL) and treated with Hydrazine monohydrate (35 μl, 0.72 mmol). The resulting mixture was stirred at 105° C. for 1 hour. The reaction mixture was cooled and diluted with water (~5 mL) and mixture extracted with DCM (2×5 mL). Combined organics were evaporated to dryness to afford the crude product, which was purified by preparative HPLC (Waters XBridge Prep C18 OBD column, 5μ silica, 19 mm diameter, 100 mm length), using decreasingly polar mixtures of water (containing 1% NH3) and acetonitrile as eluents. Fractions containing the desired compound were evaporated to dryness to afford the desired material as a white solid (13 mg, 24% yield); $^1$H NMR (400.132 MHz, DMSO) δ 1.28-1.38 (1H, m), 1.40-1.50 (1H, m), 1.49-1.76 (1H, m), 1.83-1.91 (1H, m), 3.01-3.09 (1H, m), 3.25 (3H, s), 3.26-3.37 (2H, m), 3.40-3.46 (1H, m), 3.88-3.96 (1H, m), 4.34 (2H, s), 7.22 (1H, t), 7.35-7.42 (2H, m), 7.87 (1H, dd), 8.02 (1H, d), 8.26 (1H, d), 12.68 (1H, s); m/z (LC-MS, ESI+), RT=2.24 (M+H 430.6).

(c) 7-chloro-4-(4-fluoro-3-(4-methoxypiperidine-1-carbonyl)benzyl)phthalazin-1(2H)-one (69)

(Z)-6-chloro-3-(4-fluoro-3-(4-methoxypiperidine-1-carbonyl)benzylidene)isobenzofuran-1(3H)-one (67) (25 mg, 0.06 mmol) was taken up in water (1 mL) and N,N-dimethylformamide (0.5 mL) and treated with Hydrazine monohydrate (20 μL, 0.41 mmol). The resulting mixture was stirred at 105° C. for 1 hour. The reaction mixture was cooled and diluted with water (~5 mL) and mixture extracted with DCM (2×5 mL). Combined organics were evaporated to dryness to afford the crude product, which was purified by preparative HPLC (Waters XBridge Prep C18 OBD column, 5μ silica, 19 mm diameter, 100 mm length), using decreasingly polar mixtures of water (containing 1% NH₃) and acetonitrile as eluents. Fractions containing the desired compound were evaporated to dryness to afford the desired material as a white foam (10 mg, 39% yield); ¹H NMR (400.132 MHz, DMSO) δ 1.26-1.35 (1H, m), 1.40-1.49 (1H, m), 1.67-1.74 (1H, m), 1.83-1.90 (1H, m), 2.99-3.06 (1H, m), 3.26 (3H, s), 3.26-3.36 (2H, m), 3.39-3.45 (1H, m), 3.88-3.95 (1H, m), 4.33 (2H, s), 7.22 (1H, t), 7.31 (1H, dd), 7.38-7.42 (1H, m), 7.94 (1H, dd), 8.00 (1H, d), 8.21 (1H, d), 12.72 (1H, s); m/z (LC-MS, ESI+), RT=2.23 (M+H 430.7).

Example 31

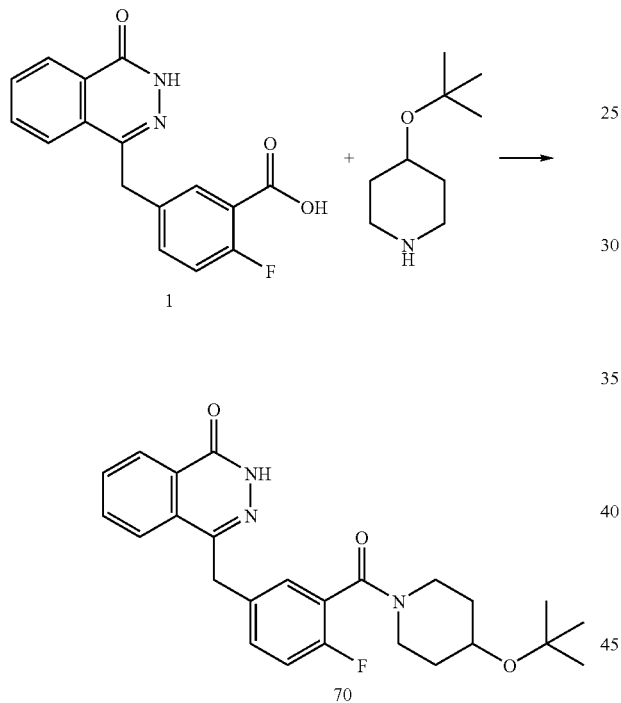

(a) 4-(3-(4-tert-butoxypiperidine-1-carbonyl)-4-fluorobenzyl)phthalazin-1(2H)-one (70) A solution of 2-fluoro-5-((4-oxo-3,4-dihydrophthalazin-1-yl)methyl)benzoic acid (1) (650 mg, 2.18 mmol) and 4-tert-butoxypiperidine (350 mg, 2.23 mmol) in N,N-dimethylacetamide (11 mL) was treated with triethylamine (0.750 mL, 5.38 mmol) and O-benzotriazol-1-yl-N,N,N',N'-tetra-methyluronium hexafluorophosphate (1.15 g, 3.03 mmol) The resulting mixture was stirred at ambient temperature overnight. The reaction mixture was poured onto water (~200 mL) and resultant solid collected by suction filtration and dried to afford the crude product, which was purified by flash silica chromatography, elution gradient 2 to 10% methanol in dichloromethane. Pure fractions were evaporated to dryness and dried under vacuum to afford the desired material as a white solid (460 mg, 48.2% yield); ¹H NMR (400.132 MHz, DMSO) δ 1.14 (9H, s), 1.19-1.38 (2H, m), 1.53-1.60 (1H, m), 1.70-1.77 (1H, m), 3.02-3.10 (1H, m), 3.16-3.28 (2H, m), 3.70-3.77 (1H, m), 4.02-4.10 (1H, m), 4.33 (2H, s), 7.20 (1H, t), 7.31-7.35 (1H, m), 7.38-7.42 (1H, m), 7.81-7.90 (2H, m), 7.97 (1H, d), 8.27 (1H, dd), 12.56 (1H, s); m/z (LC-MS, ESI+), RT=2.13 (M+H 438.2).

Example 32

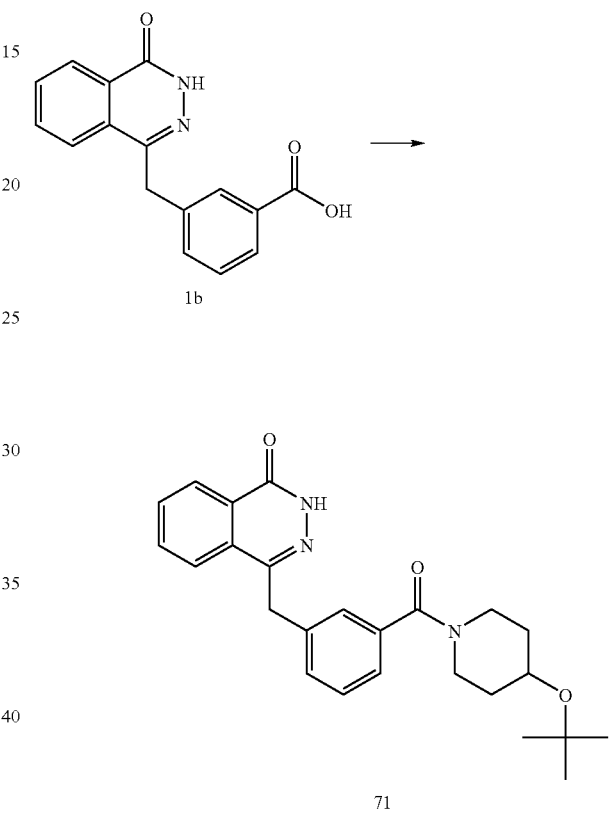

(a) 4-[[3-[4-[(2-methylpropan-2-yl)oxy]piperidine-1-carbonyl]phenyl]methyl]-2H-phthalazin-1-one (71)

To 20 ml vial was added 3-[(4-oxo-3H-phthalazin-1-yl)methyl]benzoic acid (1b) (50 mg, 0.178 mmol). To this was added N,N-dimethylacetamide (2 mL) and triethylamine (70 μL, 0.445 mmol). This mixture was allowed to stir for 5 mins before addition of O-benzotriazol-1-yl-N,N,N',N'-tetra-methyluronium hexafluorophosphate, this solution was also allowed to stir for a further 5 minutes. A solution of 4-[(2-methylpropan-2-yl)oxy]piperidine hydrochloride (35 mg, 0.178 mmol) in N,N-dimethylacetamide (1 mL) and triethylamine (25 μl, 0.179 mmol) was then added and the reaction left to stir at ambient temperature for 2 hours before being purified by preparative HPLC to afford the desired compound; m/z (LC-MS, ESI+), RT=1.74 (M+H 420.4).

Example 33

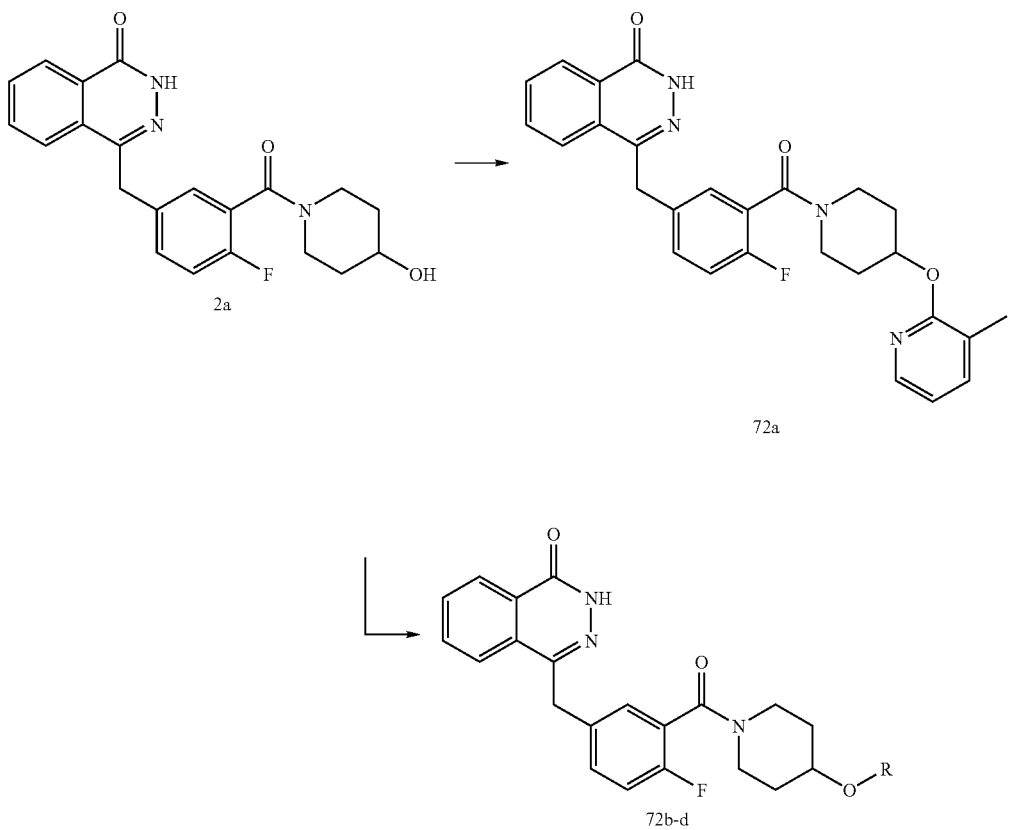

(a) 4-[[4-fluoro-3-[4-(3-methylpyridin-2-yl)oxypiperidine-1-carbonyl]phenyl]methyl]-2H-phthalazin-1-one (72a)

A solution of crude 4-[[4-fluoro-3-(4-hydroxypiperidine-1-carbonyl)phenyl]methyl]-2H-phthalazin-1-one (2a) (50 mg, 0.131 mmol) in N,N-dimethylacetamide (1 mL) was treated with sodium hydride (60% in mineral oil; 3.8 mg, 0.157 mmol) and the reaction was left stirring at ambient temperature until effervescence had stopped. 2-fluoro-3-methylpyridine (16 mg, 0.144 mmol) was then added and the reaction mixture sealed into a microwave tube, heated to 170° C. and held at that temperature for 250 seconds before cooling to ambient temperature. The mixture was then purified by preparative HPLC to afford the desired material; m/z (LC-MS, ESI+), RT=4.22 (M+H 473.2)

(b) Analogous Examples

Using a method analogous to that described for 72a, 4-[[4-fluoro-3-(4-hydroxypiperidine-1-carbonyl)phenyl]methyl]-2H-phthalazin-1-one was reacted with the appropriate fluoropyridine at 170° C., for 10 minutes, and purified by preparative HPLC to afford the required compounds.

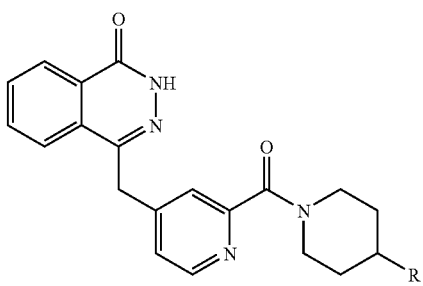

| | R | Purity | RT (min) | M + H |
|---|---|---|---|---|
| 72b | 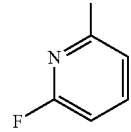 | 98 | 1.49 | 477.3 |

91
-continued

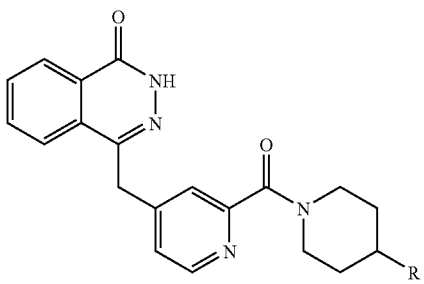

| | R | Purity | RT (min) | M + H |
|---|---|---|---|---|
| 72c | *–O–pyridyl-methyl | 98 | 1.44 | 473.3 |
| 72d | *–O–pyridyl-methyl | 96 | 1.43 | 473.3 |

Example 34

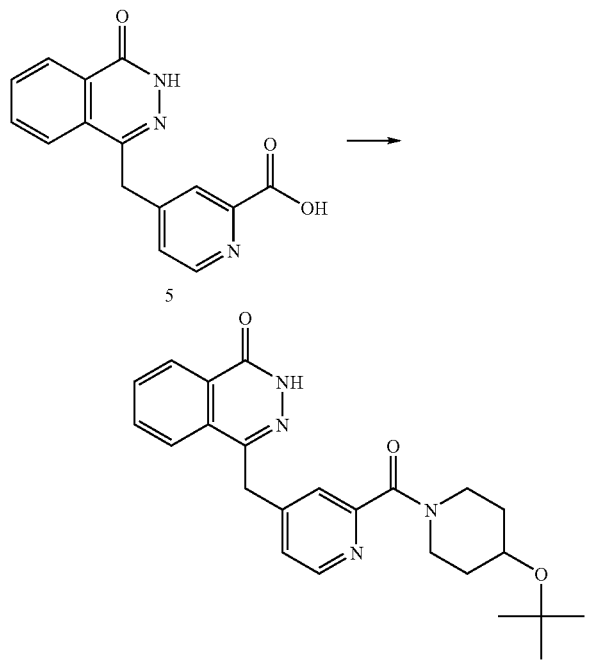

73

92

(a) 4-((2-(4-tert-butoxypiperidine-1-carbonyl)pyridin-4-yl)methyl)phthalazin-1(2H)-one (73)

A solution of 4-tert-butoxypiperidine hydrochloride (227 mg, 1.17 mmol) and triethylamine (0.327 mL, 2.35 mmol) in N,N-dimethlformamide (3 mL) was added in one portion to a stirred solution of 4-((4-oxo-3,4-dihydrophthalazin-1-yl)methyl)picolinic acid (5) (300 mg, 1.07 mmol), Triethylamine (0.327 mL, 2.35 mmol) and O-Benzotriazol-1-yl-N,N,N',N'-tetra-methyluronium hexafluorophosphate (607 mg, 1.60 mmol) in N,N-dimethlformamide (3 mL) at 25° C. The resulting solution was stirred at 25° C. for 4 hours, then The crude mixture was purified by preparative HPLC (Waters XBridge Prep C18 OBD column, 5µ silica, 30 mm diameter, 100 mm length), using decreasingly polar mixtures of water (containing 1% $NH_3$) and MeCN as eluents. Fractions containing the desired compound were evaporated to dryness and lyophilised to afford the desired compound as a solid (250 mg, 55.7% yield); $^1$H NMR (400.132 MHz, DMSO) δ 1.15 (9H, s), 1.25-1.40 (2H, m), 1.56-1.63 (1H, m), 1.71-1.79 (1H, m), 3.08-3.23 (2H, m), 3.44-3.50 (1H, m), 3.71-3.78 (1H, m), 4.01-4.08 (1H, m), 4.40 (2H, s), 7.39 (1H, dd), 7.48-7.49 (1H, m), 7.83-7.87 (1H, m), 7.90 (1H, td), 7.94-7.97 (1H, m), 8.28 (1H, dd), 8.46-8.48 (1H, m), 12.60 (1H, s); m/z (LC-MS, ESI+), RT=1.67 (M+H 421.5).

Example 35

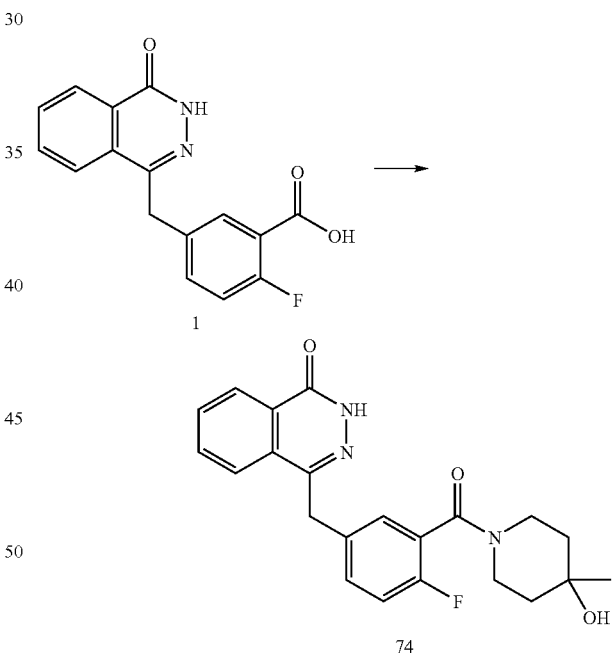

(a) 4-(4-fluoro-3-(4-hydroxy-4-methylpiperidine-1-carbonyl)benzyl)phthalazin-1(2H)-one (74)

O-Benzotriazol-1-yl-N,N,N',N'-tetra-methyluronium hexafluorophosphate (572 mg, 1.51 mmol) was added in one portion to 2-fluoro-5-((4-oxo-3,4-dihydrophthalazin-1-yl)methyl)benzoic acid (1) (300 mg, 1.01 mmol) and triethylamine (0.308 mL, 2.21 mmol) in N,N-dimethylformamide (3 mL) at 25° C. under an air atmosphere. The resulting solution was stirred at 25° C. for 10 minutes. A solution of 4-methylpiperidin-4-ol hydrochloride (154 mg, 1.02 mmol) and triethylamine (0.308 mL, 2.21 mmol) in N,N-dimethylformamide (1 mL) was added dropwise and the resulting solution stirred at 25° C. for 2 hours. The reaction mixture was diluted with DCM (100 mL), and washed sequentially with water (3×50 mL) and saturated brine (20 mL). The organic layer was dried over $MgSO_4$, filtered and evaporated to afford crude product, which was purified by preparative HPLC (Waters XBridge Prep C18 OBD column, 5μ silica, 19 mm diameter, 100 mm length), using decreasingly polar mixtures of water (containing 1% $NH_3$) and MeCN as eluents. Fractions containing the desired compound were evaporated to dryness to afford the desired material as a gum (94 mg, 23.63% yield); $^1$H NMR (400.132 MHz, DMSO) δ 1.13 (3H, s), 1.29-1.47 (4H, m), 3.20-3.28 (4H, m), 4.32 (2H, s), 4.41 (1H, s), 7.19 (1H, d), 7.31 (1H, dd), 7.38-7.42 (1H, m), 7.83 (1H, td), 7.88 (1H, td), 7.96 (1H, d), 8.27 (1H, dd), 12.56 (1H, s); m/z (LC-MS, ESI+), RT=1.45 (M+H 396.4).

Example 36

(a) Tert-butyl 4-(2-morpholino-2-oxoethoxy)piperidine-1-carboxylate (75)

Tert-butyl 4-hydroxypiperidine-1-carboxylate (10 g, 49.69 mmol), tetrabutylammonium hydrogensulfate (0.844 g, 2.48 mmol) and 2-chloro-1-morpholinoethanone (8.13 g, 49.69 mmol) were added to toluene (75 mL) to this was added NaOH (40 g, 400.03 mmol) in water (45 mL) and the reaction was stirred at 25° C. overnight. The reaction mixture was quenched with water (100 mL), extracted with $Et_2O$ (3×75 mL), the organic layer was dried over MgSO4, filtered and evaporated to afford a white solid. This was redissolved in DCM and evaporated carefully to give a yellow gum, diethyl ether was added followed by iso-hexane until a cloudy solution was observed. The system was stirred to afford a solid which was collected by filtration and dried under vacuum to give the desired compound as a white solid (15.30 g, 94% yield); $^1$H NMR (400.132 MHz, $CDCl_3$) δ 1.45 (9H, s), 1.58-1.49 (OH, m), 1.72-1.61 (2H, m), 1.89-1.82 (2H, m), 3.12-3.06 (2H, m), 3.61-3.54 (6H, m), 3.68-3.67 (4H, m), 3.80-3.72 (1H, m), 4.18 (2H, s).

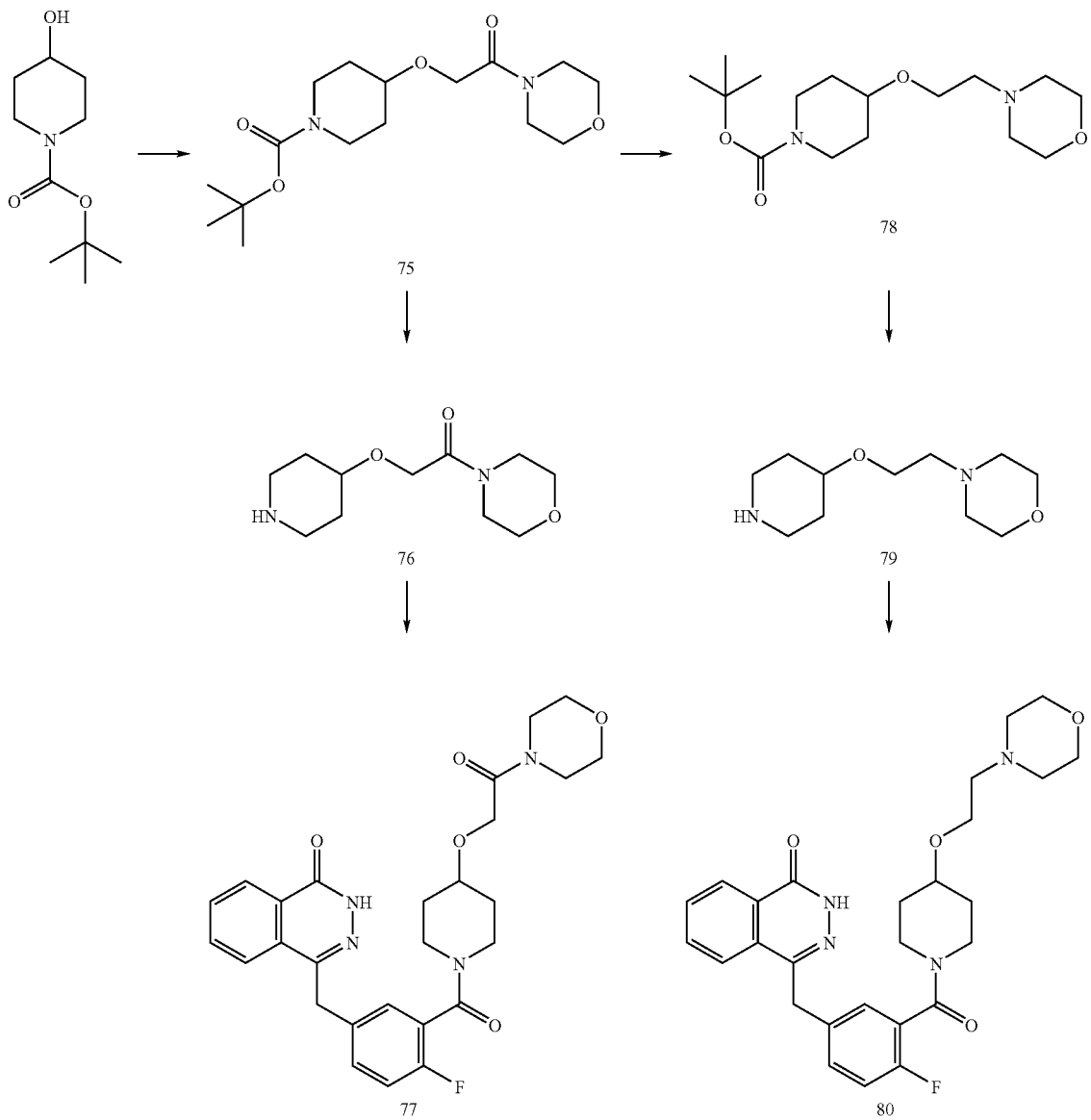

(b) 1-morpholino-2-(piperidin-4-yloxy)ethanone (76)

Tert-butyl 4-(2-morpholino-2-oxoethoxy)piperidine-1-carboxylate (75) (5 g, 15.23 mmol) was added to 6.0 HCl in propan-2-ol (30 mL, 180.00 mmol) and the reaction was stirred at 25° C. for 2 hours. The reaction mixture was evaporated to dryness and the crude material was purified by ion exchange chromatography, using an SCX column. The desired product was eluted from the column using 7M NH3/MeOH and fractions were evaporated to dryness to afford a yellow gum. The crude product was purified by distillation at 0.72 mBar, collecting fractions that distilled at 155° C. to afford the desired material as a colourless gum (1.950 g, 56.1% yield); $^1$H NMR (400.132 MHz, CDCl$_3$) δ 1.50-1.41 (2H, m), 1.96-1.89 (2H, m), 2.64-2.58 (2H, m), 3.10-3.04 (2H, m), 3.50-3.43 (1H, m), 3.63-3.56 (4H, m), 3.70-3.67 (4H, m), 4.17 (2H, s); NH proton missing.

(c) 4-(4-fluoro-3-(4-(2-morpholino-2-oxoethoxy)piperidine-1-carbonyl)benzyl)phthalazin-1(2H)-one (77)

2-fluoro-5-((4-oxo-3,4-dihydrophthalazin-1-yl)methyl)benzoic acid (1) (0.2 g, 0.67 mmol), 1-morpholino-2-(piperidin-4-yloxy)ethanone (76) (0.153 g, 0.67 mmol) and 2-(1H-benzo[d][1,2,3]triazol-1-yl)-1,1,3,3-tetramethylisouronium tetrafluoroborate (0.215 g, 0.67 mmol) were dissolved in DMF (10 mL), to this was added DIPEA (0.117 mL, 0.67 mmol) and the reaction was stirred for 1 hour. The solvent was evaporated to dryness and the gum was dissolved in acetonitrile (4 mL). The crude product was purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired material as a white foam (0.214 g, 62.8%); $^1$H NMR (400.132 MHz, CDCl$_3$) δ 1.64-1.53 (1H, m), 1.75-1.67 (2H, m), 1.86-1.75 (1H, m), 1.98-1.93 (1H, m), 3.16-3.07 (1H, m), 3.57-3.39 (3H, m), 3.64-3.58 (2H, m), 3.72-3.66 (5H, m), 4.11-3.99 (1H, m), 4.19 (2H, q), 4.27 (2H, s), 7.02 (1H, t), 7.32-7.26 (2H, m), 7.77-7.69 (3H, m), 8.49-8.44 (1H, m), 10.51 (1H, s); Very broad peaks due to rotamers; m/z (LC-MS, ESI+), RT=1.48 (M+H 509).

(d) Tert-butyl 4-(2-morpholinoethoxy)piperidine-1-carboxylate (78)

Tert-butyl 4-(2-morpholino-2-oxoethoxy)piperidine-1-carboxylate (75) (8.84 g, 26.92 mmol) was dissolved in dry THF (50 mL), to this was added borane-methyl sulfide complex (20.19 mL, 40.38 mmol) and the reaction was stirred at 40° C. for 3 hours then at ambient temperature overnight. The gummy mixture was evaporated and was quenched with 2.0 N sodium carbonate (50 mL), extracted with EtOAc (3×75 mL), the organic layer was dried over MgSO$_4$, filtered and evaporated to afford The desired material as a colourless liquid (6.50 g, 77% yield); $^1$H NMR (400.132 MHz, CDCl$_3$) δ 1.45 (9H, s), 1.54-1.45 (2H, m), 1.84-1.79 (2H, m), 2.90-2.84 (2H, m), 3.16-3.03 (6H, m), 3.79-3.67 (5H, m), 3.97 (2H, t), 4.15-4.10 (2H, m).

(e) 4-(2-(piperidin-4-yloxy)ethyl)morpholine (79)

Tert-butyl 4-(2-morpholinoethoxy)piperidine-1-carboxylate (78) (7.0 g, 22.26 mmol) was added to 6.0 HCl in propan-2-ol (30 mL, 180.00 mmol) and the reaction was stirred at 25° C. for 2 hours. The reaction mixture was evaporated to dryness and redissolved in methanol (75 mL) and water (7 mL), this was basified by stirring with solid sodium hydroxide for 1 hour. The reaction was filtered and evaporated to afford a gummy solid. This was stirred with ethyl acetate (75 mL) for 20 minutes, filtered and evaporated to afford a clear liquid. The crude product was purified by distillation at 1.2 mBar, collecting fractions that distilled at 120° C. to afford the desired material as a colourless oil (3.10 g, 65.0%); $^1$H NMR (400.132 MHz, CDCl$_3$) δ 1.47-1.38 (2H, m), 1.93-1.89 (2H, m), 2.53-2.51 (4H, m), 2.63-2.56 (4H, m), 3.08 (2H, dt), 3.38-3.31 (1H, m), 3.61 (2H, t), 3.71 (4H, dd).

(f) 4-(4-fluoro-3-(4-(2-morpholinoethoxy)piperidine-1-carbonyl)benzyl)phthalazin-1(2H)-one (80)

2-fluoro-5-((4-oxo-3,4-dihydrophthalazin-1-yl)methyl)benzoic acid (1)(0.2 g, 0.67 mmol), 4-(2-(piperidin-4-yloxy)ethyl)morpholine (79) (0.144 g, 0.67 mmol) and 2-(1H-benzo[d][1,2,3]triazol-1-yl)-1,1,3,3-tetramethylisouronium tetrafluoroborate (0.215 g, 0.67 mmol) were dissolved in DMF (10 mL), to this was added DIPEA (0.117 mL, 0.67 mmol) and the reaction was stirred for 1 hour. The solvent was evaporated to dryness and the gum was dissolved in acetonitrile (4 mL). The crude product was purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired material as a white foam (0.055 g, 16.6% yield); $^1$H NMR (400.132 MHz, CDCl$_3$) δ 1.60-1.48 (1H, m), 1.83-1.64 (2H, m), 1.94-1.88 (1H, m), 2.59-2.57 (4H, m), 2.64 (2H, t), 3.14-3.05 (1H, m), 3.49-3.37 (1H, m), 3.58-3.51 (1H, m), 3.66-3.60 (3H, m), 3.74-3.72 (4H, m), 4.06-3.94 (1H, m), 4.28 (2H, s), 7.01 (1H, t), 7.32-7.26 (2H, m), 7.77-7.70 (3H, m), 8.48-8.44 (1H, m), 10.77 (1H, s); m/z (LC-MS, ESI+), RT=1.57 (M+H 495).

Example 37

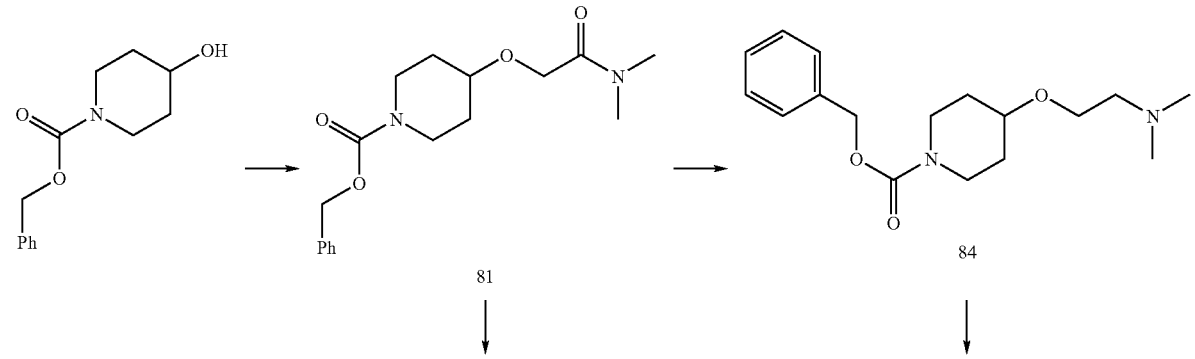

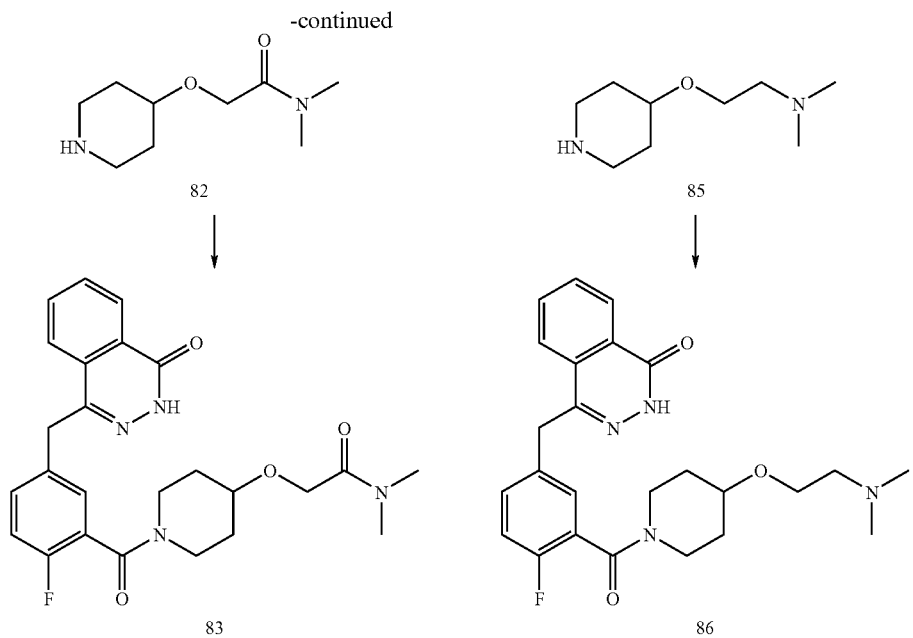

(a) Benzyl 4-(2-(dimethylamino)-2-oxoethoxy)piperidine-1-carboxylate (81)

Benzyl 4-hydroxypiperidine-1-carboxylate (5 g, 21.25 mmol), tetrabutylammonium hydrogensulfate (0.361 g, 1.06 mmol) and 2-chloro-N,N-dimethylacetamide (4.13 g, 27.63 mmol) were added to toluene (50 mL) to this was added sodium hydroxide (21 g, 210.02 mmol) in water (30 mL) and the reaction was stirred at 25° C. overnight. The reaction mixture was quenched with water (100 mL), extracted with $Et_2O$ (3×75 mL), the organic layer was dried over $MgSO_4$, filtered and evaporated to afford the desired compound as an orange liquid (6.00 g, 88% yield); $^1$H NMR (400.132 MHz, $CDCl_3$) δ 1.65-1.55 (2H, m), 1.93-1.86 (2H, m), 2.95 (3H, s), 3.03 (3H, s), 3.25-3.18 (2H, m), 3.63-3.57 (1H, m), 3.85-3.79 (2H, m), 4.17 (2H, s), 5.12 (2H, s), 7.38-7.30 (5H, m).

(b) N,N-dimethyl-2-(piperidin-4-yloxy)acetamide (82)

Benzyl 4-(2-(dimethylamino)-2-oxoethoxy)piperidine-1-carboxylate (81) (3.0 g, 9.36 mmol) and palladium on carbon (0.100 g, 0.94 mmol) were added to ethanol (40 mL). This was stirred for 3 hours under an atmosphere of hydrogen. The reaction was filtered and the solvent evaporated to afford a viscous clear oil. The crude product was purified by distillation at 0.5 mBar, collecting fractions that distilled at 90° C. to afford the desired material as a colourless oil (1.000 g, 57.3% yield); $^1$H NMR (400.132 MHz, $CDCl_3$) δ 1.51-1.42 (2H, m), 1.98-1.92 (2H, m), 2.63-2.57 (2H, m), 2.95 (3H, s), 3.10-3.05 (5H, m), 3.51-3.44 (1H, m), 4.17 (2H, s) NH proton missing.

(c) 2-(1-(2-fluoro-5-((4-oxo-3,4-dihydrophthalazin-1-yl)methyl)benzoyl)piperidin-4-yloxy)-N,N-dimethylacetamide (83)

2-fluoro-5-((4-oxo-3,4-dihydrophthalazin-1-yl)methyl) benzoic acid (1) (0.2 g, 0.67 mmol), N,N-dimethyl-2-(piperidin-4-yloxy)acetamide (82) (0.125 g, 0.67 mmol) and 2-(1H-benzo[d][1,2,3]triazol-1-yl)-1,1,3,3-tetramethylisouronium tetrafluoroborate (0.215 g, 0.67 mmol) were dissolved in DMF (10 mL), to this was added DIPEA (0.117 mL, 0.67 mmol) and the reaction was stirred for 1 hour. The solvent was evaporated to dryness and the gum was dissolved in acetonitrile (4 mL). The crude product was purified by preparative HPLC (Waters XBridge Prep C18 OBD column, 5μ silica, 19 mm diameter, 100 mm length), using decreasingly polar mixtures of water (containing 1% $NH_3$) and MeCN as eluents. Fractions containing the desired compound were evaporated to dryness to afford the desired material as a cream solid (0.191 g, 61.1% yield); $^1$H NMR (400.132 MHz, $CDCl_3$) δ 1.98-1.55 (4H, m), 2.96 (3H, s), 3.03 (3H, s), 3.17-3.06 (1H, m), 3.60-3.43 (2H, m), 3.72-3.67 (1H, m), 4.08-3.99 (1H, m), 4.19 (2H, q), 4.28 (2H, s), 7.01 (1H, t), 7.32-7.26 (2H, m), 7.78-7.70 (3H, m), 8.48-8.46 (1H, m), 10.89 (1H, s); m/z (LC-MS, ESI+), RT=1.55 (M+H 467).

(d) Benzyl 4-(2-(dimethylamino)ethoxy)piperidine-1-carboxylate (84)

Benzyl 4-(2-(dimethylamino)-2-oxoethoxy)piperidine-1-carboxylate (81) (4.5 g, 14.05 mmol) was dissolved in dry THF (50 mL), to this was added borane-methyl sulfide complex (10.53 mL, 21.07 mmol) and the reaction was stirred at 40° C. for 3 hours then at ambient temperature overnight. The gummy mixture was evaporated and was quenched with 2.0 N $Na_2CO_3$ (50 mL), extracted with EtOAc (3×75 mL), the organic layer was dried over MgSO4, filtered and evaporated to afford the desired material as a colourless liquid (4.00 g, 93% yield); $^1$H NMR (400.132 MHz, $CDCl_3$) δ 1.60-1.51 (2H, m), 1.88-1.78 (2H, m), 2.65 (6H, s), 2.97 (2H, t), 3.29-3.22 (2H, m), 3.54-3.48 (1H, m), 3.79-3.73 (2H, m), 3.85 (2H, t), 5.12 (2H, s), 7.36-7.28 (5H, m).

(e) N,N-dimethyl-2-(piperidin-4-yloxy)ethanamine (85)

Benzyl 4-(2-(dimethylamino)ethoxy)piperidine-1-carboxylate (84) (4.5 g, 14.69 mmol) and Palladium on carbon 5% (JM Type87L; 0.9 g, 0.21 mmol) in EtOH (50 mL) were stirred under an atmosphere of hydrogen at 5 bar and 50° C. for 3 hours. The reaction was filtered and the solvent evaporated to afford a yellow gum. This was dissolved in diethyl ether (50 mL) and filtered. The solvent was removed to afford an orange oil, this was purified by distillation at 1.0 mBar, collecting fractions that distilled at 70° C. to afford the desired material as a colourless liquid (1.100 g, 55.9%); $^1$H NMR (400.132 MHz, $CDCl_3$) δ 1.47-1.38 (2H, m), 1.61 (1H, s), 1.93-1.89 (2H, m), 2.27 (6H, s), 2.50 (2H, t), 2.63-2.56 (2H, m), 3.11-3.05 (2H, m), 3.38-3.31 (1H, m), 3.56 (2H, t).

(f) 4-(3-(4-(2-(dimethylamino)ethoxy)piperidine-1-carbonyl)-4-fluorobenzyl)phthalazin-1(2H)-one (86)

2-fluoro-5-((4-oxo-3,4-dihydrophthalazin-1-yl)methyl)benzoic acid (1) (0.2 g, 0.67 mmol), N,N-dimethyl-2-(piperidin-4-yloxy)ethanamine (85) (0.116 g, 0.67 mmol) and 2-(1H-benzo[d][1,2,3]triazol-1-yl)-1,1,3,3-tetramethylisouronium tetrafluoroborate (0.215 g, 0.67 mmol) were dissolved in DMF (10 mL), to this was added DIPEA (0.117 mL, 0.67 mmol) and the reaction was stirred for 1 hour. The solvent was evaporated to dryness and the gum was dissolved in acetonitrile (4 mL). The crude product was purified by preparative HPLC (Waters XBridge Prep C18 OBD column, 5μ silica, 19 mm diameter, 100 mm length), using decreasingly polar mixtures of water (containing 1% $NH_3$) and MeCN as eluents. Fractions containing the desired compound were evaporated to dryness to afford the desired material as a white solid (0.087 g, 28.7% yield); $^1$H NMR (400.132 MHz, $CDCl_3$) δ 1.62-1.51 (1H, m), 1.84-1.66 (3H, m), 1.95-1.89 (1H, m), 2.28 (6H, s), 2.52 (2H, t), 3.15-3.01 (1H, m), 3.48-3.40 (1H, m), 3.62-3.51 (3H, m), 4.07-3.98 (1H, m), 4.27 (2H, s), 7.01 (1H, t), 7.32-7.25 (2H, m), 7.77-7.70 (3H, m), 8.47-8.45 (1H, m), 10.62 (1H, s); m/z (LC-MS, ESI+), RT=1.67 (M+H 452).

Example 38

(a) Benzyl 4-(2-(3,3-difluoroazetidin-1-yl)-2-oxoethoxy)piperidine-1-carboxylate (87)

2-(1-(Benzyloxycarbonyl)piperidin-4-yloxy)acetic acid (4.12 g, 14.05 mmol), 3,3-difluoroazetidine hydrochloride (1.4 g, 10.81 mmol) and 2-(1H-benzo[d][1,2,3]triazol-1-yl)-1,1,3,3-tetramethylisouronium tetrafluoroborate (3.47 g, 10.81 mmol) were dissolved in DMF (50 mL), to this was added DIPEA (4.91 mL, 28.10 mmol) and the reaction was stirred overnight. The solvent was evaporated and the reaction mixture was quenched with 2M NaOH (50 mL), extracted with $Et_2O$ (3×50 mL), the organic layer was dried over $MgSO_4$, filtered and evaporated to afford the desired material as a yellow gum (2.59 g, 65.1% yield); $^1$H NMR (400.132 MHz, $CDCl_3$) δ 1.67-1.49 (2H, m), 1.90-1.81 (2H, m), 3.26-3.19 (2H, m), 3.58-3.51 (1H, m), 3.84-3.78 (2H, m), 4.13 (2H, s), 4.36 (2H, t), 4.60 (2H, t), 5.12 (2H, s), 7.40-7.29 (5H, m).

(b) 1-(3,3-difluoroazetidin-1-yl)-2-(piperidin-4-yloxy)ethanone (88)

Benzyl 4-(2-(3,3-difluoroazetidin-1-yl)-2-oxoethoxy)piperidine-1-carboxylate (87) (2.59 g, 7.03 mmol) and palladium on carbon (0.075 g, 0.70 mmol) were added to ethanol (40 mL). This was stirred for 3 hours under an atmosphere of $H_2$ (1.417 g, 703.09 mmol). The reaction was filtered and the solvent evaporated to afford a viscous clear oil. The crude

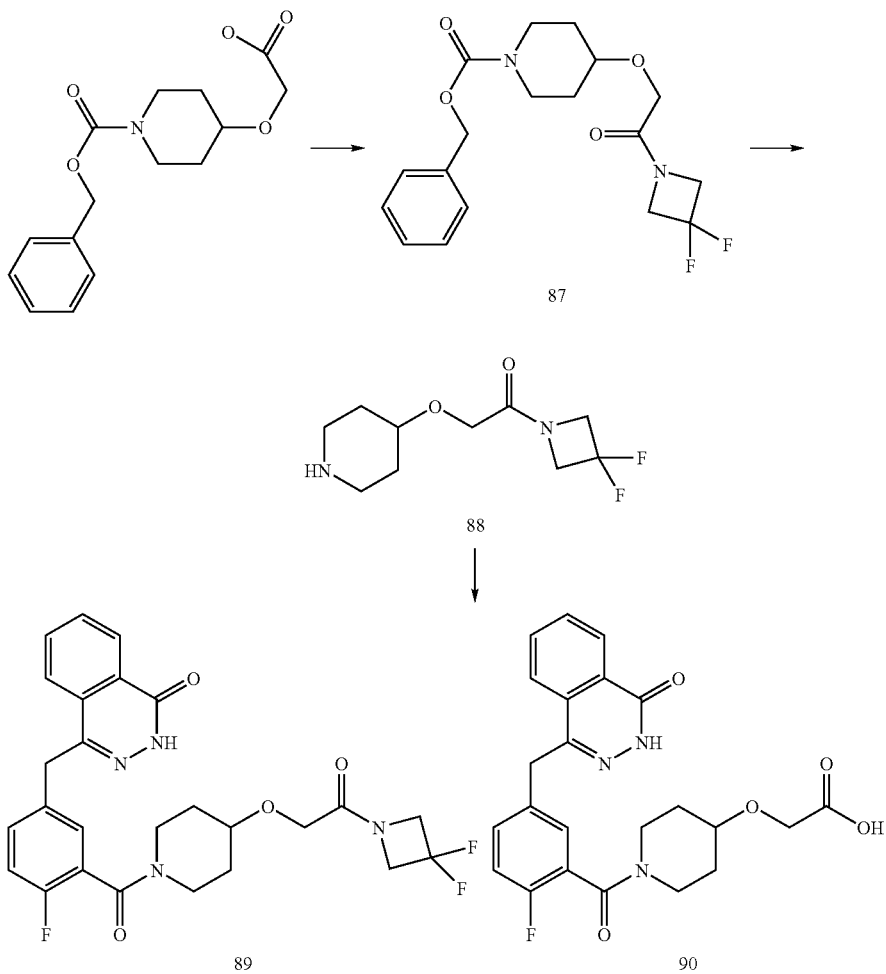

product was purified by distillation at 0.5 mBar, collecting fractions that distilled at 90° C. to afford the desired material as a colourless oil (0.540 g, 32.8% yield); $^1$H NMR (400.132 MHz, CDCl$_3$) δ 1.49-1.40 (2H, m), 1.94-1.89 (2H, m), 2.65-2.59 (2H, m), 3.10-3.05 (2H, m), 3.44-3.38 (1H, m), 4.13 (2H, s), 4.35 (2H, t), 4.64 (2H, t); NH missing (c) 4-(3-(4-(2-(3,3-difluoroazetidin-1-yl)-2-oxoethoxy)piperidine-1-carbonyl)-4-fluorobenzyl)phthalazin-1(2H)-one (89) & 2-(1-(2-fluoro-5-((4-oxo-3,4-dihydrophthalazin-1-yl)methyl)benzoyl)piperidin-4-yloxy)acetic acid (90)

2-fluoro-5-((4-oxo-3,4-dihydrophthalazin-1-yl)methyl) benzoic acid (1) (0.2 g, 0.67 mmol), 1-(3,3-difluoroazetidin-1-yl)-2-(piperidin-4-yloxy)ethanone (88) and 2-(1H-benzo[d][1,2,3]triazol-1-yl)-1,1,3,3-tetramethylisouronium tetrafluoroborate (0.215 g, 0.67 mmol) were dissolved in DMF (10 mL), to this was added DIPEA (0.117 mL, 0.67 mmol) and the reaction was stirred for 1 hour. The solvent was evaporated to dryness and the gum was dissolved in acetonitrile (4 mL). The crude product was purified by preparative HPLC (Waters XBridge Prep C18 OBD column, 5µ silica, 19 mm diameter, 100 mm length), using decreasingly polar mixtures of water (containing 1% NH$_3$) and MeCN as eluents. Fractions containing the desired compounds were evaporated to dryness to afford 4-(3-(4-(2-(3,3-difluoroazetidin-1-yl)-2-oxoethoxy)piperidine-1-carbonyl)-4-fluorobenzyl)phthalazin-1(2H)-one (89) as a white solid (0.061 g, 17.7% yield); $^1$H NMR (400.132 MHz, CDCl$_3$) δ 1.67-1.48 (2H, m), 1.86-1.75 (1H, m), 2.01-1.89 (1H, m), 3.19-3.06 (1H, m), 3.56-3.39 (2H, m), 3.66-3.57 (1H, m), 4.17-3.95 (3H, m), 4.28 (2H, s), 4.39-4.33 (2H, m), 4.62-4.57 (2H, m), 7.02 (1H, t), 7.31-7.26 (2H, m), 7.79-7.70 (3H, m), 8.48-8.46 (1H, m), 10.53 (1H, s) m/z (LC-MS, ESI+), RT=1.83 (M+H 515). and 2-(1-(2-fluoro-5-((4-oxo-3,4-dihydrophthalazin-1-yl)methyl)benzoyl)piperidin-4-yloxy)acetic acid (90) as a white solid (0.016 g, 5.50%); $^1$H NMR (400.132 MHz, CDCl3) δ 1.68-1.60 (1H, m), 1.84-1.71 (2H, m), 2.05-1.96 (1H, m), 3.16-3.04 (1H, m), 3.53-3.45 (2H, m), 3.78-3.68 (1H, m), 4.23-4.04 (3H, m), 4.32-4.28 (2H, m), 7.07-7.02 (1H, m), 7.30-7.24 (2H, m), 7.86-7.74 (3H, m), 8.47-8.42 (1H, m), 11.12 (1H, s) COOH missing; m/z (LC-MS, ESI+), RT=0.91 (M+H 440).

Example 39

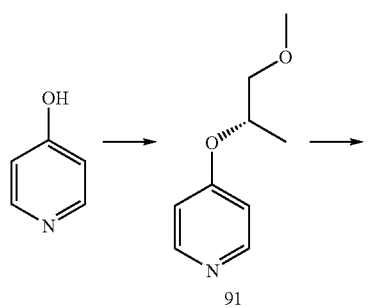

-continued

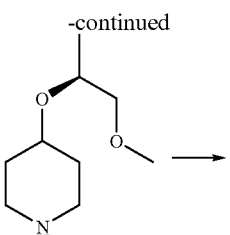

92

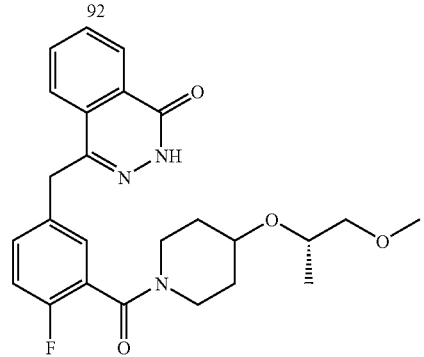

93

(a) (S)-4-(1-methoxypropan-2-yloxy)pyridine (91)

Pyridin-4-ol (10 g, 105.15 mmol), (R)-1-methoxypropan-2-ol (9.48 g, 105.15 mmol) and triphenylphosphine (30.3 g, 115.67 mmol) were added to THF (250 mL) and stirred for 10 minutes. To this was slowly added DIAD (22.49 mL, 115.67 mmol) and the reaction was stirred for 1 hour at 25° C. The solvent was evaporated and diethyl ether (100 mL) was added. To this was added a little triphenyl phosphine oxide and the reaction was stirred for 20 minutes to afford a solid, which was discarded. The solvent was evaporated and the pale yellow gum was acidified with 2.0 HCl, extracted with Et$_2$O (1×75 mL) and the aqueous was then basified with solid KOH. This was then extracted with Et$_2$O (3×75 mL), the organic layer was dried over MgSO$_4$, filtered and evaporated to afford yellow gum. This was purified by distillation at 0.43 mBar, collecting fractions that distilled at 80° C. to afford the desired material as a colourless oil (15.30 g, 87% yield); $^1$H NMR (400.132 MHz, CDCl$_3$) δ 1.34 (3H, d), 3.40 (3H, s), 3.50 (1H, dd), 3.58 (1H, dd), 4.68-4.60 (1H, m), 6.82 (2H, d), 8.40 (2H, d); m/z (LC-MS, ESI+), RT=1.28 (M+H 168).

(b) (S)-4-(1-methoxypropan-2-yloxy)piperidine (92)

(S)-4-(1-methoxypropan-2-yloxy)pyridine (91) (15 g, 89.71 mmol) and Platinum(IV) oxide in MeOH (50 mL) were stirred under an atmosphere of hydrogen at 50 bar and 80° C. for 16 hours. Analysis indicated no reaction, so 20 ml of acetic acid was added and the temperature increased to 100° C. and pressure increased to 80 bar for another 18 hrs, Still very little reaction observed. An aliquot of 5% Rhodium on alumina was added and the mixture heated overnight at 100° C., 80 bar. GCMS-2 indicated more product formation so reaction put back on at 100° C. again as the impurity peak doesn't seem to be increasing. GCMS-3 indicated more product formation so reaction put back on at 100° C. again for 48 hours as the impurity peak doesn't seem to be increasing. GCMS-4 indicated more product formation so reaction put back on at 100° C. again for 48 hours as the impurity peak doesn't seem to be increasing. GCMS-5 showed just a trace of SM with the main peak being product with the impurity slightly increased. The reaction was filtered and the solvent evaporated, the reaction was quenched with 2M NaOH (75 mL), extracted with EtOAc (3×75 mL), the organic layer was dried over MgSO4, filtered and evaporated to afford a yellow liquid. The crude product was purified by distillation at 0.89 mBar, collecting fractions that distilled at 70° C. to afford the desired compound as a colourless liquid (2.500 g, 16.08% yield); $^1$H NMR (400.132 MHz, CDCl$_3$) δ 1.14 (3H, d), 1.47-1.37 (2H, m), 1.94-1.83 (2H, m), 2.62-2.56 (2H, m), 3.10-3.06 (2H, m), 3.30-3.26 (1H, m), 3.40-3.36 (4H, m), 3.50-3.44 (1H, m), 3.75-3.66 (1H, m); NH missing.

(c) (S)-4-(4-fluoro-3-(4-(1-methoxypropan-2-yloxy)piperidine-1-carbonyl)benzyl)phthalazin-1(2H)-one (93)

2-fluoro-5-((4-oxo-3,4-dihydrophthalazin-1-yl)methyl)benzoic acid (1) (0.2 g, 0.67 mmol), (S)-4-(1-methoxypropan-2-yloxy)piperidine (92) (0.151 g, 0.87 mmol) and 2-(1H-benzo[d][1,2,3]triazol-1-yl)-1,1,3,3-tetramethylisouronium tetrafluoroborate (0.280 g, 0.87 mmol) were dissolved in DMF (10 mL), to this was added DIPEA (0.152 mL, 0.87 mmol) and the reaction was stirred for 1 hour. The solvent was evaporated to dryness and the gum was dissolved in acetonitrile (4 mL) and purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired compound as a white foam; (0.215 g, 70.7% yield) $^1$H NMR (400.132 MHz, CDCl$_3$) δ 1.13 (3H, t), 1.61-1.49 (1H, m), 1.78-1.65 (2H, m), 1.91-1.87 (1H, m), 3.17-3.01 (1H, m), 3.31-3.27 (1H, m), 3.39-3.35 (4H, m), 3.57-3.45 (2H, m), 3.72-3.67 (2H, m), 4.06-3.97 (1H, m), 4.27 (2H, s), 7.01 (1H, t), 7.31-7.26 (2H, m), 7.79-7.70 (3H, m), 8.49-8.45 (1H, m), 10.50 (1H, s); m/z (LC-MS, ESI+), RT=1.81 (M+H 454).

Example 40

(a) 3,5-dibromoisobenzofuran-1(3H)-one (94)

5-bromoisobenzofuran-1(3H)-one (E)-2,2'-(diazene-1,2-diyl)bis(2-methylpropanenitrile) (0.540 g, 3.29 mmol) and 1-bromopyrrolidine-2,5-dione (5.85 g, 32.86 mmol) were dissolved CCl4 and heated at reflux for 2 hours. The reaction was cooled and filtered, the filtrate was evaporated to afford the desired material, as a yellow solid (6.05 g, 63.1% yield), which was used directly in the next stage.

(b) (6-bromo-3-oxo-1,3-dihydroisobenzofuran-1-yl)triphenylphosphonium bromide (95)

3,5-dibromoisobenzofuran-1(3H)-one (94) (6.2 g, 21.24 mmol) and triphenylphosphine (5.57 g, 21.24 mmol) were heated at reflux in tetrahydrofuran (100 mL) overnight. The reaction was cooled and filtered to afford the desired material as a white solid (7.20 g, 71.5% yield); $^1$H NMR (400.132 MHz, CDCl$_3$) δ 7.23 (1H, s), 7.59 (1H, d), 7.72-7.67 (7H, m), 7.92-7.84 (9H, m), 10.20 (1H, s);

(c) 5-((7-bromo-4-oxo-3,4-dihydrophthalazin-1-yl)methyl)-2-fluorobenzonitrile (96)

(6-bromo-3-oxo-1,3-dihydroisobenzofuran-1-yl)triphenylphosphonium bromide (95) (9.0 g, 16.24 mmol) and 2-fluoro-5-formylbenzonitrile (2.91 g, 19.49 mmol) were dissolved DCM (60 mL), to this was added triethylamine (2.94 mL, 21.11 mmol) and the reaction was stirred overnight. The reaction mixture was quenched with water (50 mL), extracted with DCM (2×75 mL), the organic layer was dried over MgSO$_4$, filtered and evaporated to afford an orange gum. This was passed through a plug of silica eluting with ethyl acetate to afford a yellow gum. To this was added water (40 mL),

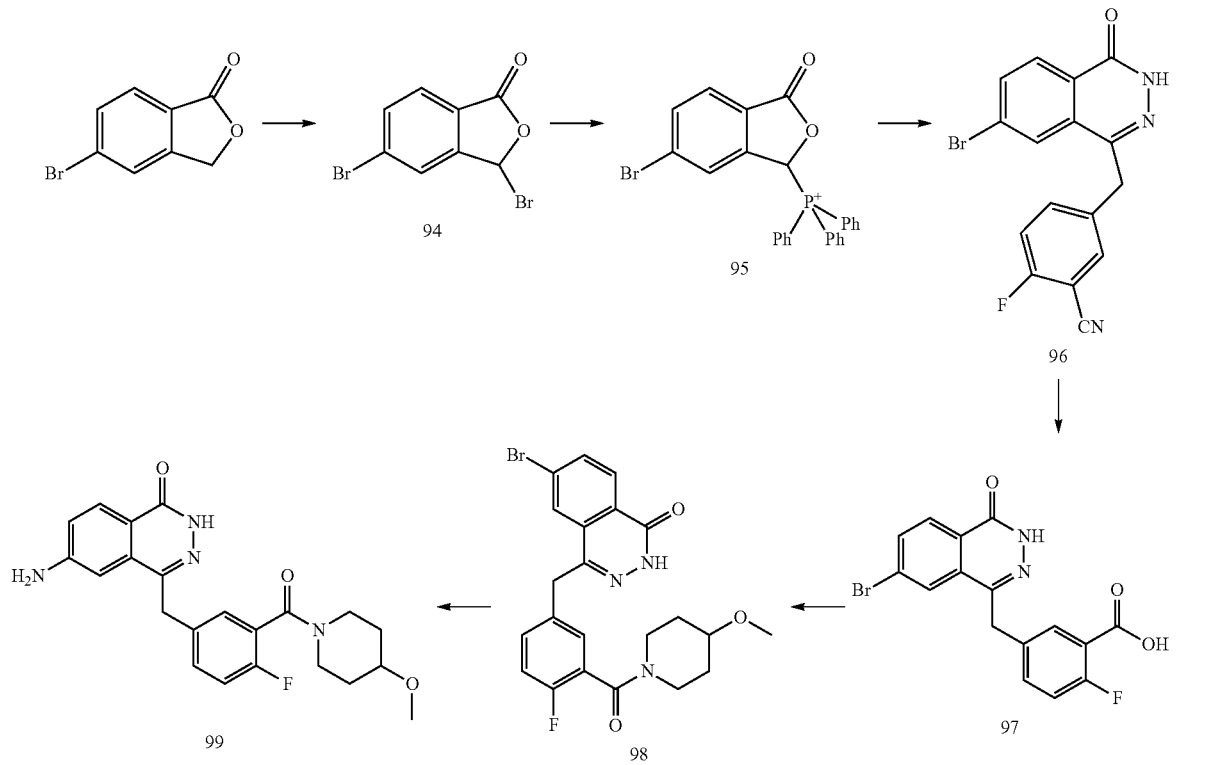

EtOH (40 mL) and DMF (4 mL). Hydrazine hydrate (8.13 g, 162.39 mmol) was added and the reaction was heated at reflux overnight. The reaction was cooled and the precipitate was collected by filtration, washed with EtOH (25 mL) and air dried to afford the desired compound as a white solid (2.410 g, 41.4% yield), which was used without further purification; ¹H NMR (400.132 MHz, DMSO) δ 4.38 (2H, s), 7.48 (1H, t), 7.75-7.71 (1H, m), 7.89 (1H, dd), 8.02 (1H, d), 8.18 (1H, d), 8.22 (1H, s), 12.64 (1H, s); m/z (LC-MS, ESI−), RT=2.18 (M−H 358).

(d) 5-((7-bromo-4-oxo-3,4-dihydrophthalazin-1-yl) methyl)-2-fluorobenzoic acid (97)

5-((7-bromo-4-oxo-3,4-dihydrophthalazin-1-yl)methyl)-2-fluorobenzonitrile (96) (2.4 g, 6.70 mmol) and potassium hydroxide (3.76 g, 67.01 mmol) were added to ethanol (20 mL) and water (80 mL) and heated at 100° C. for 5 hours. The ethanol was evaporated off and the aqueous was extracted with ethyl acetate (1×75 mL). The aqueous was then acidified to pH1 with conc HCl to afford a solid, which was filtered, washed with water and dried to the desired material as a beige solid. (2.000 g, 79% yield); ¹H NMR (400.132 MHz, DMSO) δ 4.37 (2H, s), 7.26 (1H, t), 7.61-7.57 (1H, m), 7.83-7.82 (1H, m), 8.01 (1H, d), 8.18 (1H, d), 8.22 (1H, s), 12.67 (1H, s), 13.19 (1H, s); m/z (LC-MS, ESI+), RT=0.88 (M+H 376).

(e) 6-bromo-4-(4-fluoro-3-(4-methoxypiperidine-1-carbonyl)benzyl)phthalazin-1(2H)-one (98)

5-((7-bromo-4-oxo-3,4-dihydrophthalazin-1-yl)methyl)-2-fluorobenzoic acid (97) (1.0 g, 2.65 mmol), 4-methoxypiperidine (0.336 g, 2.92 mmol) and 2-(1H-benzo[d][1,2,3]triazol-1-yl)-1,1,3,3-tetramethylisouronium tetrafluoroborate (0.936 g, 2.92 mmol) were dissolved in DMF (40 mL), to this was added DIPEA (0.509 mL, 2.92 mmol) and the reaction was stirred for 1 hour. The DMF was evaporated and the crude gum was quenched with 2M NaOH (75 mL), extracted with EtOAc (3×75 mL), the organic layer was dried over MgSO₄, filtered and evaporated to afford a brown gum. The gum was passed through a plug of silica eluting with ethyl acetate to afford a white solid, most of which was used without further purification. A sample (100 mg) was purified via preparative HPLC (Waters XTerra C18 column, 5μ silica, 19 mm diameter, 100 mm length), using decreasingly polar mixtures of water (containing 1% NH₃) and MeCN as eluents. Fractions containing the desired compound were evaporated to dryness to afford the desired material as a white solid (66 mg); ¹H NMR (400.132 MHz, CDCl₃) δ 1.62-1.48 (1H, m), 1.85-1.68 (2H, m), 1.94-1.89 (1H, m), 3.18-3.07 (1H, m), 3.35 (3H, s), 3.47-3.40 (2H, m), 3.67-3.53 (1H, m), 4.06-3.89 (1H, m), 4.23 (2H, s), 7.04 (1H, t), 7.31-7.26 (2H, m), 7.86-7.84 (2H, m), 8.33-8.31 (1H, m), 10.55 (1H, s); m/z (LC-MS, ESI+), RT=1.94 (M+H 476).

(f) 6-amino-4-(4-fluoro-3-(4-methoxypiperidine-1-carbonyl)benzyl)phthalazin-1(2H)-one (99)

6-bromo-4-(4-fluoro-3-(4-methoxypiperidine-1-carbonyl)benzyl)phthalazin-1 (2H)-one (98) (0.2 g, 0.42 mmol), diphenylmethanimine (0.076 g, 0.42 mmol) and cesium carbonate (0.275 g, 0.84 mmol) were added to dioxane (15 mL) and the system was degassed using nitrogen. To this was added diacetoxypalladium (0.019 g, 0.08 mmol) and (9,9-dimethyl-9H-xanthene-4,5-diyl)bis(diphenylphosphine) (0.073 g, 0.13 mmol), the reaction was heated at 95° C. for 2 hours. The reaction mixture was quenched with water (50 mL), extracted with EtOAc (3×50 mL), the organic layer was dried over MgSO₄, filtered and evaporated to afford brown gum. This was stirred with 2.0N HCl (5.0 mL) for 1 hour, the reaction mixture was quenched with 2M NaOH (10 mL), extracted with EtOAc (3×15 mL), the organic layer was dried over MgSO₄, filtered and evaporated to afford brown gum. The crude product was purified by preparative HPLC (Waters XBridge Prep C18 OBD column, 5μ silica, 19 mm diameter, 100 mm length), using decreasingly polar mixtures of water (containing 1% NH₃) and MeCN as eluents. Fractions containing the desired compound were evaporated to dryness to afford the desired material as a white solid (0.024 g, 13.87%); ¹H NMR (500.133 MHz, DMSO) δ 1.47-1.38 (2H, m), 1.82-1.73 (2H, m), 2.89 (3H, s), 3.23-3.16 (2H, m), 3.27 (2H, s), 3.46-3.41 (1H, m), 4.13 (2H, s), 5.78 (2H, s), 6.87 (1H, d), 7.00 (1H, dd), 7.14 (1H, t), 7.22 (1H, dd), 7.38-7.34 (1H, m), 7.93 (1H, d), 11.60 (1H, s); m/z (LC-MS, ESI+), RT=1.56 (M+H 411).

Example 41

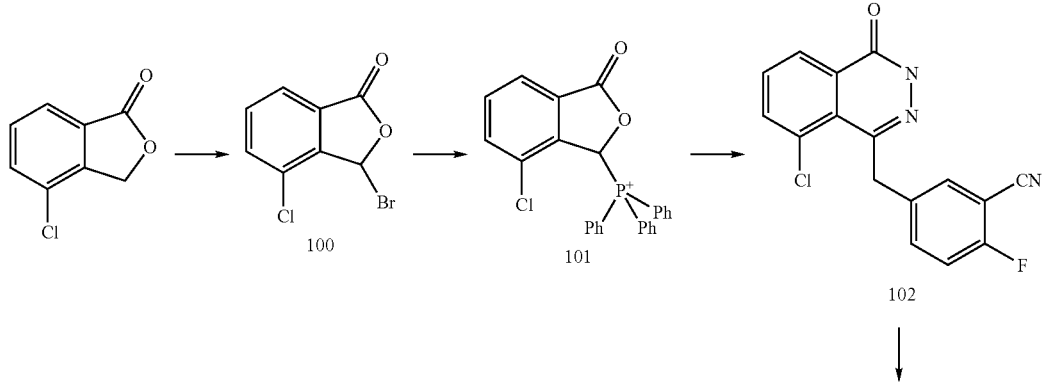

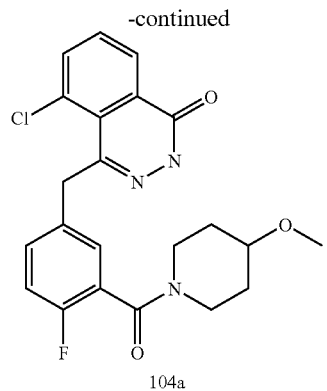

104a

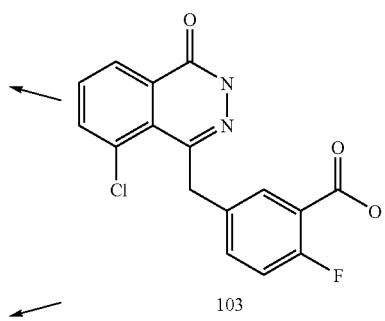

103

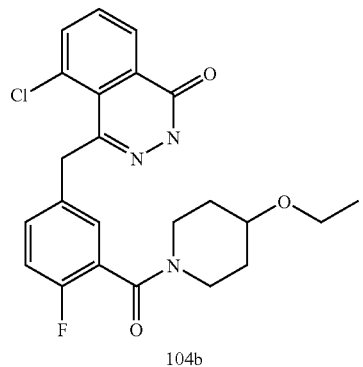

104b (a) 3-bromo-4-chloroisobenzofuran-1(3H)-one (100)

4-chloroisobenzofuran-1(3H)-one (10 g, 59.32 mmol), (E)-2,2'-(diazene-1,2-diyl)bis(2-methylpropanenitrile) (0.974 g, 5.93 mmol) and 1-bromopyrrolidine-2,5-dione (11.61 g, 65.25 mmol) were dissolved CCl4 (100 mL) and heated at reflux for 2 hours. The reaction was cooled and filtered, the filtrate was evaporated to the desired compound as a yellow gum (14.20 g, 97% yield); $^1$H NMR (400.132 MHz, CDCl$_3$) δ 7.32 (1H, s), 7.61 (1H, t), 7.73 (1H, d), 7.88 (1H, d); m/z (LC-MS, ESI+), RT=2.28 (M+H not detected).

(b) (7-chloro-3-oxo-1,3-dihydroisobenzofuran-1-yl) triphenylphosphonium bromide (101)

3-bromo-4-chloroisobenzofuran-1(3H)-one (100) (14 g, 56.57 mmol) and triphenylphosphine (14.84 g, 56.57 mmol) were dissolved THF (200 mL) and heated at reflux for 2 hours. The reaction was cooled and filtered, the filtrate was evaporated to the desired compound as a yellow gum (22.5 g, 78% yield); $^1$H NMR (400.132 MHz, CDCl$_3$) δ 7.54-7.51 (2H, m), 7.65-7.59 (7H, m), 7.79-7.74 (3H, m), 8.07-8.02 (6H, m), 10.41 (1H, s); m/z (LC-MS, ESI+), RT=2.09 (M+H not detected).

(c) 5-((8-chloro-4-oxo-3,4-dihydrophthalazin-1-yl) methyl)-2-fluorobenzonitrile (102)

(7-chloro-3-oxo-1,3-dihydroisobenzofuran-1-yl)triphenylphosphonium bromide (101) (9.3 g, 21.64 mmol) and 2-fluoro-5-formylbenzonitrile (3.55 g, 23.80 mmol) were dissolved in DCM (60 mL), to this was added triethylamine (3.92 mL, 28.13 mmol) and the reaction was stirred overnight. The reaction mixture was evaporated to afford a brown solid. To this was added water (40 mL), EtOH (40 mL) and DMF (4 mL). Hydrazine hydrate (10.83 g, 216.35 mmol) was added and the reaction was heated at reflux overnight. The reaction was cooled and the precipitate was collected by filtration, washed with EtOH (25 mL) and air dried to afford the desired compound as a yellow solid (6.10 g, 90%), which was used without further purification; $^1$H NMR (400.132 MHz, DMSO) δ 4.64 (2H, s), 7.44 (1H, t), 7.63-7.59 (1H, m), 7.78 (1H, dd), 7.81 (1H, t), 7.98 (1H, dd), 8.33 (1H, dd); m/z (LC-MS, ESI+), RT=2.17 (M−H 312).

(d) 5-((8-chloro-4-oxo-3,4-dihydrophthalazin-1-yl) methyl)-2-fluorobenzoic acid (103)

5-((8-chloro-4-oxo-3,4-dihydrophthalazin-1-yl)methyl)-2-fluorobenzonitrile (102) (6.1 g, 19.44 mmol) and potassium hydroxide (10.91 g, 194.44 mmol) were added to ethanol (30 mL) and water (70 mL) and heated at 100° C. for 5 hours. The ethanol was evaporated off and the aqueous was extracted with ethyl acetate (1×75 mL). The aqueous was then acidified to pH1 with conc HCl to afford a solid, this was filtered, washed with water and dried to afford the desired compound as a beige solid (5.73 g, 89%); $^1$H NMR (400.132 MHz, DMSO) δ 4.63 (2H, s), 7.21 (1H, s), 7.44-7.40 (1H, m), 7.64 (1H, dd), 7.82 (1H, t), 7.98 (1H, dd), 8.34 (1H, dd), 12.87 (1H, s), 13.12 (1H, s); m/z (LC-MS, ESI+), RT=0.87 (M+H 333).

(e) 5-chloro-4-(4-fluoro-3-(4-methoxypiperidine-1-carbonyl)benzyl)phthalazin-1(2H)-one (104a)

5-((8-chloro-4-oxo-3,4-dihydrophthalazin-1-yl)methyl)-2-fluorobenzoic acid (103) (0.2 g, 0.60 mmol), 4-methoxypiperidine (0.069 g, 0.60 mmol) and 2-(1H-benzo[d][1,2,3]triazol-1-yl)-1,1,3,3-tetramethylisouronium tetrafluoroborate (0.251 g, 0.78 mmol) were dissolved in DMF (10 mL), to this was added DIPEA (0.136 mL, 0.78 mmol) and the reaction was stirred for 1 hour. The solvent was evaporated to dryness and the gum was dissolved in acetonitrile (4 mL) and purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired material as a white foam (0.100 g, 38.7%); $^1$H NMR (400.132 MHz, CDCl$_3$) δ 1.60-1.49 (1H, m), 1.83-1.64 (2H, m), 1.94-1.89 (1H, m), 3.17-3.05 (1H, m), 3.35 (3H, s), 3.48-3.44 (2H, m), 3.61-3.48 (1H, m), 4.03-3.93 (1H, m), 4.65 (2H, s), 7.00 (1H, t), 7.17-7.14 (2H, m), 7.66 (1H, t), 7.80 (1H, dd), 8.49 (1H, dd) NH missing; m/z (LC-MS, ESI+), RT=1.89 (M+H 430).

(f) 5-chloro-4-(3-(4-ethoxypiperidine-1-carbonyl)-4-fluorobenzyl)phthalazin-1(2H)-one (104b)

5-((8-chloro-4-oxo-3,4-dihydrophthalazin-1-yl)methyl)-2-fluorobenzoic acid (103) (0.2 g, 0.60 mmol), 4-ethoxypiperidine (0.078 g, 0.60 mmol) and 2-(1H-benzo[d][1,2,3]triazol-1-yl)-1,1,3,3-tetramethylisouronium tetrafluoroborate (0.251 g, 0.78 mmol) were dissolved in DMF (10 mL), to this was added DIPEA (0.136 mL, 0.78 mmol) and the reaction was stirred for 1 hour. The solvent was evaporated to dryness and the gum was dissolved in acetonitrile (4 mL) and purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired compound as a white foam (0.052 g, 19.49%); $^1$H NMR (400.132 MHz, CDCl$_3$) δ 1.20 (3H, t), 1.59-1.48 (1H, m), 1.81-1.63 (2H, m), 1.94-1.89 (1H, m), 3.16-3.07 (1H, m), 3.57-3.45 (4H, m), 4.09-4.00 (1H, m), 4.65 (2H, s), 6.99 (1H, t), 7.17-7.13 (2H, m), 7.26 (1H, s), 7.66 (1H, t), 7.80 (1H, dd), 8.49 (1H, dd); NH missing; m/z (LC-MS, ESI+), RT=2.08 (M+H 444).

Example 42

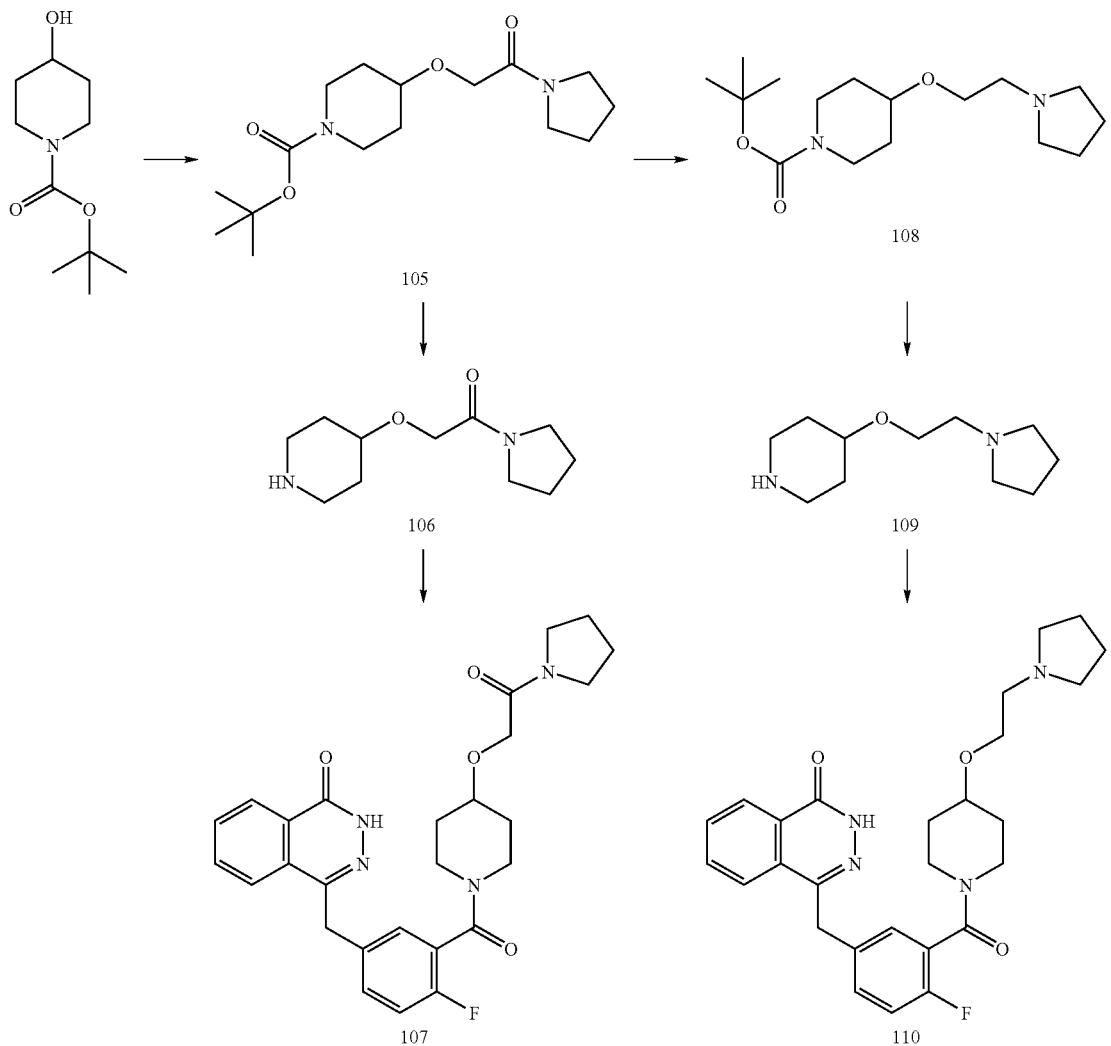

(a) Tert-butyl 4-(2-oxo-2-(pyrrolidin-1-yl)ethoxy) piperidine-1-carboxylate (105)

Tert-butyl 4-hydroxypiperidine-1-carboxylate (4 g, 19.87 mmol), tetrabutylammonium hydrogensulfate (0.337 g, 0.99 mmol) and 2-chloro-1-pyrrolidin-1-yl-ethanone (3.87 g, 25.84 mmol) were added to toluene (50 mL) to this was added NaOH (19.87 g, 198.75 mmol) in water (20 ml) and the reaction was stirred at 25° C. overnight. The reaction mixture was quenched with water (100 mL), extracted with $Et_2O$ (3×75 mL), the organic layer was dried over $MgSO_4$, filtered and evaporated to afford the desired material as an orange liquid (7.20 g, >100% yield); $^1H$ NMR (400.13 MHz, DMSO-$d_6$) δ 1.40 (9H, s), 1.86 (8H, m), 3.02 (4H, s), 3.38 (2H, t), 3.54 (1H, m), 3.60 (2H, m), 4.07 (2H, s).

(b) 2-(piperidin-4-yloxy)-1-(pyrrolidin-1-yl)ethanone (106)

A 4 N HCl solution in dioxane (3 mL, 12 mmol) was added to a solution of tert-butyl 4-(2-oxo-2-(pyrrolidin-1-yl)ethoxy)piperidine-1-carboxylate (105) (3.5 g, 11.20 mmol) in methanol (3 mL) and the reaction mixture was stirred at room temperature for 6 hours. Removal of solvent gave the desired material as its hydrochloride salt. This salt was dissolved in methanol (50 ml) and MP-carbonate (14.88 g, 33.61 mmol) was added. The resulting mixture was filtered and the solvent removed to give the desired material (1.700 g, 71.5% yield); $^1H$ NMR (400.13 MHz, DMSO-$d_6$) δ 1.34 (2H, m), 1.73 (2H, q), 1.86 (4H, q), 2.43 (2H, m), 2.94 (2H, m), 3.39 (4H, t), 4.04 (2H, s).

(c) 4-(4-fluoro-3-(4-(2-oxo-2-(pyrrolidin-1-yl) ethoxy)piperidine-1-carbonyl)benzyl)phthalazin-1(2H)-one (107)

2-fluoro-5-((4-oxo-3,4-dihydrophthalazin-1-yl)methyl) benzoic acid (1) (0.20 g, 0.67 mmol) and HBTU (0.381 g, 1.01 mmol) were added to DMA (4 mL), to this was added N-ethyl-N-isopropylpropan-2-amine (0.179 mL, 1.01 mmol) and then 2-(piperidin-4-yloxy)-1-(pyrrolidin-1-yl)ethanone (106) (0.142 g, 0.67 mmol). The reaction was stirred for 2 hours before being evaporated to dryness and purified by preparative HPLC (Waters XBridge Prep C18 OBD column, 5µ silica, 21 mm diameter, 100 mm length), using decreasingly polar mixtures of water (containing 1% NH+) and MeCN as eluents. Fractions containing the desired compound were evaporated to dryness to the desired compound as a white solid (0.168 g, 50.9%); $^1H$ NMR (400.132 MHz, CDCl$_3$) δ 1.90-1.56 (m, 6H), 2.01-1.93 (m, 2H), 3.16-3.07 (m, 1H), 3.57-3.42 (m, 6H), 3.72 (septet, J=3.6 Hz, 1H), 4.06-4.00 (m, 1H), 4.12 (q, J=11.9 Hz, 2H), 4.26 (s, 2H), 7.02 (t, J=8.8 Hz, 1H), 7.32-7.25 (m, 2H), 7.79-7.70 (m, 3H), 8.47-8.44 (m, 1H), 10.01-9.97 (m, 1H); m/z (LC-MS, ESI+), RT=1.66 (M+H 493).

(d) tert-butyl 4-(2-(pyrrolidin-1-yl)ethoxy)piperidine-1-carboxylate (108)

Tert-butyl 4-(2-oxo-2-(pyrrolidin-1-yl)ethoxy)piperidine-1-carboxylate (105)(3.5 g, 11.20 mmol) was dissolved in dry THF (50 mL), to this was added borane-methyl sulfide complex (8.40 mL, 16.81 mmol) and the reaction was stirred at 40° C. for 3 hours then at ambient temperature overnight. The gummy mixture was evaporated and was quenched with 2.0 N sodium carbonate (50 mL), extracted with EtOAc (3×75 mL), the organic layer was dried over MgSO4, filtered and evaporated to afford the desired material as a colourless liquid, which was taken through directly to the next stage; $^1H$ NMR (400.132 MHz, CDCl$_3$) δ 1.38-1.58 (m, 9H), 1.73-1.86 (m, 4H), 1.86-1.97 (m, 2H), 2.09-2.21 (m, 2H), 2.79-2.91 (m, 2H), 2.96 (t, 2H), 3.06-3.17 (m, 2H), 3.18-3.27 (m, 2H), 3.49 (septet, 2H), 3.65-3.76 (m, 2H), 3.92 (t, 1H).

(e) 1-(2-(piperidin-4-yloxy)ethyl)piperidine (109)

A 4 N HCl solution in dioxane (6 mL) was added to a solution of tert-butyl 4-(2-(piperidin-1-yl)ethoxy)piperidine-1-carboxylate (108) (6.5 g, 20.80 mmol) in MeOH (16 mL) and the reaction mixture was stirred at room temperature for 6 hours. Removal of solvent afforded the desired compound as its hydrochloride salt. This salt was dissolved in methanol (50 ml) and MP-carbonate (14.88 g, 33.61 mmol) was added. The resulting mixture was filtered and the solvent removed to give the desired material, as a clear liquid which was used without further purification; $^1H$ NMR (400.132 MHz, CDCl$_3$) δ 1.33-1.47 (2H, m), 1.50-1.71 (3H, m), 1.86-1.96 (4H, m), 2.50-2.67 (6H, m), 3.00-3.14 (4H, m), 3.34 (1H, septet), 3.55 (2H, t), 3.60 (2H, t).

(f) 4-(4-fluoro-3-(4-(2-(pyrrolidin-1-yl)ethoxy)piperidine-1-carbonyl)benzyl)phthalazin-1(2H)-one (110)

2-fluoro-5-((4-oxo-3,4-dihydrophthalazin-1-yl)methyl) benzoic acid (1) (0.20 g, 0.67 mmol) and HBTU (0.381 g, 1.01 mmol) were added to DMF (4 mL), to this was added N-ethyl-N-isopropylpropan-2-amine (0.179 mL, 1.01 mmol) and then 4-(2-(pyrrolidin-1-yl)ethoxy)piperidine (109) (0.133 g, 0.67 mmol). The reaction was stirred for 2 hours before being evaporated to dryness and purified by preparative HPLC (Waters XBridge Prep C18 OBD column, 5µ silica, 19 mm diameter, 100 mm length), using decreasingly polar mixtures of water (containing 1% NH$_3$) and MeCN as eluents. Fractions containing the desired compound were evaporated to dryness to afford the desired material as a white solid (0.287 g, 89% yield); $^1H$ NMR (400.132 MHz, CDCl$_3$) δ 1.65-1.81 (6H, m), 1.87-1.96 (3H, m), 2.53-2.61 (3H, m), 2.65-2.72 (2H, m), 3.04-3.14 (1H, m), 3.38-3.57 (3H, m), 3.61 (2H, t), 3.97-4.06 (1H, m), 4.28 (2H, s), 7.01 (1H, t), 7.21-7.33 (2H, m), 7.68-7.80 (3H, m), 8.43-8.48 (1H, m), 9.85-9.95 (1H, m); m/z (LC-MS, ESI+), RT=1.88 (M+H 479.5).

Example 43

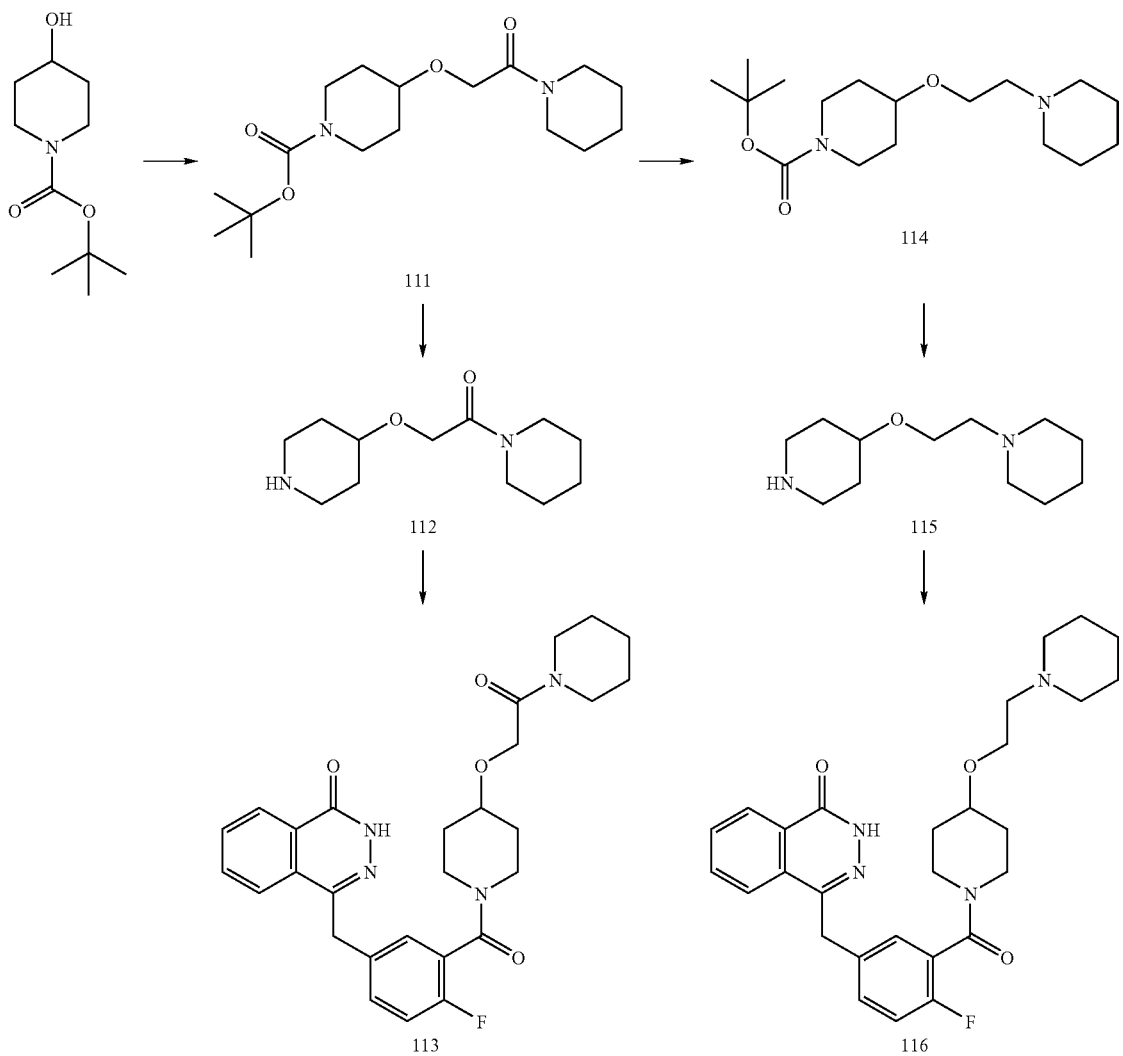

(a) tert-butyl 4-(2-oxo-2-(piperidin-1-yl)ethoxy)piperidine-1-carboxylate (111)

Tert-butyl 4-hydroxypiperidine-1-carboxylate (10 g, 49.69 mmol), tetrabutylammonium hydrogensulfate (0.844 g, 2.48 mmol) and 2-chloro-1-(piperidin-1-yl)ethanone (8.08 g, 49.69 mmol) were added to toluene (75 mL) to this was added sodium hydroxide (49.7 g, 496.86 mmol) in water (20 ml) and the reaction was stirred at 25° C. overnight. The reaction mixture was quenched with water (100 mL), extracted with $Et_2O$ (3×75 mL), the organic layer was dried over $MgSO_4$, filtered and evaporated to afford the crude product as an orange liquid (15.60 g, 96% yield); $^1H$ NMR (400.132 MHz, $CDCl_3$) δ 1.49 (9H, s), 1.51-1.60 (2H, m), 1.61-1.68 (2H, m), 1.81-1.90 (3H, m), 3.05-3.13 (2H, m), 3.35-3.47 (2H, m), 3.50-3.62 (4H, m), 3.71-3.79 (2H, m), 3.80-3.89 (2H, m), 4.13-4.19 (2H, m).

(b) 1-(piperidin-1-yl)-2-(piperidin-4-yloxy)ethanone (112)

A 4 N HCl solution in dioxane (6 mL) was added to a solution of tert-butyl 4-(2-oxo-2-(piperidin-1-yl)ethoxy)piperidine-1-carboxylate (111) (7.5 g, 22.98 mmol) in MeOH (20 mL) and the reaction mixture was stirred at room temperature for 6 hours. Removal of solvent afforded 1-(piperidin-1-yl)-2-(piperidin-4-yloxy)ethanone as its hydrochloride salt (2.300 g, 44.2%). This salt was then dissolved in methanol (50 ml) and MP-carbonate (14.88 g, 33.61 mmol) was added. The resulting mixture was filtered and the solvent removed to give the desired compound (2.300 g, 44.2%), which was used without further purification.

(c) 4-(4-fluoro-3-(4-(2-oxo-2-(piperidin-1-yl)ethoxy)piperidine-1-carbonyl)benzyl)phthalazin-1 (2H)-one (113)

2-fluoro-5-((4-oxo-3,4-dihydrophthalazin-1-yl)methyl)benzoic acid (1) (0.20 g, 0.67 mmol) and HBTU (0.381 g, 1.01 mmol) were added to DMA (4 mL), to this was added N-ethyl-N-isopropylpropan-2-amine (0.179 mL, 1.01 mmol) and then 1-(piperidin-1-yl)-2-(piperidin-4-yloxy)ethanone (112) (0.152 g, 0.67 mmol). The reaction was stirred for 2 hours before being evaporated to dryness and purified by preparative HPLC (Waters XBridge Prep C18 OBD column, 5µ silica, 19 mm diameter, 100 mm length), using decreasingly polar mixtures of water (containing 1% NH₃) and MeCN as eluents. Fractions containing the desired compound were evaporated to dryness to afford the desired material (0.303 g, 89% yield); $^1$H NMR (400.132 MHz, DMSO) δ 1.07-1.39 (8H, m), 1.46-1.56 (1H, m), 1.61-1.71 (1H, m), 2.76-2.85 (1H, m), 3.02-3.09 (2H, m), 3.10-3.20 (4H, m), 3.34-3.41 (1H, m), 3.66-3.75 (1H, m), 3.90-3.93 (2H, m), 4.08-4.12 (2H, m), 6.99 (1H, t), 7.09-7.21 (2H, m), 7.57-7.69 (1H, m), 7.72-7.76 (1H, m), 8.02-8.06 (2H, m), 12.34 (1H, s); m/z (LC-MS, ESI+), RT=1.76 (M+H 507.5).

(d) tert-butyl 4-(2-(piperidin-1-yl)ethoxy)piperidine-1-carboxylate (114)

Tert-butyl 4-(2-oxo-2-(piperidin-1-yl)ethoxy)piperidine-1-carboxylate (111) (7.5 g, 22.98 mmol) was dissolved in dry THF (100 mL), to this was added borane-methyl sulfide complex (17.23 mL, 34.46 mmol) and the reaction was stirred at 40° C. for 3 hours then at ambient temperature overnight. The gummy mixture was evaporated and was quenched with 2.0 N sodium carbonate (50 mL), extracted with EtOAc (3×75 mL), the organic layer was dried over MgSO4, filtered and evaporated to afford tert-butyl 4-(2-(piperidin-1-yl)ethoxy)piperidine-1-carboxylate (7.3 g, 95% yield) as a colourless liquid and used without further purification.

(e) 1-(2-(piperidin-4-yloxy)ethyl)piperidine (115)

A 4 N HCl solution in dioxane (6 mL) was added to a solution of tert-butyl 4-(2-(piperidin-1-yl)ethoxy)piperidine-1-carboxylate (114)(6.5 g, 20.80 mmol) in MeOH (16 mL) and the reaction mixture was stirred at room temperature for 6 hours. Removal of solvent afforded 1-(2-(piperidin-4-yloxy)ethyl)piperidine as its hydrochloride salt (0.540 g, 12.22%). This salt was then dissolved in methanol (50 ml) and MP-carbonate (14.88 g, 33.61 mmol) was added. The resulting mixture was filtered and the solvent removed to give the desired material a colourless liquid which was used without further purification; $^1$H NMR (400.132 MHz, CDCl₃) δ 1.33-1.47 (2H, m), 1.50-1.71 (3H, m), 1.86-1.96 (4H, m), 2.50-2.67 (6H, m), 3.00-3.14 (4H, m), 3.34 (1H, septet), 3.55 (2H, t), 3.60 (2H, t).

(f) 4-(4-fluoro-3-(4-(2-(piperidin-1-yl)ethoxy)piperidine-1-carbonyl)benzyl)phthalazin-1(2H)-one (116)

2-fluoro-5-((4-oxo-3,4-dihydrophthalazin-1-yl)methyl) benzoic acid (1)(0.20 g, 0.67 mmol) and HBTU (0.381 g, 1.01 mmol) were added to DMA (4 mL), to this was added N-ethyl-N-isopropylpropan-2-amine (0.179 mL, 1.01 mmol) and then 1-(2-(piperidin-4-yloxy)ethyl)piperidine (115) (0.214 g, 1.01 mmol). The reaction was stirred for 2 hours before being evaporated to dryness and purified by preparative HPLC (Waters XBridge Prep C18 OBD column, 5µ silica, 19 mm diameter, 100 mm length), using decreasingly polar mixtures of water (containing 1% NH₃) and MeCN as eluents. Fractions containing the desired compound were evaporated to dryness to afford the desired compound (0.069 g, 20.74% yield); $^1$H NMR (400.132 MHz, CDCl₃) δ 1.36-1.45 (2H, m), 1.64-1.94 (8H, m), 2.37-2.50 (4H, m), 2.55 (2H, t), 3.03-3.15 (1H, m), 3.37-3.49 (1H, m), 3.50-3.65 (4H, m), 3.92-4.04 (1H, m), 4.30 (2H, s), 7.00 (1H, t), 7.21-7.32 (2H, m), 7.68-7.79 (3H, m), 8.43-8.49 (1H, m), 10.49 (1H, s); m/z (LC-MS, ESI+), RT=2.01 (M+H 493.5).

Example 44

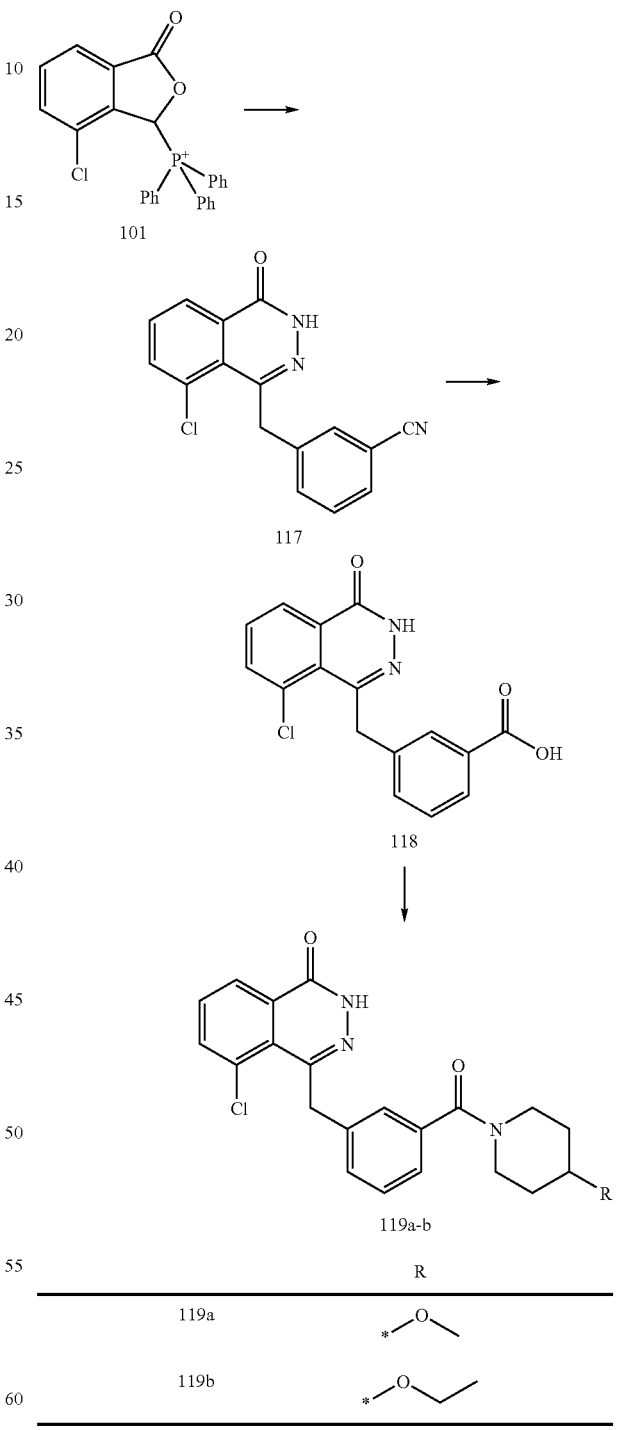

(a) 3-((8-chloro-4-oxo-3,4-dihydrophthalazin-1-yl) methyl)benzonitrile (117)

(7-chloro-3-oxo-1,3-dihydroisobenzofuran-1-yl)triphenylphosphonium bromide (101) (10 g, 23.26 mmol) and 3-formylbenzonitrile (3.20 g, 24.43 mmol) were dissolved DCM (60 mL), to this was added triethylamine (4.22 mL, 30.24 mmol) and the reaction was stirred overnight. The reaction mixture was filtered to afford a white solid. To this was added water (40 mL), EtOH (40 mL) and DMF (4 mL). Hydrazine hydrate (11.65 g, 232.64 mmol) was added and the reaction was heated at reflux overnight. The reaction was cooled and the precipitate was collected by filtration, washed with EtOH (25 mL) and air dried to afford the desired material as a white solid (3.75 g, 54.5% yield), which was used without further purification; $^1$H NMR (400.132 MHz, DMSO) δ 4.66 (2H, s), 7.53-7.47 (2H, m), 7.68-7.66 (2H, m), 7.81 (1H, t), 7.97 (1H, d), 8.33 (1H, d), 12.55 (1H, s); m/z (LC-MS, ESI−), RT=2.04 (M−H 294).

(b) 3-((8-chloro-4-oxo-3,4-dihydrophthalazin-1-yl)methyl)benzoic acid (118)

3-((8-chloro-4-oxo-3,4-dihydrophthalazin-1-yl)methyl)benzonitrile (117) (3.75 g, 12.68 mmol) and potassium hydroxide (7.11 g, 126.81 mmol) were added to ethanol (30 mL) and water (70 mL) and heated at 100° C. for 5 hours. The ethanol was evaporated off and the aqueous was extracted with ethyl acetate (1×75 mL). The aqueous was then acidified to pH1 with conc HCl to afford a solid, this was filtered, washed with water and dried to afford the desired material as a beige solid (3.81 g, 95% yield); $^1$H NMR (400.132 MHz, DMSO) δ 4.67 (2H, s), 7.42-7.41 (2H, m), 7.72 (1H, s), 7.79-7.76 (1H, m), 7.81 (1H, t), 7.97 (1H, dd), 8.34 (1H, dd), 12.88 (1H, s); m/z (LC-MS, ESI+), RT=0.92 (M+H 315).

(c) 5-chloro-4-(3-(4-methoxypiperidine-1-carbonyl)benzyl)phthalazin-1(2H)-one (119a)

3-((8-chloro-4-oxo-3,4-dihydrophthalazin-1-yl)methyl)benzoic acid (118) (200 mg, 0.64 mmol) and 4-methoxypiperidine (73.2 mg, 0.64 mmol) were added to DMF (5 mL), to this was added N-ethyl-N-isopropylpropan-2-amine (0.170 mL, 0.95 mmol) and then HBTU (362 mg, 0.95 mmol). The reaction mixture was stirred for four hours at 0° C. The crude mixture was purified by preparative LCMS (Waters XBridge Prep C18 OBD column, 5μ silica, 30 mm diameter, 100 mm length), using decreasingly polar mixtures of water (containing 1% NH$_3$) and MeCN as eluents. Fractions containing the desired compound were evaporated to dryness to afford the desired material as a white crystalline solid (62.2 mg, 23.76% yield); $^1$H NMR (400.132 MHz, CDCl$_3$) δ 1.62-2.00 (3H, m), 3.02-3.29 (2H, m), 3.35 (3H, s), 3.37-3.65 (3H, m), 3.87-4.08 (1H, m), 4.69 (2H, s), 7.15-7.24 (3H, m), 7.29-7.34 (1H, m), 7.65 (1H, t), 7.77-7.81 (1H, m), 8.48 (1H, m), 9.85-10.01 (1H, m); m/z (LC-MS, ESI+), RT=1.80 (M+H 412.1).

(d) 5-chloro-4-(3-(4-ethoxypiperidine-1-carbonyl)benzyl)phthalazin-1(2H)-one (119bd)

3-((8-chloro-4-oxo-3,4-dihydrophthalazin-1-yl)methyl)benzoic acid (118) (200 mg, 0.64 mmol) and 4-ethoxypiperidine were added to DMF (5 mL), to this was added N-ethyl-N-isopropylpropan-2-amine (0.170 mL, 0.95 mmol) and then HBTU (362 mg, 0.95 mmol). The solvent was removed and the crude product dissolved in acetonitrile and purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired material as a white solid (111 mg, 41.0% yield); $^1$H NMR (400.132 MHz, DMSO) δ 1.11 (3H, t), 1.17-1.46 (2H, m), 1.58-1.92 (2H, m), 2.97-3.42 (4H, m), 3.42-3.55 (3H, m), 4.68 (2H, s), 7.13 (1H, s), 7.21 (2H, t), 7.35 (1H, t), 7.81 (1H, t), 7.94-7.99 (1H, m), 8.32-8.36 (1H, m), 12.91 (1H, s); m/z (LC-MS, ESI+), RT=1.96 (M+H 426.7)

Example 45

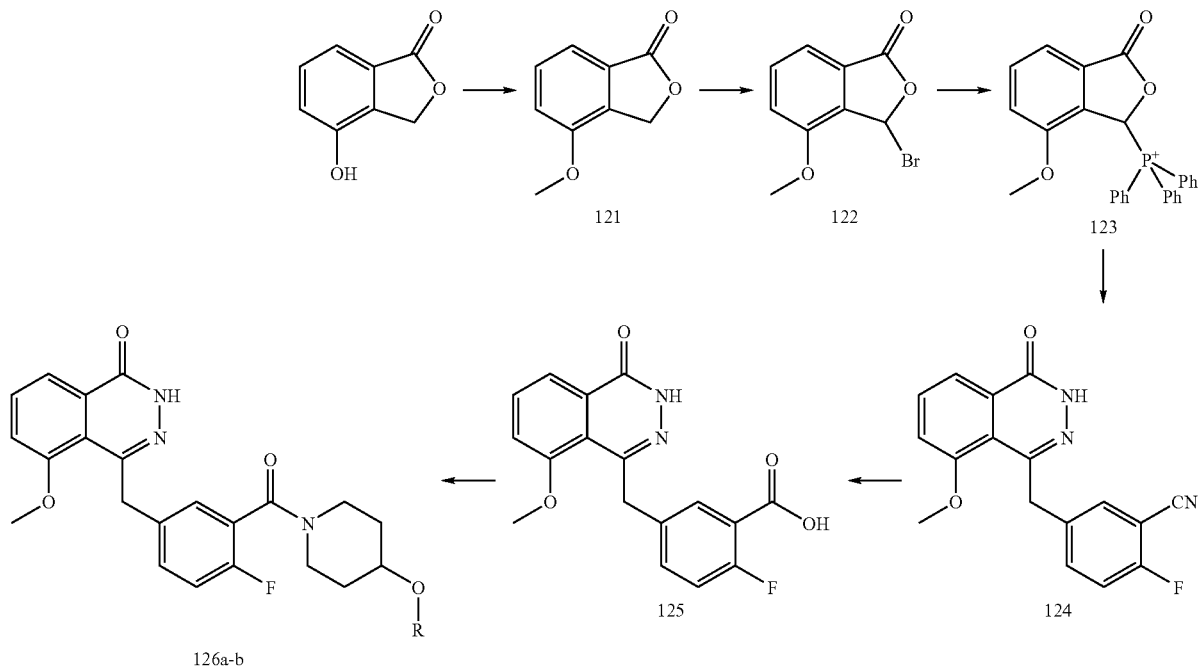

(a) 4-methoxyisobenzofuran-1(3H)-one (121)

Iodomethane (1.313 mL, 20.78 mmol) was added to 4-hydroxyisobenzofuran-1(3H)-one (3.12 g, 20.78 mmol) and potassium carbonate (5.74 g, 41.56 mmol) in DMF (50 mL) at 21° C. under air. The resulting solution was stirred overnight. The solvent was removed to give a yellow solid which was then quenched with potassium carbonate (70 ml). The mixture was extracted ethyl acetate (3×75 ml). The combined extracts were evaporated to give the desired material as a yellow solid (3.18 g, 93% yield), which was used without further purification; $^1$H NMR (400.132 MHz, CDCl$_3$) δ 3.30 (2H, s), 5.37 (2H, s), 7.31-7.42 (2H, m), 7.51-7.61 (1H, m).

(b) 3-bromo-4-methoxyisobenzofuran-1(3H)-one (122)

4-methoxyisobenzofuran-1(3H)-one (121) (3.18 g, 19.37 mmol) and 1-bromopyrrolidine-2,5-dione (3.62 g, 20.34 mmol) were dissolved in carbon tetrachloride (40 mL) and heated reflux. (E)-2,2'-(diazene-1,2-diyl)bis(2-methylpropanenitrile) (0.318 g, 1.94 mmol) was added and the reaction stirred overnight at 80° C. The reaction was allowed to cool and filtered. The solvent removed to afford the desired material as a orange solid (3.15 g, 66.9%), which was used without further purification; $^1$H NMR (400.132 MHz, DMSO) δ 3.91 (3H, s), 6.66 (1H, s), 7.35-7.40 (2H, m), 7.57-7.65 (1H, m).

(c) (7-methoxy-3-oxo-1,3-dihydroisobenzofuran-1-yl)triphenylphosphonium bromide (123)

3-bromo-4-methoxyisobenzofuran-1(3H)-one (122) (3.15 g, 12.96 mmol) and triphenylphosphine (3.40 g, 12.96 mmol) were dissolved THF (50 mL) and heated at reflux over the weekend. The reaction was cooled and filtered to afford the desired material as a white solid (3.50 g, 53.4%); $^1$H NMR (400.132 MHz, CDCl$_3$) δ 3.42 (3H, s), 7.10 (1H, d), 7.22-7.28 (1H, m), 7.47-7.53 (1H, m), 7.59-7.65 (6H, m), 7.74-7.80 (3H, m), 7.91-8.00 (6H, m), 9.80 (1H, s).

(d) 2-fluoro-5-((8-methoxy-4-oxo-3,4-dihydrophthalazin-1-yl)methyl)benzonitrile (124)

(7-methoxy-3-oxo-1,3-dihydroisobenzofuran-1-yl)triphenylphosphonium bromide (123) (3.5 g, 6.93 mmol) and 2-fluoro-5-formylbenzonitrile (1.033 g, 6.93 mmol) were dissolved DCM (30 mL), to this was added triethylamine (1.255 mL, 9.00 mmol) and the reaction was stirred overnight. The solvent was removed to afford a white solid. To this was added water (20 mL), EtOH (20 mL) and DMF (2 mL). Hydrazine hydrate (3.36 mL, 69.26 mmol) was added and the reaction was heated at reflux overnight. The reaction was cooled and the precipitate was collected by filtration, washed with EtOH (25 mL) and air dried to afford the desired material as a white solid (2.70 g, >100%), which was used without further purification; $^1$H NMR (400.132 MHz, DMSO) δ 3.79 (3H, s), 4.40 (2H, s), 7.31-7.39 (1H, m), 7.47-7.59 (2H, m), 7.66-7.73 (2H, m), 7.78-7.82 (1H, m), 12.40-12.62 (1H, m).

(e) 2-fluoro-5-((8-methoxy-4-oxo-3,4-dihydrophthalazin-1-yl)methyl)benzoic acid (125)

2-fluoro-5-((8-methoxy-4-oxo-3,4-dihydrophthalazin-1-yl)methyl)benzonitrile (124) (2.7 g, 8.73 mmol) and potassium hydroxide (4.90 g, 87.30 mmol) were added to ethanol (20 mL) and water (50 mL) and heated at 100° C. for 5 hours. The ethanol was evaporated off and the aqueous was extracted with ethyl acetate (1×75 mL). The aqueous was then acidified to pH1 with conc HCl to afford a solid, this was filtered, washed with water and dried to afford the desired material as a white solid (2.370 g, 83%); $^1$H NMR (400.132 MHz, DMSO) δ 3.82 (3H, s), 4.40 (2H, s), 7.16-7.23 (1H, m), 7.40-7.46 (2H, m), 7.64-7.68 (1H, m), 7.76 (1H, t), 7.84-7.88 (1H, m), 12.96-13.28 (1H, m), 12.59-12.63 (1H, m).

(f) 4-(4-fluoro-3-(4-methoxypiperidine-1-carbonyl)benzyl)-5-methoxyphthalazin-1(2H)-one (126a)

2-fluoro-5-((8-methoxy-4-oxo-3,4-dihydrophthalazin-1-yl)methyl)benzoic acid (125) and 4-methoxypiperidine were added to DMF (5 mL), to this was added N-ethyl-N-isopropylpropan-2-amine (0.163 mL, 0.91 mmol) and then HBTU (347 mg, 0.91 mmol). The solvent was removed and the residue was dissolved in acetonitrile. A white solid precipitated, which was filtered and dried to afford the desired material as a white crystalline solid (140 mg, 54.0% yield); $^1$H NMR (400.132 MHz, CDCl$_3$) δ 1.49-1.60 (1H, m), 1.62-1.83 (2H, m), 1.86-1.96 (1H, m), 3.07-3.19 (1H, m), 3.32-3.36 (3H, m), 3.41-3.62 (3H, m), 3.78-3.82 (3H, m), 3.94-4.04 (1H, m), 4.36-4.46 (2H, m), 6.93-7.00 (1H, m), 7.10-7.30 (3H, m), 7.64-7.72 (1H, m), 8.00-8.12 (1H, m), 9.98-10.07 (1H, m); m/z (ES+) (M+H)$^+$=426.4; HPLC RT=1.71 min.

(g) 4-(3-(4-ethoxypiperidine-1-carbonyl)-4-fluorobenzyl)-5-methoxyphthalazin-1(2H)-one (126b)

2-fluoro-5-((8-methoxy-4-oxo-3,4-dihydrophthalazin-1-yl)methyl)benzoic acid (125) (200 mg, 0.61 mmol) and 4-ethoxypiperidine (79 mg, 0.61 mmol) were added to DMF (5 mL), to this was added N-ethyl-N-isopropylpropan-2-amine (0.163 mL, 0.91 mmol) and then HBTU (347 mg, 0.91 mmol). The solvent was then removed to give a brown solid, which was dissolved in acetonitrile. A white solid precipitated, which was filtered and dried to afford the desired material as a white crystalline solid (200 mg, 74.7% yield); $^1$H NMR (400.132 MHz, CDCl$_3$) δ 1.20 (3H, t), 1.46-1.62 (1H, m), 1.63-1.82 (2H, m), 1.87-1.96 (1H, m), 3.07-3.18 (1H, m), 3.43-3.59 (5H, m), 3.77-3.82 (3H, m), 3.99-4.11 (1H, m), 4.45 (2H, s), 6.91-7.02 (1H, m), 7.11-7.28 (3H, m), 7.62-7.71 (1H, m), 8.03-8.08 (1H, m), 10.29 (1H, s); m/z (ES+) (M+H)$^+$=440.41; HPLC RT=1.87 min.

Example 46

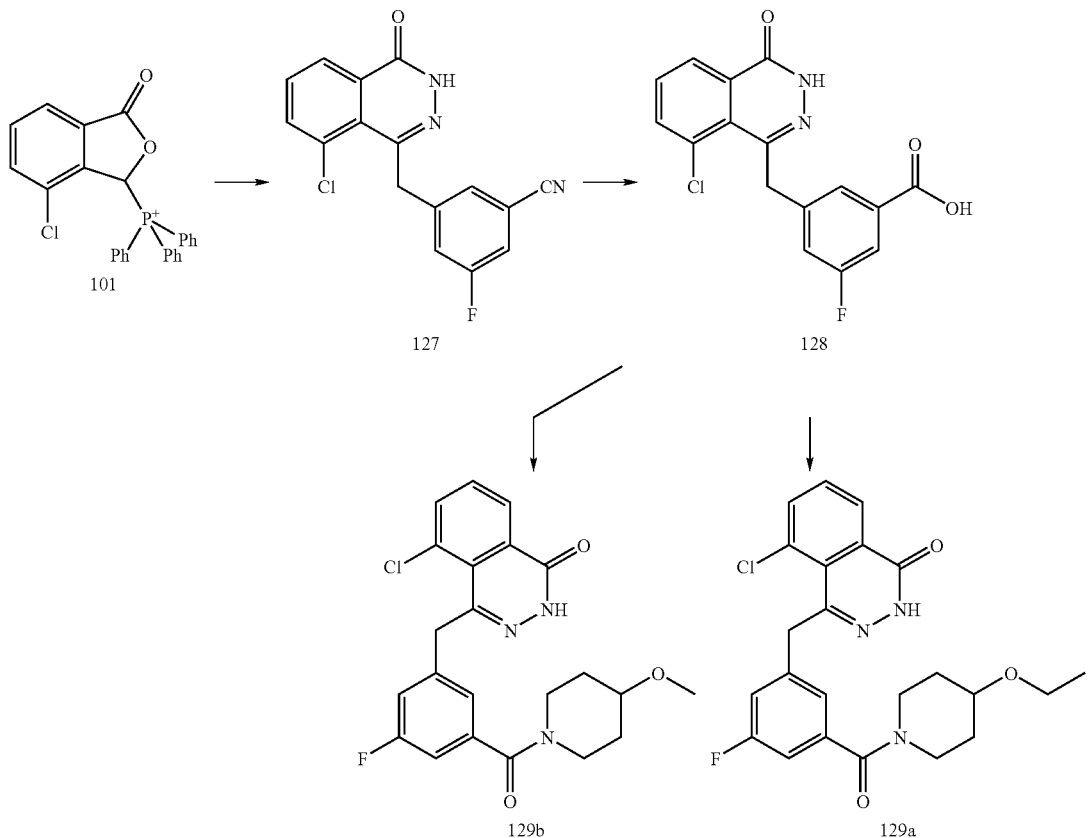

(a) 3-((8-chloro-4-oxo-3,4-dihydrophthalazin-1-yl)methyl)-5-fluorobenzonitrile (127)

(7-chloro-3-oxo-1,3-dihydroisobenzofuran-1-yl)triphenylphosphonium bromide (101) (2.88 g, 6.71 mmol) and 3-fluoro-5-formylbenzonitrile (1.0 g, 6.71 mmol) were dissolved DCM (60 mL), to this was added triethylamine (1.215 mL, 8.72 mmol) and the reaction was stirred overnight. The reaction mixture was evaporated to afford a brown solid. To this was added water (40 mL), EtOH (40 mL) and DMF (4 mL). Hydrazine hydrate (3.36 g, 67.06 mmol) was added and the reaction was heated at reflux overnight. The reaction was cooled and the precipitate was collected by filtration, washed with EtOH (25 mL) and air dried to afford the desired material as a yellow solid (1.260 g, 59.9% yield), which was used without further purification; $^1$H NMR (400.132 MHz, DMSO) δ 4.68 (2H, s), 7.49 (1H, d), 7.58 (1H, s), 7.68 (1H, d), 7.82 (1H, t), 7.99 (1H, dd), 8.34 (1H, dd), 12.82 (1H, s); m/z (LC-MS, ESI-), RT=2.21 (M-H 312).

(b) 3-((8-chloro-4-oxo-3,4-dihydrophthalazin-1-yl)methyl)-5-fluorobenzoic acid (128)

3-((8-chloro-4-oxo-3,4-dihydrophthalazin-1-yl)methyl)-5-fluorobenzonitrile (127) (1.26 g, 4.02 mmol) and potassium hydroxide (2.253 g, 40.16 mmol) were added to ethanol (30 mL) and water (70 mL) and heated at 100° C. for 5 hours. The ethanol was evaporated off and the aqueous was extracted with ethyl acetate (1×75 mL). The aqueous was then acidified to pH1 with conc HCl to afford a solid, this was filtered, washed with water and dried to afford the desired compound as a beige solid (1.280 g, 96% yield); $^1$H NMR (400.132 MHz, DMSO) δ 4.69 (2H, s), 7.35 (1H, d), 7.50 (1H, d), 7.58 (1H, s), 7.82 (1H, t), 7.99 (1H, d), 8.34 (1H, d), 12.87 (1H, s); m/z (LC-MS, ESI+), RT=0.99 (M+H 333).

(c) 5-chloro-4-(3-(4-ethoxypiperidine-1-carbonyl)-5-fluorobenzyl)phthalazin-1(2H)-one (129a)

3-((8-chloro-4-oxo-3,4-dihydrophthalazin-1-yl)methyl)-5-fluorobenzoic acid (128), 4-ethoxypiperidine and 2-(1H-benzo[d][1,2,3]triazol-1-yl)-1,1,3,3-tetramethylisouronium tetrafluoroborate were dissolved in DMF (10 mL), to this was added DIPEA and the reaction was stirred for 1 hour. The solvent was evaporated to dryness and the gum was dissolved in acetonitrile (4 mL) and purified by preparative HPLC (Waters XBridge Prep C18 OBD column, 5μ silica, 19 mm diameter, 100 mm length), using decreasingly polar mixtures of water (containing 1% NH$_3$) and MeCN as eluents. Fractions containing the desired compound were evaporated to dryness to afford the desired compound as a white foam (130 mg); $^1$H NMR (400.132 MHz, CDCl$_3$) δ 1.20 (3H, t), 2.00-1.38 (4H, m), 3.29-3.05 (1H, m), 3.57-3.34 (5H, m), 4.08-3.91 (1H, m), 4.68 (2H, s), 6.90 (1H, d), 6.97-6.94 (2H, m), 7.67 (1H, t), 7.80 (1H, d), 8.50 (1H, dd); NH missing; m/z (LC-MS, ESI+), RT=2.06 (M+H 444).

(d) 5-chloro-4-(3-fluoro-5-(4-methoxypiperidine-1-carbonyl)benzyl)phthalazin-1(2H)-one (129b)

3-((8-chloro-4-oxo-3,4-dihydrophthalazin-1-yl)methyl)-5-fluorobenzoic acid (128), 4-methoxypiperidine and 2-(1H-benzo[d][1,2,3]triazol-1-yl)-1,1,3,3-tetramethylisouronium tetrafluoroborate were dissolved in DMF (10 mL), to this was added DIPEA and the reaction was stirred for 1 hour. The solvent was evaporated to dryness and the gum was dissolved in acetonitrile (4 mL) and purified by preparative HPLC (Waters XBridge Prep C18 OBD column, 5μ silica, 19 mm diameter, 100 mm length), using decreasingly polar mixtures of water (containing 1% $NH_3$) and MeCN as eluents. Fractions containing the desired compound were evaporated to dryness to afford the desired compound as a white foam (67.0 mg); $^1$H NMR (400.132 MHz, $CDCl_3$) δ 1.89-1.40 (4H, m), 3.17-3.06 (1H, m), 3.34 (3H, s), 3.58-3.42 (3H, m), 4.00-3.84 (1H, m), 4.67 (2H, s), 6.97-6.89 (3H, m), 7.67 (1H, t), 7.81 (1H, d), 8.49 (1H, d), 10.29 (1H, s); m/z (LC-MS, ESI+), RT=1.93 (M+H 430).

Example 47 a) Resynthesis of 2b

O-Benzotriazol-1-yl-tetramethyluronium hexafluorophosphate (45.5 g, 119.86 mmol) was added portionwise to a solution of 2-fluoro-5-((4-oxo-3,4-dihydrophthalazin-1-yl)methyl)benzoic acid (1) (27.5 g, 92.20 mmol), 4-methoxypiperidine (11.68 g, 101.42 mmol) and triethylamine (30.8 mL, 221.28 mmol) in DMA (450 mL) at 20° C. under nitrogen. The resulting solution was stirred at 20° C. for 21 hours. The solution was poured into water (2.5 liters) and extracted with EtOAc (×3), the combined extracts washed with brine (×3), dried ($MgSO_4$), filtered and evaporated to a gum. The crude product was purified by flash silica chromatography, elution gradient 0 to 100% EtOAc in isohexane. Pure fractions were evaporated to dryness and slurried with EtOAc to afford 4-(4-fluoro-3-(4-methoxypiperidine-1-carbonyl)benzyl)phthalazin-1(2H)-one (2b) (22.45 g, 61.6%) as a white solid after filtration and vacuum drying.

b) Slurrying of 2b to Produce Hydrate

A suspension of 2b as made in step a) was prepared at a concentration of ~25 mg/ml in water, and stirred at constant temperature between 20 and 50° C. for about 48 hours. The desired hydrate was then separated from the water by filtration.

c) Resynthesis of 2f

A solution of 2-fluoro-5-((4-oxo-3,4-dihydrophthalazin-1-yl)methyl)benzoic acid (1) (27.07 g, 90.76 mmol) and 4-ethoxypiperidine (12.11 g, 93.73 mmol) in N,N-dimethylacetamide (422 ml) was treated with triethylamine (31.6 ml, 226.89 mmol) and stirred for 5 minutes before portionwise addition, over 10 minutes, of O-benzotriazol-1-yl-N,N,N',N'-tetra-methyluronium hexafluorophosphate (48.6 g, 128.15 mmol). The resulting solution was stirred at ambient temperature, under nitrogen, overnight, before being poured onto water (2.5 L). The mixture was split into two batches and each batch was extracted with ethyl acetate (2×750 mL). Combined extracts were washed with brine (~500 mL per batch) and dried over magnesium sulfate, filtered and evaporated to afford an amber gum (54 g), which was purified by flash silica chromatography, eluting isocratically with neat EtOAc. Pure fractions were evaporated to dryness to afford a sticky foam, which was dissolved, with gentle heating in a small amount (~50 mL) of EtOAc. This solution was then concentrated a little by rotary evaporation and left to stand. The resultant solid was slurried in ethyl acetate for ~7 hours before standing overnight. The solid was then collected by suction filtration and dried, under vacuum, at 55° C., for several hours to afford the product as a white solid (20.1 g). This material required further purification, thus material was taken up in diethyl ether (~75-100 mL) and stirred for 2 hours. Solid was then again collected by suction filtration and dried before combining with material which had been kept separate and slurried in ethyl acetate (~60 mL) for several hours. Mixture was stood over a weekend before collecting solid by suction filtration, washing with a little more ethyl acetate and drying under vacuum, at 55° C., to constant weight to afford 4-(3-(4-ethoxypiperidine-1-carbonyl)-4-fluorobenzyl)phthalazin-1(2H)-one (2f) (21.70 g, 58.4%) as a white solid.

Example 48

Inhibitory Action

In order to assess the inhibitory action of the compounds, the following assay was used to determine $IC_{50}$ values.

Mammalian PARP, isolated from Hela cell nuclear extract, was incubated with Z-buffer (25 mM Hepes (Sigma); 12.5 mM $MgCl_2$ (Sigma); 50 mM KCl (Sigma); 1 mM DTT (Sigma); 10% Glycerol (Sigma) 0.001% NP-40 (Sigma); pH 7.4) in 96 well FlashPlates (TRADE MARK) (NEN, UK) and varying concentrations of said inhibitors added. All compounds were diluted in DMSO and gave final assay concentrations of between 10 and 0.01 μM, with the DMSO being at a final concentration of 1% per well. The total assay volume per well was 40 μl.

After 10 minutes incubation at 30° C. the reactions were initiated by the addition of a 10 μl reaction mixture, containing NAD (5 μM), $^3$H-NAD and 30 mer double stranded DNA-oligos. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 μl 30% acetic acid to each well. The plates were then shaken for 1 hour at room temperature.

The plates were transferred to a TopCount NXT (TRADE MARK) (Packard, UK) for scintillation counting. Values recorded are counts per minute (cpm) following a 30 second counting of each well.

The % enzyme activity for each compound is then calculated using the following equation:

$$\% \text{ Inhibition} = 100 - \left(100 \times \frac{(cpm \text{ of unknowns} - \text{mean negative } cpm)}{(\text{mean positive } cpm - \text{mean neagative } cpm)}\right)$$

$IC_{50}$ values (the concentration at which 50% of the enzyme activity is inhibited) were calculated, which are determined over a range of different concentrations, normally from 10 μM down to 0.001 μM. Such $IC_{50}$ values are used as comparative values to identify increased compound potencies.

| Compound | IC$_{50}$ (nM) |
|---|---|
| 2a | 7 |
| 2b | 5 |
| 2c | 4 |
| 2d | 4 |
| 2e | 4 |
| 2f | 3 |
| 2g | 4 |
| 2h | 4 |
| 2i | 4 |
| 2j | 5 |
| 4a | 13 |
| 4b | 5 |
| 4c | 16 |
| 6a | 4 |
| 6b | 7 |
| 6c | 16 |
| 6d | 7 |
| 6e | 10 |
| 6f | 8 |
| 7 | 8 |
| 8a | 3 |
| 8b | 2 |
| 8c | 5 |
| 8d | 4 |
| 8e | 5 |
| 8f | 2 |
| 9 | 7 |
| 10 | 3 |
| 11 | 4 |
| 12 | 7 |
| 15 | 10 |
| 16 | 6 |
| 19 | 5 |
| 20 | 5 |
| 24 | 6 |
| 25 | 7 |
| 26a | 4 |
| 26b | 10 |
| 26c | 3 |
| 26d | 6 |
| 26e | 6 |
| 26f | 5 |
| 26g | 7 |
| 26h | 3 |
| 26i | 2 |
| 26j | 5 |
| 26k | 1 |
| 26l | 5 |
| 26m | 7 |
| 29 | 3 |
| 35a | 479 |
| 36 | 4 |
| 37 | 5 |
| 39 | 5 |
| 40 | 6 |
| 46 | 11 |
| 47a | 10 |
| 47b | 30 |
| 52a | 152 |
| 52b | 55 |
| 54 | 18 |
| 56 | 14 |
| 58 | 19 |
| 60 | 26 |
| 63 | 69 |
| 65 | 40 |
| 68 | 24 |
| 69 | 8 |
| 70 | 6 |
| 71 | 9 |
| 72a | 664 |
| 72b | 677 |
| 72c | 1739 |
| 72d | 1028 |
| 73 | 5 |
| 74 | 8 |
| 77 | 8 |
| 80 | 11 |
| 83 | 14 |
| 86 | 18 |
| 89 | 7 |
| 90 | 9 |
| 93 | 8 |
| 98 | 135 |
| 99 | 11 |
| 104a | 9 |
| 104b | 7 |
| 107 | 9 |
| 110 | 22 |
| 113 | 8 |
| 116 | 46 |
| 119a | 21 |
| 119b | 13 |
| 126a | 6 |
| 126b | 6 |
| 129a | 4 |
| 129b | 23 |

Potentiation Factor

The Potentiation Factor (PF$_{50}$) for compounds is calculated as a ratio of the IC$_{50}$ of control cell growth divided by the IC$_{50}$ of cell growth+PARP inhibitor. Growth inhibition curves for both control and compound treated cells are in the presence of the alkylating agent methyl methanesulfonate (MMS). The test compounds were used at a fixed concentration of 0.2 micromolar. The concentrations of MMS were over a range from 0 to 10 μg/ml.

Cell growth was assessed using the sulforhodamine B (SRB) assay (Skehan, P., et al., (1990) New calorimetric cytotoxicity assay for anticancer-drug screening. J. Natl. Cancer Inst. 82, 1107-1112). 2,000 HeLa cells were seeded into each well of a flat-bottomed 96-well microtiter plate in a volume of 100 μl and incubated for 6 hours at 37° C. Cells were either replaced with media alone or with media containing PARP inhibitor at a final concentration of 30 nM or 200 nM. Cells were allowed to grow for a further 1 hour before the addition of MMS at a range of concentrations (typically 0, 1, 2, 3, 5, 7 and 10 μg/ml) to either untreated cells or PARP inhibitor treated cells. Cells treated with PARP inhibitor alone were used to assess the growth inhibition by the PARP inhibitor.

Cells were left for a further 16 hours before replacing the media and allowing the cells to grow for a further 72 hours at 37° C. The media was then removed and the cells fixed with 100 μl of ice cold 10% (w/v) trichloroacetic acid. The plates were incubated at 4° C. for 20 minutes and then washed four times with water. Each well of cells was then stained with 100 μl of 0.4% (w/v) SRB in 1% acetic acid for 20 minutes before washing four times with 1% acetic acid. Plates were then dried for 2 hours at room temperature. The dye from the stained cells was solubilized by the addition of 100 μl of 10 mM Tris Base into each well. Plates were gently shaken and left at room temperature for 30 minutes before measuring the optical density at 564 nM on a Microquant microtiter plate reader.

| Patent | PF$_{50}$ (30 nM) |
|---|---|
| 2b | 3.0 |
| 2c | 1.9 |
| 2d | 2.1 |

| Patent | |
|---|---|
| 2e | 1.6 |
| 2f | 14.1 |
| 2g | 4.3 |
| 2h | 2.9 |
| 2i | 16.7 |
| 2j | 3.0 |
| 4a | 1.2 |
| 4b | 2.2 |
| 4c | 1.2 |
| 6a | 1.7 |
| 6b | 1.5 |
| 6c | 1.2 |
| 6d | 1.4 |
| 6e | 1.5 |
| 6f | 1.8 |
| 7 | 4.0 |
| 8a | 1.6 |
| 8b | 23.6 |
| 8c | 12.2 |
| 8d | 1.2 |
| 8e | 1.4 |
| 8f | 4.1 |
| 9 | 1.3 |
| 10 | 3.1 |
| 11 | 33.6 |
| 12 | 2.1 |
| 15 | 4.4 |
| 16 | 3.4 |
| 19 | 2.5 |
| 20 | 2.0 |
| 24 | 1.5 |
| 25 | 2.1 |
| 26a | 3.7 |
| 26b | 1.5 |
| 26c | 32.4 |
| 26d | 4.0 |
| 26e | 2.7 |
| 26f | 4.4 |
| 26g | 1.6 |
| 26h | 12.7 |
| 26i | 8.0 |
| 26j | 1.2 |
| 26k | 26.8 |
| 26l | 1.2 |
| 26m | 2.4 |
| 29 | 25.9 |
| 36 | 14.5 |
| 37 | 1.7 |
| 39 | 1.4 |
| 40 | 2.2 |
| 46 | 20.1 |
| 47a | 1.8 |
| 54 | 1.3 |
| 58 | 1.0 |
| 60 | 1.0 |
| 63 | 1.0 |
| 69 | 1.7 |
| 70 | 32.1 |
| 71 | 4.0 |
| 73 | 6.2 |
| 74 | 1.5 |
| 77 | 3.1 |
| 80 | 1.5 |
| 83 | 1.7 |
| 89 | 1.9 |
| 90 | 1.1 |
| 93 | 2.8 |
| 99 | 1.0 |
| 104a | 1.3 |
| 104b | 2.2 |
| 107 | 1.7 |
| 113 | 5.8 |
| 119a | 1.0 |
| 119b | 1.2 |
| 126a | 11.0 |
| 126b | 7.4 |
| 129a | 1.0 |

| Patent | $PF_{50}$ (200 nM) |
|---|---|
| 2a | 3 |
| 2b | 15 |
| 2c | 7 |
| 2d | 11 |
| 2e | 8 |
| 2f | 25 |
| 6a | 4.2 |
| 6b | 3.5 |
| 6c | 1.5 |
| 6d | 3.5 |
| 6e | 1.9 |
| 6f | 5.0 |
| 36 | 24.3 |
| 37 | 10.6 |
| 40 | 19.8 |
| 46 | 3.24 |
| 70 | 19.5 |
| 71 | 8.9 |
| 73 | 27.8 |
| 113 | 23.1 |

Example 49

Cells from the Hela cell line known as KBA1, which expressed high P-glycoprotein (ABC1a and ABC1b transporter glycoproteins also known as MDR1a and MDR1b) and the matched non-P-glycoprotein expressing line known as KB31, were seeded onto 96 well tissue culture plates with 80 μl per well of $1.00 \times 10^4$ cells/ml=800 cells/well [DMEM, 10% FBS, PSG] and left to adhere for 4 hours. After the incubation period 10 μl per well of 200 μM Verapamil (giving a final conc. of 20 μM) a known inhibitor of P-gp or vehicle media were added to various wells of the cell plates. The 96 well plates were left in the incubator for 1 hour prior to 10 μl of test compound (or the known substrate Etoposide as a reference control) or 10 μl PBS/1% DMSO vehicle (control wells) being added into either Verapamil containing or media control wells. The test compounds were tested over a range of different concentrations, normally from 100 μM down to 0.3 μM.

The cell plates were then incubated for 5 days prior to cell growth being assessed using the Sulforhodamine B (SRB) assay as described previously. The P-gp substrate activity for each compound was calculated using the cell growth activity of the tests compounds on the KBA1 cells in the presence or absence (control wells) of Verapamil. The Dose Modification Ratio (DMR) is calculated from the KBA1 where for each test compound a ratio of the $IC_{50}$ of the compound in the absence of Verapamil is divided by the $IC_{50}$ of cell growth in the presence of Verapamil. Compound that are not substrates for P-gp have a DMR of <1.5 while those compounds which are actively effluxed by P-gp generally show a DMR of >1.5 and more typically greater than 2.

Compound 2b has a DMR of 1.3 and compound 2f has a DMR of 1.0.

Example 50

The solubility of the test compounds was measured following a method described in Leach, A., et al., J Med Chem (2006), 49(23), 6672-6682:

Solubility values are determined from agitation of compounds in 0.1 M phosphate buffer at pH 7.4 for 24 hours at 25°

C. The supernatant is separated from undissolved material by double centrifugation and subsequently analysed and quantified against a standard of known concentration in DMSO using generic HPLC-UV methodology coupled with mass spectral peak identification.

Compound 2b has a solubility of 1070 µMol, and compound 2f has a solubility of 211 µMol.

The invention claimed is:

1. A compound of the formula (I):

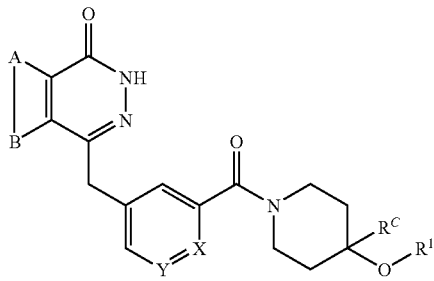

wherein:
- A and B together represent an optionally substituted benzene ring;
- X and Y are selected from CH and CH, CF and CH, CH and CF and N and CH respectively;
- $R^C$ is selected from H, $C_{1-4}$ alkyl; and
- $R^1$ is selected from $C_{1-7}$ alkyl, $C_{3-20}$ heterocyclyl and $C_{5-20}$ aryl, which groups are optionally substituted.

2. The compound according to claim 1, wherein the benzene ring is unsubstituted.

3. The compound according to claim 1, wherein the benzene ring bears one or two substituents selected from the group consisting of: halo, $NH_2$ and $C_{1-4}$ alkoxy.

4. The compound according to claim 1, wherein Y is CH.

5. The compound according to claim 1, wherein X is CH or CF.

6. The compound according to claim 1, wherein X is N.

7. The compound according to claim 1, wherein $R^1$ is a saturated $C_{1-7}$ alkyl group.

8. The compound according to claim 7, wherein $R^1$ is methyl or ethyl.

9. The compound according to claim 1, wherein $R^1$ is a $C_6$ aryl group.

10. The compound according to claim 9, wherein the $C_6$ aryl group is selected from phenyl, pyridyl, pyridazinyl, pyrimidinyl and pyrazinyl.

11. A pharmaceutical composition comprising a compound according to claim 1 and a pharmaceutically acceptable carrier or diluent.

* * * * *